(12) United States Patent
Tsien et al.

(10) Patent No.: US 7,906,636 B2
(45) Date of Patent: *Mar. 15, 2011

(54) MONOMERIC AND DIMERIC FLUORESCENT PROTEIN VARIANTS AND METHODS FOR MAKING SAME

(75) Inventors: Roger Y. Tsien, La Jolla, CA (US);
Robert E. Campbell, Edmonton (CA);
Nathan C. Shaner, La Jolla, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/618,624

(22) Filed: Nov. 13, 2009

(65) Prior Publication Data
US 2010/0227400 A1 Sep. 9, 2010

Related U.S. Application Data

(63) Continuation of application No. 10/931,304, filed on Aug. 30, 2004, now Pat. No. 7,687,614, which is a continuation-in-part of application No. 10/209,208, filed on Jul. 29, 2002, now Pat. No. 7,005,511, which is a continuation-in-part of application No. 10/121,258, filed on Apr. 10, 2002, now Pat. No. 7,157,566, which is a continuation-in-part of application No. 09/866,538, filed on May 24, 2001, now Pat. No. 6,852,849, which is a continuation-in-part of application No. 09/794,308, filed on Feb. 26, 2001, now Pat. No. 7,022,826.

(51) Int. Cl.
*C07H 21/04* (2006.01)
*A61K 38/00* (2006.01)

(52) U.S. Cl. ........ 536/23.1; 435/69.1; 435/106; 435/440; 435/6; 530/350

(58) Field of Classification Search ........................ None
See application file for complete search history.

(56) References Cited

U.S. PATENT DOCUMENTS

| | | | |
|---|---|---|---|
| 5,625,048 | A | 4/1997 | Tsien et al. |
| 5,981,200 | A | 11/1999 | Tsien et al. |
| 6,020,192 | A | 2/2000 | Muzyczka et al. |
| 6,140,132 | A | 10/2000 | Tsien et al. |
| 6,852,849 | B2 | 2/2005 | Tsien et al. |
| 6,969,597 | B2 | 11/2005 | Lukyanov et al. |
| 7,005,511 | B2 | 2/2006 | Tsien et al. |

FOREIGN PATENT DOCUMENTS

| | | |
|---|---|---|
| WO | WO 96/23810 A1 | 8/1996 |
| WO | WO 00/34318 A | 6/2000 |
| WO | WO 00/34326 | 6/2000 |
| WO | WO 00/34526 A1 | 6/2000 |
| WO | WO 01/62919 A1 | 8/2001 |
| WO | WO 01/96373 A3 | 12/2001 |
| WO | WO 02/068605 A2 | 9/2002 |

OTHER PUBLICATIONS

Attachment 1: ClonTech (Jan. 2002), DsRed Subcellular Localization Vectors, "New Products," pp. 1-2.
Attachment 2: pQE-30 and pQE-31 (2003) from Qiagen.
Baird et al., "Biochemistry, Mutagenesis, and Oligomerization of DsRed, a Red Fluorescent Protein from Coral." *Proc. Natl. Acad. Sci., USA*, 2000, vol. 97, pp. 11984-11989.
Baird et al., "Circular Permutation and Receptor Insertion within Green Fluorescent Proteins." *Proc. Natl. Acad. Sci.*, USA, 1999, vol. 96, pp. 11241-11246.
Baird, "Designing Fluorescent Biosensors by Exploiting Structure-Function Relationships in Fluorescent Proteins." *Ph.D. Thesis*, Biomedical Sciences, University of California, San Diego, 2001.
BD Biosciences/Clontech, Product Literature, "Living Colors DsRed C-Terminal Fusion Vector." *CLONTECHniques*, Jan. 2000, p. 22.
BD Biosciences/Clontech, Product Literature, "Living Colors DsRed Express." *CLONTECHniques*, Jul. 2002, pp. 16-17.
BD Biosciences/Clontech, Product Literature, "Living Colors HcRed: Novel Far-Red Fluorescent Protein for Real-Time Expression Studies." *CLONTECHniques*, Apr. 2002.
BD Biosoiences/Clontech, Product Literature, "Living Colors Red Fluorescent Protein." *CLONTECHniques*, Oct. 1999, vol. XIV, No. 4, pp. 2-6.
BD Biosciences/Clontech, Product Literature, "Mercury DsRed I Signaling Probes." *CLONTECHniques*, Apr. 2000, pp. 22-23.
Bevis et el., "Rapidly Maturing Variants of the Discosoma Red Fluorescent Protein (DsRed)." *Nat. Biotechnol.*, vol. 20, pp. 83-87.
Campbell et al., "A Monomeric Red Fluorescent protein." *PNAS*, 2002, vol. 99, No. 12, pp. 7877-7882.
Gavin et al., "An Approach for Reducing Unwanted Oligomerisation of DsRed Fusion Proteins." *Biochemical and Biophysical Res. Comm.*, 2002, vol. 298, pp. 707-713.
Gross et al, "The Structure of the Chromophore Within DsRed, A Red Fluorescent Protein from Coral." *PNAS*, 2000, vol. 97, pp. 11990-11995.
Gurskaya et al, "GFP-like Chromoproteins as a Source of Far-Red Fluorescent Proteins," *FEBS Lett.*, 2001, vol. 507, pp. 16-20.
Heim et al., "Improved Green Fluorescence." *Nature*, 1995, vol. 373, pp. 663-664.
Heim et al., "Wavelength Mutations and Posttranslational Autoxidation of Green Fluorescent Protein." *PNAS*, 1994, vol. 91, pp. 12501-12504.

(Continued)

Primary Examiner — Anand U Desai
Assistant Examiner — Samuel Liu
(74) Attorney, Agent, or Firm — Morgan, Lewis & Bockius LLP; Annette S. Parent

(57) ABSTRACT

The present invention relates generally to fluorescent proteins and fluorescent protein variants, and more specifically to monomeric and dimeric forms of Anthozoan fluorescent proteins. In one aspect, the present invention provides variants of fluorescent proteins, where the variants have a reduced propensity to tetramerize, and form dimeric or monomeric structures. In a further aspect, the present invention provides variants of fluorescent proteins, the variants being characterized by more efficient maturation than corresponding fluorescent proteins from which they are derived. The invention also relates to methods of making and using such fluorescent proteins and fluorescent protein variants, including fluorescent protein monomers and dimers.

8 Claims, 64 Drawing Sheets

OTHER PUBLICATIONS

Labas et al., "Diversity and Evolution of the Green Fluorescent Protein Family." *PNAS*, 2002, vol. 99, pp. 4256-4261.

Lauf et al., "Expression of Fluorescently Tagged Connexins: A Novel Approach to Rescue Function of Oligomeric DsRed-Tagged Proteins." *FEBS Lett.*, 2001, vol. 498, pp. 11-15.

Lukyanov et al., "Natural Animal Coloration Can Be Determined by a Nonfluorescent Green Fluorescent Protein Homolog." *J. Biol. Chem.*, 2000, vol. 275, pp. 25879-25882.

Lukyanoy, S.A. et al; "Novel fluorescent protein from non-bioluminescent Discosoma sp. red, useful for fluorescent labeling and as markers"; 2000, attachment for sequence alignment between SEQ ID No. 56 and SEQ ID No. 8, 3 pages.

Matz et al. "Fluorescent Proteins from NonBioluminescent Anthozoa Species," Nature Biotechnology, 1999, vol. 17, No. 10, pp. 969-973.

Miyawaki and Tsien, "Monitoring Protein Conformations and Interactions by Fluorescence Resonance Energy Transfer Between Mutants of Green Fluorescent Protein." *Methods Enzyrnol., Application of Chimeras in Cell Physiology*, 2000, vol. 327, pp. 472-500.

Miyawaki et al., "Dynamic and Quantitative Ca2+ Measurements Using Improved Cameleons." *PNAS*, 96: 2135-2140, 1999.

Ormö et al. "Crystal Structure of the Aequorea Victoria Green Fluorescent Protein," Science, 1996, vol. 273, pp. 1392-1395.

Prasher et al., "Summary Structure of the *Aequorea Victoria* Green-Fluorescent Protein." *Gene*, 1992, vol. 111, pp. 229-233, 1992.

Remington, "Negotiating the Speed Bumps to Fluorescence." *Nat. Biotechnol.*, 2002, vol. 20, pp. 28-29.

Roth, "Purification and Protease Susceptibility of the Green-Fluorescent Protein of *Aequorea* with a Note on Hlistaura." *Thesis from the Graduate Program in Biochemistry* at Rutgers, The State University of New Jersey, 1985.

Smialowski, Pawel, Dissertation of Technische Universitat Munchen, 2004, "Structural and Functional Studies on Photoactive Proteins and Proteins Involved in Cell Differentiation," pp. 1-138.

Terskikh et al., "Analysis of DsRed Mutants, Space Around the Fluorophore Accelerates Fluorescence Development." *J. Biol. Chem.*, 2002, vol. 277, pp. 7633-7636.

Tsien, "Rosy Dawn for Fluorescent Proteins." *Nature Biotechnology*, 1999 vol. 17, pp. 956-957.

Verkhusha et al., "Kinetic Analysis of Maturation and Denaturation of DsRed, a Coral-Derived Red Fluorescent Protein." *Biochemistry*, 2001, vol. 66, No. 12, pp. 1342-1351.

Wall et al., "The Structural Basis for Red Fluorescence in the Tetrameric GFP Homolog DsRed." *Nature Struct. Biol.*, 2000, vol. 7, pp. 1133-1138.

Wang et al. Directed molecular evolution by somatic hypermutation, Protein Eng, Des. Sel., 2004, vol. 17, No. 9, pp. 659-664.

Wiehler et al., "Mutants of Discosoma Red Fluorescent protein with a GFP-like Chromophore." *FEBS Letters*, 2001, vol. 487, pp. 384-389.

Yang et al., "The Molecular Structure of Green Fluorescent Protein." *Nature Biotechnology* 1996, vol. 14, pp. 1246-1251.

Yanushevich, et al. "A Strategy far the Generation of Non-Aggregating Mutants of Anthozoa Fluorescent Proteins," 2002, FEBS Letters 511, pp. 11-14.

Yarbrough et al. Refined crystal structure of DsRed, a red fluorescent protein from coral, at 2.0-A resolution, Proc. Natl. Acad. Sci. USA, 2001, vol. 98, No. 2, pp. 462-467.

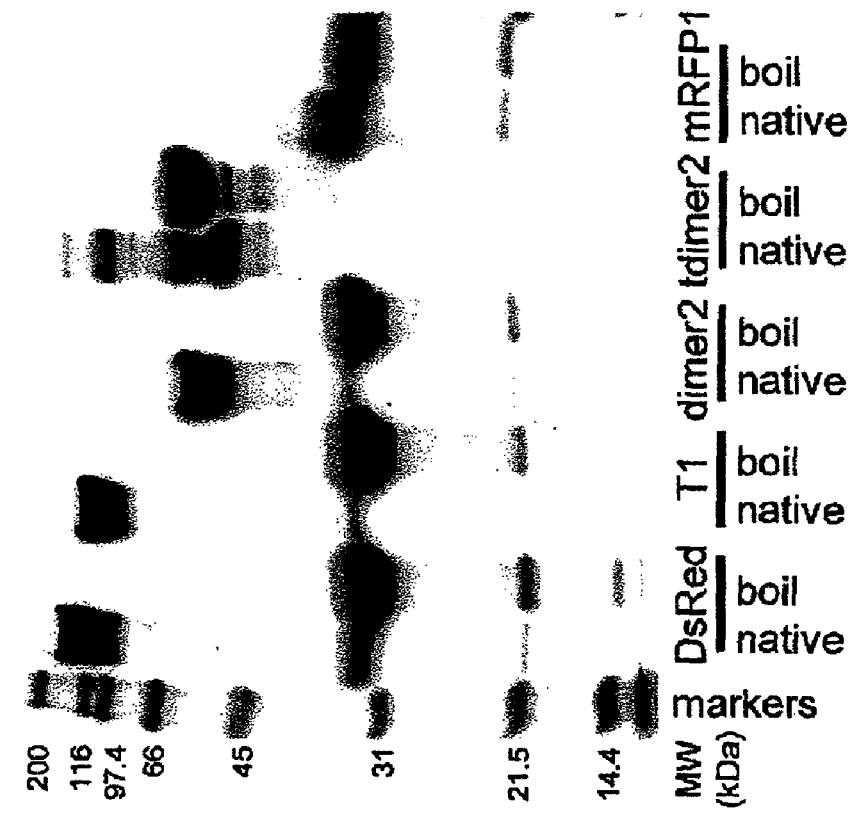
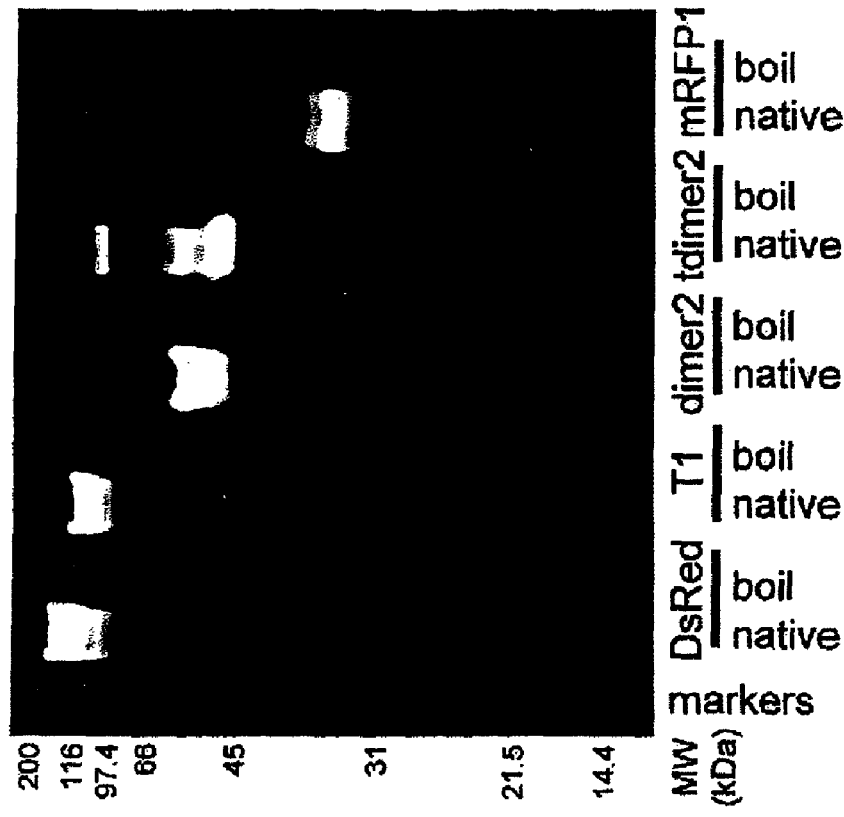

FIG. 10A

| Library* | Template | Method† | Targeted positions | Top clone‡ | Name |
|---|---|---|---|---|---|
| D1 | T1§ + I125R | MOE | I161/K163/S179/S197 | T1 + S117C_rev/I125R/K163Q/S179T/S197T | dimer1 |
| D2 | dimer1 | EPM | n/a | dimer1 + V71A/S131P | dimer1.02 |
| D3 | dimer1.02 | MOE | K70/S197/T217 | dimer1.02 + K70R/F118L/T217S | dimer1.56 |
| D4 | dimer1.56 | MOE | C117/F118/F124/V127T | dimer1.56 + R70K_rev/C117T/F118L/V127T | dimer2 |
| D5 | T1 + I125R | MOE | I161/K163/S179/S197/H222G/F224G | a. T1 + S117C_rev/F124L/I125R/K163Q/S179T/S197T/H222G/F224G | a.HF2Ga |
|  |  |  |  | b. As in a with K163H | b.HF2Gb |
| M1 | dimer1 | MOE | E144/A145/S146/I161/H162/K163/A164/H222G/F224G | dimer1 + E144A/A145R/H162K/K163M/A164R/H222G/F224G | mRFP0.1 |
| M2 | mRFP0.1 | EPM | n/a | mRFP0.1 + Y192C | mRFP0.2 |
| M3 | dimer1.56 & HF2Ga & HF2Gb & mRFP0.2 | MOE | C117/F124/V127T/S131/H162/K163/A164/Y192A/Y194A/H222G/F224G | mRFP0.2 + K70R/C117E/F124L/V127T/A144E_rev/R145A_rev/Y192A/Y194A/T217S | mRFP0.3 |

*Libraries are labeled either 'M' or 'D' if they are composed of monomers or dimers respectively. †In each round libraries were constructed by either multiple overlap extension (MOE) or error-prone PCR mutagenesis (EPM). ‡Unless otherwise indicated, the top clone contains all mutations present in the starting template. All mutations are relative to wild type DsRed except reversions, which are identified with the subscript 'rev'. § The T1 construct used in this work differs from the original T1 construct(7) by the absence of the P(−4)L mutation and the inserted valine residue (V1a) which is present in all constructs except mRFP1.

| Library[*] | Template | Method[†] | Targeted positions | Top clone[‡] | Name |
|---|---|---|---|---|---|
| M4 | mRFP0.3 | MOE | K70/V71/K83/ Y192/Y194/V195/ S197/ T217/L223/ L225 | a. mRFP0.3 + K83I/ L223E/L225A | a. mRFP0.4a |
| | | | | b. mRFP0.3 + R70K rev/ V71A/ K83L/Y194K/ V195T/S197I/T217A/ H222C/ L223T/L225A | b. mRFP0.4b |
| M5 | mRFP0.4a & mRFP0.4b | EPM | n/a | a. mRFP0.4a + F177S | a. mRFP0.5a |
| | | | | b. mRFP0.4b + L150M/ V156A | b. mRFP0.5b |
| M6 | mRFP0.5a & mRFP0.5b | MOE | L174/ V175/F177/ F180 | mRFP0.5b + L174D/ V175A/F177V/I180T | mRFP0.6 |
| M7 | mRFP0.6 | MOE | V1a del/A145/R149/L150/ R153/V156/H222 | mRFP0.6 + V1a del/ R153E/H222S | mRFP1 |

*Libraries are labeled either 'M' or 'D' if they are composed of monomers or dimers respectively. †In each round libraries were constructed by either multiple overlap extension (MOE) or error-prone PCR mutagenesis (EPM). ‡Unless otherwise indicated, the top clone contains all mutations present in the starting template. All mutations are relative to wild type DsRed except reversions, which are identified with the subscript 'rev'. §The T1 construct used in this work differs from the original T1 construct(7) by the absence of the P(-4)L mutation and the inserted valine residue (V1a) which is present in all constructs except mRFP1.

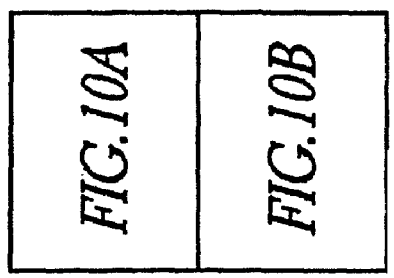

| FIG.11A | FIG.11B | FIG.11C |

| Library | Primer pairs for fragment amplification | Positions | Codon * | Possible substitutions |
|---|---|---|---|---|
| D1 | 1. PRSET_BamH1_FW/I161X_K163X_RV<br>2. I161X_K163X_FW/S179X_RV<br>3. S179X_FW/S197X_A_RV<br>4. S197X_A_FW/PRSET_EcoR1_RV | I161<br>K163<br>S179<br>S197 | VYC<br>MWS<br>NCC<br>NCC | T/I/A/V/R/L<br>Q/H/L/K/N/M/I<br>A/S/T/P<br>A/S/T/P |
| D3 | 1. PRSET_BamH1_FW/S197X_B_RV<br>2. S197X_B_FW/T217X_RV<br>3. T217X_FW/PRSET_EcoR1_RV | K70†<br>S197<br>T217 | ARG<br>NNK<br>DYC | K/R<br>All 20 a.a.<br>A/T/S/V/I/F |
| D4 | 1. PRSET_BamH1_FW/C117X_V127T_RV<br>2. C117X_V127T_FW/PRSET_EcoR1_RV | C117<br>F118<br>F124<br>V127 | RVS<br>NTS<br>NTS<br>ACC | T/K/S/N/R/A/E/G/D<br>L/M/V/I/F<br>L/M/V/I/F<br>T |
| D5 | 1. PRSET_BamH1_FW/I161X_K163X_RV<br>2. I161X_K163X_FW/S179X_RV<br>3. S179X_FW/S197X_RV<br>4. S197X_FW/H222G_F224G_RV | I161<br>K163<br>S179<br>S197<br>H222<br>F224 | VYC<br>MWS<br>NCC<br>NCC<br>GGC<br>GGC | T/I/A/V/P/L<br>Q/H/L/K/N/M/I<br>A/S/T/P<br>A/S/T/P<br>G<br>G |

*The standard mixed base definitions are R = A/G, Y = C/T, M = A/C, K = G/T, S = C/G, W = A/T, H = A/C/T, B = C/G/T, V=A/C/G, D=A/G/T, N=A/C/G/T  Multiple templates were used to introduce these K70 substitutions.

FIG. 11B

| Library | Primer pairs for fragment amplification | Positions | Codon * | Possible substitutions |
|---|---|---|---|---|
| M1 | 1. PRSET_BamH1_FW/E144X_A164X_RV<br>2. E144X_A164X_FW/H222G_F224G_RV | E144<br>A145<br>S146<br>I61<br>H162<br>K163<br>A164<br>H222<br>F224 | VVS<br>VVS<br>ASC<br>NHC<br>ARG<br>NWS<br>ARG<br>GGC<br>GGC | G/R/A/P/T/E/Q/K/S/D/H/N<br>G/R/A/P/T/E/Q/K/S/D/H/N<br>S/T<br>N/D/H/Y/T/A/P/S/I/L/V/F<br>K/R<br>K/E/Q/M/V/L/N/D/H/Y/I/F<br>K/R<br>G<br>G |
| M3 | 1. PRSET_BamH1_FW/C117X_S131X_RV<br>2. C117X_S131X_FW/H162X_A164X_RV<br>3. H162X_A164X_FW/Y192A_Y194A_RV<br>4. Y192A_Y194A_FW/H222G_F224G_RV | C117<br>F124<br>V127<br>S131<br>H162<br>K163<br>A164<br>Y192<br>Y194<br>H222<br>F224 | RVS<br>NTS<br>ACC<br>YCC<br>ARG<br>MWS<br>ARG<br>GCC<br>GCC<br>GGC<br>GGC | T/K/S/N/R/A/E/G/D<br>L/M/V/I/F<br>T<br>S/P<br>K/R<br>Q/H/L/K/N/M/I<br>K/R<br>A<br>A<br>G<br>G |

*The standard mixed base definitions are R = A/G, Y = C/T, M = A/C, K = G/T, S = C/G, W = A/T, H = A/C/T, B = C/G/T, V=A/C/G, D=A/G/T, N=A/C/G/T Multiple templates were used to introduce these K70 substitutions.

FIG. 11C

| Library | Primer pairs for fragment amplification | Positions | Codon * | Possible substitutions |
|---|---|---|---|---|
| M4 | 1. PRSET_BamH1_FW/K70X_K83X_RV<br>2. K70X_K83X_FW/Y192X_S197X_RV<br>3. Y192X_S197X_FW/T217X_L225X_RV | K70<br>V71<br>K83<br>Y192<br>Y194<br>V195<br>S197<br>T217<br>L223<br>L225 | ARG<br>GYC<br>WWK<br>RMS<br>RMS<br>RYC<br>RYC<br>DCC<br>RMS<br>RMS | K/R<br>V/A<br>N/K/I/M/Y/F/L<br>E/D/A/K/N/T<br>E/D/A/K/N/T<br>T/I/A/V<br>T/I/A/V<br>S/T/A<br>E/D/A/K/N/T<br>E/D/A/K/N/T |
| M6 | 1. PRSET_BamH1_FW/L174X_I180X_RV<br>2. L174X_I180X_FW/PRSET_EcoR1_RV | L174<br>V175<br>F177<br>I180 | VVC<br>NYC<br>NYC<br>AYC | A/D/G/H/N/P/R/S/T<br>P/T/S/A/L/I/F/V<br>P/T/S/A/L/I/F/V<br>I/T |
| M7 | 1. PRSET_BamH1_FW/A145X_V156X_RV<br>2. A145X_V156X_FW/PRSET_EcoR1_RV<br>then<br>3. V1a_del_FW/H222S_REV | V1a<br>A145<br>R149<br>L150<br>R153<br>V156<br>H222 | deletion<br>SCC<br>CRS<br>NTS<br>VAS<br>RBC<br>TCC | deletion<br>A/P<br>Q/H/R/R<br>L/M/V/I/F<br>E/Q/D/H/K/N<br>V

FIG. 12A

| Primer Name | Sequence | SEQ ID No. |
|---|---|---|
| Primers for General Use | | |
| PRSET_BamH1_FW | GTA CGA CGA TGA CGA TAA GGA TCC | 41 |
| PRSET_EcoR1_RV | GCA GCC GGA TCA AGC TTC GAA TTC | 42 |
| Primers Used to Construct Libraries for DsRed Dimer Evolution | | |
| N42X_V44X_FW | CGC CCC TAC GAG GGC CAC MWS ACC VYC AAG CTG AAG GTG ACC AAGG | 43 |
| N42X_V44X_RV | CCT TGG TCA CCT TCA GCT TGR BGG TSW KGT GGC CCT CGT AGG GGC G | 44 |
| K70X_V71X_FW | CAG TTC CAG TAC GGC TCC NNK NYC TAC GTG AAG CAC CCC GCC | 45 |
| K70X_V71X_RV | GGC GGG GTG CTT CAC GTA GRN MNN GGA GCC GTA CTG GAA CTG | 46 |
| C117X_V127T_FW | CAG GAC GGC RVS NTS ATC TAC AAG GTG AAG NTS CGC GGC ACC AAC TTC | 47 |
| C117X_V127T_RV | GAA GTT GGT GCC GCG SAN CTT GTA GAT SAN SBY GCC GTC CTG | 48 |
| I161X_K163X_FW | GGC GTG CTG AAG GGC GAG VYC CAC MWS GCC CTG AAG GTG GAC G | 49 |
| I161X_K163X_RV | CGT CCT TCA GCT TCA GGG CSW KGT GGR BCT CGC CCT TCA GCA CGC C | 50 |
| S179X_FW | GGT GGA GTT CAA GNC CAT CTA CAT GGC CAA G | 51 |
| S179X_RV | CTT GGC CAT GTA GAT GGN CTT GAA CTC CACC | 52 |
| S197X_A_FW | CTA CTA CTA CGT GGA CNC CAA GCT GGA CAT CAC C | 53 |
| S197X_A_RV | P-GGT GAT GTC CAG CTT GKN GTC CAC GTA GTA G | 54 |
| S197_B_FW | C TAC TAC TAC GTG GAC NNK AAG CTG GAC ATC ACC | 55 |
| S197_B_RV | GGT GAT GTC CAG CTT MNN GTC CAC GTA GTA G | 56 |
| T217X_FW | CAG TAC GAG CGC NCC GAG GGC CGC CAC | 57 |
| T217X_RV | GTG GCG GCC CTC GGN GCG CTC GTA CTG | 58 |

The standard mixed base definitions are R = A/G, Y = C/T, M = A/C, K = G/T, S = C/G, W = A/T, H = A/C/T, B = C/G/T, V = A/C/G, D = A/G/T, N=A/C/G/T.

FIG. 12B

| Primer Name | Sequence | SEQ ID No. |
|---|---|---|
| Primers used for DsRed Monomer Evolution | | |
| K70X_K83X_FW | AAG CAC CCC GCC GAC ATC CCC GAC TAC WWK AAG CTG TCC | 59 |
| K70X_K83X_RV | GAT GTC GGC GGG GTG CTT CAC GTA GRC CYT GGA GCC GTA CTG | 60 |
| C117X_S131X_FW | GTG AAG NTS CGC GGC ACC AAC TTC CCC YCC GAC GGC CCC | 61 |
| C117X_S131X_RV | GAA GTT GGT GCC GCG SAN CTT CAC CTT GTA GAT GAA SBY GCC GTC CTG | 62 |
| E144X_A164X_FW | CTG TAC CCC CGC GAC GGC GTG CTG AAG GGC GAG NHC ARG NWS ARG | 63 |
| E144X_A164X_RV | CTT CAG GCC GTC GCG GGG GTA CAG GCC CTC GGT GST SBB SBB CCA GCC CAT RGT CTT CTG | 64 |
| A145X_V156X_FW | TCC ACC GAG CRS NTS TAC CCC VAS GAC GGC RBC CTG AAG GGC | 65 |
| A145X_V156X_RV | GCC GTC STB GGG GTA SAN SYG CTC GGT GGA GGS CTC CCA GCC | 66 |
| H162X_A164X_FW | CTG AAG GGC GAG ATC ARG MWS ARG CTG AAG GAC | 67 |
| H162X_A164X_RV | GTC CTT CAG CYT SWK CYT GAT CTC GCC CTT CAG | 68 |
| L174X_180X_FW | GGC CAC TAC VVC NYC GAG NYC AAG ACC AYC TAC ATG GCC | 69 |
| L174X_180X_RV | GGC CAT GTA GRT GGT CTT GRN CTC GRN GBB GTA GTG GCC | 70 |
| Y192A_Y194A_FW | GTG CAG CTG CCC GGC GCC TAC GCC GTG GAC GCC AAG CTG | 71 |
| Y192A_Y194A_RV | CAG CTT GGT GTC CAC GGC GTA GGC GCC GGG CAG CTG CAC | 72 |
| Y192X_S197X_FW | GGC RMS TAC RYC GAC RYC AAG CTG GAC ATC ACC | 73 |
| Y192X_S197X_RV | CTT GRY GTC GRY SKY GTA SKY GCC SKY GCC CAG CTG CAC | 74 |
| T217X_L225X_RV | C GAA TTC TTA SKY GCC SKY GCC GTG GCC CTC GGH GCG CTC | 75 |
| H222G_F224G_RV | P-GCT TCG AAT TCT TAC AGG CCC AGG CCG TGG CGG CCC TCG G | 76 |
| V1a_del_FW | AAG GAT CCG ATG GCC TCC TCC GAG GAC GTC | 77 |
| H222S_REV | TTC GAA TTC TTA GGC GCC GGT GGA GTG GCG GCC | 78 |

The standard mixed base definitions are R = A/G, Y = C/T, M = A/C, K = G/T, S = C/G, W = A/T, H = A/C/T, B = C/G/T, V = A/C/G, D = A/G/T, N = A/C/G/T.

FIG. 13

| Construct/Injection | Number of Cells (and %) Showing Lucifer Yellow Passage | Did not pass lucifer yellow |
|---|---|---|
| Cx43-mRFP1 | 8 (100%) | 0 |
| Cx43-mRFP0.5a | 36 (100%) | 0 |
| Cx43-tdimer2(12)* | 13 (33.5%) | 27 |
| Cx43-dimer2 | 16 (35%) | 29 |
| Cx43-T1 | 1 (2.5%) | 38 |
| Injected untransfected cells | 0 (0%) | 22 |
| Injected transfected cell in contact with an untransfected cell. | 0 (0%) | 76 |

* Found one obvious gap junction with Cx43-tdimer2(12)

FIG. 14

| | Excitation maximum (nm) | Emission maximum (nm) | $\varepsilon$ ($M^{-1}cm^{-1}$) | Quantum Yield (QY) | QY of photobleach | $pK_a$ | $t_{0.5}$ for maturation at 37°C |
|---|---|---|---|---|---|---|---|
| DsRed* | 558 | 583 | $57 \times 10^3$ | 0.79 | $2.7 \times 10^{-7}$ | 4.7 | ~10 h |
| T1 | 555 | 584 | $35 \times 10^3$ | 0.51 | $2.1 \times 10^{-7}$ | 4.8 | <1 h |
| dimer2 | 552 | 579 | $60 \times 10^3$ | 0.69 | $2.5 \times 10^{-7}$ | 4.9 | ~2 h |
| tdimer2(12) | 552 | 579 | $120 \times 10^3$ | 0.68 | $2.0 \times 10^{-7}$ | 4.8 | ~2 h |
| mRFP1 | 584 | 607 | $44 \times 10^3$ | 0.25 | $2.9 \times 10^{-6}$ | 4.5 | <1 h |

*Published values for the $\varepsilon$ and QY of photobleach of DsRed are highly variable, suggesting that these values depend critically on the conditions of the purification or handling. All values were determined in parallel on identically treated

FIG. 15

| Mutation | Red Species | | Green Species | | Maturation Speed | Red/Green Ratio |
|---|---|---|---|---|---|---|
| | Exc (nm) | Em (nm) | Exc (nm) | Em (nm) | | |
| None | 558 | 583 | 475 | 499 | ++ | 840 |
| K83R | 558 | 582 | 480 | 499 | -- | 0.05 |
| K83E | 550 | 584 | 474 | 497 | - | 0.43 |
| K83N | 558 | 592 | 474 | 497 | - | 9.8 |
| K83P | 558 | 594 | 474 | 497 | - | 3.3 |
| K83F | 560 | 594 | 474 | 499 | -- | 0.29 |
| K83W | 562 | 594 | 478 | 501 | - | 0.44 |
| K83M | 564 | 602 | 474 | 499 | -- | 49 |
| Y120H | 562 | 600 | 478 | 499 | - | 0.4 |
| S197T | 558 | 584 | 478 | 499 | + | 53 |
| K70R | 562 | 585 | 480 | 503 | - | 13.8 |
| K70M | N/a | n/a | 480 | 499 | n/a | 0 |

FIG. 16 nucleotide sequence of the *Discosoma* wild-type red fluorescent protein open reading frame atggtgtcttccaagaatgttatcaagagtgttcatgaggtttaaggttcgcatgaaaga
acggtcaatgggcacgagtttgaaatagaaggcgaagagaggagaggggaggccatacgaaggc
cacaataccgtaaagcttaaggtaaccaaggggggaccttttgccatttgcttgggatatt
ttgtcaccacaatttcagtatgtgaagcaaggtatatgtcaagcaccctgccgacatacca
gactataaaagctgtcattcctgaagatttaaatgggaaaggtcatgaactttgaa
gacggtggcgtcgttactgtaacccagattccagtttgcaggatgctgtgtttcatctac
aaggtcaagttcattggcgtgaactttcctccgatggacctgtttatgcaaaagaagaca
atgggctgggaagccagcactgagctgaaagacgtgtatcctcgtgatggcgtgttgaaaggagag
attcataaggctctgaagctgaaagactgaagctaccagctactactatgttgactccaaactggat
tacatggcaaagaagccacgaagactatacaatcgtttgagcagtatgaaagaaccgagggacgc
caccatctgtttcctttaa

FIG. 17 amino acid sequence of the *Discosoma* wild-type red fluorescent protein

M R S S K N V I K E F M R F K V R M E G
T V N G H E F E I E G E G E G R P Y E G
H N T V K L K V T K G G P L P F A W D I
L S P Q F Q Y G S K V Y V K H P A D I P
D Y K K L S F P E G F K W E R V M N F E
D G G V V T V T Q D S S L Q D G C F I Y
K V K F I G V N F P S D G P V M Q K K T
M G W E A S T E R L Y P R D G V L K G E
I H K A L K L K D G G H Y L V E F K S I
Y M A K K P V Q L P G Y Y Y V D S K L D
I T S H N E D Y T I V E Q Y E R T E G R
H H L F L

FIG. 18 nucleotide sequence of the *Discosoma* variant fast T1 red fluorescent protein open reading frame atggcctcctccgaggacgtcatcaaggagttcatgcgcttcaaggtgcgcatggagggc
tccgtgaacggccacgagttcgagatcgagggcgagggcgagggccgcccctacgagggc
acccagaccgccaagctgaaggtgaccaagggcggccccctgccctttcgcctgggacatc
ctgtccccccagttccagtacggctccaaggtgtacgtgaagcaccccgccgacatcccc
gactacaagaagctgtcctttcccgagggcttcaagtgggagcgcgtgatgaacttcgag
gacggcggcgtggtgaccgtgacccagcagactcctcccgcaggacgctccttcatctac
aaggtgaagttcatcggggcctccaccgagcctctacccccgcgtaatgcagagaagaagact
atgggctgggaggcctccaccgagcgcctgtacccccgcgacggcgtgctgaagggcgag
atccacaaggccctgaagctgaaggacggcggccactacctggtgagtttcaagtccatc
tacatggccaagaagcccgtgcagctgcccgcgtactactacgtggactgctccaagctggac
atcacctcccacaacgaggactacaccatcgtggagcagtacgagcgcgccgagggcccgc
caccacacctgttcctgtag

FIG. 19 amino acid sequence of the *Discosoma* variant fast T1 red fluorescent protein

| | P-4L | R2A | K5E | N6D | | T21S | H41T | N42Q | V44A | | | |
|---|---|---|---|---|---|---|---|---|---|---|---|---|
| T1 (as received from B. Glick) | P-4L | R2A | K5E | N6D | | T21S | H41T | N42Q | V44A | | | |
| T1 + I125R (after subcloning into our preferred vector) | V1a | R2A | K5E | N6D | | T21S | H41T | N42Q | V44A | | | |
| dimer1 | V1a | R2A | K5E | N6D | | T21S | H41T | N42Q | V44A | | | |
| dimer1.02 | V1a | R2A | K5E | N6D | | T21S | H41T | N42Q | V44A | | | V71A |
| 1.26 | V1a | R2A | K5E | N6D | | T21S | H41T | N42Q | V44A | | | V71A |
| 1.28 | V1a | R2A | K5E | N6D | | T21S | H41T | N42Q | V44A | K47R | | V71A |
| 1.34 | V1a | R2A | K5E | N6D | | T21S | H41T | N42Q | V44A | | K70R | V71A |
| dimer1.58 | V1a | R2A | K5E | N6D | | T21S | H41T | N42Q | V44A | | K70R | V71A |
| 1.61 | V1a | R2A | K5E | N6D | | T21S | H41T | N42Q | V44A | | K70R | |
| 1.76 | V1a | R2A | K5E | N6D | | T21S | H41T | N42Q | V44A | | K70R | |
| dimer2 | V1a | R2A | K5E | N6D | | T21S | H41T | N42Q | V44A | | | V71A |
| non-aggregating mutations | | X | X | X | | | | | | | | |
| AB interface | | | | | | | | | | | | |
| AC interface | | | | | | | | | | | | |
| external to barrel | X | | | | | X | X | | | | | |
| internal to barrel | | | | | | | | X | X | | | X |
| | | | | | | | | | | | | |
| mRFP0.1 | V1a | R2A | K5E | N6D | | T21S | H41T | N42Q | V44A | | | |
| mRFP0.2 | V1a | R2A | K5E | N6D | | T21S | H41T | N42Q | V44A | | | |
| mRFP0.3 | V1a | R2A | K5E | N6D | | T21S | H41T | N42Q | V44A | | K70R | |
| mRFP0.4a | V1a | R2A | K5E | N6D | | T21S | H41T | N42Q | V44A | | K70R | |
| mRFP0.4b | V1a | R2A | K5E | N6D | | T21S | H41T | N42Q | V44A | | | V71A |
| mP11 | V1a | R2A | K5E | N6D | | T21S | H41T | N42Q | V44A | | K70R | |
| mP17 | V1a | R2A | K5E | N6D | | T21S | H41T | N42Q | V44A | | K70R | |
| m1.01 | V1a | R2A | K5E | N6D | | T21S | H41T | N42Q | V44A | | K70R | |
| m1.02 | V1a | R2A | K5E | N6D | | T21S | H41T | N42Q | V44A | | K70R | |
| mRFP0.5a | V1a | R2A | K5E | N6D | | T21S | H41T | N42Q | V44A | | K70R | |
| m1.12 | V1a | R2A | K5E | N6D | | T21S | H41T | N42Q | V44A | | K70R | |
| mRFP0.5b | V1a | R2A | K5E | N6D | | T21S | H41T | N42Q | V44A | | | V71A |
| m1.15 | V1a | R2A | K5E | N6D | F11S | T21S | H41T | N42Q | V44A | | K70R | |
| m1.19 | V1a | R2A | K5E | N6D | | T21S | H41T | N42Q | V44A | | K70R | |
| mRFP0.6 | V1a | R2A | K5E | N6D | | T21S | H41T | N42Q | V44A | | | V71A |
| m124 | V1a | R2A | K5E | N6D | | T21S | H41T | N42Q | V44A | | | V71A |
| m131 | V1a | R2A | K5E | N6D | | T21S | H41T | N42Q | V44A | | | V71A |
| m141 | V1a | R2A | K5E | N6D | | T21S | H41T | N42Q | V44A | | | V71A |
| m163 | V1a | R2A | K5E | N6D | | T21S | H41T | N42Q | V44A | | | V71A |
| m173 | V1a | R2A | K5E | N6D | | T21S | H41T | N42Q | V44A | | | V71A |
| m187 | V1a | R2A | K5E | N6D | | T21S | H41T | N42Q | V44A | | | V71A |
| m193 | V1a | R2A | K5E | N6D | | T21S | H41T | N42Q | V44A | | | V71A |
| m200 | V1a | R2A | K5E | N6D | | T21S | H41T | N42Q | V44A | | | V71A |
| m205 | V1a | R2A | K5E | N6D | | T21S | H41T | N42Q | V44A | | | V71A |
| m220 | V1a | R2A | K5E | N6D | | T21S | H41T | N42Q | V44A | | | V71A |
| mRFP1 | | R2A | K5E | N6D | | T21S | H41T | N42Q | V44A | | | V71A |
| non-aggregating mutations | | X | X | X | | | | | | | | |
| AB interface | | | | | | | | | | | | |
| AC interface | | | | | | | | | | | | |
| external to barrel | | | | | | X | X | | | | | |
| internal to barrel | | | | | | | | X | X | | | X |

FIG. 20B

| Name | | | | | | | | | | |
|---|---|---|---|---|---|---|---|---|---|---|
| T1 (as received from B. Glick) | | C117S | | | | | | | | |
| T1 → H25R (after subcloning into our preferred vector) | | C117S | | I125R | | | | | | |
| dimer1 | | | | I125R | | | | | | |
| dimer1.02 | | | | I125R | | S131P | | | | |
| 1.25 | | | | I125R | | S131P | | | | |
| 1.28 | D78G | | | I125R | | S131P | | | | |
| 1.34 | | | | I125R | | S131P | | | | |
| dimer1.56 | | | F118L | I125R | | S131P | | | | |
| 1.61 | | | | I125R | | S131P | | | | |
| 1.76 | | | F118L | I125R | | S131P | | | | |
| dimer2 | | C117T | F118L | I125R | V127T | S131P | | | | |
| non-aggregating mutations | | | | | | | | | | |
| AB interface | | | | X | X | | | | | |
| AC interface | | | | | | | | | | |
| external to barrel | | X | | | X | | | | | |
| internal to barrel | | | X | | | | | | | |
| mRFP0.1 | | | | I125R | | | E144A | A145R | | |
| mRFP0.2 | | | | I125R | | | E144A | A145R | | |
| mRFP0.3 | | C117E | F124L | I125R | V127T | | | | | |
| mRFP0.4a | K83I | C117E | F124L | I125R | V127T | | | | | |
| mRFP0.4b | K83L | C117E | F124L | I125R | V127T | | | | | |
| mP11 | K83I | C117E | F124L | I125R | V127T | | | | | |
| mP17 | K83I | C117E | F124L | I125R | V127T | | | | | |
| m1.01 | K83I | C117E | F124L | I125R | V127T | | | | | |
| m1.02 | K83I | C117E | F124L | I125R | V127T | | | | | |
| mRFP0.5a | K83I | C117E | F124L | I125R | V127T | | | | | |
| m1.12 | K83I | C117E | F124L | I125R | V127T | | | | | |
| mRFP0.5b | K83L | C117E | F124L | I125R | V127T | | | | | L150M |
| m1.15 | K83I | C117E | F124L | I125R | V127T | | | | | |
| m1.19 | K83I | C117E | F124L | I125R | V127T | | | | | |
| mRFP0.6 | K83L | C117E | F124L | I125R | V127T | | | | | L150M |
| m124 | K83L | C117E | F124L | I125R | V127T | | | | | L150M |
| m131 | K83L | C117E | F124L | I125R | V127T | | | | | |
| m141 | K83L | C117E | F124L | I125R | V127T | | | | | |
| m163 | K83L | C117E | F124L | I125R | V127T | | | A145P | | L150M |
| m173 | K83L | C117E | F124L | I125R | V127T | | | | | L150M |
| m187 | K83L | C117E | F124L | I125R | V127T | | | | R149H | L150M |
| m193 | K83L | C117E | F124L | I125R | V127T | | | | | L150M |
| m200 | K83L | C117E | F124L | I125R | V127T | | | A145P | R149H | L150M |
| m205 | K83L | C117E | F124L | I125R | V127T | | | A145P | R149H | |
| m229 | K83L | C117E | F124L | I125R | V127T | | | | | L150M |
| mRFP1 | K83L | C117E | F124L | I125R | V127T | | | | | L150M |
| non-aggregating mutations | | | | | | | | | | |
| AB interface | | | | X | X | | | | | |
| AC interface | | | | | | | | | | |
| external to barrel | | X | | | | | | | | |
| internal to barrel | X | | | X | | | | | | X |

FIG. 20C

| Variant | R153 | V156 | H162 | K163 | A164 | K168 | L174 | V175 | F177 | S179 | I180 |
|---|---|---|---|---|---|---|---|---|---|---|---|
| T1 (as received from B. Glick) | | | | | | | | | | | |
| T1 + I125R (after subcloning into our preferred vector) | | | | | | | | | | | |
| dimer1 | | | | K163Q | | | | | | S179T | |
| dimer1.82 | | | | K163Q | | | | | | S179T | |
| 1.26 | | | | K163Q | | | | | | S179T | |
| 1.28 | | | | K163Q | | | | | | S179T | |
| 1.34 | | | | K163Q | | K168R | | | | S179T | |
| dimer1.56 | | | | K163Q | | | | | | S179T | |
| 1.61 | | | | K163Q | | | | | | S179T | |
| 1.78 | | | | K163Q | | | | | | S179T | |
| dimer2 | | | | K163Q | | | | | | S179T | |
| non-aggregating mutations | | | | | | | | | | | |
| AB interface | | | | | | | | | | | |
| AC interface | | | | | | | | | | | |
| external to barrel | | | | | | | | | | | |
| internal to barrel | | | | X | | | | | | X | |
| | | | | | | | | | | | |
| mRFP0.1 | | | H162K | K163M | A164R | | | | | S179T | |
| mRFP0.2 | | | H162K | K163M | A164R | | | | | S179T | |
| mRFP0.3 | | | H162K | K163M | A164R | | | | | S179T | |
| mRFP0.4a | | | H162K | K163M | A164R | | | | | S179T | |
| mRFP0.4b | | | H162K | K163M | A164R | | | | | S179T | |
| mP11 | | | H162K | K163M | A164R | | | | | S179T | |
| mP17 | | | H162K | K163M | A164R | | | | | S179T | |
| m1.01 | | | H162K | K163M | A164R | | | | F177C | S179T | |
| m1.02 | | | H162K | K163M | A164R | | | V175A | | S179T | |
| mRFP0.5a | | | H162K | K163M | A164R | | | | F177S | S179T | |
| m1.12 | | | H162K | K163T | A164R | | | | | S179T | |
| mRFP0.5b | | V156A | H162K | K163M | A164R | | | | | S179T | |
| m1.15 | | | H162K | K163M | A164R | | | V175A | | S179T | |
| m1.19 | | | H162K | K163M | A164R | | L174P | | | S179T | |
| mRFP0.6 | | V156A | H162K | K163M | A164R | | L174D | V175A | F177V | S179T | I180T |
| m124 | | V156A | H162K | K163M | A164R | | L174A | V175A | F177V | S179T | I180T |
| m131 | | | H162K | K163M | A164R | | L174G | | F177T | S179T | |
| m141 | | V156A | H162K | K163M | A164R | | L174T | V175A | F177V | S179T | |
| m163 | R153E | V156A | H162K | K163M | A164R | | L174D | V175A | F177V | S179T | |
| m173 | R153E | V156A | H162K | K163M | A164R | | L174D | V175A | F177V | S179T | I180T |
| m187 | R153E | V156S | H162K | K163M | A164K | | L174G | | F177T | S179T | |
| m193 | R153E | V156A | H162R | K163M | A164R | | L174D | V175A | F177V | S179T | I180T |
| m200 | R153E | | H162K | K163M | A164R | | L174G | | F177T | S179T | |
| m205 | R153E | V156A | H162K | K163M | A164R | | L174D | V175A | F177V | S179T | I180T |
| m220 | R153E | V156A | H162R | K163M | A164R | | L174D | V175A | F177V | S179T | I180T |
| mRFP1 | R153E | V156A | H162K | K163M | A164R | | L174D | V175A | F177V | S179T | I180T |
| non-aggregating mutations | | | | | | | | | | | |
| AB interface | | | | | | | | | | | X |
| AC interface | X | | X | | X | | X | | | | |
| external to barrel | | X | | | | | | | | | |
| internal to barrel | | | | X | | | | | X | X | |

FIG. 20D

| | | | | | | | | | | |
|---|---|---|---|---|---|---|---|---|---|---|
| T1 (as received from B. Glick) | | | | | T217A | | | | | |
| T1 + I125R (after subcloning into our preferred vector) | | | | | T217A | | | | | |
| dimer1 | | | | S197T | T217A | | | | | |
| dimer1.02 | | | | S197T | T217A | | | | | |
| 1.26 | | | | S197T | T217S | | | | | |
| 1.28 | | | | S197A | T217A | | | | | |
| 1.34 | | | | S197T | T217A | | | | | |
| dimer1.56 | | | | S197T | T217S | | | | | |
| 1.61 | | | | S197T | T217A | | | | | |
| 1.76 | | | | S197T | T217S | | | | | |
| dimer2 | | | | S197T | T217S | | | | | |
| non-aggregating mutations | | | | | | | | | | |
| AB interface | | | | | | | | | | |
| AC interface | | | | | | | | | | |
| external to barrel | | | | | | | | | | |
| internal to barrel | | | | X | X | | | | | |
| | | | | | | | | | | |
| mRFP0.1 | | | | S197T | T217A | | H222G | | F224G | |
| mRFP0.2 | Y192C | | | S197T | T217A | | H222G | | F224G | |
| mRFP0.3 | Y192A | Y194A | | S197T | T217S | | H222G | | F224G | |
| mRFP0.4a | Y192A | Y194A | | S197T | T217S | | H222G | L223E | F224G | L225A |
| mRFP0.4b | Y192A | Y194K | V195T | S197T | T217A | | H222C | L223T | F224G | L225A |
| mP11 | Y192A | Y194A | | S197T | T217S | | H222G | L223A | F224G | L225A |
| mP17 | Y192A | Y194A | | S197T | T217S | | H222G | L223T | F224G | L225E |
| m1.01 | Y192A | Y194A | | S197T | T209S | T217S | R220H | H222G | L223E | F224G | L225A |
| m1.02 | Y192A | Y194A | | S197T | T217S | | H222G | L223E | F224G | L225A |
| mRFP0.5a | Y192A | Y194A | | S197T | T217S | | H222G | L223E | F224G | L225A |
| m1.12 | Y192A | Y194A | | S197T | T217S | | H222G | L223E | F224G | L225A |
| mRFP0.5b | Y192A | Y194K | V195T | S197T | T217A | | H222C | L223T | F224G | L225A |
| m1.15 | Y192A | Y194A | | S197T | T217S | | H222G | L223E | F224G | L225A |
| m1.19 | Y192A | Y194A | | S197T | T217S | | H222G | L223E | F224G | L225A |
| mRFP0.6 | Y192A | Y194K | V195T | S197T | T217A | | H222C | L223T | F224G | L225A |
| m124 | Y192A | Y194K | V195T | S197T | T217A | | H222C | L223T | F224G | L225A |
| m131 | Y192A | Y194K | V195T | S197T | T217A | | H222C | L223T | F224G | L225A |
| m141 | Y192A | Y194K | V195T | S197T | T217A | | H222C | L223T | F224G | L225A |
| m163 | Y192A | Y194K | V195T | S197T | T217A | | H222C | L223T | F224G | L225A |
| m173 | Y192A | Y194K | V195T | S197T | T217A | | H222C | L223T | F224G | L225A |
| m187 | Y192A | Y194K | V195T | S197T | T217A | | H222G | L223T | F224G | L225E |
| m193 | Y192A | Y194K | V195T | S197T | T217A | | H222G | L223S | F224G | L225E |
| m200 | Y192A | Y194K | V195T | S197T | T217S | | H222G | L223T | F224G | L225T |
| m205 | Y192A | Y194K | V195T | S197T | T217A | | H222G | L223T | F224G | L225T |
| m220 | Y192A | Y194K | V195T | S197T | T217A | | H222G | L223S | F224G | L225E |
| mRFP1 | Y192A | Y194K | V195T | S197T | T217A | | H222S | L223T | F224G | L225A |
| non-aggregating mutations | | | | | | | | | | |
| AB interface | | | | | | | | | | |
| AC interface | X | X | | | | | X | X | X | X |
| external to barrel | | | | | | | | | | |
| internal to barrel | | | X | X | X | | | | | |

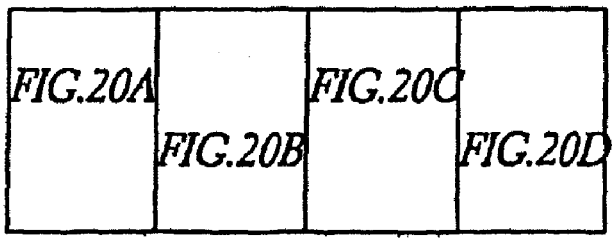

FIG. 20 — FIG.20A, FIG.20B, FIG.20C, FIG.20D

FIG. 21 nucleotide sequence of the *Discosoma* variant red fluorescent protein dimer2 open reading frame

```
atggtggcctcctccgaggacgtcatcaaagagttcatgcgcttcaaggtgcgcatggag
ggctccgtgaacggccacgagttcgagatcgagggcgagggcgagggccgcccctacgag
ggcacccagaccgccaagctgaaggtgaccaagggtggccccctgcccttcgcctgggac
atcctgtcccccagttccagtacggctccaaggcgtacgtgaagcacccgccgacatc
cccgactacaagaagctgtccttcccggagggcttcaagtgggagcgcgtgatgaacttc
gaggacggcggcgtgaccgtgaccaggactcccctgcaggacggcactcgctgatc
tacaaggtgaagttccgggaccaccttcccccgacggcctgtaccccgacggcgtgaagggc
accatgggctgggaggcctccaccgagcgcctgtacccccgacggcgtgctgaaggggc
gagatccaccagccctgaagctgaaggacggcgccactacctggtggagttcaagacc
atctacatggccaagaagcccgtgcagctgccgctactactacgtggacaccagctg
gacatcacctcccacaacgaggactacaccatcgtggaacagtacgagcgctccgagggc
cgccaccacctgttcctgtag
```

FIG. 22A amino acid sequence of the *Discosoma* variant red fluorescent protein dimer2

Amino acid sequence of the GFP termini and illustrates their locations at the N- and C-terminal ends of a fluorescent protein (SEQ ID NO: 14 and SEQ ID NO:91).

```
wtDsRed     1 2 3 4 5 6 7 8 9 10... 220           225
            M R S S K N V I K E ...  R H H L F L mRFP1       M A S S E D V I K E ...  R H S T G A

"GFP termini":
1 1a2 3 4 5 6 6a6b6c6d7 8 9 10... 220           225
M V S K G E E N N M A V I K E ...  R H S T G G M D E L Y K
```

The underlined residues were copied from the N- and C-termini of EGFP
and replace the corresponding amino acids in DsRed and mRFP1.

FIG. 23 nucleotide sequence of the *Discosoma* variant red fluorescent protein mRFP1 open reading frame atggcctcctccgaggacgtcatcaaggagttcatgcgcttcaaggtgcgcatggagggc
tccgtgaacggccacgagttcgagatcgagggcgagggcgagggccgcccctacgagggc
acccagaccgccaagctgaaggtgaccaagggtggccccctgcccttcgcctgggacatc
ctgtcccctcagttccagtacggctccaaggcctacgtgaagcaccccgcagacatccccc
gactacttgaagctgtccttccccgagggcttcaagtgggagcgcgtgatgaacttcgag
gacggcggtgtgatcaccgtgacccagggactctccctgcaggacggcgagttcatctac
aaggtgaagctgcgcggcaccaacttccccctgacgccccgtaatgcagaagaagacc
atgggctgggaggcctccaccgagctgaagtaccccgaggacggcgccctgaaggggcgag
atcaagatgaggctgaagctgaaggaggacggcgccctgaagctgcgcgactacgaccacc
tacatggccaagaagcccgtgcagctgccggcctacaagaccgatcaagctggac
atcacctcccacaacgaggactacaccatcgtgaacagtacgagcgccgagggccgc
cactccaccggcgcctaa

FIG. 24 amino acid sequence of the *Discosoma* variant red fluorescent protein mRFP1

```
M A S S E D V I K E
F M R F K V R M E G
S V N G H E F E I E
G E G R P Y E G T Q
T A K L K V T K G G
P L P F A W D I L S
P Q F Q Y G S K A Y
V K H P A D I P D Y
L K L S F P E G F K
W E R V M N F E D G
G V T V T Q D S S L
Q D G E F I Y K V K
L R G T N F P S D G
P V M Q K K T M G W
E A S T E R M Y P E
D G A L K G E I K M
R L K L K D G G H Y
D A E V K T T Y M A
K K P V Q L P G A Y
K T D I K L D I T S
H N E D Y T I V E Q
Y E R A E G R H S T
G A
```

FIG. 25 nucleotide sequence of a modified *Discosoma* wild-type red fluorescent protein open reading frame with humanized codon usage atggtgcgctcctccaagaacgtcatcaaggagttcatgcgcttcaaggtgcgcatggag
ggcaccgtgaacggccacgagttcgagatcgagggcgagggcgagggccgcccctacgag
ggccacaacaccgtgaagctgaaggtgaccaaggcgccccctgccctcgcctgggac
atcctgtccccccagttccagtacggctccaagtgtacgtgaagcaccccgccgacatc
cccgactacaagaagctgtccttccccgagggcttcaagtggagcgcgtgatgaacttc
gaggacggcggcgtggtgaccgtgaccagactcctcctgcagacgctgcttcatc
tacaaggtgaagttcatcggcgtgaacttcccctccgacgccgtaatgcagaagaag
accatgggctgggagggcctccaccgagcgcctgtaccccgacggcgtgctgaaggc
gagatccacaaggccctgaagctgaaggacggccactacctgtggagttcaagtcc
atctacatggccaagaagcccgtgcagctgcccggctactactgtgactccaagctg
gacatcacctcccacaacgaggactacaccatcgtggagcagtacgagcgcaccgaggc
cgccaccctgttcctgtag

FIG. 30 mRFP1.1 amino acid sequence

```
M S A V S D Y K M H M F E E K M E R V R M E G
S T N Q G K G V G K I K T G P G Y K P A Y P D
T L T S H V K V L T F V G A K W K S A V D I I
L D P Y K L M E S S P A G P E S D G W N P F P
D D L G F A R G L E T F D D V M P Y D E L E E
D K G V L S K A S Q N S P K W G H K N P K G Y
K M K G V K L K F E E S M E E L A A F K V M T
M I W K R P K K R K Y G R G Q K D R K G I Y E
I Y M M A E N P D Q F E G P P V T D K T A E T
Y H A T L D A L V L R Y V A D G E V G L D R D
H H S S K Y K T T D G V E D V G Y G T I G
                                      L
```

FIG. 31 mRFP1.1 DNA sequence

```
atggcctcctccgaggacgtcatcaaggagttcatgcgcttcaaggtgcgcatggagggc
tccgtgaacggccacgagttcgagatcgagggcgagggcgagggccgcccctacgagggc
acccagaccgccaagctgaaggtgaccaagggcggccccctgcccttcgcctgggacatc
ctgtcccctcagttcatgtacggctccaaggcctacgtgaagcaccccgcccgacatcccc
gactacttgaagctgtccttcccccgagggcttcaagtgggagcgcgtgatgaacttcgag
gacggcggcgtggtgaccgtgacccagctgtccccctgcgaagactcgagttcatctac
aaggtgaagctgcgcggcaccaacttcccctccgacggccccgtaatgcagaagaagacc
atgggctgggaggcctccacggagctgaagatgtaccccgaggacggcgccctgaagggcgag
atcaagatgaggctgaagctgaaggacggcggccactacgacgccgaggtcaagaccacc
tacatggccaagaagcccgtgcagctgcccggcgcctacaagaccgacatcaagctggac
atcacctcccacaacgaggactacaccatcgtggaacagtacgagcgcgccgagggccgc
cactcccaccgggcctaa
```

FIG. 32
Table of properties of DsRed variants

| Class | designation | mutations | advantages |
|---|---|---|---|
| dimer | dimer2.2MMM (dimer3) (mTomato) | dimer2 + GFP termini + V22M, Q66M, V104L, F124M | highest EC, improved QY from dimer2, ex/em most similar to wtDsRed, least green component of any new clones tested (less green component than wtDsRed or dimer2) |
| mRFP | mRFP1.5 | mRFP1.0 + GFP termini+ins(DNMA) after E6, Q66M, R17H, Q66M, T147S, M163Q, M182K | red-shifted ~5nm with respect to mRFP1.0, significantly reduced green component, nearly complete maturation |
| mOFP | OrS4-9 | mRFP1.0 + GFP termini+ins(NNMA) after E6, V7I, T21S, Q66T, T147S, M182K, T195V | Blue-shifted relative to mRFP and wtDsRed, higher QY than mRFP1.0/1.5, reduced pH sensitivity compared with original orange mRFP variants |
| mYOFP | Y1.3 (mYOFp13) (mBanana) | mRFP1.0 + GFP termini+ins(NNMA) after E6, Q66C, A77T, D78G, L83F, T108A, T147S, D124S, V127T, M182K, K194I, T195A, D196G, I197E, L199I, Q213L | Largest blue-shift of any mRFP variant, high QY, reduced pH sensitivity compared with original yellow mRFP variants |
| mFRFP | mFRFP (F2Q6) (mGrape2) | mRFP1.0 + GFP termini+ins(NNMA) after E6, V7I, E32K, Q66M, A77P, L83M, R125H, T147S, M150L, I161V, T195L, I197Y | Largest red-shift of any mRFP variant, seems to have nearly complete maturation |

FIG. 33

```
atggtgagcaagggcgaggaggtcatcaaagagttcatgcgcttcaaggtgcgcatggag
 M  V  S  K  G  E  E  V  I  K  E  F  M  R  F  K  V  R  M  E ggctccatgaacggccacgagttcgagatcgagggcgagggcgagggccgcccctacgag
 G  S  M  N  G  H  E  F  E  I  E  G  E  G  E  G  R  P  Y  E ggcacccagaccgccaagctgaaggtgaccaagggcggccccctgcccttcgcctgggac
 G  T  Q  T  A  K  L  K  V  T  K  G  G  P  L  P  F  A  W  D atcctgtcccccagttcatgtacggctccaaggcgtacgtgaagcaccccgccgacatc
 I  L  S  P  Q  F  M  Y  G  S  K  A  Y  V  K  H  P  A  D  I cccgattacaagaagctgtccttccccgagggcttcaagtgggagcgcgtgatgaacttc
 P  D  Y  K  K  L  S  F  P  E  G  F  K  W  E  R  V  M  N  F gaggacggcggtctggtgaccgtgacccaggactcctccctgcaggacggcacgctgatc
 E  D  G  G  L  V  T  V  T  Q  D  S  S  L  Q  D  G  T  L  I tacaaggtgaagatgcgcggcaccaacttccccccgacggccccgtaatgcagaagaag
 Y  K  V  K  M  R  G  T  N  F  P  P  D  G  P  V  M  Q  K  K accatgggctgggaggcctccaccgagcgcctgtaccccgcgacggcgtgctgaagggc
 T  M  G  W  E  A  S  T  E  R  L  Y  P  R  D  G  V  L  K  G gagatccaccaggccctgaagctgaaggacggcggccactacctggtggagttcaagacc
 E  I  H  Q  A  L  K  L  K  D  G  G  H  Y  L  V  E  F  K  T atctacatggccaagaagcccgtgcaactgcccggctactactacgtggacaccaagctg
 I  Y  M  A  K  K  P  V  Q  L  P  G  Y  Y  Y  V  D  T  K  L gacatcacctcccacaacgaggactacaccatcgtggaacagtacgagcgctccgagggc
 D  I  T  S  H  N  E  D  Y  T  I  V  E  Q  Y  E  R  S  E  G cgccaccacctgttcctgtacggcatggacgagctgtacaagtaa
 R  H  H  L  F  L  Y  G  M  D  E  L  Y  K  -
```

FIG. 34

```
atggtgagcaagggcgaggaggataacatggccatcatcaaggagttcatgcgcttcaag
 M  V  S  K  G  E  E  D  N  M  A  I  I  K  E  F  M  R  F  K gtgcacatggagggctccgtgaacggccacgagttcgagatcgagggcgagggcgagggc
 V  H  M  E  G  S  V  N  G  H  E  F  E  I  E  G  E  G  E  G cgcccctacgagggcacccagaccgccaagctgaaggtgaccaagggtggccccctgccc
 R  P  Y  E  G  T  Q  T  A  K  L  K  V  T  K  G  G  P  L  P ttcgcctgggacatcctgtcccctcagttcatgtacggctccaaggcctacgtgaagcac
 F  A  W  D  I  L  S  P  Q  F  M  Y  G  S  K  A  Y  V  K  H cccgccgacatccccgactacttgaagctgtccttccccgagggcttcaagtgggagcgc
 P  A  D  I  P  D  Y  L  K  L  S  F  P  E  G  F  K  W  E  R gtgatgaacttcgaggacggcggcgtggtgaccgtgacccaggactcctccctgcaggac
 V  M  N  F  E  D  G  G  V  V  T  V  T  Q  D  S  S  L  Q  D ggcgagttcatctacaaggtgaagctgcgcggcaccaacttcccctccgacggccccgta
 G  E  F  I  Y  K  V  K  L  R  G  T  N  F  P  S  D  G  P  V atgcagaagaagaccatgggctgggaggcctcctccgagcggatgtaccccgaggacggc
 M  Q  K  K  T  M  G  W  E  A  S  S  E  R  M  Y  P  E  D  G gccctgaagggcgagatcaagcagaggctgaagctgaaggacggcggccactacgacgct
 A  L  K  G  E  I  K  Q  R  L  K  L  K  D  G  G  H  Y  D  A gaggtcaagaccacctacaaggccaagaagcccgtgcagctgcccggcgcctacaagacc
 E  V  K  T  T  Y  K  A  K  K  P  V  Q  L  P  G  A  Y  K  T gacatcaagttggacatcacctcccacaacgaggactacaccatcgtggaacagtacgaa
 D  I  K  L  D  I  T  S  H  N  E  D  Y  T  I  V  E  Q  Y  E cgcgccgagggccgccactccaccggcggcatggacgagctgtacaagtaa
 R  A  E  G  R  H  S  T  G  G  M  D  E  L  Y  K  -
```

FIG. 35

```
atggtgagcaagggcgaggagaataacatggccatcatcaaggagttcatgcgcttcaag
 M  V  S  K  G  E  E  N  N  M  A  I  I  K  E  F  M  R  F  K gtacgcatggagggctccgtgaacggccacgagttcgagattgagggcgagggcgagggc
 V  R  M  E  G  S  V  N  G  H  E  F  E  I  E  G  E  G  E  G cgccctacgagggcacccagaccgccaagttgaaggtgaccaagggtggccgcctgccc
 R  P  Y  E  G  T  Q  T  A  K  L  K  V  T  K  G  G  P  L  P ttcgcctgggacatcctgtcccctcagttcacctacggctccaaggcctacgtgaagcac
 F  A  W  D  I  L  S  P  Q  F  T  Y  G  S  K  A  Y  V  K  H cccgccgacatccccgactacttgaagctgtccttccccgagggcttcaagtgggaacgc
 P  A  D  I  P  D  Y  L  K  L  S  F  P  E  G  F  K  W  E  R gtgatgaacttcgaggacggcggcgtggtgaccgtgacacaggactcctccctgcaggac
 V  M  N  F  E  D  G  G  V  V  T  V  T  Q  D  S  S  L  Q  D ggcgagttcatctacaaggtgaagctgcgcggcaccaacttcccctccgacggccccgta
 G  E  F  I  Y  K  V  K  L  R  G  T  N  F  P  S  D  G  P  V atgcagaagaagaccatgggctgggaggcctcctccgagcggatgtaccccgaggacggc
 M  Q  K  K  T  M  G  W  E  A  S  S  E  R  M  Y  P  E  D  G gccctgaagggcgagatcaagatgaggctgaagctgaaggacggcggccactacgacgct
 A  L  K  G  E  I  K  M  R  L  K  L  K  D  G  G  H  Y  D  A gaggtcaagaccacctacaaggccaagaagcccgtgcagctgcccggcgcctacaaggtc
 E  V  K  T  T  Y  K  A  K  K  P  V  Q  L  P  G  A  Y  K  V gacatcaagctggacatcacctcccacaacgaggactacaccatcgtggaacagtacgaa
 D  I  K  L  D  I  T  S  H  N  E  D  Y  T  I  V  E  Q  Y  E cgcgccgagggccgccactccaccggcggcatggacgagctgtacaagtaa
 R  A  E  G  R  H  S  T  G  G  M  D  E  L  Y  K  -
```

FIG. 36

```
atggtgagcaagggcgaggagaataacatggccgtcatcaaggagttcatgcgcttcaag
 M  V  S  K  G  E  E  N  N  M  A  V  I  K  E  F  M  R  F  K gtgcgcatggagggctccgtgaacggccacgagttcgagatcgagggcgagggcgagggc
 V  R  M  E  G  S  V  N  G  H  E  F  E  I  E  G  E  G  E  G cgcccctacgagggcacccagaccgccaagctgaaggtgaccaagggtggccccctgccc
 R  P  Y  E  G  T  Q  T  A  K  L  K  V  T  K  G  G  P  L  P ttcgcctgggacatcctgtcccctcagttctgctacggctccaaggcctacgtgaagcac
 F  A  W  D  I  L  S  P  Q  F  C  Y  G  S  K  A  Y  V  K  H cccactggtatccccgactacttcaagctgtccttccccgagggcttcaagtgggagcgc
 P  T  G  I  P  D  Y  F  K  L  S  F  P  E  G  F  K  W  E  R gtgatgaacttcgaggacggcggcgtggtgaccgtggctcaggactcctccctgcaggac
 V  M  N  F  E  D  G  G  V  V  T  V  A  Q  D  S  S  L  Q  D ggcgagttcatctacaaggtgaagctgcgcggcaccaacttcccctccgacggccccgta
 G  E  F  I  Y  K  V  K  L  R  G  T  N  F  P  S  D  G  P  V atgcagaagaagaccatgggctgggaggcctcctccgagcggatgtaccccgaggacggc
 M  Q  K  K  T  M  G  W  E  A  S  S  E  R  M  Y  P  E  D  G gccctgaagggcgagatcaagatgaggctgaagctgaaggacggcggccactacagcgcc
 A  L  K  G  E  I  K  M  R  L  K  L  K  D  G  G  H  Y  S  A gagaccaagaccacctacaaggccaagaagcccgtgcagttgcccggcgcctacatagcc
 E  T  K  T  T  Y  K  A  K  K  P  V  Q  L  P  G  A  Y  I  A ggcgagaagatcgacatcacctcccacaatgaggactacactatcgtggaattgtacgag
 G  E  K  I  D  I  T  S  H  N  E  D  Y  T  I  V  E  L  Y  E cgcgccgagggccgccactccaccggcggcatggacgagctgtacaagtaa
 R  A  E  G  R  H  S  T  G  G  M  D  E  L  Y  K  -
```

FIG. 37

```
atggtgagcaagggcgaggagaataacatggccgtcatcaaggagttcatgcgcttcaag
 M  V  S  K  G  E  E  N  N  M  A  V  I  K  E  F  M  R  F  K gtgcgcatggagggctccgtgaacggccacgagttcgagatcgagggcaagggcgagggc
 V  R  M  E  G  S  V  N  G  H  E  F  E  I  E  G  K  G  E  G cgcccctacgagggcacccagaccgccaagctgaaggtgaccaagggcggccccctgccc
 R  P  Y  E  G  T  Q  T  A  K  L  K  V  T  K  G  G  P  L  P ttcgcctgggacatcctgtcccctcagttcatgtacggctccaaggcctacgtgaagcac
 F  A  W  D  I  L  S  P  Q  F  M  Y  G  S  K  A  Y  V  K  H cccccigacatccccgactacatgaagctgtccttccccgagggcttcaagtgggagcgc
 P  P  D  I  P  D  Y  M  K  L  S  F  P  E  G  F  K  W  E  R gtgatgaacttcgaggacggcggcgtggtgaccgtgacccaggactcctccctgcaggac
 V  M  N  F  E  D  G  G  V  V  T  V  T  Q  D  S  S  L  Q  D ggcgagttcatctacaaggtgaagctgcacggcaccaacttcccctccgacggccccgta
 G  E  F  I  Y  K  V  K  L  H  G  T  N  F  P  S  D  G  P  V atgcagaagaagaccatgggctgggaggcctcctccgagcggttgtaccccgaggacggc
 M  Q  K  K  T  M  G  W  E  A  S  S  E  R  L  Y  P  E  D  G gccctgaagggcgaggtcaagatgaggctgaagctgaaggacggcggccactacgacgcc
 A  L  K  G  E  V  K  M  R  L  K  L  K  D  G  G  H  Y  D  A gaggtcaagaccacctacatggccaagaagcccgtgcagctgcccggcgcctacaagctc
 E  V  K  T  T  Y  M  A  K  K  P  V  Q  L  P  G  A  Y  K  L gactacaagctggacatcacctcccacaacgaggactacaccatcgtggaacagtacgag
 D  Y  K  L  D  I  T  S  H  N  E  D  Y  T  I  V  E  Q  Y  E cgcgccgagggccgccactccaccggcggcatggacgagctgtacaagtaa
 R  A  E  G  R  H  S  T  G  G  M  D  E  L  Y  K  -
```

FIG. 38

```
atggtgagcaagggcgaggaggataacatggccatcatcaaggagttcatgcgcttcaag
 M  V  S  K  G  E  E  D  N  M  A  I  I  K  E  F  M  R  F  K gtgcacatggagggctccgtgaacggccacgagttcgagatcgagggcgagggcgagggc
 V  H  M  E  G  S  V  N  G  H  E  F  E  I  E  G  E  G  E  G cgcccctacgagggcacccagaccgccaagctgaaggtgaccaagggtggccccctgccc
 R  P  Y  E  G  T  Q  T  A  K  L  K  V  T  K  G  G  P  L  P ttcgcctgggacatcctgtcccctcagttcatgtacggctccaaggcctacgtgaagcac
 F  A  W  D  I  L  S  P  Q  F  M  Y  G  S  K  A  Y  V  K  H cccgccgacatccccgactacttgaagctgtccttccccgagggcttcaagtgggagcgc
 P  A  D  I  P  D  Y  L  K  L  S  F  P  E  G  F  K  W  E  R gtgatgaacttcgaggacggcggcgtggtgaccgtgacccaggactcctccctgcaggac
 V  M  N  F  E  D  G  G  V  V  T  V  T  Q  D  S  S  L  Q  D ggcgagttcatctacaaggtgaagctgcgcggcaccaacttcccctccgacggccccgta
 G  E  F  I  Y  K  V  K  L  R  G  T  N  F  P  S  D  G  P  V atgcagaagaagaccatgggctgggaggcctcctccgagcggatgtaccccgaggacggc
 M  Q  K  K  T  M  G  W  E  A  S  S  E  R  M  Y  P  E  D  G gccctgaagggcgagatcaagcagaggctgaagctgaaggacggcggccactacgacgct
 A  L  K  G  E  I  K  Q  R  L  K  L  K  D  G  G  H  Y  D  A gaggtcaagaccacctacaaggccaagaagcccgtgcagctgcccggcgcctacaacgtc
 E  V  K  T  T  Y  K  A  K  K  P  V  Q  L  P  G  A  Y  N  V aacatcaagttggacatcacctcccacaacgaggactacaccatcgtggaacagtacgaa
 N  I  K  L  D  I  T  S  H  N  E  D  Y  T  I  V  E  Q  Y  E cgcgccgagggccgccactccaccggcggcatggacgagctgtacaagtaa
 R  A  E  G  R  H  S  T  G  G  M  D  E  L  Y  K  -
```

FIG. 39

```
atggtgagcaagggcgaggagaataacatg
M   V   S   K   G   E   E   N   N   M gccatcatcaaggagttcatgcgcttcaaggtgcgcatggagggctccgtgaacggccac
A   I   I   K   E   F   M   R   F   K   V   R   M   E   G   S   V   N   G   H gagttcgagatcgagggcgagggcgagggccgcccctacgagggctttcagaccgctaag
E   F   E   I   E   G   E   G   E   G   R   P   Y   E   G   F   Q   T   A   K ctgaaggtgaccaagggtggccccctgcccttcgnctgggacatcctgtcccctcagttc
L   K   V   T   K   G   G   P   L   P   F   X   W   D   I   L   S   P   Q   F acctacggctccaaggcctacgtgaagcaccccgccgacatccccgactacttgaagctg
T   Y   G   S   K   A   Y   V   K   H   P   A   D   I   P   D   Y   L   K   L tccttccccgagggcttcaagtgggagcgcgtgatgaacttcgaggacggcggcgtggtg
S   F   P   E   G   F   K   W   E   R   V   M   N   F   E   D   G   G   V   V accgtgacccaggactcctccctgcaggacggcgagttcatctacaaggtgaagctgcgc
T   V   T   Q   D   S   S   L   Q   D   G   E   F   I   Y   K   V   K   L   R ggcaccaacttcccctccgacggccccgtaatgcagaagaagaccatgggctgggaggcc
G   T   N   F   P   S   D   G   P   V   M   Q   K   K   T   M   G   W   E   A tcctccgagcggatgtaccccgaggacggcgccctgaagggcgagatcaagatgaggctg
S   S   E   R   M   Y   P   E   D   G   A   L   K   G   E   I   K   M   R   L aagctgaaggacggcggccactacacctccgaggtcaagaccacctacaaggccaagaag
K   L   K   D   G   G   H   Y   T   S   E   V   K   T   T   Y   K   A   K   K cccgtgcagctgcccggcgcctacatcgtcggcatcaagttggacatcacctcccacaac
P   V   Q   L   P   G   A   Y   I   V   G   I   K   L   D   I   T   S   H   N gaggactacaccatcgtggaacagtacgaacgcgccgagggccgccactccaccggcggc
E   D   Y   T   I   V   E   Q   Y   E   R   A   E   G   R   H   S   T   G   G atggacgagcttaagtaa
M   D   E   L   K   -
```

FIG. 40

```
atggtgagcaagggcgaggagaataacatggccatcatcaaggagttcatgcgcttcaag
 M  V  S  K  G  E  E  N  N  M  A  I  I  K  E  F  M  R  F  K gtgcgcatggagggctccgtgaacggccacgagttcgagatcgagggcgagggcgagggc
 V  R  M  E  G  S  V  N  G  H  E  F  E  I  E  G  E  G  E  G cgcccctacgagggcacccagaccgccaagctgaaggtgaccaagggtggccccctgccc
 R  P  Y  E  G  T  Q  T  A  K  L  K  V  T  K  G  G  P  L  P ttcgcctgggacatcctaaccccaacttcacctacggctccaaggcctacgtgaagcac
 F  A  W  D  I  L  T  P  N  F  T  Y  G  S  K  A  Y  V  K  H cccgccgacatccccgactacttgaagctgtccttccccgagggcttcaagtgggagcgc
 P  A  D  I  P  D  Y  L  K  L  S  F  P  E  G  F  K  W  E  R gtgatgaacttcgaggacggcggcgtggtgaccgtgacccaggactcctccctgcaggac
 V  M  N  F  E  D  G  G  V  V  T  V  T  Q  D  S  S  L  Q  D ggcgagttcatctacaaggtgaagctgcgcggcaccaacttccctccgacggccccgta
 G  E  F  I  Y  K  V  K  L  R  G  T  N  F  P  S  D  G  P  V atgcagaagaagaccatgggctgggaggcctcctccgagcggatgtaccccgaggacggc
 M  Q  K  K  T  M  G  W  E  A  S  S  E  R  M  Y  P  E  D  G gccctgaagggcgagatcaagatgaggctgaagctgaaggacggcggccactacgacgct
 A  L  K  G  E  I  K  M  R  L  K  L  K  D  G  G  H  Y  D  A gaggtcaagaccacctacaaggccaagaagcccgtgcagctgcccggcgcctacatcgtc
 E  V  K  T  T  Y  K  A  K  K  P  V  Q  L  P  G  A  Y  I  V ggcatcaagttggacatcacctcccacaacgaggactacaccatcgtggaactgtacgaa
 G  I  K  L  D  I  T  S  H  N  E  D  Y  T  I  V  E  L  Y  E cgcgccgagggccgccactccaccggcggcatggacgagctgtacaagtaa
 R  A  E  G  R  H  S  T  G  G  M  D  E  L  Y  K  -
```

FIG. 41 mStrawberry amino acid and DNA sequence (SEQ ID NO: 98 and SEQ ID NO: 99)

```
atggtgagcaagggcgaggagaataacatggccatcatcaaggagttcatgcgcttcaag
 M  V  S  K  G  E  E  N  N  M  A  I  I  K  E  F  M  R  F  K gtgcgcatggagggctccgtgaacggccacgagttcgagatcgagggcgagggcgagggc
 V  R  M  E  G  S  V  N  G  H  E  F  E  I  E  G  E  G  E  G cgcccctacgagggcacccagaccgccaagctgaaggtgaccaagggtggccccctgccc
 R  P  Y  E  G  T  Q  T  A  K  L  K  V  T  K  G  G  P  L  P ttcgcctgggacatcctaacccccaacttcacctacggctccaaggcctacgtgaagcac
 F  A  W  D  I  L  T  P  N  F  T  Y  G  S  K  A  Y  V  K  H cccgccgacatccccgactacttgaagctgtccttccccgagggcttcaagtgggagcgc
 P  A  D  I  P  D  Y  L  K  L  S  F  P  E  G  F  K  W  E  R gtgatgaacttcgaggacggcggcgtggtgaccgtgacccaggactcctccctgcaggac
 V  M  N  F  E  D  G  G  V  V  T  V  T  Q  D  S  S  L  Q  D ggcgagttcatctacaaggtgaagctgcgcggcaccaacttcccctccgacggccccgta
 G  E  F  I  Y  K  V  K  L  R  G  T  N  F  P  S  D  G  P  V atgcagaagaagaccatgggctgggaggcctcctccgagcggatgtaccccgaggacggc
 M  Q  K  K  T  M  G  W  E  A  S  S  E  R  M  Y  P  E  D  G gccctgaagggcgagatcaagatgaggctgaagctgaaggacggcggccactacgacgct
 A  L  K  G  E  I  K  M  R  L  K  L  K  D  G  G  H  Y  D  A gaggtcaagaccacctacaaggccaagaagcccgtgcagctgcccggcgcctacatcgtc
 E  V  K  T  T  Y  K  A  K  K  P  V  Q  L  P  G  A  Y  I  V ggcatcaagttggacatcacctcccacaacgaggactacaccatcgtggaactgtacgaa
 G  I  K  L  D  I  T  S  H  N  E  D  Y  T  I  V  E  L  Y  E cgcgccgagggccgccactccaccggcggcatggacgagctgtacaagtaa
 R  A  E  G  R  H  S  T  G  G  M  D  E  L  Y  K  -
```

FIG. 42

```
atggcctcctccgaggacgtcatcaaggagttcatgcgcttcaaggtgcgcatggagggc
 M  A  S  S  E  D  V  I  K  E  F  M  R  F  K  V  R  M  E  G tccgtgaacggccacgagttcgagatcgagggcgagggcgagggccgcccctacgagggc
 S  V  N  G  H  E  F  E  I  E  G  E  G  E  G  R  P  Y  E  G acccagaccgccaagctgaaggtgaccaagggcggccccctgcccttcgcctgggacatc
 T  Q  T  A  K  L  K  V  T  K  G  G  P  L  P  F  A  W  D  I ctgtcccctcagttctgttacggctccaaggcctacgtgaagcaccccgccgacatcccc
 L  S  P  Q  F  C  Y  G  S  K  A  Y  V  K  H  P  A  D  I  P gactacttgaagctgtccttccccgagggcttcaagtgggagcgcgtgatgaacttcgag
 D  Y  L  K  L  S  F  P  E  G  F  K  W  E  R  V  M  N  F  E gacggcggcgtggtgaccgtgacccaggactcctccctgcaggacggcgagttcatctac
 D  G  G  V  V  T  V  T  Q  D  S  S  L  Q  D  G  E  F  I  Y aaggtgaagctgcgcggcaccaacttcccctccgacggccccgtaatgcagaagaagacc
 K  V  K  L  R  G  T  N  F  P  S  D  G  P  V  M  Q  K  K  T atgggctgggaggcctcctccgagcggatgtaccccgaggacggcgccctgaagggcgag
 M  G  W  E  A  S  S  E  R  M  Y  P  E  D  G  A  L  K  G  E atcaagatgaggctgaagctgaaggacggcggccactacgacgccgaggtcaagaccacc
 I  K  M  R  L  K  L  K  D  G  G  H  Y  D  A  E  V  K  T  T tacatggccaagaagcccgtgcagctgcccggcgcctacaagaccgacatcaagctggac
 Y  M  A  K  K  P  V  Q  L  P  G  A  Y  K  T  D  I  K  L  D atcacctcccacaacgaggactacaccatcgtggaattgtacgagcgcgccgagggccgc
 I  T  S  H  N  E  D  Y  T  I  V  E  L  Y  E  R  A  E  G  R cactccaccggcgcctaa
 H  S  T  G  A  -
```

FIG. 43

```
atggtgagcaagggcgaggagaataacatggccatcatcaaggagttcatgcgcttcaag
 M  V  S  K  G  E  E  N  N  M  A  I  I  K  E  F  M  R  F  K gtgcgcatggagggctccgtgaacggccacgagttcgagatcgagggcgagggcgagggc
 V  R  M  E  G  S  V  N  G  H  E  F  E  I  E  G  E  G  E  G cgcccctacgagggctttcagaccgctaagctgaaggtgaccaagggtggccccctgccc
 R  P  Y  E  G  F  Q  T  A  K  L  K  V  T  K  G  G  P  L  P ttcgcctgggacatcctgtcccctcagttcacctacggctccaaggcctacgtgaagcac
 F  A  W  D  I  L  S  P  Q  F  T  Y  G  S  K  A  Y  V  K  H cccgccgacatccccgactacttcaagctgtccttccccgagggcttcaagtgggagcgc
 P  A  D  I  P  D  Y  F  K  L  S  F  P  E  G  F  K  W  E  R gtgatgaacttcgaggacggcggcgtggtgaccgtgacccaggactcctccctgcaggac
 V  M  N  F  E  D  G  G  V  V  T  V  T  Q  D  S  S  L  Q  D ggcgagttcatctacaaggtgaagctgcgcggcaccaacttcccctccgacggccccgta
 G  E  F  I  Y  K  V  K  L  R  G  T  N  F  P  S  D  G  P  V atgcagaagaagaccatgggctgggaggcctcctccgagcggatgtaccccgaggacggc
 M  Q  K  K  T  M  G  W  E  A  S  S  E  R  M  Y  P  E  D  G gccctgaagggcgagatcaagatgaggctgaagctgaaggacggcggccactacacctcc
 A  L  K  G  E  I  K  M  R  L  K  L  K  D  G  G  H  Y  T  S gaggtcaagaccacctacaaggccaagaagcccgtgcagctgcccggcgcctacatcgtc
 E  V  K  T  T  Y  K  A  K  K  P  V  Q  L  P  G  A  Y  I  V ggcatcaagttggacatcacctcccacaacgaggactacaccatcgtggaacagtacgaa
 G  I  K  L  D  I  T  S  H  N  E  D  Y  T  I  V  E  Q  Y  E cgcgccgagggccgccactccaccggcggcatggacgagctgtacaagtaa
 R  A  E  G  R  H  S  T  G  G  M  D  E  L  Y  K
```

FIG. 44

```
atggcctcctccgaggacgtcatcaaggagttcatgcgcttcaaggtgcgcatggagggc
 M  A  S  S  E  D  V  I  K  E  F  M  R  F  K  V  R  M  E  G tccgtgaacggccacgagttcgagatcgagggcgagggcgagggccgcccctacgagggc
 S  V  N  G  H  E  F  E  I  E  G  E  G  E  G  R  P  Y  E  G acccagaccgccaagctgaaggtgaccaagggcggccccctgcccttcgcctgggacatc
 T  Q  T  A  K  L  K  V  T  K  G  G  P  L  P  F  A  W  D  I ctgtcccctcagttcatgtggggctccaaggcctacgtgaagcaccccgccgacatcccc
 L  S  P  Q  F  M  W  G  S  K  A  Y  V  K  H  P  A  D  I  P gactacttgaagctgtccttccccgagggcttcaagtgggagcgcgtgatgaacttcgag
 D  Y  L  K  L  S  F  P  E  G  F  K  W  E  R  V  M  N  F  E gacggcggcgtggtgaccgtgacccaggactcctccctgcaggacggcgagttcatctac
 D  G  G  V  V  T  V  T  Q  D  S  S  L  Q  D  G  E  F  I  Y aaggtgaagctgcgcggcaccaacttcccctccgacggccccgtaatgcagaagaagacc
 K  V  K  L  R  G  T  N  F  P  S  D  G  P  V  M  Q  K  K  T atgggctgggcggccaccaccgagcggatgtaccccgaggacggcgccctgaagggcgag
 M  G  W  A  A  T  T  E  R  M  Y  P  E  D  G  A  L  K  G  E atcaagatgaggctgaagctgaaggacggcggccactacgacgccgaggtcaagaccacc
 I  K  M  R  L  K  L  K  D  G  G  H  Y  D  A  E  V  K  T  T tacatggccaagaagcccgtgcagctgcccggcgcctacaagattgacgggaagctggac
 Y  M  A  K  K  P  V  Q  L  P  G  A  Y  K  I  D  G  K  L  D atcacctcccacaacgaggactacaccatcgtggaacagtacgagcgcgccgagggccgc
 I  T  S  H  N  E  D  Y  T  I  V  E  Q  Y  E  R  A  E  G  R cactccaccggcgcctaa
 H  S  T  G  A  -
```

FIG. 45

```
atggtgagcaagggcgaggaggtcatcaaagagttcatgcgcttcaaggtgcgcatggag
 M  V  S  K  G  E  E  V  I  K  E  F  M  R  F  K  V  R  M  E ggctccatgaacggccacgagttcgagatcgagggcgagggcgagggccgcccctacgag
 G  S  M  N  G  H  E  F  E  I  E  G  E  G  E  G  R  P  Y  E ggcacccagaccgccaagctgaaggtgaccaagggcggccccctgcccttcgcctgggac
 G  T  Q  T  A  K  L  K  V  T  K  G  G  P  L  P  F  A  W  D atcctgtcccccagttcatgtacggctccaaggcgtacgtgaagcaccccgccgacatc
 I  L  S  P  Q  F  M  Y  G  S  K  A  Y  V  K  H  P  A  D  I cccgattacaagaagctgtccttccccgagggcttcaagtgggagcgcgtgatgaacttc
 P  D  Y  K  K  L  S  F  P  E  G  F  K  W  E  R  V  M  N  F gaggacggcggtctggtgaccgtgacccaggactcctccctgcaggacggcacgctgatc
 E  D  G  G  L  V  T  V  T  Q  D  S  S  L  Q  D  G  T  L  I tacaaggtgaagatgcgcggcaccaacttcccccccgacggccccgtaatgcagaagaag
 Y  K  V  K  M  R  G  T  N  F  P  P  D  G  P  V  M  Q  K  K accatgggctgggaggcctccaccgagcgcctgtaccccgcgacggcgtgctgaagggc
 T  M  G  W  E  A  S  T  E  R  L  Y  P  R  D  G  V  L  K  G gagatccaccaggccctgaagctgaaggacggcggccactacctggtggagttcaagacc
 E  I  H  Q  A  L  K  L  K  D  G  G  H  Y  L  V  E  F  K  T atctacatggccaagaagcccgtgcaactgcccggctactactacgtggacaccaagctg
 I  Y  M  A  K  K  P  V  Q  L  P  G  Y  Y  Y  V  D  T  K  L gacatcacctcccacaacgaggactacaccatcgtggaacagtacgagcgctccgagggc
 D  I  T  S  H  N  E  D  Y  T  I  V  E  Q  Y  E  R  S  E  G cgccaccacctgttcctggggcatggcaccggcagcaccggcagcggcagctccggcacc
 R  H  H  L  F  L  G  H  G  T  G  S  T  G  S  G  S  S  G  T gcctcctccgaggacaacaacatggccgtcatcaaagagttcatgcgcttcaaggtgcgc
 A  S  S  E  D  N  N  M  A  V  I  K  E  F  M  R  F  K  V  R atggagggctccatgaacggccacgagttcgagatcgagggcgagggcgagggccgcccc
 M  E  G  S  M  N  G  H  E  F  E  I  E  G  E  G  E  G  R  P
```

FIG. 45 (cont')

```
tacgagggcacccagaccgccaagctgaaggtgaccaagggcggccccctgcccttcgcc
 Y  E  G  T  Q  T  A  K  L  K  V  T  K  G  G  P  L  P  F  A tgggacatcctgtcccccagttcatgtacggctccaaggcgtacgtgaagcaccccgcc
 W  D  I  L  S  P  Q  F  M  Y  G  S  K  A  Y  V  K  H  P  A gacatccccgattacaagaagctgtccttccccgagggcttcaagtgggagcgcgtgatg
 D  I  P  D  Y  K  K  L  S  F  P  E  G  F  K  W  E  R  V  M aacttcgaggacggcggtctggtgaccgtgacccaggactcctccctgcaggacggcacg
 N  F  E  D  G  G  L  V  T  V  T  Q  D  S  S  L  Q  D  G  T ctgatctacaaggtgaagatgcgcggcaccaacttccccccgacggccccgtaatgcag
 L  I  Y  K  V  K  M  R  G  T  N  F  P  P  D  G  P  V  M  Q aagaagaccatgggctgggaggcctccaccgagcgcctgtaccccgcgacggcgtgctg
 K  K  T  M  G  W  E  A  S  T  E  R  L  Y  P  R  D  G  V  L aagggcgagatccaccaggccctgaagctgaaggacggcggccactacctggtggagttc
 K  G  E  I  H  Q  A  L  K  L  K  D  G  G  H  Y  L  V  E  F aagaccatctacatggccaagaagcccgtgcaactgcccggctactactacgtggacacc
 K  T  I  Y  M  A  K  K  P  V  Q  L  P  G  Y  Y  Y  V  D  T aagctggacatcacctcccacaacgaggactacaccatcgtggaacagtacgagcgctcc
 K  L  D  I  T  S  H  N  E  D  Y  T  I  V  E  Q  Y  E  R  S gagggccgccaccacctgttcctgtacggcatggacgagctgtacaagtaa
 E  G  R  H  H  L  F  L  Y  G  M  D  E  L  Y  K  -
```

FIG. 46

```
atggcctcctccgaggacgtcatcaaggagttcatgcgcttcaaggtgcgcatggagggc
 M  A  S  S  E  D  V  I  K  E  F  M  R  F  K  V  R  M  E  G tccgtgaacggccacgagttcgagatcgagggcgagggcgagggccgcccctacgagggc
 S  V  N  G  H  E  F  E  I  E  G  E  G  E  G  R  P  Y  E  G acccagaccgccaagctgaaggtgaccaagggcggccccctgcccttcgcctgggacatc
 T  Q  T  A  K  L  K  V  T  K  G  G  P  L  P  F  A  W  D  I ctgtcccctcagttcatgtacggctccaaggcctacgtgaagcaccccgccgacatcccc
 L  S  P  Q  F  M  Y  G  S  K  A  Y  V  K  H  P  A  D  I  P gactacctgaagctgtccttccccgagggcttcaagtgggagcgcgtgatgaacttcgag
 D  Y  L  K  L  S  F  P  E  G  F  K  W  E  R  V  M  N  F  E gacggcggcgtggtgaccgtgacccaggactcctccctgcaggacggcgagttcatctac
 D  G  G  V  V  T  V  T  Q  D  S  S  L  Q  D  G  E  F  I  Y aaggtgaagctgcgcggcaccaacttcccctccgacggccccgtaatgcagaagaagacc
 K  V  K  L  R  G  T  N  F  P  S  D  G  P  V  M  Q  K  K  T atgggctgggaggcctcctccgagcggctgtaccccgaggacggcgccctgaagggcgag
 M  G  W  E  A  S  S  E  R  L  Y  P  E  D  G  A  L  K  G  E atcaagatgaggctgaagctgaaggacggcggccactacgacgccgaggccaagaccacc
 I  K  M  R  L  K  L  K  D  G  G  H  Y  D  A  E  A  K  T  T tacatggccaagaagcccgtgcagctgcccggcgcctacaagctcgactacaagctggac
 Y  M  A  K  K  P  V  Q  L  P  G  A  Y  K  L  D  Y  K  L  D atcacctcccacaacgaggactacaccatcgtggaacagtacgagcgcgccgagggccgc
 I  T  S  H  N  E  D  Y  T  I  V  E  Q  Y  E  R  A  E  G  R cactccaccggcgcctaa
 H  S  T  G  A  -
```

```
DsRed         MRSSKN------VIKEFMRFKVRMEGTVNGHEFEIEGEGEGRPYEGHNTVKLKVTKGGPLP  55
mRFP1         MASS--------VIKEFMRFKVRMEG-VNGHEFEIEGEGEGRPYEG-QTAKLKVTKGGPLP  55
mCherry       M-----------IKEFMRFKVRMEGSVNGHEFEIEGEGEGRPYEGTQTAKLKVTKGGPLP  55
mStrawberry   M----------IIKEFMRFKVRMEGSVNGHEFEIEGEGEGRPYEGTQTAKLKVTKGGPLP  55
mTangerine    MASSED------VIKEFMRFKVRMEGSVNGHEFEIEGEGEGRPYEGTQTAKLKVTKGGPLP  55
mOrange       M----------IIKEFMRFKVRMEGSVNGHEFEIEGEGEGRPYEGTQTAKLKVTKGGPLP  55
mBanana       M-----------VIKEFMRFKVRMEGSVNGHEFEIEGEGEGRPYEGTQTAKLKVTKGGPLP  55
mHoneydew     MASSED------VIKEFMRFKVRMEGSVNGHEFEIEGEGEGRPYEGTQTAKLKVTKGGPLP  55

DsRed         FAWDILSPQFQYGSKVYVKHPADIPDYKKLSFPEGFKWERVMNFEDGGVVTVTQDSSLQD  115
mRFP1         FAWDILSPQFQYGSKAYVKHPADIPDYLKLSFPEGFKWERVMNFEDGGVVTVTQDSSLQD  115
mCherry       FAWDILSPQFMYGSKAYVKHPADIPDYLKLSFPEGFKWERVMNFEDGGVVTVTQDSSLQD  115
mStrawberry   FAWDILSPQFMYGSKAYVKHPADIPDYLKLSFPEGFKWERVMNFEDGGVVTVTQDSSLQD  115
mTangerine    FAWDILSPQFMYGSKAYVKHPADIPDYLKLSFPEGFKWERVMNFEDGGVVTVTQDSSLQD  115
mOrange       FAWDILSPQFTYGSKAYVKHPADIPDYLKLSFPEGFKWERVMNFEDGGVVTVTQDSSLQD  115
mBanana       FAWDILSPQFCYGSKAYVKHPTGIPDYKKLSFPEGFKWERVMNFEDGGVVTVAQDSSLQD  115
mHoneydew     FAWDILSPQFMWGSKAYVKHPADIPDYLKLSFPEGFKWERVMNFEDGGVVTVTQDSSLQD  115

DsRed         GCFIYKVKFIGVNFPSDGPVMQKKTMGWEASTERLYPRDGVLKGEIHKALKLKDGGHYLV  175
mRFP1         GEFIYKVKFIGVNFPSDGPVMQKKTMGWEASTERLYPEDGALKGEIKMRLKLKDGGHYDA  175
mCherry       GEFIYKVKLRGTNFPSDGPVMQKKTMGWEASSERMYPEDGALKGEIKQRLKLKDGGHYDA  175
mStrawberry   GEFIYKVKLRGTNFPSDGPVMQKKTMGWEASSERMYPEDGALKGEIKMRLKLKDGGHYDA  175
mTangerine    GEFIYKVELRGTNFPSDGPVMQKKTMGWEASSERMYPEDGALKGEIKMRLKLKDGGHYDA  175
mOrange       GEFIYKVKLRGTNFPSDGPVMQKKTMGWEASSERMYPEDGALKGEIKMRLKLKDGGHYTV  175
mBanana       GEFIYKVKLRGTNFPSDGPVMQKKTMGWEASSERMYPEDGALKGEIKMRLKLKDGGHYSA  175
mHoneydew     GEFIYKVKLRGTNFPSDGPVMQKKTMGWKASSERMYPEDGALKGEIKMRLKLKDGGHYDA  175

DsRed         EFKSIYMAKKPVQLPGYYYVDSKLDITSHNEDYTIVEQYERTEGRHHLFL---------  225
mRFP1         EVKTTYMAKKPVQLPGAYKTDIKLDITSHNEDYTIVEQYERAEGRHSTGG-------  225
mCherry       EVKTTYKAKKPVQLPGAYKTNIKLDITSHNEDYTIVEQYERAEGRHSTGGMDELYK-  231
mStrawberry   EVKTTYKAKKPVQLPGAYKTDIKLDITSHNEDYTIVEQYERAEGRHSTGGMDELYK-  231
mTangerine    EVKTTYMAKKPVQLPGAYKTDIKLDITSHNEDYTIVEQYERAEGRHSTGA-------  225
mOrange       EVKTTYMAKKPVQLPGAYKTDIKLDITSHNEDYTIVEQYERAEGRHSTGGMDELYK-  231
mBanana       EVKTTYKAKKPVQLPGAYIAMEKIDITSHNEDYTIVELYERAEGRHSTGGMDELYK-  231
mHoneydew     EVKTTYMAKKPVQLPGAYKTDIKLDITSHNEDYTIVEQYERAEGRHSTGA-------  225
```

MONOMERIC AND DIMERIC FLUORESCENT PROTEIN VARIANTS AND METHODS FOR MAKING SAME

CROSS-REFERENCES TO RELATED APPLICATIONS

This application is a continuation of U.S. patent application Ser. No. 10/931,304 filed Aug. 30, 2004 and issued as U.S. Pat. No. 7,687,614, which is a continuation-in-part of U.S. patent application Ser. No. 10/209,208 filed Jul. 29, 2002 and issued as U.S. Pat. No. 7,005,511, which is a continuation-in-part application of U.S. patent application Ser. No. 10/121,258 filed Apr. 10, 2002 and issued as U.S. Pat. No. 7,157,566, which is a continuation-in-part of U.S. patent application Ser. No. 09/866,538, filed May 24, 2001 and issued as U.S. Pat. No. 6,852,849, which is a continuation-in-part of U.S. patent application Ser. No. 09/794,308, filed Feb. 26, 2001 and issued as U.S. Pat. No. 7,022,826, and claims priority under 35 U.S.C. §120 to all of which applications, the disclosures of which are hereby expressly incorporated by reference in their entirety.

STATEMENT AS TO RIGHTS TO INVENTIONS MADE UNDER FEDERALLY SPONSORED RESEARCH OR DEVELOPMENT

This invention was made in part with Government support under Grant No. NS27177, awarded by the National Institute of Neurological Disorders and Stroke, and under Grant No. GM62114-01, awarded by the National Institute of General Medical Sciences. The Government may have certain rights in this invention.

BACKGROUND OF THE INVENTION

1. Field of the Invention

The present invention relates generally to variant fluorescent proteins, and more specifically to Anthozoan fluorescent proteins that have a reduced propensity to oligomerize, where such proteins form monomeric and/or dimeric structures. The invention also relates to methods of making and using such fluorescent protein monomers and dimers. In particular, the present invention relates generally to variant red fluorescent proteins (RFPs), and more specifically to Anthozoan fluorescent proteins (AnFP), having at least one amino acid alteration that results in more efficient maturation than the corresponding wild-type protein or another variant RFP from which such variants derive. The invention further concerns RFP variants that additionally have reduced propensity tetramerize, and thus form predominantly monomeric and/or dimeric structures. The invention also relates to methods of making and using such RFP variants.

2. Description of the Related Art

The identification and isolation of fluorescent proteins in various organisms, including marine organisms, has provided a valuable tool to molecular biology. The green fluorescent protein (GFP) of the jellyfish *Aequorea victoria*, for example, has become a commonly used reporter molecule for examining various cellular processes, including the regulation of gene expression, the localization and interactions of cellular proteins, the pH of intracellular compartments, and the activities of enzymes.

The usefulness of *Aequorea* GFP has led to the identification of numerous other fluorescent proteins in an effort to obtain proteins having different useful fluorescence characteristics. In addition, spectral variants of *Aequorea* GFP have been engineered, thus providing proteins that are excited or fluoresce at different wavelengths, for different periods of time, and under different conditions. The identification and cloning of a red fluorescent protein from *Discosoma* coral, termed DsRed or drFP583, has raised a great deal of interest due to its ability to fluoresce at red wavelengths.

The DsRed from *Discosoma* (Matz et al., *Nature Biotechnology* 17:969-973 [1999]) holds great promise for biotechnology and cell biology as a spectrally distinct companion or substitute for the green fluorescent protein (GFP) from the *Aequorea* jellyfish (Tsien, *Ann. Rev. Biochem.*, 67:509-544 [1998]). GFP and its blue, cyan, and yellow variants have found widespread use as genetically encoded indicators for tracking gene expression and protein localization and as donor/acceptor pairs for fluorescence resonance energy transfer (FRET). Extending the spectrum of available colors to red wavelengths would provide a distinct new label for multicolor tracking of fusion proteins and together with GFP (or a suitable variant) would provide a new FRET donor/acceptor pair that should be superior to the currently preferred cyan/yellow pair (Mizuno et al., *Biochemistry* 40:2502-2510 [2001]). However, there are problems associated with the use of DsRed as a fluorescent reporter, including its slow and inefficient chromophore maturation and its tendency to oligomerize.

All coelenterate fluorescent proteins cloned to date display some form of quaternary structure, including the weak tendency of *Aequorea* green fluorescent protein (GFP) to dimerize, the obligate dimerization of *Renilla* GFP, and the obligate tetramerization of the *Discosoma* DsRed (Baird et al., *Proc. Natl. Acad. Sci. USA* 97:11984-11989 [2000]; and Vrzheshch et al., *FEBS Lett.*, 487:203-208 [2000]). While the weak dimerization of *Aequorea* GFP has not impeded its acceptance as an indispensable tool of cell biology, the obligate tetramerization of DsRed has greatly hindered its development from a scientific curiosity to a generally applicable and robust tool, most notably as genetically encoded fusion tag. Thus, one problem with DsRed is its tendency to oligomerize.

DsRed tetramerization presents an obstacle—for the researcher who wishes to image the subcellular localization of a red fluorescent chimera, as the question exists as to what extent will fusing tetrameric DsRed to the protein of interest affect the location and function of the latter. Furthermore, it can be difficult in some cases to confirm whether a result is due, for example, to a specific interaction of two proteins under investigation, or whether a perceived interaction is an artifact caused by the oligomerization of fluorescent proteins linked to each of the two proteins under investigation. There have been several published reports (see, e.g., Mizuno et al., *Biochemistry* 40:2502-2510 [2001]; and Lauf et al., *FEBS Lett.*, 498:11-15 [2001]) and many unpublished anecdotal communications, in which DsRed chimeras have been described as forming intracellular aggregates that have lost their biological activity. In addition to its tendency to oligomerize, DsRed also suffers from slow and incomplete maturation (Baird et al., *Proc. Natl. Acad. Sci. USA* 97:11984-11989 [2000]).

One approach to overcome these shortcomings has been to continue the search for DsRed homologues in sea coral and anemone; an approach that has yielded several red shifted proteins (Fradkov et al., *FEBS Lett.*, 479:127-130 [2000]; and Lukyanov et al., *J Biol. Chem.*, 275:25879-25882 [2000]). However, the fundamental problem of tetramerization has yet to be overcome. The only published progress towards decreasing the oligomeric state of a red fluorescent protein involved an engineered DsRed homologue, commercially available as HcRed1 (CLONTECH), which was converted to a dimer with a single interface mutation (Gurskaya et al., *FEBS Lett.*, 507:16-20 [2001]). Although HcRed1 has the additional benefit of being 35 nm red-shifted from DsRed, it is limited by a low extinction coefficient (20,000 M−1 cm$^{-1}$) and quantum yield (0.015) (CLONTECH Laboratories Inc., (2002) Living Colors User Manual Vol. II: Red Fluorescent Protein [Becton, Dickinson and Company], p. 4) making the protein problematic to use in experimental systems.

A methionine at position 66 of a tetrameric nonfluorescent chromoprotein from *Anemonia sulcata* was converted to a fluorescent protein through the introduction of two mutations (Lukyanov, K. A., Fradkov, A. F., Gurskaya, N. G., Matz, M. V., Labas, Y. A., Savitsky, A. P.; Markelov, M. L., Zaraisky, A. G., Zhao, X., Fang, Y. et al. (2000) *J. Biol. Chem.* 275, 25879-25882). Introduction of a methionine at position 66 apparently improved the fluorescent properties of both a green (zFP506) and a cyan (amFP486) tetrameric fluorescent protein though no details have been published (Yanushevich, Y. G., Staroverov, D. B., Savitsky, A. P., Fradkov, A. F., Gurskaya, N. G., Bulina, M. E., Lukyanov, K. A. & Lukyanov, S. A. (2002) *FEES Lett.* 511, 11-14).

Most previous attempts to improve the rate and/or extent of maturation of DsRed (Verkhusha et al., *J. Biol. Chem.*, 276: 29621-29624 [2001]; and Terskikh et al., *J. Biol. Chem.*, 277:7633-7636 [2002]) including the commercially available DsRed2 (CLONTECH, Palo Alto, Calif.), have provided only modest improvements. Recently, an engineered. variant of DsRed, known as T1 has become available, and which matures more rapidly, but appears to suffer from an incomplete maturation (Bevis and Glick, *Nat. Biotechnol.*, 20:83-87 [2002]). Thus; like DsRed, a significant fraction of the T1 protein remains as the green fluorescent intermediate in the aged tetramer.

Thus, there exists a need in the art for the development of red fluorescent polypeptides for use in scientific applications without technical limitations due to oligomerization, especially tetramerization, and due to inefficient and slow chromophore maturation. There exists a need for methods to produce fluorescent proteins having reduced propensity for oligomerization, especially reduced propensity for tetramerization. There exists a need for methods to produce red fluorescent proteins (RFPs) exhibiting more efficient chromophore maturation than wild-type RFPs or other RPF variants. Furthermore, there exists a need for RFPs that additionally have reduced propensity for oligomerization, such as, e.g., tetramerization. There also exists a need for RFP variants with improved efficiency of maturation that demonstrate useful fluorescence in a monomeric state in experimental systems. There exists a need for methods to produce fluorescent proteins that demonstrate useful fluorescence in a monomeric state in experimental systems. The present invention satisfies these needs and provides additional advantages.

BRIEF SUMMARY OF THE INVENTION

Variants of red fluorescent proteins (RFPs) that have a reduced propensity to oligomerize are disclosed herein. For example, the variant RFPs disclosed in the present application have a propensity to form monomers and dimers, where the native form of the RFP has a propensity to form tetrameric structures.

Aspects of the present invention concern variants of red fluorescent proteins (RFPs) comprising at least one amino acid alteration resulting in more efficient chromophore maturation than a corresponding wild-type or variant RFP. For example, in one aspect, the present invention concerns RFP variants that have a reduced propensity to form tetramers as compared to a corresponding wild-type or variant RF. Thus, certain RFP variants of the invention have a propensity to form monomers and dimers, although the native form of the RFP has a propensity to form tetrameric structures. In some embodiments, the present invention concerns RFP variants that, in addition to showing more efficient chromophore maturation, also have a reduced propensity to form tetramers. In some aspects, the present invention further concerns RFP variants that show have improved quantum yield, improved extinction coefficient, or improvements in other measurable characteristics of a fluorescent protein as compared to a corresponding wild-type or variant RF. Some aspects of the present invention concern RFP variants that show more efficient maturation, have a reduced propensity to form tetramers, and in addition have improved quantum yield, improved extinction coefficient, or improvements in other measurable characteristics of a fluorescent protein as compared to a corresponding wild-type or variant RF.

In some aspects, the invention concerns an Anthozoan fluorescent protein (AnFP) having a reduced propensity to oligomerize, comprising at least one mutation within the wild-type AnFP amino acid sequence that reduces or eliminates the ability of the fluorescent protein to tetramerize and/ or dimerize, as the case may be. The AnFP preferably is the red fluorescent protein of *Discosoma* (DsRed) of SEQ ID NO: 1, but is by no means so limited. In some embodiments, the invention concerns an Anthozoan fluorescent protein (AnFP), e.g., DsRed, comprising at least one amino acid substitution within the AB and/or AC interface of said fluorescent protein (e.g., DsRed) that reduces or eliminates the degree of oligomerization of said fluorescent protein.

In other embodiments, the variant AnFP (e.g., DsRed) having a reduced propensity to oligomerize is a monomer in which the interfaces between the oligomeric subunits are disrupted by introducing mutations; e.g., substitutions, which interfere with oligomerization (including dimerization), and, if necessary, introducing further mutations needed to restore or improve fluorescence which might have been partially or completely lost as a result of disrupting the interaction of the subunits.

Aspects of the invention specifically include dimeric and monomeric variants of other fluorescent proteins in addition to DsRed, such as fluorescent proteins from other species and fluorescent proteins that have fluorescence emission spectra in wavelengths other than red. For example, green fluorescent proteins and fluorescent proteins from *Renilla* sp. find equal use with the invention. Furthermore, fluorescent proteins that normally have the propensity to form tetramers and/or dimers find equal use with the invention.

In a particular embodiment, the fluorescent protein is DsRed, and a DsRed variant having a reduced propensity to oligomerize (in this case, tetramerize) is prepared by first replacing at least one key residue in the AC and/or AB interface of the wild-type protein, thereby creating a dimer or monomer form, followed by the introduction of further mutation(s) to restore or improve red fluorescence properties.

In one aspect, the invention provides variant fluorescent proteins, including but not limited to DsRed, comprising amino acid substitutions relative to the respective wild-type sequences, where the substitutions impart the advantageous properties to the polypeptide variants. These amino acid substitutions can reside at any position within the polypeptide, and are not particularly limited to any type of substitution (conservative or non-conservative). In one embodiment, the mutations restoring or improving fluorescence are amino acid substitutions within the plane of the chromophore and/or just above the plane of the chromophore and/or just below the plane of the chromophore of the fluorescent protein.

In one aspect, the invention provides a polynucleotide sequence encoding a *Discosoma* red fluorescent protein (DsRed) variant having a reduced propensity to oligomerize, comprising one or more amino acid substitutions at the AB interface, at the AC interface, or at the AB and AC interfaces of the wild-type DsRed amino acid sequence of SEQ ID NO: 1, where the substitutions result in reduced propensity of the DsRed variant to form tetramers, wherein said variant displays detectable fluorescence of at least one red wavelength. In one embodiment, this protein sequence has at least about 80% sequence identity with the amino acid sequence of SEQ ID NO: 1. In another embodiment, the fluorescent protein has detectable fluorescence that matures at a rate at least about 80% as fast as the rate of fluorescence maturation of wild-type DsRed of SEQ ID NO: 1, while in another embodiment the protein has improved fluorescence maturation relative to DsRed of SEQ ID NO: 1. In still another embodiment, the protein substantially retains the fluorescence properties of DsRed of SEQ ID NO: 1.

In some embodiments, the fluorescent protein variant has a propensity to form dimers. Some proteins contain substitutions in the AB interface and form an AC dimer.

In some embodiments, the fluorescent protein variant comprises amino acid substitutions that are at one or more of the residues 2, 5, 6, 21, 41, 42, 44, 117, 125, and 217 of SEQ ID NO: 1.

In some embodiments, the fluorescent protein variant comprises at least nine amino acid substitutions that are at residues 2, 5, 6, 21, 41, 42, 44, 117, and 217, and additionally at least one more substitution including substitution at residue 125 of SEQ ID NO: 1. The protein can optionally further comprise at least one additional amino acid substitution that is at residue 71, 118, 163, 179, 197, 127, or 131 of SEQ ID NO: 1. In some embodiments, any one or more of said substitutions is optionally selected from R2A, K5E, N6D, T21S, H41T, N42Q, V44A, V7 1A, C117T, F118L, I125R, V127T, S131P, K163Q/M, S179T, S197T, and T217A/S.

The invention provides fluorescent protein variants that can be the proteins dimer1, dimer1.02, dimer1.25, dimer1.26, dimer 1.28, dimer1.34, dimer1.56, dimer1.61, or dimer1.76, as provided in FIGS. 20A-D. In some embodiments, the protein variant is dimer2 (SEQ ID NO: 6), or dimer 2.2MMM (also termed dimer3 or dTomato) (SEQ ID NO: 81), or tdTomato (SEQ ID NO: 106).

The invention also provides fluorescent protein variants that can be variants of the protein dimer2 (SEQ ID NO: 6). A variant of dimer2 (SEQ ID NO:6) may have about 80% sequence identity, or about 90%, or about 95% sequence identity with SEQ ID NO:6, and may comprise one or more amino acid substitutions selected from amino acid substitutions at positions 22, 66, 105, and 124, and may also include terminal amino acid additions or substitutions comprising one or more amino acids homologous to the N- and/or C-terminal amino acids of GFP (e.g., SEQ ID NO: 14 at the N-terminus and/or SEQ ID NO: 91 or SEQ ID NO:110 at the C-terminus). In still other embodiments, the substitutions in the dimeric protein is optionally selected from one or more of V22M, Q66M, V104L, and F124M. For example, in an embodiment, the protein variant is dimer2.2MMM (dimer3) (dTomato) (SEQ ID NO: 81).

In some embodiments, the fluorescent dimeric protein variant has at least about 90% sequence identity with the amino acid sequence of SEQ ID NO: 1, while in other embodiments, the protein has at least about 95% sequence identity with the amino acid sequence of SEQ ID NO: 1.

In still other embodiments, the fluorescent protein variant is a monomer. In this embodiment, the amino acid substitutions are in the AB interface and the AC interface.

In some embodiments, the monomeric protein variant comprises at least 14 amino acid substitutions that are at residues 2, 5, 6, 21, 41, 42, 44, 71, 117, 127, 163, 179, 197, and 217, and additionally at least one more substitution that is at residue 125 of SEQ ID NO: 1. In other embodiments, the monomeric protein optionally further comprises at least one additional amino acid substitution at residue 83, 124, 125, 150, 153, 156, 162, 164, 174, 175, 177, 180, 192, 194, 195, 222, 223, 224, and 225 of SEQ ID NO: 1. In still other embodiments, the substitutions in the monomeric protein is optionally selected from R2A, K5E, N6D, T21S, H41T, N42Q, V44A, V71A, K83L, C117E/T, F124L, I125R, V127T, L150M, R153E, V156A, H162K, K163Q/M, L174D, V175A, F177V, 5179T, I180T, Y192A, Y194K, V195T, S197A/T/I, T217A/S, H222S, L223T, F224G, L225A.

In some embodiments, the monomeric protein variant is selected from mRFP0.1, mRFP0.2, mRFP0.3, mRFP0.4a, mRFP0.4b, mP11, mP17, m1.01, m1.02, mRFP0.5a, m1.12, mRFP0.5b, m1.15, m1.19, mRFP0.6, m124, m131, m141, m163, m173, m187, m193, m200, m205 and m220, as provided in FIGS. 20A-20D. In some embodiments, the monomeric variant is mRFP1 (SEQ ID NO: 8), or is mRFP1.5 (SEQ ID NO: 83) or is another monomeric variant.

In some embodiments, the monomeric variant is a variant of mRFP1 (SEQ ID NO: 8) or related fluorescent proteins. A variant of mRFP1 (SEQ ID NO: 8) may have 80%, or 90%, or 95% sequence identity with SEQ ID NO: 8, and may comprise one or more amino acid substitutions selected from amino acid substitutions at positions 7, 17, 21, 32, 66, 77, 78, 83, 108, 125, 147, 150, 161, 163, 174, 177, 182, 194, 195, 196, 197, 199 and 213, and may also include terminal amino acid additions or substitutions selected from one or more amino acids homologous to the amino acids at the GFP terminus (e.g., SEQ ID NO: 14, SEQ ID NO:91 and SEQ ID NO:91), the amino acids DNMA (SEQ ID NO:111), and the amino acids NNMA (SEQ ID NO:112). Such insertions are preferably after amino acid E6. In still other embodiments, the substitutions in the monomeric protein is optionally selected from one or more of V7I, R17H, T21S, E32K, Q66T/M, A77T/P, D78G, L83F/M, T108A, R125H, T147S, M150L, I161V, M163Q, D174S, V177T, M182K, K194I, T195V/A/L, D195A, D196G, I197E/Y, L199I, and Q213L. In some embodiments, the protein variant is selected from mRFP1.5 (SEQ ID NO: 83), OrS4-9 (SEQ ID NO: 85), Y1.3 (mYOFP1.3) (mBanana) (SEQ ID NO: 87), mFRFP (F2Q6) (mGrape2) (SEQ ID NO: 89), mRFP2 (mCherry) (SEQ ID NO: 92), mOFP (74-11) (SEQ ID NO: 94), mROFP (A2/6-6) (SEQ ID NO: 96), mStrawberry (SEQ ID NO:98), mTangerine (SEQ ID NO: 100), mOrange (mOFP1) (SEQ ID NO: 102), mHoneydew (SEQ ID NO:104), and mGrape1 (SEQ ID NO: 108). In a specific embodiment, the variant comprises an amino acid sequence that is at least 90% or 95% identical over the entire length of SEQ ID NO:8.

In some embodiments, the monomeric variant has at least about 90% sequence identity with the amino acid sequence of SEQ ID NO: 1, while in other embodiments, the protein has at least about 95% sequence identity with the amino acid sequence of SEQ ID NO: 1.

The present invention also provides tandem dimer forms of DsRed, comprising two DsRed protein variants operatively linked by a peptide linker. The peptide linker can be of variable length, where, for example, the peptide linker is about 10 to about 25 amino acids long, or about 12 to about 22 amino acids long. In some embodiments, the peptide linker is selected from GHGTGSTGSGSS (SEQ ID NO: 17), RMGSTSGSTKGQL (SEQ ID NO: 18), and RMGSTSGSGKPGSGEGSTKGQL (SEQ ID NO: 19).

In some embodiments, the tandem dimer subunit is selected from dimer1, dimer1.02, dimer1.25, dimer1.26, dimer 1.28, dimer1.34, dimer1.56, dimer1.61, dimer1.76, dimer2, dimer 2.2MMM (dimer 3) (dTomato) SEQ ID NO: 81) and tdTomato (SEQ ID NO: 106), as provided in FIGS. 20A-20D and FIGS. 32-33. The tandem dimer can be a homodimer or a heterodimer. In some embodiments, the tandem dimer comprises at least one copy of dimer2 (SEQ ID NO: 6), dimer 2.2MMM (dimer 3) (dTomato) (SEQ ID NO: 81), or may be tdTomato (SEQ ID NO: 106).

The present application also provides fusion proteins between any protein of interest operatively joined to at least one fluorescent protein variant of the invention. This fusion protein can optionally contain a peptide tag, and this tag can optionally be a polyhistidine peptide tag.

The present application also provides polynucleotides that encode each of the fluorescent protein variants described or taught herein. Furthermore, the present invention provides the fluorescent protein variants encoded by any corresponding polynucleotide described or taught herein. Such polypeptides can include dimeric variants, tandem dimer variants, or monomeric variants.

In other embodiments, the invention provides kits comprising at least one polynucleotide sequence encoding a fluorescent protein variant of the invention. Alternatively, or in addition, the kits can provide the fluorescent protein variant itself.

In other embodiments, the present invention provides vectors that encode the fluorescent protein variants described or taught herein. Such vectors can encode dimeric variants, tandem dimer variants, or monomeric variants, or fusion proteins comprising these variants. The invention also provides suitable expression vectors. In other embodiments, the invention provides host cells comprising any of these vectors.

In another embodiment, the invention provides a method for the generation of a dimeric or monomeric variant of a fluorescent protein which has propensity to tetramerize or dimerize, comprising the steps of mutagenizing at least one amino acid residue in the fluorescent protein to produce a dimeric variant, if the protein had the propensity to tetramerize, and a monomeric variant, if the protein had the propensity to dimerize; and mutagenizing at least one additional amino acid residue to yield a dimeric or monomeric variant, which retains the qualitative ability to fluoresce in the same wavelength region as the non-mutagenized fluorescent protein.

In an optional variation of this method, an additional step can be added, essentially introducing a further mutation into a dimeric variant produced from a fluorescent protein that had the propensity to form tetramers to produce a monomeric variant. In some embodiments, this additional step can come after the first mutagenizing step.

In some embodiments, this method can result in dimeric or monomeric variants having improved fluorescence intensity or fluorescence maturation relative to the non-mutagenized fluorescent protein.

The mutagenesis used in the present method can be by multiple overlap extension with semidegenerate primers, error-prone PCR, site directed mutagenesis, or by a combination of these. The results of this mutagenesis can produce protein variants that have a propensity to form dimers or monomers.

In some embodiments of this method, the fluorescent protein is an Anthozoan fluorescent protein, and optionally, the Anthozoan fluorescent protein fluoresces at a red wavelength. The Anthozoan fluorescent protein can be *Discosoma* DsRed.

In other embodiments, the fluorescent protein variants of the invention can be used in various applications. In one embodiment, the invention provides a method for the detection transcriptional activity, where the method uses a host cell comprising a vector encoding a variant DsRed fluorescent protein operably linked to at least one expression control sequence, and a means to-assay said variant fluorescent protein fluorescence. In this method, assaying the fluorescence of the variant fluorescent protein produced by the host cell is indicative of transcriptional activity.

In other embodiments the invention also provides a a polypeptide probe suitable for use in fluorescence resonance energy transfer (FRET), comprising at least one fluorescent protein variant of the invention.

In still another embodiment, the invention provides a method for the analysis of in vivo localization or trafficking of a polypeptide of interest, where the method uses a fluorescent fusion protein of the invention in a host cell or tissue, and where the fusion protein can be visualized in the host cell or tissue.

In a further aspect, the invention concerns further improved variants of red fluorescent proteins (RFPs) that have reduced propensity to-oligomerize. In particular, the invention concerns RFP variants that not only have a propensity to form monomers and dimers, where the native form of the RFP has a propensity to form tetrameric structures, but are additionally characterized by more efficient maturation than the corresponding non-oligomerizing variants from which they derive. Such variants are typically brighter than the corresponding non-oligomerizing variants, where brightness is typically expressed as the product of the extinction coefficient (EC) and the quantum yield (QY) at the desired red wavelength.

The invention further provides a polynucleotide encoding a variant of a red fluorescent protein (RFP) having a propensity to form tetrameric structures, comprising at least one amino acid alteration resulting in more efficient maturation into the desired red species from the immature green species, and at least one further amino acid alteration resulting in a reduced propensity to tetramerize. The amino acid alteration may be substitution, insertion and/or deletion, and preferably is substitution.

Thus, in one aspect the invention concerns a polynucleotide encoding a variant of a red fluorescent protein (RFP) having a propensity to form tetrameric structures, comprising at least one amino acid alteration resulting in higher fluorescence intensity at red wavelength, and at least one further amino acid alteration resulting in a reduced propensity to tetramerize.

In a particular embodiment, the polynucleotide encodes a *Discosoma* red fluorescent protein (DsRed) variant.

In another embodiment, the polynucleotide encodes a DsRed variant, in which the amino acid substitution resulting in more efficient maturation is at position 66 of wild-type DsRed of SEQ ID NO: 1. A particular substitution is a Q66M substitution within SEQ ID NO: 1. In another embodiment, the polynucleotide encodes a DsRed variant, in which the amino acid substitution resulting in more efficient maturation is at position 147 of wild-type DsRed of SEQ ID NO: 1. The substitution at position 147 preferably is a T147S substitution, but other substitutions are also possible at this position and are specifically included within the scope of the present invention. In a further embodiment, the polynucleotide of the invention encodes a DsRed variant comprising a substitution at both position 66 and position 147 within SEQ ID NO: 1. In a preferred embodiment, the polynucleotide of the invention encodes a DsRed variant comprising a Q66M and a T147S substitution.

The polynucleotides of the invention encoding DsRed variants comprising at least one amino acid alteration resulting in improved efficiency of chromophore maturation into the desired red form, such as, for example, a Q66M substitution, may additionally contain codons for any of the other amino acid substitutions, alone or in any combination, discussed hereinabove and throughout the present disclosure, in connection with other embodiments. In particular, such polynucleotides (e.g. those encoding a DsRed variant with a Q66M mutation alone or in combination with a T147S substitution) may encode DsRed variants further comprising one or more substitutions at the AB interface, at the AC interface, or at the AB and AC interfaces of the wild-type DsRed amino acid sequence of SEQ ID NO: 1, where the substitutions result in reduced propensity of the DsRed variant to form tetramers.

In a particular embodiment, such polynucleotides encode DsRed variants additionally comprising one or more substitutions at an amino acid position selected from the group consisting of 42, 44, 71, 83, 124, 150, 163, 175, 177, 179, 195, 197, 217, 2, 5, 6, 125, 127, 180, 153, 162, 164, 174, 192, 194, 222, 223, 224, 225, 21, 41, 117, and 156 within the wild-type DsRed amino acid sequence of SEQ ID NO: 1. Possible substitutions at the indicated positions include, without limitation, one or more substitutions selected from the group consisting of N42Q, V44A, V71A, K83L, F124L, L150M, K163M, V175A, F177V, S179T, V195T, S197I, T217A, R2A, K5E, N6D, I125R, V127T, I180T, R153E, H162K, A164R, L174D, Y192A, Y194K, H222S, L223T, F224G, L225A, T21S, H41T, C117E, and V156A within the wild-type DsRed amino acid sequence of SEQ ID NO: 1.

Thus, polynucleotides encoding DsRed variants comprising the following substitutions: N42Q, V44A, V71A, K83L, F124L, L150M, K163M, V175A, F177V, S179T, V195T, S197I, T217A, R2A, K5E, N6D, I125R, V127T, I180T, R153E, H162K, A164R, L174D, Y192A, Y194K, H222S, L223T, F224G, L225A, T21S, H41T, C117E, and V156A within the wild-type DsRed amino acid sequence of SEQ ID NO: 1, are specifically within the scope of the invention.

Preferred dimeric embodiments of the invention include a polynucleotide encoding a dimer2 (SEQ ID NO:6), a polynucleotide encoding a dimer2.2MMM (dimer3) (dTomato) (peptide SEQ ID NO: 81, DNA SEQ ID NO: 82), and a polynucleotide encoding a tdTomato (peptide SEQ ID NO: 106, DNA SEQ ID NO: 107). Preferred monomeric embodiments of the invention include a polynucleotide encoding a mRFP1.1 shown in FIG. 30 (SEQ ID NO: 79), a polynucleotide encoding a mRFP1.5 (SEQ ID NO: 83), a polynucleotide encoding a OrS4-9 (SEQ ID NO: 85), a polynucleotide encoding a Y1.3 (SEQ ID NO: 87), a polynucleotide encoding a F2Q6 (SEQ ID NO: 89), a polynucleotide encoding a mRFP2 (mCherry) (SEQ ID NO: 92), a polynucleotide encoding a mOFP (74-11) (SEQ ID NO: 94), a polynucleotide encoding a mROFP (A2/6-6) (SEQ ID NO: 96), a polynucleotide encoding a mStrawberry (SEQ ID NO:98), a polynucleotide encoding a mTangerine (SEQ ID NO: 100), a polynucleotide encoding a mOrange (mOFP1) (SEQ ID NO: 102), a polynucleotide encoding a mHoneydew (SEQ. ID NO:104), and a polynucleotide encoding a mGrape1 (SEQ ID NO:108).

In another aspect, the invention concerns a polynucleotide encoding a fusion protein, comprising at least one DsRed protein variant encoded by the polynucleotides discussed above, operatively joined to at least one other polypeptide of interest. In particular embodiments, such fusion proteins may comprising either the Q66M or T147S substitution, or both, as a tandem dimer.

The invention further concerns polypeptides encoded by the polynucleotides discussed above, vectors containing such polynucleotides (including expression vectors), and recombinant host cells transformed with such polynucleotides or vectors.

The invention, in a different aspect, concerns a kit comprising at least one polynucleotide or polypeptide discussed above.

In yet another aspect, the invention concerns a method for the detection transcriptional activity, comprising:

(a) providing a host cell comprising a vector, wherein said vector comprises nucleotide sequence encoding a DsRed fluorescent protein variant comprising at least one amino acid alteration resulting in higher fluorescence intensity at red wavelength, and at least one further amino acid alteration resulting in a reduced propensity to tetramerize operably linked to at least one expression control sequence, and a means to assay said variant fluorescent protein fluorescence, and (b) assaying fluorescence of said variant fluorescent protein produced by said host cell, where variant fluorescent protein fluorescence is indicative of transcriptional activity.

In a further aspect, the invention concerns a method for the detection of protein-protein interactions, comprising detection of energy transfer from a fluorescent or bioluminescent protein fusion to a fusion protein as discussed above.

In a still further aspect, the invention concerns a method for the analysis of in vivo localization or trafficking of a polypeptide of interest, comprising the steps of:

(a) providing a polynucleotide encoding a fusion protein, comprising at least one DsRed protein variant encoded by the polynucleotides discussed above, operatively joined to at least one other polypeptide of interest and a host cell or tissue, and (b) visualizing said fusion protein that is expressed in said host cell or tissue.

BRIEF DESCRIPTION OF THE DRAWINGS

FIG. 2A shows the tetramer of DsRed with the residues mutated in T1 indicated in blue for external residues and green for those internal to the β-barrel. FIG. 2B shows the AC dimer of DsRed with all mutations present in dimer2 represented as in FIG. 2A and the intersubunit linker present in tdimer2(12) shown as a dotted line. FIG. 2C shows the mRFP1 monomer of DsRed with all mutations present in mRFP1 represented as in FIG. 2A.

FIG. 6A shows two contacting cells transfected with Cx43-mRFP1 and connected by a single large gap junction. FIG. 6B shows one cell microinjected with lucifer yellow at the point indicated by an asterisk and the dye quickly passing (1-2 sec) to the adjacent cell. FIG. 6C shows four neighboring cells transfected with Cx43-dimer2. The bright line between the two right-most cells is the result of having two fluorescent membranes in contact and is not a gap junction. FIG. 6D shows microinjected dye slowly passing to an adjacent cell (observed approximately one third of the time). FIG. 6E shows two adjacent cells transfected with Cx43-T1 and displaying the typical perinuclear localized aggregation. FIG. 6F shows no dye passed between neighboring cells.

FIGS. 8A and 8B show SDS-PAGE analysis of DsRed, T1, dimer2, tdimer2(12), and mRFP1 polypeptides. The oligomeric state of each protein is demonstrated by running each protein (20 μg) both not boiled and boiled on a 12% SDS-PAGE Tris-HCl precast gel (BioRad). FIG. 8A shows the gel prior to Coomasie staining, which was imaged with excitation at 560 nm and emission at 610 nm. The tandem dimer tdimer2 (12) has a small tetrameric component due a fraction of the covalent tandem pairs participating in intermolecular dimer pairs. Fluorescent proteins that are not boiled do not necessarily migrate at their expected molecular weight. FIG. 8B shows the same gel as in FIG. 8A after Coomasie staining. The band at ~20 kDa results from partial hydrolysis of the mainchain acylimine linkage in protein containing a red chromophore.

In FIG. 9A, the quadrants corresponding to T1, dimer2, and mRFP1 all appear of similar brightness when excited at 540 nm and imaged with a 575 nm (long pass) emission filter. Almost no fluorescence is visible for identically treated E. coli transformed with DsRed. In FIG. 9B, when excited at 560 nm and imaged with a 610 (long pass) filter, mRFP1 appears brighter due to its 25 nm red shift. In FIG. 9C, the monomer mRFP1 does not contain a green fluorescent component and is thus very dim in comparison to T1 and dimer2 when excited at 470 nm, a wavelength suitable for excitation of EGFP. FIG. 9D shows a digital color photograph of the same plate taken after 5 days at room temperature reveals the orange and purple hues of T1 and mRFP1, respectively.

FIGS. 10A and 10B show a table describing the protocols and multiple libraries created during evolution of dimer1 and mRFP1, as well as other intermediate forms. The templates, method of mutagenesis, targeted positions within the DsRed polypeptide, and resulting clones are indicated.

FIGS. 11A-11C show a table providing a key to the primer pairs used in the mutagenesis protocols, as well as the target codon positions.

FIGS. 12A and 12B provide the PCR primer sequences (SEQ ID NS:41-78) listed in FIGS. 11A-11C.

FIG. 13 shows a table describing the results of a series of experiments testing the functionality of various DsRed chimeric molecules. The chimeric molecules comprise a DsRed sequence and the Cx43 polypeptide. The plasmids encoding the fusion polypeptides were transfected into HeLa cells, and the ability of the expressed fusion polypeptides to form functional gap junctions was assayed by the microinjection of lucifer yellow dye. Passage of the dye from one HeLa cell to an adjacent HeLa cell indicates the presence of a functional gap junction, and thus, a functional fusion polypeptide.

FIG. 14 shows various biophysical properties of wild-type DsRed, T1, dimer2, tdimer2(12), and mRFP1 polypeptides.

FIG. 15 shows a table providing excitation/emission wavelength values, relative maturation speed and red/green ratio values of red and green fluorescent protein species.

FIG. 16 provides the nucleotide sequence of the Discosoma sp. wild-type red fluorescent protein open reading frame (DsRed) (SEQ ID NO:2).

FIG. 17 provides the amino acid sequence of the Discosoma sp. wild-type red fluorescent protein (DsRed) (SEQ ID NO:1).

FIG. 18 provides the nucleotide sequence of the Discosoma sp. variant fast T1 red fluorescent protein (SEQ ID NO:5).

FIG. 19 provides the amino acid sequence of the Discosoma sp. variant fast T1 red fluorescent protein (SEQ ID NO:4).

FIGS. 20A-20D provide a table showing the amino acid substitutions identified during the construction of variant DsRed proteins. Also shown are the substitutions originally contained in the fast T1 DsRed variant.

FIG. 21 provides the nucleotide sequence of the Discosoma variant red fluorescent protein dimer2 open reading frame (SEQ ID NO:7).

FIG. 22A provides the amino acid sequence of the Discosoma variant red fluorescent protein dimer2 (SEQ ID NO:6).

FIG. 22B provides the amino acid sequence of the GFP termini and illustrates their locations at the N-terminal (SEQ ID NO: 14; underlined) and C-terminal (SEQ ID NO: 91; underlined) ends of a fluorescent protein. wtDsRed =SEQ ID NOS:113 and 114; mRFP1 =SEQ ID NOS:115 and 116; "GFP termini" =SEQ ID NOS:117 and 118.

FIG. 23 provides the nucleotide sequence of the Discosoma variant red fluorescent protein mRFP1 open reading frame (SEQ ID NO:9).

FIG. 24 provides the amino acid sequence of the *Discosoma* variant red fluorescent protein mRFP1 (SEQ ID NO:8).

FIG. 25 provides the nucleotide sequence of a modified *Discosoma* wild-type red fluorescent protein open reading frame with humanized codon usage (SEQ ID NO:23).

FIG. 30 provides the amino acid sequence of mRFP1.1 (SEQ ID NO:79).

FIG. 31 provides the nucleotide sequence of mRFP1.1 (SEQ ID NO:80).

FIG. 32 shows a table of properties of DsRed variants, providing excitation wavelengths and emission wavelengths (as ex/em in nm) extinction coefficients (as $M^{-1}cm^{-1}$), quantum yield, listing of mutations with respect to the parent sequence (e.g., ins (DNMA) (SEQ ID NO:111)), ins (NNMA) (SEQ ID NO:112), and comments on the properties of the listed DsRed variants.

FIG. 33 provides the amino acid sequence and DNA sequence of dimer2.2MMM (dimer3) (dTomato) (SEQ ID NO: 81 and SEQ ID NO: 82).

FIG. 34 provides the amino acid sequence and DNA sequence of mRFP1.5 (SEQ ID NO: 83 and SEQ ID NO: 84).

FIG. 35 provides the amino acid sequence and DNA sequence of OrS4-9 (SEQ ID NO: 85 and SEQ ID NO: 86).

FIG. 36 provides the amino acid sequence and DNA sequence of Y13 (mYOFP1.3) (mBanana) (SEQ ID NO:87 and SEQ ID NO:88). Y1.3 (mYOFP1.3) (mBanana) amino acid and DNA sequence (SEQ ID NO:87 and SEQ ID NO:88).

FIG. 37 provides the amino acid sequence and DNA sequence of mFRFP (F2Q6) (mGrape2) (SEQ ID NO: 89 and SEQ ID NO: 90).

FIG. 38 provides the amino acid sequence and DNA sequence of mRFP2 (mCherry) (SEQ ID NO: 92 and SEQ ID NO: 93).

FIG. 39 provides the amino acid sequence and DNA sequence of mOFP (74-11) (SEQ ID NO: 94) and (SEQ ID NO: 95).

FIG. 40 provides the amino acid sequence and DNA sequence of mROFP (A2/6-6) (SEQ ID NO: 96 and SEQ ID NO: 97).

FIG. 41 provides the amino acid sequence and DNA sequence of mStrawberry (SEQ ID NO: 98 and SEQ ID NO: 99).

FIG. 42 provides the amino acid sequence and DNA sequence of mTangerine (SEQ ID NO: 100 and SEQ ID NO: 101).

FIG. 43 provides the amino acid sequence and DNA sequence of mOrange (MOFP1) (SEQ ID NO: 102 and SEQ ID NO: 103).

FIG. 44 provides the amino acid sequence and DNA sequence of mHoneydew (SEQ ID NO: 104 and SEQ ID NO: 105).

FIG. 45 provides the amino acid sequence and DNA sequence of tdTomato (SEQ ID NO: 106 and SEQ ID NO: 107).

FIG. 46 provides the amino acid sequence and DNA sequence of mGrape1 (SEQ ID NO: 108 and SEQ ID NO: 109).

FIG. 48A provides sequence alignment of new mRFP variants with wild-type DsRed (SEQ ID NO:1) and mRFP1 (SEQ ID NO:8). Internal residues are shaded. mRFP1 mutations are shown in blue, and critical mutations in mCherry (SEQ ID NO:92), mStrawberry (SEQ ID NO:98), mTangerine (SEQ ID NO:100), mOrange (SEQ ID NO:102), mBanana (SEQ ID NO:87), and mHoneydew (SEQ ID NO:119) are shown in colors corresponding to the color of each variant. GFP-type termini on new mRFP variants are shown in green.

DETAILED DESCRIPTION OF THE INVENTION

Definitions

Figure 1:
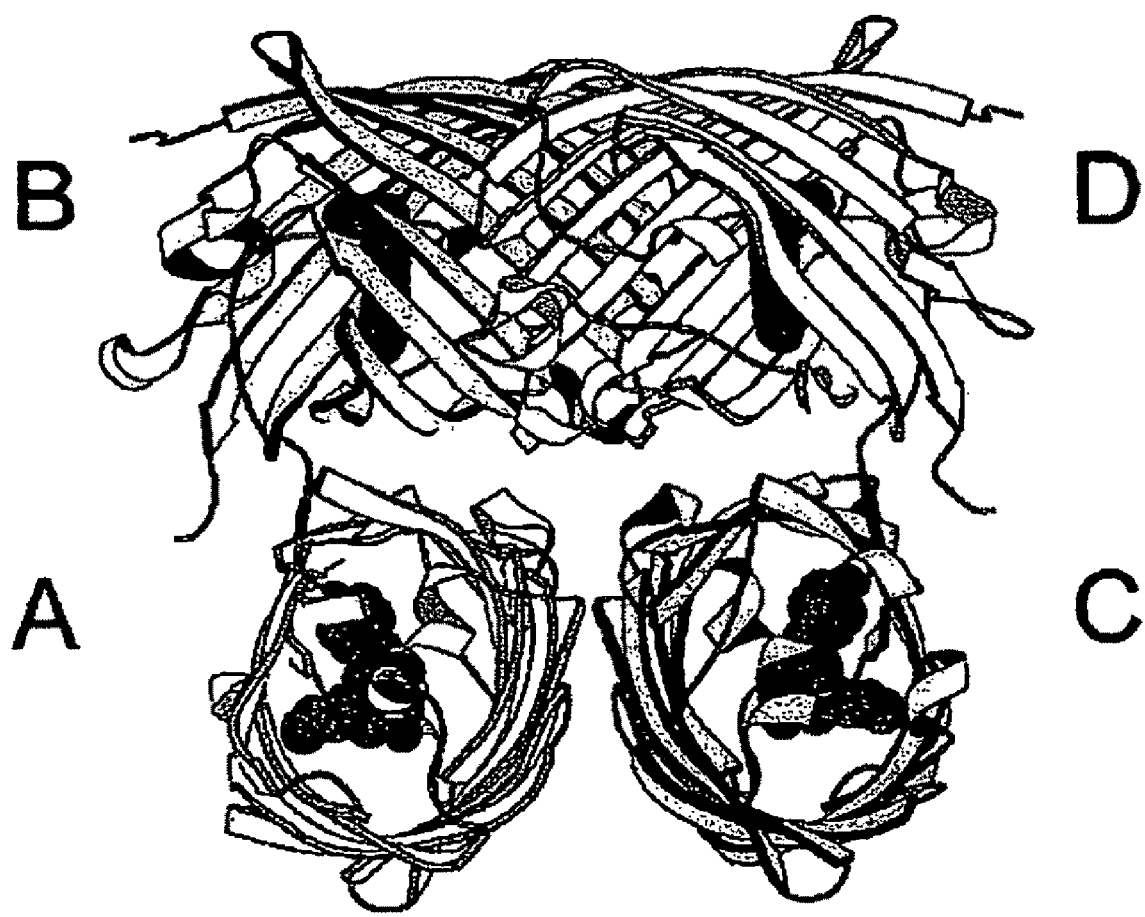
FIG. 1 illustrates the tetrameric form of DsRed (PDB identification code 1G7K). The A-C and B-D interfaces are equivalent, as are the A-B and C-D interfaces.

Unless specifically indicated otherwise, all technical and scientific terms used herein have the same meaning as commonly understood by those of ordinary skill in the art to which this invention belongs. In addition, any method or material similar or equivalent to a method or material described herein can be used in the practice the present invention. For purposes of the present invention, the following terms are defined.

The term "nucleic acid molecule" or "polynucleotide" refers to a deoxyribonucleotide or ribonucleotide polymer in either single-stranded or double-stranded form, and, unless specifically indicated otherwise, encompasses polynucleotides containing known analogs of naturally occurring nucleotides that can function in a similar manner as naturally occurring nucleotides. It will be understood that when a nucleic acid molecule is represented by a DNA sequence, this also includes RNA molecules having the corresponding RNA sequence in which "U" (uridine) replaces "T" (thymidine).

The term "recombinant nucleic acid molecule" refers to a non-naturally occurring nucleic acid molecule containing two or more linked polynucleotide sequences. A recombinant nucleic acid molecule can be produced by recombination methods, particularly genetic engineering techniques, or can be produced by a chemical synthesis method. A recombinant nucleic acid molecule can encode a fusion protein, for example, a fluorescent protein variant of the invention linked to a polypeptide of interest. The term "recombinant host cell" refers to a cell that contains a recombinant nucleic acid molecule. As such, a recombinant host cell can express a polypeptide from a "gene" that is not found within the native (non-recombinant) form of the cell.

Reference to a polynucleotide "encoding" a polypeptide means that, upon transcription of the polynucleotide and translation of the mRNA produced therefrom, a polypeptide is produced. The encoding polynucleotide is considered to include both the coding strand, whose nucleotide sequence is identical to an mRNA, as well as its complementary strand. It will be recognized that such an encoding polynucleotide is considered to include degenerate nucleotide sequences, which encode the same amino acid residues. Nucleotide sequences encoding a polypeptide can include polynucleotides containing introns as well as the encoding exons.

The term "expression control sequence" refers to a nucleotide sequence that regulates the transcription or translation of a polynucleotide or the localization of a polypeptide to which to which it is operatively linked. Expression control sequences are "operatively linked" when the expression control sequence controls or regulates the transcription and, as appropriate, translation of the nucleotide sequence (i.e., a transcription or translation regulatory element, respectively), or localization of an encoded polypeptide to a specific compartment of a cell. Thus, an expression control sequence can be a promoter, enhancer, transcription terminator, a start codon (ATG), a splicing signal for intron excision and maintenance of the correct reading frame, a STOP codon, a ribosome binding site, or a sequence that targets a polypeptide to a particular location, for example, a cell compartmentalization signal, which can target a polypeptide to the cytosol, nucleus, plasma membrane, endoplasmic reticulum, mitochondrial membrane or matrix, chloroplast membrane or lumen, medial trans-Golgi cisternae, or a lysosome or endosome. Cell compartmentalization domains are well known in the art and include, for example, a peptide containing amino acid residues 1 to 81 of human type II membrane-anchored protein galactosyltransferase, or amino acid residues 1 to 12 of the presequence of subunit IV of cytochrome c oxidase (see, also, Hancock et al., *EMBO J.* 10:4033-4039, 1991; Buss et al., *Mol. Cell. Biol.* 8:3960-3963, 1988; U.S. Pat. No. 5,776,689, each of which is incorporated herein by reference).

The term "operatively linked" or "operably linked" or "operatively joined" or the like, when used to describe chimeric proteins, refer to polypeptide sequences that are placed in a physical and functional relationship to each other. In a most preferred embodiment, the functions of the polypeptide components of the chimeric molecule are unchanged compared to the functional activities of the parts in isolation. For example, a fluorescent protein of the present invention can be fused to a polypeptide of interest. In this case, it is preferable that the fusion molecule retains its fluorescence, and the polypeptide of interest retains its original biological activity. In some embodiments of the present invention, the activities of either the fluorescent protein or the protein of interest can be reduced relative to their activities in isolation. Such fusions can also find use with the present invention. As used herein, the chimeric fusion molecules of the invention can be in a monomeric state, or in a multimeric state (e.g., dimeric).

In another example, the tandem dimer fluorescent protein variant of the invention comprises two "operatively linked" fluorescent protein units. The two units are linked in such a way that each maintains its fluorescence activity. The first and second units in the tandem dimer need not be identical. In another embodiment of this example, a third polypeptide of interest can be operatively linked to the tandem dimer, thereby forming a three part fusion protein.

The term "oligomer" refers to a complex formed by the specific interaction of two or more polypeptides. A "specific interaction" or "specific association" is one that is relatively stable under specified conditions, for example, physiologic conditions. Reference to a "propensity" of proteins to oligomerize indicates that the proteins can form dimers, trimers, tetramers, or the like under specified conditions. Generally, fluorescent proteins such as GFPs and DsRed have a propensity to oligomerize under physiologic conditions although, as disclosed herein, fluorescent proteins also can oligomerize, for example, under pH conditions other than physiologic conditions. The conditions under which fluorescent proteins oligomerize or have a propensity to oligomerize can be determined using well known methods as disclosed herein or otherwise known in the art.

As used herein, a molecule that has a "reduced propensity to oligomerize" is a molecule that shows a reduced propensity to foam structures with multiple subunits in favor of forming structures with fewer subunits. For example, a molecule that would normally form tetrameric structures under physiological conditions shows a reduced propensity to oligomerize if the molecule is changed in such a way that it now has a preference to form monomers, dimers or trimers. A molecule that would normally form dimeric structures under physiological conditions shows a reduced propensity to oligomerize if the molecule is changed in such a way that it now has a preference to form monomers. Thus, "reduced propensity to oligomerize" applies equally to' proteins that are normally dimers and to proteins that are normally tetrameric.

As used herein, the term "non-tetramerizing" refers to protein forms that produce trimers, dimers and monomers, but not tetramers. Similarly, "non-dimerizing" refers to protein forms that remain monomeric.

As used herein, the term "efficiency of (chromophore) maturation" with reference to a red fluorescent protein (RFP) indicates the percentage of the protein that has matured from a species with a green fluorescent protein (GFP)-like absorbance spectrum to the final RFP absorbance spectrum. Accordingly, efficiency of maturation is determined after allowing sufficient time for the maturation process to be practically (e.g.>95%) complete. Preferably, the resultant RFP, e.g. DsRed, will contain at least about 80%, more preferably at least about 85%, even more preferably at least about 90%, even more preferably at least about 95%, still more preferably at least about 98%, most preferably at least about 99% of the red fluorescent species.

As used herein, the term "brightness," with reference to a fluorescent protein, is measured as the product of the extinction coefficient (EC) at a given wavelength and the fluorescence quantum yield (QY).

The term "probe" refers to a substance that specifically binds to another substance (a "target"). Probes include, for example, antibodies, polynucleotides, receptors and their ligands, and generally can be labeled so as to provide a means to identify or isolate a molecule to which the probe has specifically bound. The term "label" refers to a composition that is detectable with or without the instrumentation, for example, by visual inspection, spectroscopy, or a photochemical, biochemical, immunochemical or chemical reaction. Useful labels include, for example, phosphorus-32, a fluorescent dye, a fluorescent protein, an electron-dense reagent, an enzymes (such as is commonly used in an ELISA), a small molecule such as biotin, digoxigenin, or other haptens or peptide for which an antiserum or antibody, which can be a monoclonal antibody, is available. It will be recognized that a fluorescent protein variant of the invention, which is itself a detectable protein, can nevertheless be labeled so as to be detectable by a means other than its own fluorescence, for example, by incorporating a radionuclide label or a peptide tag into the protein so as to facilitate, for example, identification of the protein during its expression and isolation of the expressed protein, respectively. A label useful for purposes of the present invention generally generates a measurable signal such as a radioactive signal, fluorescent light, enzyme activity, and the like, either of which can be used, for example, to quantitate the amount of the fluorescent protein variant in a sample.

The term "nucleic acid probe" refers to a polynucleotide that binds to a specific nucleotide sequence or sub-sequence of a second (target) nucleic acid molecule. A nucleic acid probe generally is a polynucleotide that binds to the target nucleic acid molecule through complementary base pairing. It will be understood that a nucleic acid probe can specifically bind a target sequence that has less than complete complementarity with the probe sequence, and that the specificity of binding will depend, in part, upon the stringency of the hybridization conditions. A nucleic acid probes can be labeled as with a radionuclide, a chromophore, a lumiphore, a chromogen, a fluorescent protein, or a small molecule such as biotin; which itself can be bound, for example, by a streptavidin complex, thus providing a means to isolate the probe, including a target nucleic acid molecule specifically bound by the probe. By assaying for the presence or absence of the probe, one can detect the presence or absence of the target sequence or sub-sequence. The term "labeled nucleic acid probe" refers to a nucleic acid probe that is bound, either directly or through a linker molecule, and covalently or through a stable non-covalent bond such as an ionic, van der Waals or hydrogen bond, to a label such that the presence of the probe can be identified by detecting the presence of the label bound to the probe.

The term "polypeptide" or "protein" refers to a polymer of two or more amino acid residues. The terms apply to amino acid polymers in which one or more amino acid residue is an artificial chemical analogue of a corresponding naturally occurring amino acid, as well as to naturally occurring amino acid polymers. The term "recombinant protein" refers to a protein that is produced by expression of a nucleotide sequence encoding the amino acid sequence of the protein from a recombinant DNA molecule.

The term "isolated" or "purified" refers to a material that is substantially or essentially free from components that normally accompany the material in its native state in nature. Purity or homogeneity generally are determined using analytical chemistry techniques such as polyacrylamide gel electrophoresis, high performance liquid chromatography, and the like. A polynucleotide or a polypeptide is considered to be isolated when it is the predominant species present in a preparation. Generally, an isolated protein or nucleic acid-molecule represents greater than 80% of the macromolecular species present in a preparation, often represents greater than 90% of all macromolecular species present, usually represents greater than 95%, of the macromolecular species, and, in particular, is a polypeptide or polynucleotide that purified to essential homogeneity such that it is the only species detected when examined using conventional methods for determining purity of such a molecule.

The term "naturally-occurring" is used to refer to a protein, nucleic acid molecule, cell, or other material that occurs in nature. For example, a polypeptide or polynucleotide sequence that is present in an organism, including in a virus. A naturally occurring material can be in its form as it exists in nature, and can be modified by the hand of man such that, for example, is in an isolated form.

The term "antibody" refers to a polypeptide substantially encoded by an immunoglobulin gene or immunoglobulin genes, or antigen-binding fragments thereof, which specifically bind and recognize an analyte (antigen). The recognized immunoglobulin genes include the kappa, lambda, alpha, gamma, delta, epsilon and mu constant region genes, as well as the myriad immunoglobulin variable region genes. Antibodies exist as intact immunoglobulins and as well characterized antigen-binding fragments of an antibody, which can be produced by digestion with a peptidase or can using recombinant DNA methods. Such antigen-binding fragments of an antibody include, for example, Fv, Fab' and $F(ab)'_2$ fragments. The term "antibody," as used herein, includes antibody fragments either produced by the modification of whole antibodies or those synthesized de novo using recombinant DNA methodologies. The term "immunoassay" refers to an assay that utilizes an antibody to specifically bind an analyte. An immunoassay is characterized by the use of specific binding properties of a particular antibody to isolate, target, and/or quantify the analyte.

The term "identical," when used in reference to two or more polynucleotide sequences or two or more polypeptide sequences, refers to the residues in the sequences that are the same when aligned for maximum correspondence. When percentage of sequence identity is used-in reference to a polypeptide, it is recognized that one or more residue positions that are not otherwise identical can differ by a conservative amino acid substitution, in which a first amino acid residue is substituted for another amino acid residue having similar chemical properties such as a similar charge or hydrophobic or hydrophilic character and, therefore, does not change the functional properties of the polypeptide. Where polypeptide sequences differ in conservative substitutions, the percent sequence identity can be adjusted upwards to correct for the conservative nature of the substitution. Such an adjustment can be made using well known methods, for example, scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions can be calculated using any-well known algorithm (see, for example, Meyers and Miller, *Comp. Appl. Biol. Sci.* 4:11-17, 1988; Smith and Waterman, *Adv. Appl. Math.* 2:482, 1981; Needleman and Wunsch, *J. Mol. Biol.* 48:443, 1970; Pearson and Lipman, *Proc. Natl. Acad. Sci., USA* 85:2444 (1988); Higgins and Sharp, *Gene* 73:237-244, 1988; Higgins and Sharp, *CABIOS* 5:151-153; 1989; Corpet et al., *Nucl. Acids Res.* 16:10881-10890, 1988; Huang, et al., *Comp. Appl. Biol. Sci.* 8:155-165, 1992; Pearson et al., *Meth. Mol. Biol.,* 24:307-331, 1994). Alignment also can be performed by simple visual inspection and manual alignment of sequences.

The term "conservatively modified variation," when used in reference to a particular polynucleotide sequence, refers to different polynucleotide sequences that encode identical or essentially identical amino acid sequences, or where the polynucleotide does not encode an amino acid sequence, to essentially identical sequences. Because of the degeneracy of the genetic code, a large number of functionally identical polynucleotides encode any given polypeptide. For instance, the codons CGU, CGC, CGA, CGG, AGA, and AGG all encode the amino acid arginine. Thus, at every position where an arginine is specified by a codon, the codon can be altered to any of the corresponding codons described without altering the encoded polypeptide. Such nucleotide sequence variations are "silent variations," which can be considered a species of "conservatively modified variations." As such, it will be recognized that each polynucleotide sequence disclosed herein as encoding a fluorescent protein variant also describes every possible silent variation. It will also be recognized that each codon in a polynucleotide, except AUG, which is ordinarily the only codon for methionine, and UUG, which is ordinarily the only codon for tryptophan, can be modified to yield a functionally identical molecule by standard techniques. Accordingly, each silent variation of a polynucleotide that does not change the sequence of the encoded polypeptide is implicitly described herein. Furthermore, it will be recognized that individual substitutions, deletions or additions that alter, add or delete a single amino acid or a small percentage of amino acids (typically less than 5%, and generally less than 1%) in an encoded sequence can be considered conservatively modified variations, provided alteration results in the substitution of an amino acid with a chemically similar amino acid.

Conservative amino acid substitutions providing functionally similar amino acids are well known in the art, including the following six groups, each of which contains amino acids that are considered conservative substitutes for each another:

1) Alanine (Ala, A), Serine (Ser, S), Threo nine (Thr, T);
2) Aspartic acid (Asp, D), Glutamic acid (Glu, E);
3) Asparagine (Asn, N), Glutamine (Gln, Q);
4) Arginine (Arg, R), Lysine (Lys, K);
5) Isoleucine (Ile, I), Leucine (Leu, L), Methionine (Met, M), Valine (Val, V); and
6) Phenylalanine (Phe, F), Tyrosine (Tyr, Y), Tryptophan (Trp, V).

Two or more amino acid sequences or two or more nucleotide sequences are considered to be "substantially identical" or "substantially similar" if the amino acid sequences or the nucleotide sequences share at least 80% sequence identity with each other, or with a reference sequence over a given comparison window. Thus, substantially similar sequences include those having, for example, at least 85% sequence identity, at least 90% sequence identity, at least 95% sequence identity, or at least 99% sequence identity.

A subject nucleotide sequence is considered "substantially complementary" to a reference nucleotide sequence if the complement of the subject nucleotide sequence is substantially identical to the reference nucleotide sequence. The term "stringent conditions" refers to a temperature and ionic conditions used in a nucleic acid hybridization reaction. Stringent conditions are sequence dependent and are different under different environmental parameters. Generally, stringent conditions are selected to be about 5° C. to 20° C. lower than the thermal melting point (Tm) for the specific sequence at a defined ionic strength and pH. The ™ is the temperature, under defined ionic strength and pH, at which 50% of the target sequence hybridizes to a perfectly matched probe.

The term "allelic variants" refers to polymorphic forms of a gene at a particular genetic locus, as well as cDNAs derived from mRNA transcripts of the genes, and the polypeptides encoded by them. The term "preferred mammalian codon" refers to the subset. of codons from among the set of codons encoding an amino acid that are most frequently used in proteins expressed in mammalian cells as chosen from the following list: Gly (GGC, GGG); Glu (GAG); Asp (GAC); Val (GUG, GUC); Ala (GCC, GCU); Ser (AGC, UCC); Lys (AAG); Asn (AAC); Met (AUG); Ile (AUC); Thr (ACC); Trp (UGG); Cys (UGC); Tyr (UAU, UAC); Leu (CUG); Phe (UUC); Arg (CGC, AGG, AGA); Gln (CAG); His (CAC); and Pro (CCC).

Fluorescent molecules are useful in fluorescence resonance energy transfer, FRET, which involves a donor molecule and an acceptor molecule. To optimize the efficiency and detectability of FRET between a donor and acceptor molecule, several factors need to be balanced. The emission spectrum of the donor should overlap as much as possible with the excitation spectrum of the acceptor to maximize the overlap integral. Also, the quantum yield of the donor moiety and the extinction coefficient of the acceptor should be as high as possible to maximize $R_o$, which represents the distance at which energy transfer efficiency is 50%. However, the excitation spectra of the donor and acceptor should overlap as little as possible so that a wavelength region can be found at which the donor can be excited efficiently without directly exciting the acceptor because fluorescence arising from direct excitation of the acceptor can be difficult to distinguish from fluorescence arising from FRET. Similarly, the emission spectra of the donor and acceptor should overlap as little as possible so that the two emissions can be clearly distinguished. High fluorescence quantum yield of the acceptor moiety is desirable if the emission from the acceptor is to be measured either as the sole readout or as part of an emission ratio. One factor to be considered in choosing the donor and acceptor pair is the efficiency of fluorescence resonance energy transfer between them. Preferably, the efficiency of FRET between the donor and acceptor is at least 10%, more preferably at least 50% and even more preferably at least 80%.

The term "fluorescent property" refers to the molar extinction coefficient at an appropriate excitation wavelength, the fluorescence quantum efficiency, the shape of the excitation spectrum or emission spectrum, the excitation wavelength maximum and emission wavelength maximum, the ratio of excitation amplitudes at two different wavelengths, the ratio of emission amplitudes at two different wavelengths, the excited state lifetime, or the fluorescence anisotropy. A measurable difference in any one of these properties between wild type *Aequorea* GFP and a spectral variant, or a mutant thereof, is useful. A measurable difference can be determined by determining the amount of any quantitative fluorescent property, e.g., the amount of fluorescence at a particular wavelength, or the integral of fluorescence over the emission spectrum. Determining ratios of excitation amplitude or emission amplitude at two different wavelengths ("excitation amplitude ratioing" and "emission amplitude ratioing", respectively) are particularly advantageous because the ratioing process provides an internal reference and cancels out variations in the absolute brightness of the excitation source, the sensitivity of the detector, and light scattering or quenching by the sample.

As used herein, the term "fluorescent protein" refers to any protein that can fluoresce when excited with an appropriate electromagnetic radiation, except that chemically tagged proteins, wherein the fluorescence is due to the chemical tag, and polypeptides that fluoresce only due to the presence of certain amino acids such as tryptophan or tyrosine, whose emission peaks at ultraviolet wavelengths (i.e., less that about 400 nm) are not considered fluorescent proteins for purposes of the present invention. In general, a fluorescent protein useful for preparing a composition of the invention or for use in a method of the invention is a protein that derives its fluorescence from autocatalytically forming a chromophore. A fluorescent protein can contain amino acid sequences that are naturally occurring or that have been engineered (i.e., variants or mutants). When used in reference to a fluorescent protein, the term "mutant" or "variant" refers to a protein that is different from a reference protein. For example, a spectral variant of Aequorea GFP can be derived from the naturally occurring GFP by engineering mutations such as amino acid substitutions into the reference GFP protein. For example ECFP is a spectral variant of GFP that contains substitutions with respect to GFP (compare SEQ ID NOs: 10 and 11).

Many cnidarians use green fluorescent proteins as energy transfer acceptors in bioluminescence. The term "green fluorescent protein" is used broadly herein to refer to a protein that fluoresces green light, for example, Aequorea GFP (SEQ ID NO: 10). GFPs have been isolated from the Pacific Northwest jellyfish, Aequorea victoria, the sea pansy, Renilla reniformis, and Phialidium gregarium (Ward et al., Photochem. Photobiol. 35:803-808, 1982; Levine et al., Comp. Biochem. Physiol. 72B:77-85, 1982, each of which is incorporated herein by reference). Similarly, reference is made herein to "red fluorescent proteins", which fluoresce red, "cyan fluorescent proteins," which fluoresce cyan, and the like. RFPs, for example, have been isolated from the corallimorph Discosoma (Matz et al., Nature Biotechnology 17:969-973 [1999]). The term "red fluorescent protein," or "RFP" is used in the broadest sense and specifically covers the Discosoma RFP (DsRed), and red fluorescent proteins from any other species, such as coral and sea anemone, as well as variants thereof as long as they retain the ability to fluoresce red light.

The term "coral" as used herein encompasses species within the class Anthozoa, and includes specifically both corals and corallimorphs.

A variety of Aequorea GFP-related fluorescent proteins having useful excitation and emission spectra have been engineered by modifying the amino acid sequence of a naturally occurring GFP from A. victoria (see Prasher et al., Gene 111:229-233, 1992; Heim et al., Proc. Natl. Acad. Sci. USA 91:12501-12504, 1994; U.S. Pat. No. 5,625,048; International application PCT/US95/14692, now published as PCT WO96/23810, each of which is incorporated herein by reference). As used herein, reference to a "related fluorescent protein" refers to a fluorescent protein that has a substantially identical amino acid sequence when compared to a reference fluorescent protein. In general, a related fluorescent protein, when compared to the reference fluorescent protein sequence, has a contiguous sequence of at least about 150 amino acids that shares at least about 85% sequence identity with the reference fluorescent protein, and particularly has a contiguous sequence of at least about 200 amino acids that shares at least about 95% sequence identity with the reference fluorescent protein. Thus, reference is made herein to an "Aequorea-related fluorescent protein" or to a "GFP-related fluorescent protein," which is exemplified by the various spectral variants and GFP mutants that have amino acid sequences that are substantially identical to A. victoria GFP (SEQ ID NO: 10), to a "Discosoma-related fluorescent protein" or a "DsRed-related fluorescent related protein," which is exemplified by the various mutants that have amino acid sequences substantially identical to that of DsRed (SEQ ID NO: 1), and the like, for example, a Renilla-related fluorescent protein or a Phialidium-related fluorescent protein.

The term "mutant" or "variant" also is used herein in reference to a fluorescent protein that contains a mutation with respect to a corresponding wild type fluorescent protein. In addition, reference is made herein to a "spectral variant" or "spectral mutant" of a fluorescent protein to indicate a mutant fluorescent protein that has a different fluorescence characteristic with respect to the corresponding wild type fluorescent protein. For example, CFP, YFP, ECFP (SEQ ID NO: 11), EYFP-V68L/Q69K (SEQ ID NO: 12), and the like are GFP spectral variants.

Aequorea GFP-related fluorescent proteins include, for example, wild type (native) Aequorea victoria GFP (Prasher et al., supra, 1992; see, also, SEQ ID NO: 10), allelic variants of SEQ ID NO: 10, for example, a variant having a Q80R substitution (Chalfie et al., Science 263:802-805, 1994, which is incorporated herein by reference); and spectral variants of GFP such as CFP, YFP, and enhanced and otherwise modified forms thereof (U.S. Pat. Nos. 6,150,176; 6,124,128; 6,077,707; 6,066,476; 5,998,204; and 5,777,079, each of which is incorporated herein by reference), including GFP-related fluorescent proteins having one or more folding mutations, and fragments of the proteins that are fluorescent, for example, an A. victoria GFP from which the two N-terminal amino acid residues have been removed. Several of these fluorescent proteins contain different aromatic amino acids within the central chromophore and fluoresce at a distinctly shorter wavelength than the wild type GFP species. For example, the engineered GFP proteins designated P4 and P4-3 contain, in addition to other mutations, the substitution Y66H; and the engineered GFP proteins designated W2 and W7 contain, in addition to other mutations, Y66W.

The term "non-tetramerizing fluorescent protein" is used broadly herein to refer to normally tetrameric fluorescent proteins that have been modified such that they have a reduced propensity to tetramerize as compared to a corresponding unmodified fluorescent protein. As such, unless specifically indicated otherwise, the term "non-tetramerizing fluorescent protein" encompasses dimeric fluorescent proteins, tandem dimer fluorescent proteins, as well as fluorescent proteins that remain monomeric.

As used herein, the term "aggregation" refers to the tendency of an expressed protein to form insoluble precipitates or visible punctae and is to be distinguished from "oligomerization". In particular, mutations that reduce aggregation, e.g., increase the solubility of the protein, do not necessarily reduce oligomerization, i.e., convert tetramers to dimers or monomers.

DESCRIPTION OF THE PREFERRED EMBODIMENTS

The present invention provides fluorescent protein variants that can be derived from fluorescent proteins that have a propensity to dimerize or tetramerize. As disclosed herein, in one embodiment of the invention, a fluorescent protein variant of the invention can be derived from a naturally occurring fluorescent protein or from a spectral variant or mutant thereof, and contains at least one mutation that reduces or eliminates the propensity of the fluorescent protein to oligomerize. In particular, the present invention provides dimeric and monomeric red fluorescent proteins (RFP) and RFP variants with reduced propensity to oligomerize. As disclosed herein, in a further embodiment of the invention, a fluorescent protein is provided having improved efficacy of maturation. In particular, the present invention provides dimeric and monomeric red fluorescent proteins (RFP) and RFP variants with improved efficacy of maturation. In embodiments of the invention, fluorescent protein variants are provided which contain at least one mutation that reduces or eliminates the propensity of the fluorescent protein to oligomerize and which contain at least one mutation that improves the efficacy of maturation of fluorescence in the protein variant—as compared to other variants including the parent protein.

The cloning of a red fluorescent protein from *Discosoma* (DsRed) raised a great deal of interest due to its tremendous potential as a tool for the advancement of cell biology. However, a careful investigation of the properties of this protein revealed several problems that would preclude DsRed from being as widely accepted as the *Aequorea* GFP and its blue, cyan, and yellow variants, which have found widespread use as both genetically encoded indicators for tracking gene expression and as donor/acceptor pairs for fluorescence resonance energy transfer (FRET). Extending the spectrum of available colors to red wavelengths would provide a distinct new label for multicolor tracking of fusion proteins and together with GFP would provide a new FRET donor/acceptor pair that would be superior to the currently preferred cyan/yellow pair.

The three most pressing problems with the 28 kDa DsRed are its strong tendency to oligomerize, its slow maturation, and its inefficient maturation from a species with a GFP-like spectrum to the ultimate RFP spectrum.

A variety of techniques have been used to determine that DsRed is an obligate tetramer both in vitro and in vivo. For numerous reasons, the oligomeric state of DsRed is problematic for applications in which it is fused to a protein of interest in order to monitor trafficking or interactions of the latter. Using purified protein, it was shown that DsRed requires greater than 48 hours to reach >90% of its maximal red fluorescence (see below). During the maturation process, a green intermediate initially accumulates and is slowly converted to the final red form. However, the conversion of the green component does not proceed to completion and thus a fraction of aged DsRed remains green. The primary disadvantage of the incomplete maturation is an excitation spectrum that extends well into the green wavelengths due to energy transfer between the green and red species within the tetramer. This is a particularly serious problem due to overlap with the excitation spectra of potential FRET partners such as GFP.

The original report of the cloning of DsRed provided an in vivo application marking the fates of *Xenopus* blastomeres after 1 week of development (Matz et al., *Nature Biotechnology* 17:969-973 [1999]). As disclosed herein, DsRed has been characterized with respect to the time the red fluorescence takes to appear, the pH sensitivity of the chromophore, how strongly the chromophore absorbs light and fluoresces, how readily the protein photobleaches, and whether the protein normally exists as a monomer or an oligomer in solution. The results demonstrate that DsRed provides a useful complement to or alternative for GFP and its spectral mutants. In addition, DsRed mutants that are non-fluorescent or that are blocked or slowed in converting from green to red emission were characterized, including mutants in which the eventual fluorescence is substantially red-shifted from wild type DsRed (see, Baird et al., *Proc. Natl. Acad. Sci., USA* 97:11984-11989, 2000; Gross et al., *Proc. Natl. Acad. Sci., USA* 97:11990-11995, 2000, each of which is incorporated herein by reference).

Red Fluorescent Protein Variants with Improved Efficacy of Maturation

The present invention provides RFP variants that show more efficient chromophore maturation than a reference wild-type or variant RFP, as a result of at least one amino acid alteration within the reference (wild-type or variant) sequence.

The wild-type RFP protein typically consists of about 70% red protein with about 30% contamination by the green, immature form of the protein. Through careful mass spectrometric and biochemical investigations, it has been determined that the Cα-N bond of Q66 in DsRed is oxidized as the protein matures into its red form, which, in turn, led to a further investigation of the role of the amino acid at-position 66 as it relates to chromophore maturation. By site-directed mutagenesis, it was determined that the substitution of methionine (M) for the native glutamine (Q) at amino acid position 66 yielded a protein that showed a deeper pink color than the wild-type protein, and contained less of the immature green form than wild-type DsRed. In addition, the Q66M DsRed variant was found to mature more quickly than wild-type DsRed. Additional experiments have shown that the Q66M mutation retained its advantageous properties, also when introduced into non-tetramerizing, i.e. dimeric or monomeric DsRed variants, which contained additional mutations. Further details of these findings are set forth in the Examples below: Thus, an RFP variant of the invention can be derived from—a naturally occurring (wild-type) RFP or from a spectral variant or mutant thereof, and contains at least one mutation that makes chromophore maturation more efficient.

While the invention is illustrated with reference to the Q66M mutation in DsRed, it will be understood that it is not so limited. Mutations of other amino acids within the wild-type DsRed sequence that play a role in chromophore structure, orientation and/or maturation can also yield DsRed variants with improved maturation efficiency. Similarly, amino acid alterations (e.g. substitutions) at corresponding (homologous) positions or regions in other RFPs can produce RFP variants showing an improvement in maturation efficiency. All of such variants, alone or in combination with other mutations (substitutions, insertions and/or deletions) within the wild-type RFP sequence, are specifically within the scope of the invention. Thus an additional exemplary amino acid alteration that is believed to improve maturation of both the wild-type DsRed protein and DsRed variants, including Q66M DsRed is a substitution at amino acid position 147 of wild-type DsRed. A preferred substitution at this position is T147S, but other substitutions resulting in similar improvements in spectral properties and, in particular, in the efficiency and potentially speed of maturation, are also possible. Especially, substitution of amino acids with similar properties of threonine (T) are expected to yield such variants.

In a specific embodiment, the invention concerns RFP variants with improved maturation efficiency that have a reduced propensity to tetramerize, as a result of one or more further mutations within the RFP molecule. In particular, in this embodiment, the invention concerns non-tetramerizing, such as dimeric or monomeric, DsRed variants that show enhanced maturation efficiency relative to the corresponding non-tetramerizing DsRed variant. Further details about the design and preparation of such variants are provided below.

In brief, the RFP variants of the invention can be derived from RFPs that have a propensity to dimerize or tetramerize. As disclosed herein, an RFP variant of the invention can be derived from a naturally occurring RFP or from a spectral variant or mutant thereof, and contains at least one mutation that enhances maturation efficiency, and optionally at least one additional mutation that reduces or eliminates the propensity of the RFP to oligomerize.

A fluorescent protein variant of the invention can be derived from any fluorescent protein that is known to oligomerize, including, for example, a green fluorescent protein (GFP) such as an *Aequorea victoria* GFP (SEQ ID NO: 10), a *Renilla reniformis* GFP, a *Phialidium gregarium* GFP; a red fluorescent protein (RFP) such as a *Discosoma* RFP (SEQ ID NO: 1); or a fluorescent protein related to a GFP or an RFP. Thus, the fluorescent protein can be a cyan fluorescent protein (CFP), a yellow fluorescent protein (YFP), an enhanced GFP (EGFP; SEQ ID NO: 13), an enhanced CFP (ECFP; SEQ ID NO: 11), an enhanced YFP (EYFP; SEQ ID NO: 15), a DsRed fluorescent protein (SEQ ID NO: 1), a homologue in any other species, or a mutant or variant of such fluorescent proteins.

As disclosed herein, the propensity of the fluorescent protein variant of the invention to oligomerize is reduced or eliminated. There are two basic approaches to reduce the propensity of the fluorescent protein, e.g., RFP such as DsRed, to form intermolecular oligomers, (1) oligomerization can be reduced or eliminated by introducing mutations into appropriate regions of the fluorescent protein, e.g., an RFP molecule, and (2) two subunits of the fluorescent protein can operatively link, e.g., link RFP to each other by a linker, such as a peptide linker. If oligomerization is reduced or eliminated by following approach (1), it is usually necessary to introduce additional mutations into the molecule, in order to restore fluorescence, which is typically lost or greatly impaired as a result of introducing mutations at the oligomer interfaces.

Red Fluorescent Protein Variants with Reduced Propensity to Oligomerize

The present invention provides fluorescent protein variants where the degree of oligomerization of the fluorescent protein is reduced or eliminated by the introduction of amino acid substitutions to reduce or abolish the propensity of the constituent monomers to tetramerize. In one embodiment, the resulting structures have a propensity to dimerize. In other embodiments, the resulting structures have a propensity to remain monomeric.

Various dimer forms can be created. For example, an AB orientation dimer can be formed, or alternatively, an AC orientation dimer can be formed. However, with the creation of dimeric forms, fluorescence or the rate of maturation of fluorescence, can be lost. The present invention provides methods for the generation of dimeric forms that display detectable fluorescence, and furthermore, fluorescence that has advantageous rates of maturation.

In one embodiment, the dimer is an intermolecular dimer. Furthermore, the dimer can be a homodimer (comprising two molecules of the identical species) or a heterodimer (comprising two molecules of different species). In a preferred embodiment, dimers will spontaneously form in physiological conditions. As used herein, the molecules that form such types of structures are said to have a reduced tendency to oligomerize, as the monomeric units have reduced or non-existent ability to form tetrameric intermolecular oligomers.

A non-limiting, illustrative example of such a dimeric red fluorescent protein variant is described herein, and is termed "dimer2." The dimer2 nucleotide sequence is provided in SEQ ID NO: 7 and FIG. 21. The dimer2 polypeptide is provided in SEQ ID NO: 6 and FIG. 22.

In an attempt to produce a still further advantageous form of the DsRed variant dimer, a novel strategy to synthesize a "tandem" DsRed variant dimer was devised. This approach utilized covalent tethering of two engineered monomeric DsRed units to yield a dimeric form of DsRed with advantageous properties. The basic strategy was to fuse two copies of an AC dimer with a polypeptide linker such that the critical dimer interactions could be satisfied through intramolecular contacts with the tandem partner encoded within the same polypeptide. Such operably linked homodimers or heterodimers are referred to herein as "tandem dimers," and have a substantially reduced propensity to form tetrameric structures.

Illustrative examples of such tandem red fluorescent protein variant dimers include, without limitation, two monomeric units of the dimer2 species (SEQ ID NO: 6) operably covalently linked by a peptide linker, preferably about 9 to about 25, more preferably about 9 to 20 amino acid residues in length. Such linkers finding use with the invention include, but are not limited to, for example, the 9 residue linker RMGTGSGQL (SEQ ID NO: 16), the 12 residue linker GHGTGSTGSGSS (SEQ ID NO: 17), the 13 residue linker RMGSTSGSTKGQL (SEQ ID NO: 18), or the 22 residue linker RMGSTSGSGKPGSGEGSTKGQL (SEQ ID NO: 19). As noted above, the subunits of such tandem dimers preferably contain mutations relative to the wild-type DsRed sequence of SEQ ID NO: 1, in order to preserve/restore fluorescent properties. An illustrative example of the tandem red fluorescent protein dimers herein is a dimer composed of two monomers, wherein at least one of the monomers is a variant DsRed, which has an amino acid sequence of SEQ ID NO: 6, operatively linked by a peptide linker, preferably about 9 to about 25, more preferably about 10 to about 20 amino acid residues in length, including any of the 9, 12, 13, and 22 residue linkers above. Yet another illustrative example of a tandem red fluorescent protein dimer herein is a tandem dimer composed of two identical or different DsRed variant monomeric subunits at least one of which contains, for example, the following substitutions within the DsRed polypeptide of SEQ ID NO: 1: N42Q, V44A, V71A, F118L, K163Q, S179T, S197T, T217S (mutations internal to the β-barrel); R2A, K5E and N6D (aggregation reducing mutations); I125R and V127T (AB interface mutations); and T21S, H41T, C117T and S131P (miscellaneous surface mutations). Just as in the other illustrative dimers, the two monomeric subunits may be fused by a peptide linker, preferably about 9 to about 25, more preferably about 10 to about 25 amino acid residues in length, such as any of the 9, 12, 13, and 22 residue linkers above. Shorter linkers are generally preferable to longer linkers, as long as they do not significantly slow affinity maturation or otherwise interfere with the fluorescent and spectral properties of the dimer. As noted above, the two monomeric subunits within a dimer may be identical or different. Thus, for example, one subunit may be the wild-type DsRed monomer of SEQ ID NO: 1 operatively linked to a variant DsRed polypeptide, such as any of the DsRed variants listed above or otherwise disclosed herein. The monomers should be linked such that the critical dimer interactions are satisfied through intramolecular contacts with the tandem partner. The peptide linkers are preferably protease resistant. The peptide linkers specifically disclosed herein are only illustrative. One skilled in the art will understand that other peptide linkers, preferably protease resistant linkers, are also suitable for the purpose of the present invention. See, e.g., Whitlow et al., *Protein Eng* 6:989-995 (1993).

In one embodiment, disclosed in more detail in the examples below, a novel approach was used to overcome the intermolecular oligomerization propensity of wild-type DsRed by linking the C-terminus of the A subunit to the N-terminus of the B subunit through a flexible linker to produce tandem dimers. Based on the crystal structure of DsRed tetramer, a 10 to 20 residue linkers, such as an 18 residue linker (Whitlow et al., *Prot. Eng.* 6:989-995, 1993, supra, which is incorporated herein by reference) was predicted to be long enough to extend from the C-terminus of the A subunit to the N-terminus of the C subunit (about 30 Å), but not to the N-terminus of the B subunit (greater than 70 Å). As such, 'oligomerization' in the tandem dimers is intramolecular, i.e., the tandem dimer of DsRed (tDsRed), for example, is encoded by a single polypeptide chain. Furthermore, a combination of tDsRed with the I125R mutant (tDsRed-I125R) resulted in another dimeric red fluorescent protein. It should be recognized that this strategy can be generally applied to any protein system in which the distance between the N-terminus of one protein and the C-terminus of a dimer partner is known, such that a linker having the appropriate length can be used to operatively link the monomers. In particular, this strategy can be useful for other modifying other fluorescent proteins that have interesting spectral properties, but form obligate dimers that are difficult to disrupt using the targeted mutagenesis method disclosed herein.

Mutagenesis Strategy to Produce Dimeric and Monomeric Red Fluorescent Proteins

The present invention provides variant fluorescent proteins that have a reduced propensity to form tetrameric oligomers (i.e., the propensity to form tetramers is reduced or eliminated) due to the presence of one or more mutations in the fluorescent protein. As disclosed herein, mutations were introduced into DsRed, and DsRed mutants having reduced oligomerization activity were identified, including, for example, a DsRed-I125R mutant of DsRed of SEQ ID NO: 20. The strategy for producing the DsRed mutants involved introducing mutations in DsRed that were predicted to interfere with the dimer interfaces (A-B or A-C, see FIGS. 1 and 2) and thus prevent formation of the tetramer. This strategy resulted in the production of DsRed mutants that had a reduced propensity to form tetramers by disrupting the A-B interface, for example, using the single replacement of isoleucine 125 with an arginine (I125R).

The basic strategy for decreasing the oligomeric state of DsRed was to replace key dimer interface residues with charged amino acids, preferably arginine. It is contemplated that dimer formation would require the targeted residue to interact with the identical residue of the dimer partner through symmetry. The resulting high energetic cost of placing two positive charges in close proximity should disrupt the interaction. Initial attempts to break apart the DsRed AC interface (see FIG. 2A) with the single mutations T147R, H162R, and F224R, consistently gave non-fluorescent proteins. The AB interface however, proved somewhat less resilient and could be broken with the single mutation I125R to give a poorly red fluorescent dimer that suffered from an increased green component and required more than 10 days to fully mature.

Illustrative examples of mutations (amino acid substitutions) which can further improve the fluorescent properties of I125R include mutations in at least one of amino acid positions 163, 179 an 217 within SEQ ID NO: 1. In a preferred embodiment, the I125R variant comprises at least one of the K163Q/M, S179T and T217S substitutions. Further illustrative variants may contain additional mutations at position N42 and/or C44 within SEQ ID NO: 1. Yet another group of illustrative DsRed dimers comprise additional mutations at least one of residues I161 and S197 within SEQ ID NO: 1. Specific examples of DsRed variants obtained by this mutagenesis approach include DsRed-I125R, S179T, T217A, and DsRed-I125R, K163Q, T217A, and others (see, e.g., the Examples below).

Figure 2A:
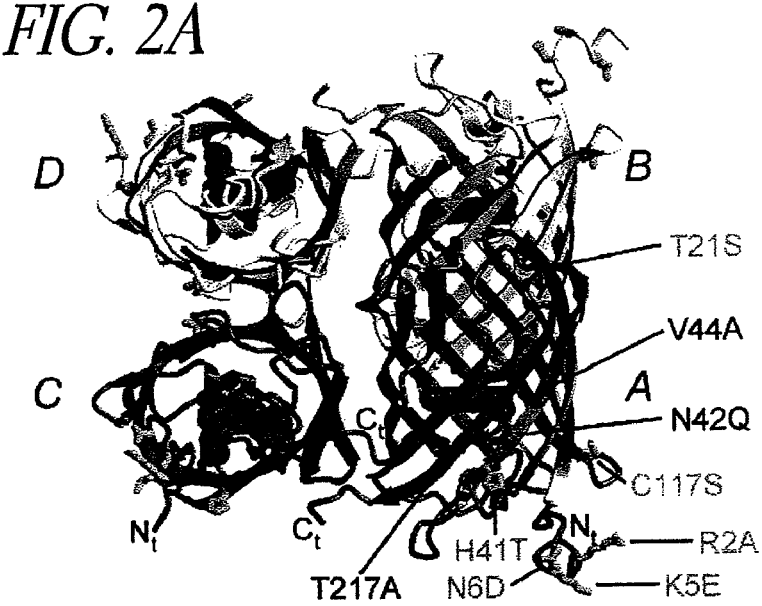
FIGS. 2A-2C show graphical representations of the tetramer, dimer and monomer forms of DsRed, respectively, based on the x-ray crystal structure of DsRed. Residues 1-5 were not observed in the crystal structure but have been arbitrarily appended for the sake of completeness. The DsRed chromophore is represented in red and the four chains of the tetramer are labeled following the convention of Yarbrough et al. (Yarbrough et al., *Proc. Natl. Acad. Sci. USA* 98:462-467 [2001]).

It is noted that there exists an inconsistency in the naming convention of the DsRed subunits in the prior art. As shown in FIG. 1, one convention assigns the A-B-C-D subunits as shown. However, a different convention is also recognized, which is shown in FIG. 2. When viewing the model of FIG. 1, the AC interface of that figure is equivalent to the AB interface shown in FIG. 2A. With the exception of FIG. 1, reference to subunit interfaces in the present application is according to the convention used in FIG. 2.

Figures 11, 11A:
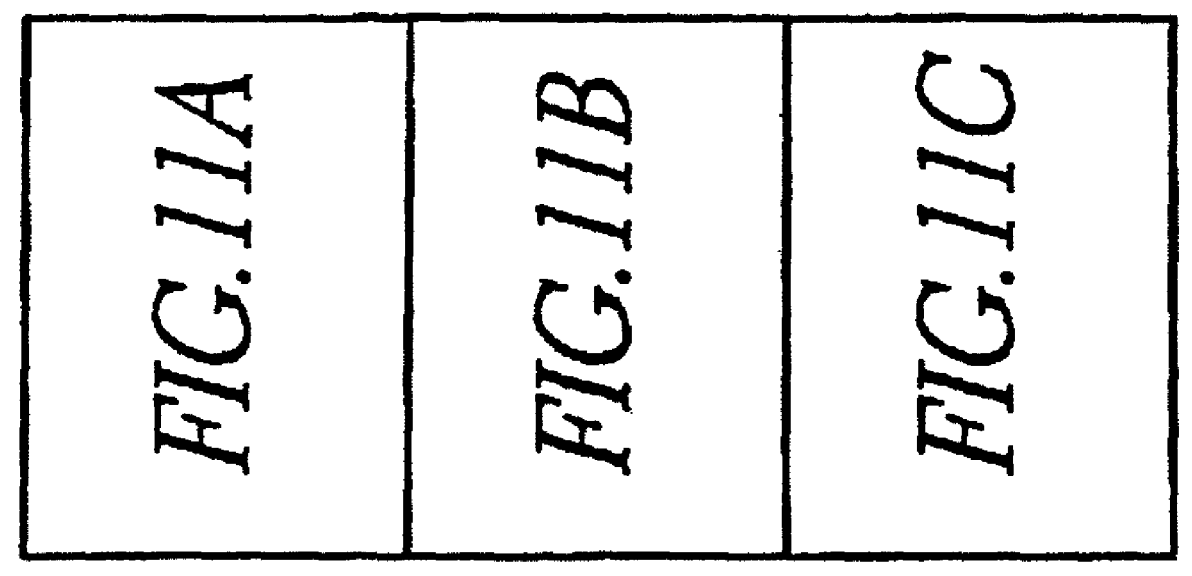

A similar directed mutagenesis strategy starting from T1-I125R (see FIG. 10A, library D1) was undertaken and eventually identified dimer1. Dimer1 was somewhat better than wt DsRed both in terms of brightness and rate of maturation but had a substantial green peak equivalent to that of T1. Dimer1 was also somewhat blue-shifted with an excitation maximum at 551 nm and an emission maximum at 579 nm. Error prone PCR on dimer1 (FIG. 10A, library D2) resulted in the discovery of dimer1.02 containing the mutation V71A in the hydrophobic core of the protein and effectively no green component in the excitation spectra. A second round of random mutagenesis (FIG. 10A, library D3) identified the mutations K70R which further decreased the green excitation, S197A which red-shifted the dimer back to DsRed wavelengths and T217S which greatly improved the rate of maturation. Unfortunately, K70R and S197A matured relatively slowly and T217S had a green excitation peak equivalent to DsRed. Using dimer1.02 as the template, two more rounds of directed mutagenesis were performed; the first focusing on the three positions identified above (FIG. 11A, library D3) and the second on C117, F118, F124, and V127 (FIG. 10A, library D4).

Figure 2B:
Figure 2C:
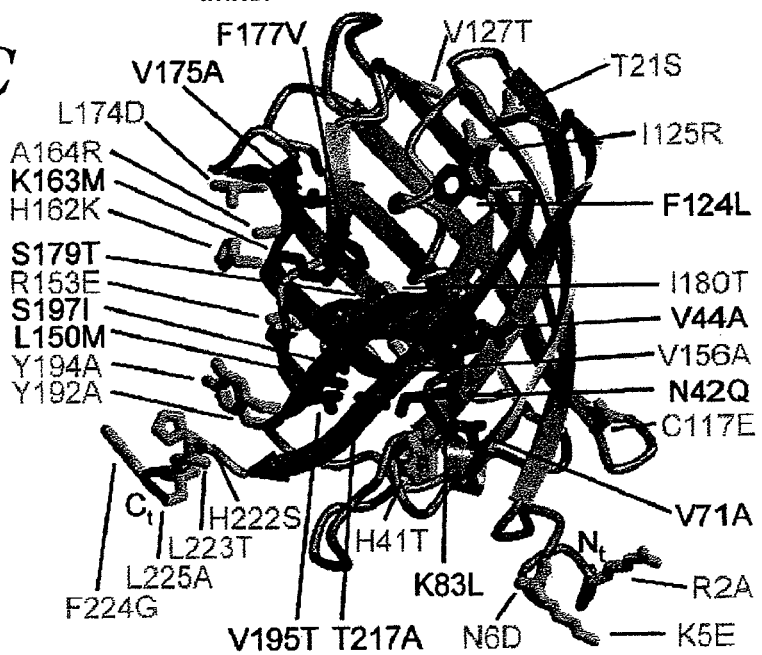

Continuing with the directed evolution strategy for a total of 4 generations, an optimal dimeric variant was produced, which was designated dimer2 (illustrated in FIG. 2B). This variant contains 17 mutations, of which eight are internal to the β-barrel (N42Q, V44A, V71A, F118L, K163Q, S179T, S197T and T217S), three are the aggregation reducing mutations found in T1 (R2A, K5E and N6D and see Bevis and Glick, Nat. Biotechnol., 20:83-87 [2002]; and Yanushevich et al., *FEBS Lett.*, 511:11-14 [2002]), two are AB interface mutations (I125R and V127T), and 4 are miscellaneous surface mutations (T21S, H41T, C117T and S131P). The dimer2 nucleotide sequence is provided in SEQ ID NO: 7 and FIG. 21. The dimer2 polypeptide is provided in SEQ ID NO: 6 and FIG. 22.

A product of the mutagenesis approach described above is a monomeric red fluorescent protein, designated mRFP1, which contains the following mutations within the wild-type DsRed sequence of SEQ ID NO: 1: N42Q, V44A, V71A, K83L, F124L, L150M, K163M, V175A, F177V, S179T, V195T, S197I, T217A, R2A, K5E, N6D, I125R, V127T; I180T, R153E, H162K, A164R; L174D, Y192A, Y194K, H222S, L223T, F224G, L225A, T21S, H41T, C117E, and V156A. Of these, the first 13 mutations are internal to the β-barrel. Of the remaining 20 external mutations, 3 are aggregation reducing mutations (R2A, K5E, and N6D), 3 are AB interface mutations (I125R, V127T, and I180T), 10 are AC interface mutations (R153E, H162K, A164R, L174D, Y192A, Y194K, H222S, L223T, F224G, and L225A), and 4 are additional beneficial mutations (T21S, H41T, C117E, and V156A). The mRFP1 nucleotide sequence is provided in SEQ ID NO: 9 and FIG. 23. The mRFP1 polypeptide is provided in SEQ ID NO: 8 and FIG. 24.

Other variants, including variants related to mRFP1, may also be produced by such methods (see, e.g., the Examples below). Thus, although mRFP1 is believed to be optimized in many aspects, a person skilled in the art will appreciate that other mutations within these and other regions of the wild-type DsRed amino acid sequence (SEQ ID NO: 1) may also yield monomeric DsRed variants retaining the qualitative red fluorescing properties of the wild-type DsRed protein. Accordingly, mRFP1 serves merely as an illustration, and embodiments of the invention are by no means intended to be limited to this particular monomer.

For example, the monomeric DsRed variants herein, e.g. mRFP1, can be further modified to alter the spectral and/or fluorescent properties of DsRed. For example, based upon experience with GFP, it is known that in the excited state, electron density tends to shift from the phenolate towards the carbonyl end of the chromophore. Therefore, placement of increasing positive charge near the carbonyl end of the chromophore tends to decrease the energy of the excited. state and cause a red-shift in the absorbance and emission wavelength maximum of the protein. Decreasing a positive charge near the carbonyl end of the chromophore tends to have the opposite effect, causing a blue-shift in the protein's wavelengths. Similarly, mutations have been introduced into DsRed to produce mutants having altered fluorescence characteristics.

Amino acids with charged (ionized D, E, K, and R), dipolar (H, N, Q, S, T, and uncharged D, E and K), and polarizable side groups (e.g., C, F, H, M, W and Y) are useful for altering the ability of fluorescent proteins to oligomerize, especially when they substitute an amino acid with an uncharged, non-polar or non-polarizable side chain.

Similarly, monomers of other oligomerizing fluorescent proteins can also be prepared following a similar mutagenesis strategy, as illustrated in the Examples below, and these and other fluorescent protein monomers are intended to be within the scope of the present invention.

Variant Anthozoan Fluorescent Proteins

It is contemplated that the mutagenesis methods provided by the present invention can be used to generate advantageous fluorescent protein variants that have reduced ability to oligomerize (i.e., tetramerize), and also find uses analogous to the uses of the *Discosoma* DsRed variant proteins. It is known in the art that the DsRed protein is a member of a family of highly related homologous proteins sharing high degrees of amino acid identity and protein structure (see, e.g., Labas et al., *Proc. Natl. Acad. Sci. USA* 99:4256-4261 [2002]; and Yanushevich et al., *FEBS Letters* 511:11-14 [2002]). These alternative fluorescent proteins are additionally advantageous since they have the ability to fluoresce at different wavelengths than does *Discosoma* DsRed. If dimeric or monomeric forms of these proteins can be produced, they will have great experimental potential as fluorescent markers.

Anthozoan species from which related fluorescent proteins have been identified include, but are not limited to, *Anemonia* sp., *Clavularia* sp., *Condylactis* sp., *Heteractis* sp., *Renilla* sp., *Ptilosarcus* sp., *Zoonthus* sp., *Scolymia* sp., *Montastraea* sp., *Ricordea* sp., *Goniopara* sp., and others.

Fusion Proteins Comprising the Tandem Dimers and Monomers

Fluorescent proteins fused to target proteins can be prepared, for example using recombinant DNA methods, and used as markers to identify the location and amount of the target protein produced. Accordingly, the present invention provides fusion proteins comprising a fluorescent protein variant moiety and a polypeptide of interest. The polypeptide of interest can be of any length, for example, about 15 amino acid residues, about 50 residues, about 150 residues, or up to about 1000 amino acid residues or more, provided that the fluorescent protein component of the fusion protein can fluoresce or can be induced to fluoresce when exposed to electromagnetic radiation of the appropriate wavelength. The polypeptide of interest can be, for example, a peptide tag such as a polyhistidine sequence, a c-myc epitope, a FLAG epitope, and the like; can be an enzyme, which can be used to effect a function in a cell expressing a fusion protein comprising the enzyme or to identify a cell containing the fusion protein; can be a protein to be examined for an ability to interact with one or more other proteins in a cell, or any other protein as disclosed herein or otherwise desired.

As disclosed herein, the *Discosoma* (coral) red fluorescent protein, DsRed, can be used as a complement to or alternative for a GFP or spectral variant thereof. In particular, the invention encompasses fusion proteins of any of the tandem dimeric and monomeric DsRed fluorescent proteins discussed above, and variants thereof, which has altered spectral and/or fluorescent characteristics.

A fusion protein, which includes a fluorescent protein variant operatively linked to one or more polypeptides of interest also is provided. The polypeptides of the fusion protein can be linked through peptide bonds, or the fluorescent protein variant can be linked to the polypeptide of interest through a linker molecule. In one embodiment, the fusion protein is expressed from a recombinant nucleic acid molecule containing a polynucleotide encoding a fluorescent protein variant operatively linked to one or more polynucleotides encoding one or more polypeptides of interest.

A polypeptide of interest can be any polypeptide, including, for example, a peptide tag such as a polyhistidine peptide, or a cellular polypeptide such as an enzyme, a G-protein, a growth factor receptor, or a transcription factor; and can be one of two or more proteins that can associate to form a complex. In one embodiment, the fusion protein is a tandem fluorescent protein variant construct, which includes a donor fluorescent protein variant, an acceptor fluorescent protein variant, and a peptide linker moiety coupling said donor and said acceptor, wherein cyclized, amino acids of the donor emit light characteristic of said donor, and wherein the donor and the acceptor exhibit fluorescence resonance energy transfer when the donor is excited, and the linker moiety does not substantially emit light to excite the donor. As such, a fusion protein of the invention can include two or more operatively linked fluorescent protein variants, which can be linked directly or indirectly, and can further comprise one or more polypeptides of interest.

Preparation of DsRed Dimers and Monomers

The present invention also provides polynucleotides encoding fluorescent protein variants, where the protein can be a dimeric fluorescent protein, a tandem dimeric fluorescent protein, a monomeric protein, or a fusion protein comprising a fluorescent protein operatively linked to one or more polypeptides of interest. In the case of the tandem dimer the entire dimer may be encoded by one polynucleotide molecule. If the linker is a non-peptide linker, the two subunits will be encoded by separate polynucleotide molecules, produced separately, and subsequently linked by methods known in the art.

The invention further concerns vectors containing such polynucleotides, and host cell containing a polynucleotide or vector. Also provided is a recombinant nucleic acid molecule, which includes at least one polynucleotide encoding a fluorescent protein variant operatively linked to one or more other polynucleotides. The one or more other polynucleotides can be, for example, a transcription regulatory element such as a promoter or polyadenylation signal sequence, or a translation regulatory element such as a ribosome binding site. Such a recombinant nucleic acid molecule can be contained in a vector, which can be an expression vector, and the nucleic acid molecule or the vector can be contained in a host cell.

The vector generally contains elements required for replication in a prokaryotic or eukaryotic host system or both, as desired. Such vectors, which include plasmid vectors and viral vectors such as bacteriophage, baculovirus, retrovirus, lentivirus, adenovirus, vaccinia virus, semliki forest virus and adeno-associated virus vectors, are well known and can be purchased from a commercial source (Promega, Madison Wis.; Stratagene, La Jolla Calif.; GIBCO/BRL, Gaithersburg Md.) or can be constructed by one skilled in the art (see; for example, *Meth. Enzymol.*, Vol. 185, Goeddel, ed. (Academic Press, Inc., 1990); Jolly, *Canc. Gene Ther.* 1:51-64, 1994; Flotte, *J. Bioenerg. Biomemb.* 25:37-42, 1993; Kirshenbaum et al.; *J. Clin. Invest.* 92:381-387, 1993; each of which is incorporated herein by reference).

A vector for containing a polynucleotide encoding a fluorescent protein variant can be a cloning vector or an expression vector, and can be a plasmid vector, viral vector, and the like. Generally, the vector contains a selectable marker independent of that encoded by a polynucleotide of the invention, and further can contain transcription or translation regulatory elements, including a promoter sequence, which can provide tissue specific expression of a polynucleotide operatively linked thereto, which can, but need not, be the polynucleotide encoding the fluorescent protein variant, for example, a tandem dimer fluorescent protein, thus providing a means to select a particular cell type from among a mixed population of cells containing the introduced vector and recombinant nucleic acid molecule contained therein.

Where the vector is a viral vector, it can be selected based on its ability to infect one or few specific cell types with relatively high efficiency. For example, the viral vector also can be derived from a virus that infects particular cells of an organism of interest, for example, vertebrate host cells such as mammalian host cells. Viral vectors have been developed for use in particular host systems, particularly mammalian systems and include, for example, retroviral vectors, other lentivirus vectors such as those based on the human immunodeficiency virus. (HIV), adenovirus vectors, adeno-associated virus vectors, herpesvirus vectors, vaccinia virus vectors, and the like (see Miller and Rosman, *BioTechniques* 7:980-990, 1992; Anderson et al., *Nature* 392:25-30 Suppl., 1998; Verma and Somia, *Nature* 389:239-242; 1997; Wilson, *New Engl. J. Med.* 334:1185-1187 (1996), each of which is incorporated herein by reference).

Recombinant production of a fluorescent protein variant, which can be a component of a fusion protein, involves expressing a polypeptide encoded by a polynucleotide. A polynucleotide encoding the fluorescent protein variant is a useful starting material. Polynucleotides encoding fluorescent protein are disclosed herein or otherwise known in the art, and can be obtained using routine methods, then can be modified such that the encoded fluorescent protein lacks a propensity to oligomerize. For example, a polynucleotide encoding a GFP can be isolated by PCR of cDNA from *A. victoria* using primers based on the DNA sequence of *Aequorea* GFP (SEQ ID NO: 21). A polynucleotide encoding the red fluorescent protein from *Discosoma* (DsRed) can be similarly isolated by PCR of cDNA of the *Discosoma* coral, or obtained from the commercially available DsRed2 or HcRed1 (CLONTECH). PCR methods are well known and routine in the art (see, for example, U.S. Pat. No. 4,683,195; Mullis et al., *Cold Spring Harbor Symp. Quant. Biol.* 51:263, 1987; Erlich, ed., "PCR Technology" (Stockton Press, NY, 1989)). A variant form of the fluorescent protein then can be made by site-specific mutagenesis of the polynucleotide encoding the fluorescent protein. Similarly, a tandem dimer fluorescent protein can be expressed from a polynucleotide prepared by PCR or obtained otherwise, using primers that can encode, for example, a peptide linker, which operatively links a first monomer and at least a second monomer of a fluorescent protein.

The construction of expression vectors and the expression of a polynucleotide in transfected cells involves the use of molecular cloning techniques also well known in the art (see Sambrook et al., In "Molecular Cloning: A Laboratory Manual" (Cold Spring Harbor Laboratory Press 1989); "Current Protocols in Molecular Biology" (eds., Ausubel et al.; Greene Publishing Associates, Inc., and John Wiley & Sons, Inc. 1990 and supplements). Expression vectors contain expression control sequences operatively linked to a polynucleotide sequence of interest, for example, that encodes a fluorescent protein variant, as indicated above. The expression vector can be adapted for function in prokaryotes or eukaryotes by inclusion of appropriate promoters, replication sequences, markers, and the like. An expression vector can be transfected into a recombinant host cell for expression of a fluorescent protein variant, and host cells can be selected, for example, for high levels of expression in order to obtain a large amount of isolated protein. A host cell can be maintained in cell culture, or can be a cell in vivo in an organism. A fluorescent protein variant can be produced by expression from a polynucleotide encoding the protein in a host cell such as *E. coli. Aequorea* GFP-related fluorescent proteins, for example, are best expressed by cells cultured between about 15° C. and 30° C., although higher temperatures such as 37° C. can be used. After synthesis; the fluorescent proteins are stable at higher temperatures and can be used in assays at such temperatures.

An expressed fluorescent protein variant, which can be a tandem dimer fluorescent protein or a non-oligomerizing monomer, can be operatively linked to a first polypeptide of interest, further can be linked to a second polypeptide of interest, for example, a peptide tag, which can be used to facilitate isolation of the fluorescent protein variant, including any other polypeptides linked thereto. For example, a polyhistidine tag containing, for example, six histidine residues (SEQ ID NO:120), can be incorporated at the N-terminus or C-terminus of the fluorescent protein variant, which then can be isolated in a single step using nickel-chelate chromatography. 'Additional peptide tags, including a c-myc peptide, a FLAG epitope, or any ligand (or cognate receptor), including any peptide epitope (or antibody, or antigen binding fragment thereof, that specifically binds the epitope are well known in the art and similarly can be used. (see, for example, Hopp et al., *Biotechnology* 6:1204 (1988); U.S. Pat. No. 5,011,912, each of which is incorporated herein by reference).

Kits of the Invention

The present invention also provides kits to facilitate and/or standardize use of compositions provided by the present invention, as well as facilitate the methods of the present invention. Materials and reagents to carry out these various methods can be provided in kits to facilitate execution of the methods. As used herein, the term "kit" is used in reference to a combination of articles that facilitate a process, assay, analysis or manipulation.

Kits can contain chemical reagents (e.g., polypeptides or polynucleotides) as well as other components. In addition, kits of the present invention can also include, for example but not limited to, apparatus and reagents for sample collection and/or purification, apparatus and reagents for product collection and/or purification, reagents for bacterial cell transformation, reagents for eukaryotic cell transfection, previously transformed or transfected host cells, sample tubes, holders, trays, racks, dishes, plates, instructions to the kit user, solutions, buffers or other chemical reagents, suitable samples to be used for standardization, normalization, and/or control samples. Kits of the present invention can also be packaged for convenient storage and safe shipping, for example, in a box having a lid.

In some embodiments, for example, kits of the present invention can provide a fluorescent protein of the invention, a polynucleotide vector (e.g., a plasmid) encoding a fluorescent protein of the invention, bacterial cell strains suitable for propagating the vector, and reagents for purification of expressed fusion proteins. Alternatively, a kit of the present invention can provide the reagents necessary to conduct mutagenesis of an Anthozoan fluorescent protein in order to generate a protein variant having a reduced propensity to oligomerize.

A kit can contain one or more compositions of the invention, for example, one or a plurality of fluorescent protein variants, which can be a portion of a fusion protein, or one or a plurality of polynucleotides that encode the polypeptides. The fluorescent protein variant can be a mutated fluorescent protein having a reduced propensity to oligomerize, such as a non-oligomerizing monomer, or can be a tandem dimer fluorescent protein and, where the kit comprises a plurality of fluorescent protein variants, the plurality can be a plurality of the mutated fluorescent protein variants, or of the tandem dimer fluorescent proteins, or a combination thereof.

A kit having features of the invention also can contain one or a plurality of recombinant nucleic acid molecules, which encode, in part, fluorescent protein variants, which can be the same or different, and can further include, for example, an operatively linked second polynucleotide containing or encoding a restriction endonuclease recognition site or a recombinase recognition site, or any polypeptide of interest. In addition, the kit can contain instructions for using the components of the kit, particularly the compositions of the invention that are contained in the kit.

Such kits can be particularly useful where they provide a plurality of different fluorescent protein variants because the artisan can conveniently select one or more proteins having the fluorescent properties desired for a particular application. Similarly, a kit containing a plurality of polynucleotides encoding different fluorescent protein variants provides numerous advantages. For example, the polynucleotides can be engineered to contain convenient restriction endonuclease or recombinase recognition sites, thus facilitating operative linkage of the polynucleotide to a regulatory element or to a polynucleotide encoding a polypeptide of interest or, if desired, for operatively linking two or more the polynucleotides encoding the fluorescent protein variants to each other.

Uses of Fluorescent Protein Variants

A fluorescent protein variant having features of the invention is useful in any method that employs a fluorescent protein. Thus, the fluorescent protein variants, including the monomeric, dimeric, and tandem dimer fluorescent proteins, are useful as fluorescent markers in the many ways fluorescent markers already are used, including, for example, coupling fluorescent protein variants to antibodies, polynucleotides or other receptors for use in detection assays such as immunoassays or hybridization assays, or to track the movement of proteins in cells. For intracellular tracking studies, a first (or other) polynucleotide encoding the fluorescent protein variant is fused to a second (or other) polynucleotide encoding a protein of interest and the construct, if desired, can be inserted into an expression vector. Upon expression inside the cell, the protein of interest can be localized based on fluorescence, without concern that localization of the protein is an artifact caused by oligomerization of the fluorescent protein component of the fusion protein. In one embodiment of this method, two proteins of interest independently are fused with two fluorescent protein variants that have different fluorescent characteristics.

Fluorescent protein variants having features of the invention are useful in systems to detect induction of transcription. For example, a nucleotide sequence encoding a non-oligomerizing monomeric, dimeric or tandem dimeric fluorescent protein can be fused to a promoter or other expression control sequence of interest, which can be contained in an expression vector, the construct can be transfected into a cell, and induction of the promoter (or other regulatory element) can be measured by detecting the presence or amount of fluorescence, thereby allowing a means to observe the responsiveness of a signaling pathway from receptor to promoter.

A fluorescent protein variant of the invention also is useful in applications involving FRET, which can detect events as a function of the movement of fluorescent donors and acceptors towards or away from each other. One or both of the donor/acceptor pair can be a fluorescent protein variant. Such a donor/acceptor pair provides a wide separation between the excitation and emission peaks of the donor, and provides good overlap between the donor emission spectrum and the acceptor excitation spectrum. Variant red fluorescent proteins or red-shifted mutants as disclosed herein are specifically disclosed as the acceptor in such a pair.

FRET can be used to detect cleavage of a substrate having the donor and acceptor coupled to the substrate on opposite sides of the cleavage site. Upon cleavage of the substrate, the donor/acceptor pair physically separate, eliminating FRET. Such an assay can be performed, for example, by contacting the substrate with a sample, and determining a qualitative or quantitative change in FRET (see, for example, U.S. Pat. No. 5,741,657, which is incorporated herein by reference). A fluorescent protein variant donor/acceptor pair also can be part of a fusion protein coupled by a peptide having a proteolytic cleavage site (see, for example, U.S. Pat. No. 5,981,200, which is incorporated herein by reference). FRET also can be used to detect changes in potential across a membrane. For example, a donor and acceptor can be placed on opposite sides of a membrane such that one translates across the membrane in response to a voltage change, thereby producing a measurable FRET (see, for example, U.S. Pat. No. 5,661,035, which is incorporated herein by reference).

In other embodiments, a fluorescent protein of the invention is useful for making fluorescent sensors for protein kinase and phosphatase activities or indicators for, small ions and molecules such as $Ca^{2+}$, $Zn^{2+}$, cyclic 3',5'-adenosine monophosphate, and cyclic 3',5'-guanosine monophosphate.

Fluorescence in a sample generally is measured using a fluorimeter, wherein excitation radiation from an excitation source having a first wavelength, passes through excitation optics, which cause the excitation radiation to excite the sample. In response, a fluorescent protein variant in the sample emits radiation having a wavelength that is different from the excitation wavelength. Collection optics then collect the emission from the sample. The device can include a temperature controller to maintain the sample at a specific temperature while it is being scanned, and can have a multi-axis translation stage, which moves a microtiter plate holding a plurality of samples in order to position different wells to be exposed. The multi-axis translation stage, temperature controller, auto-focusing feature, and electronics associated with imaging and data collection can be managed by an appropriately programmed digital computer, which also can transform the data collected during the assay into another format for presentation. This process can be miniaturized and automated to enable screening many thousands of compounds in a high throughput format. These and other methods of performing assays on fluorescent materials are well known in the art (see, for example, Lakowicz, "Principles of Fluorescence Spectroscopy" (Plenum Press 1983); Herman, "Resonance energy transfer microscopy" In "Fluorescence Microscopy of Living Cells in Culture" Part B, *Meth. Cell Biol.* 30:219-243 (ed. Taylor and Wang; Academic Press 1989); Turro, "Modem Molecular Photochemistry" (Benjamin/Cummings Publ. Co., Inc. 1978), pp. 296-361, each of which is incorporated herein by reference).

Accordingly, the present invention provides a method for identifying the presence of a molecule in a sample. Such a method can be performed, for example, by linking a fluorescent protein variant of the invention to the molecule, and detecting fluorescence due to the fluorescent protein variant in a sample suspected of containing the molecule. The molecule to be detected can be a polypeptide, a polynucleotide, or any other molecule, including, for example, an antibody, an enzyme, or a receptor, and the fluorescent protein variant can be a tandem dimer fluorescent protein.

The sample to be examined can be any sample, including a biological sample, an environmental sample, or any other sample for which it is desired to determine whether a particular molecule is present therein. Preferably, the sample includes a cell or an extract thereof. The cell can be obtained from a vertebrate, including a mammal such as a human, or from an invertebrate, and can be a cell from a plant or an animal. The cell can be obtained from a culture of such cells, for example, a cell line, or can be isolated from an organism. As such, the cell can be contained in a tissue sample, which can be obtained from an organism by any means commonly used to obtain a tissue sample, for example, by biopsy of a human. Where the method is performed using an intact living cell or a freshly isolated tissue or organ sample, the presence of a molecule of interest in living cells can be identified, thus providing a means to determine, for example, the intracellular compartmentalization of the molecule. The use of the fluorescent protein variants of the invention for such a purpose provides a substantial advantage in that the likelihood of aberrant identification or localization due to oligomerization the fluorescent protein is greatly minimized.

A fluorescent protein variant can be linked to the molecule directly or indirectly, using any linkage that is stable under the conditions to which the protein-molecule complex is to be exposed. Thus, the fluorescent protein and molecule can be linked via a chemical reaction between reactive groups present on the protein and molecule, or the linkage can be mediated by linker moiety, which contains reactive groups specific for the fluorescent protein and the molecule. It will be recognized that the appropriate conditions for linking the fluorescent protein variant and the molecule are selected depending, for example, on the chemical nature of the molecule and the type of linkage desired. Where the molecule of interest is a polypeptide, a convenient means for linking a fluorescent protein variant and the molecule is by expressing them as a fusion protein from a recombinant nucleic acid molecule, which comprises a polynucleotide encoding, for example, a tandem dimer fluorescent protein operatively linked to a polynucleotide encoding the polypeptide molecule.

A method of identifying an agent or condition that regulates the activity of an expression control sequence also is provided. Such a method can be performed, for example, by exposing a recombinant nucleic acid molecule, which includes a polynucleotide encoding a fluorescent protein variant operatively linked to an expression control sequence, to an agent or condition suspected of being able to regulate expression of a polynucleotide from the expression control sequence, and detecting fluorescence of the fluorescent protein variant due to such exposure. Such a method is useful, for example, for identifying chemical or biological agents, including cellular proteins, that can regulate expression from the expression control sequence, including cellular factors involved in the tissue specific expression from the regulatory element. As such, the expression control sequence can be a transcription regulatory element such as a promoter, enhancer, silencer, intron splicing recognition site, polyadenylation site, or the like; or a translation regulatory element such as a ribosome binding site.

Fluorescent protein variants having features the invention also are useful in a method of identifying a specific interaction of a first molecule and a second molecule. Such a method can be performed, for example, by contacting the first molecule, which is linked to a donor first fluorescent protein variant, and the second molecule, which is linked to an acceptor second fluorescent protein variant, under conditions that allow a specific interaction of the first molecule and second molecule; exciting the donor; and detecting fluorescence or luminescence resonance energy transfer from the donor to the acceptor, thereby identifying a specific interaction of the first molecule and the second molecule. The conditions for such an interaction can be any conditions under which is expected or suspected that the molecules can specifically interact. In particular, where the molecules to be examined are cellular molecules, the conditions generally are physiological conditions. As such, the method can be performed in vitro using conditions of buffer, pH, ionic strength, and the like, that mimic physiological conditions, or the method can be performed in a cell or using a cell extract.

Luminescence resonance energy transfer entails energy transfer from a chemiluminescent, bioluminescent, lanthanide, or transition metal donor to the red fluorescent protein moiety. The longer wavelengths of excitation of red fluorescent proteins permit energy transfer from a greater variety of donors and over greater distances than possible with green fluorescent protein variants. Also, the longer wavelengths of emission is more efficiently detected by solid-state photodetectors and is particularly valuable for in vivo applications where red light penetrates tissue far better than shorter wavelengths. Chemiluminescent donors include but are not limited to luminol derivatives and peroxyoxalate systems. Bioluminescent donors include but are not limited to aequorin, obelin, firefly luciferase, *Renilla* luciferase, bacterial luciferase, and variants thereof. Lanthanide donors include but are not limited to terbium chelates containing ultraviolet-absorbing sensitizer chromophores linked to multiple liganding groups to shield the metal ion from solvent water. Transition metal donors include but are not limited to ruthenium and osmium chelates of oligopyridine ligands. Chemiluminescent and bioluminescent donors need no excitation light but are energized by addition of substrates, whereas the metal-based systems need excitation light but offer longer excited state lifetimes, facilitating time-gated detection to discriminate against unwanted background fluorescence and scattering.

The first and second molecules can be cellular proteins that are being investigated to determine whether the proteins specifically interact, or to confirm such an interaction. Such first and second cellular proteins can be the same, where they are being examined, for example, for an ability to oligomerize, or they can be different where the proteins are being examined as specific binding partners involved, for example, in an intracellular pathway. The first and second molecules also can be a polynucleotide and a polypeptide, for example, a polynucleotide known or to be examined for transcription regulatory element activity and a polypeptide known or being tested for transcription factor activity. For example, the first molecule can comprise a plurality of nucleotide sequences, which can be random or can be variants of a known sequence, that are to be tested for transcription regulatory element activity, and the second molecule can be a transcription factor, such a method being useful for identifying novel transcription regulatory elements having desirable activities.

The present invention also provides a method for determining whether a sample contains an enzyme. Such a method can be performed, for example, by contacting a sample with a tandem fluorescent protein variant of the invention; exciting the donor, and determining a fluorescence property in the sample, wherein the presence of an enzyme in the sample results in a change in the degree of fluorescence resonance energy transfer. Similarly, the present invention relates to a method for determining the activity of an enzyme in a cell. Such a method can be performed, for example, providing a cell that expresses a tandem fluorescent protein variant construct, wherein the peptide linker moiety comprises a cleavage recognition amino acid sequence specific for the enzyme coupling the donor and the acceptor; exciting said donor, and determining the degree of fluorescence resonance energy transfer in the cell, wherein the presence of enzyme activity in the cell results in a change in the degree of fluorescence resonance energy transfer.

Also provided is a method for determining the pH of a sample. Such a method can be performed, for example, by contacting the sample—with a first fluorescent protein variant, which can be a tandem dimer fluorescent protein, wherein the emission intensity of the first fluorescent protein variant changes as pH vanes between pH 5 and pH 10; exciting the indicator; and determining the intensity of light emitted by the first fluorescent protein variant. at a first wavelength, wherein the emission intensity of the first fluorescent protein variant indicates the pH of the sample. The first fluorescent protein variant useful in this method, or in any method of the invention, can comprise two DsRed monomers as set forth in SEQ ID NO: 8. It will be recognized that such fluorescent protein variants similarly are useful, either alone or in combination, for the variously disclosed methods of the invention.

The sample used in a method for determining the pH of a sample can be any sample, including, for example, a biological tissue sample, or a cell or a fraction thereof. In addition, the method can further include contacting the sample with a second fluorescent protein variant, wherein the emission intensity of the second fluorescent protein variant changes as pH vanes from 5 to 10, and wherein the second fluorescent protein variant emits at a second wavelength that is distinct from the first wavelength; exciting the second fluorescent protein variant; determining the intensity of light emitted by the second fluorescent protein variant at the second wavelength; and comparing the fluorescence at the second wavelength to the fluorescence at the first wavelength. The first (or second) fluorescent protein variant can include a targeting sequence, for example, a cell compartmentalization domain such a domain that targets the fluorescent protein variant in a cell to the cytosol, the endoplasmic reticulum, the mitochondrial matrix, the chloroplast lumen, the medial trans-Golgi cisternae, a lumen of a lysosome, or a lumen of an endosome. For example, the cell compartmentalization domain can include amino acid residues 1 to 81 of human type H membrane-anchored protein galactosyltransferase, or amino acid residues 1 to 12 of the presequence of subunit IV of cytochrome c oxidase.

The following Examples are provided to further illustrate certain embodiments and aspects of the present invention. It is not intended that these Examples should limit the scope of any aspect of the invention. Although specific reaction conditions and reagents are described, it is clear that one familiar with the art would recognize alternative or equivalent conditions that also find use with the invention, where the alternative or equivalent conditions do not depart from the scope of the invention.

Example 1

Construction of Dimeric and Monomeric Red Fluorescent Proteins DsRed Mutagenesis and Screening The DsRed gene was amplified from vector pDsRed-N1 (CLONTECH, Palo Alto, Calif.) or the T1 variant (provided by B.S. Glick, University of Chicago) and subcloned into pRSET$_B$ (Invitrogen™; see Baird et al., *Proc. Natl. Acad. Sci. USA* 97:11984-11989 [2000]). The pRSET$_B$ vector produces 6×His (SEQ ID NO:120) tagged fusion proteins, where an N-terminal polyhistidine tag having the following sequence is coupled to the suitably subcloned sequence:

MRGSHHHHHHGMASMTGGQQMGRDLYDDDDKDP    (SEQ ID NO: 22)

This resulting construct was used as the template for introduction of the I125R mutant using the QuikChange™ Site Directed Mutagenesis Kit (Stratagene®), according to the manufacturer's instructions. The complete DsRed wild-type cDNA and polypeptide sequences are provided in GenBank Accession Number AF168419. This nucleotide sequence is also provided in FIG. 16 and SEQ ID NO: 2. A variation of this nucleotide sequence is also known (Clontech), where various nucleotide positions been amended to accommodate mammalian codon usage utilization preferences. This nucleotide sequence is provided in FIG. 25 and SEQ ID NO: 23. The corresponding polypeptide encoded by both of these nucleotide sequences is provided in FIG. 17 and SEQ ID NO: 1.

Figure 19:
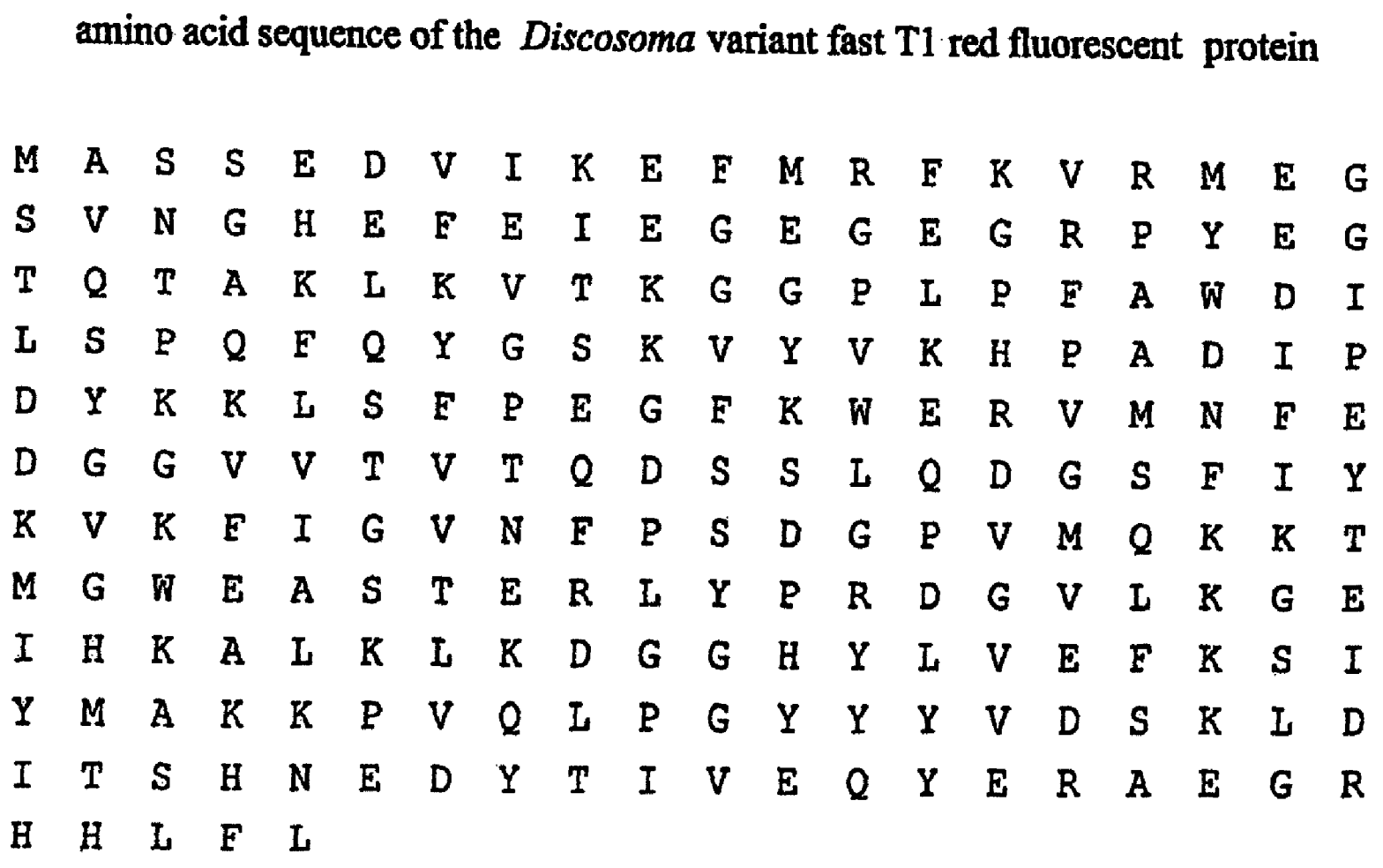

Similarly, the DsRed T1 variant cDNA nucleotide sequence is provided in FIG. 18 and SEQ ID NO: 5. The corresponding polypeptide is provided in FIG. 19 and SEQ ID NO: 4.

As used herein, the numbering of amino acids in DsRed or mRFP1 variants conforms to the wild-type sequence of DsRed, in which residues 66-68 of wild-type DsRed (Gln-Tyr-Gly) are homologous to the chromophore-forming residues 65-67 of GFP (Ser-Tyr-Gly). The amino-terminal polyhistidine tag is numbered −33 to −1. When amino acid residues are inserted at or near position 6, they are numbered to preserve the DsRed numbering for the rest of the protein; for example, where NNMA (SEQ ID NO:112) or DNMA (SEQ ID NO:111) are inserted at position 6, residues NNMA (or DNMA) are numbered as residues 6a, 6b, 6c, and 6d.

Error prone PCR Mutagenesis—Error prone PCR was performed essentially as described in Griesbeck et al. (*J. Biol. Chem.*, 276:29188-29194 [2001]). Briefly, the cDNA encoding DsRed in the vector pRSET$_B$ (Invitrogen™) was subjected to error-prone PCR using Taq DNA polymerase. The 5' primer included a BamHI site and ended at the starting Met of the DsRed, and the 3' primer included an EcoRI site and ended at the stop codon, theoretically allowing mutagenesis of every base of DsRed open reading frame, except for the initiator methionine. The PCR reactions (38 cycles with annealing at 55° C.) were run in four 100 μL batches, each containing 10 μL of 10×PCR buffer with $Mg^{2+}$ (Roche Molecular Biochemicals), 150 μM $Mn^{2+}$, 250 μM of three nucleotides, 50 μM of the remaining nucleotide, and 5 ng of template DNA.

Mutagenized PCR products were combined, purified by agarose gel electrophoresis, digested with BamHI and EcoRI, and isolated by QIAGEN® QIAquick™ DNA purification spin column following the manufacturer's instructions. The resulting fragments were ligated into $pRSET_B$, and the crude ligation mixture was transformed into E. coli BL21(DE3) Gold (Stratagene®) by electroporation.

Overlap Extension PCR Mutagenesis—Semi-random mutations at multiple distant locations were introduced by overlap extension PCR with multiple fragments essentially as described in Ho et al., Gene 77:51-59 (1989). Briefly, two to four pairs of sense and antisense oligonucleotide primers (Invitrogen™ or GenBase), with semi-degenerate codons at positions of interest, were used for PCR amplification of the DsRed template with Pfu DNA polymerase (Stratagene®) in individual reactions. The resulting overlapping fragments were gel purified using QIAGEN® gel extraction kit and recombined by overlap extension PCR with Pfu or Taq DNA polymerase (Roche).

Full length genes were digested with BamHI/EcoRI (New England BioLabs®) and ligated into $pRSET_B$ with T4 ligase (New England BioLabs®). Chemically competent E. coli JM109(DE3) were transformed and grown on LB/agar at 37° C.

Bacterial Fluorescence Screening—Bacteria plated on LB/agar plates were screened essentially as described in Baird et al., Proc. Natl. Acad. Sci. USA 96:11241-11246 (1999). Briefly, the bacterial plates were illuminated with a 150-W Xe lamp using 470 nm (40 nm bandwidth), 540 nm (30 nm bandwidth), or 560 nm (40 nm bandwidth) excitation filters and 530 nm (40 nm bandwidth), 575 nm (long pass), or 610 nm (long pass) emission filters. Fluorescence was imaged by a cooled charge-coupled device camera (Sensys Photometrics, Tucson, Ariz.) and were processed using Metamorph software (Universal Imaging, West Chester, Pa.).

Fluorescent colonies of interest were cultured overnight in 2 ml of LB supplemented with ampicillin. Bacteria were pelleted by centrifugation and imaged again to ensure that the protein was expressed well in culture. For fast maturing proteins a fraction of the cell pellet was extracted with B-per II (Pierce) and complete spectra obtained. DNA was purified from the remaining pellet by QIAGEN® QIAprep® plasmid isolation spin column according to the manufacturer's instructions and submitted for DNA sequencing. To determine the oligomeric state of DsRed mutants, a single colony of E. coli was restreaked on LB/agar and allowed to mature at room temperature. After 2 days to 2 weeks the bacteria were scraped from the plate, extracted with B-per II, analyzed (not boiled) by SDS-PAGE (BioRad), and the gel imaged with a digital camera.

Bacterial Transformations and DsRed Protein Purification

Ligation mixtures were transformed into Escherichia coli BL21(DE3) Gold (Stratagene) by electroporation in 10% glycerol with a ligation mixture (0.1 cm cuvette, 12.5 kV/cm, 200Ω, 25 μF).

Protein was expressed and purified essentially as-described in Baird et al., Proc. Natl. Acad. Sci. USA 96:11241-11246 (1999). Briefly, when cultured for protein expression, transformed bacteria were grown to an $OD_{600}$ of 0.6 in LB containing 100 mg/liter ampicillin, at which time they were induced with 1 mM isopropyl β-D-thiogalactoside. Bacteria were allowed to express recombinant protein for 6 hr at room temperature and then overnight at 4° C. The bacteria then were pelleted by centrifugation, resuspended in 50 mM Tris-HCl/300 mM NaCl, and lysed by a French press. The bacterial lysates were centrifuged at 30,000×g for 30 min, and the proteins were purified from the supernatants using Ni-NTA resin (QIAGEN®).

Spectroscopy of purified protein was typically performed in 100 mM KCl, 10 mM MOPS, pH 7.25, in a fluorescence spectrometer (Fluorolog-2, Spex Industries). All DNA sequencing was performed by the Molecular Pathology Shared Resource, University of California, San Diego, Cancer Center.

Construction of DsRed Tandem Dimers and Constructs for Mammalian Cell Expression, Including Chimeric Constructs To construct tandem dimers of DsRed protein, dimer2 in $pRSET_B$ was amplified in two separate PCR reactions. In the first reaction, the 5' BamHI and a 3' SphI site were introduced while in the second reaction a 5' SacI and a 3' EcoRI site were introduced. The construct was assembled in a 4-part ligation containing the digested dimer2 genes, a synthetic linker with phosphorylated sticky ends, and digested $pRSET_B$. Four different linkers were used, which encoded polypeptides of various lengths. These were:

| Linker | Polypeptide Sequence | SEQ ID NO |
|---|---|---|
| 9 a.a. residue linker | RMGTGSGQL | 16 |
| 12 a.a. residue linker | GHGTGSTGSGSS | 17 |
| 13 a.a. residue linker | RMGSTSGSTKGQL | 18 |
| 22 a.a. residue linker | RMGSTSGSGKPGSGEGSTKGL | 19 |

("a.a." indicates amino acid)

For expression in mammalian cells, DsRed variants were amplified from $pRSET_B$ with a 5' primer that encoded a KpnI restriction site and a Kozak sequence. The PCR product was digested, ligated into pcDNA3, and used to transform E. coli DH5α.

A gene encoding a chimeric fusion polypeptide comprising DsRed and connexin43 (Cx43) was constructed. To produce these fusions, Cx43 was first amplified with a T primer encoding a seven-residue linker ending in a BamHI site. The construct was assembled in a 3-part ligation containing KpnI/BamHI digested Cx43, BamHI/EcoRI digested enhanced GFP, and digested pcDNA3. For all other fusion proteins (Cx43-T1, -dimer2, -tdimer2(12) and -mRFP1) the gene for the fluorescent protein was ligated into the BamHI/EcoRI digested Cx43-GFP vector.

DsRed Protein Variant Production and Characterization

DsRed variants were expressed essentially as described in Baird et al., Proc. Natl. Acad. Sci. USA 96:11241-11246 (1999). All proteins were purified by Ni-NTA chromatography (QIAGEN®) according to the manufacturer's instructions and dialyzed into 10 mM Tris, pH 7.5 or phosphate buffered saline supplemented with 1 mM EDTA. All biochemical characterization experiments were performed essentially as described in Baird et al., Proc. Natl. Acad. Sci. USA 97:11984-11989 (2000).

The maturation time courses were determined on a Safire 96 well plate reader with monochromators (TECAN, Austria). Aqueous droplets of purified, protein in phosphate-buffered saline were formed under mineral oil in a chamber on the fluorescence microscope stage. For reproducible results it proved essential to pre-extract the oil with aqueous buffer, which would remove any traces of autoxidized or acidic contaminants. The droplets were small enough (5-10 μm diameter) so that all the molecules would see the same incident intensity. The absolute excitation irradiance in photons/(cm$^2$·s·nm) as a function of wavelength was computed from the spectra of a xenon lamp, the transmission of the excitation filter, the reflectance of the dichroic mirror, the manufacturer-supplied absolute spectral sensitivity of a miniature integrating-sphere detector (SPD024 head and ILC1700 meter, International Light Corp., Newburyport, Mass.), and the measured detector current. The predicted rate of initial photon emission (before any photobleaching had occurred) was calculated from the excitation irradiance and absorbance spectrum (both as functions of wavelength), and the quantum yield. These rates varied. from 180s$^{-1}$ for mHoneydew to 3300s$^{-1}$ for mStrawberry. To normalize the observed photobleaching time courses to a common arbitrary standard of 1000 emitted photons/sec, the time axes were correspondingly scaled by factors of 0.18 to 3.3, assuming that emission and photobleach rates are both proportional to excitation intensity at intensities typical of microscopes with arc lamp sources, as is known to be the case for GFP.

Analytical Ultracentrifugation—Purified, recombinant DsRed was dialyzed extensively against PBS, pH 7.4 or 10 mM Tris, 1 mM EDTA, pH 7.5. Sedimentation equilibrium experiments were performed on a Beckman Optima XL-I analytical ultracentrifuge at 20° C. measuring absorbance at 558 nm as a function of radius. Samples of DsRed were normalized to 3.57 μM (0.25 absorbance units), and from this, 125 μL aliquots were loaded into six channel cells. The data were analyzed globally at 10K, 14K, and 20K rpm by non-linear least-squares analysis using the ORIGIN software package supplied by Beckman. The goodness of fit was evaluated on the basis of the magnitude and randomness of the residuals, expressed as the difference between the experimental data and the theoretical curve and also by checking each of the fit parameters for physical reasonability.

Absorption/Fluorescence Spectra and Extinction Coefficients—Fluorescence spectra were taken with a Fluorolog spectrofluorimeter (Spex Industries, Edison, N.J.). Absorbance spectra of proteins were taken with a Cary ITV-V is spectrophotometer. For quantum yield determination, the fluorescence of a solution of DsRed or DsRed variant in PBS was compared with equally absorbing solutions of rhodamine B and rhodamine 101 in ethanol. Corrections were included in the quantum yield calculation for the refractive index difference between ethanol and water. For extinction coefficient determination, native protein absorbance was measured with the spectrophotometer, and protein concentration was measured by the BCA method (Pierce).

Mammalian Cell Imaging and Microinjection

HeLa cells were transfected with DsRed variants or Cx43-DsRed fusions in pcDNA3 through the use of Fugene 6 transfection reagent (Roche). Transfected cells were grown for 12 hours to 2 days in DMEM at 37° C. before imaging using a Zeiss Axiovert 35 fluorescence microscope with cells in glucose-supplemented HBSS at room temperature. Individual cells expressing Cx43 fused to a DsRed variant, or contacting non-transfected cells for control experiments, were microinjected with a 2.5% solution of lucifer yellow (Molecular Probes, Eugene, Oreg.). Images were acquired and processed with the Metafluor software package (Universal Imaging, West Chester, Pa.).

Results

Stepwise Evolution of DsRed Molecules

The present invention provides methods for the stepwise evolution of tetrameric DsRed to a dimer and then either to a genetic fusion of two copies of the protein, i.e., a tandem dimer, or to a true monomer designated mRFP1. Each subunit interface was disrupted by insertion of arginines, which initially crippled the resulting protein, but red fluorescence could be rescued by random and directed mutagenesis totaling 17 substitutions in the dimer and 33 substitutions in mRFP1 Fusions of the gap junction protein.connexin43 to mRFP1 formed fully functional junctions, whereas analogous fusions to the tetramer and dimer failed. Although mRFP1 has somewhat lower extinction coefficient, quantum yield, and photostability than DsRed, mRFP1 matures >10× faster, so that it shows similar brightness in living cells. In addition, the excitation and emission peaks of mRFP1, 584 and 607 nm, are ~25 nm red shifted from DsRed, which should confer greater tissue penetration and spectral separation from autofluorescence and other fluorescent proteins.

The consensus view is that a monomeric form of DsRed will be essential if it is to ever reach its full potential as a genetically encoded red fluorescent tag (Remington, Nat. Biotechnol., 20:28-29 [2002]). The present invention provides a directed evolution and preliminary characterization of the first monomeric red fluorescent protein. The present invention provides an independent alternative to GFP in the construction of fluorescently tagged fusion proteins.

Directed and Random Evolution of a Dimer of DsRed

The basic strategy for decreasing the oligomeric state of DsRed was to replace key hydrophobic residues at the dimer interface by charged residues such as arginine. The high energetic cost of burying a charged residue within a nonpolar hydrophobic interface or of placing two positive charges in close proximity should disrupt the interaction. Initial attempts to break apart the DsRed AC interface (see FIG. 2A) with the single mutations T147R, H162R, and F224R, consistently gave non-fluorescent proteins. The AB interface however, proved somewhat less resilient and could be broken with the single mutation I125R to give a poorly red fluorescent dimer that suffered from an increased green component and required more than 10 days to fully mature.

Figure 7:
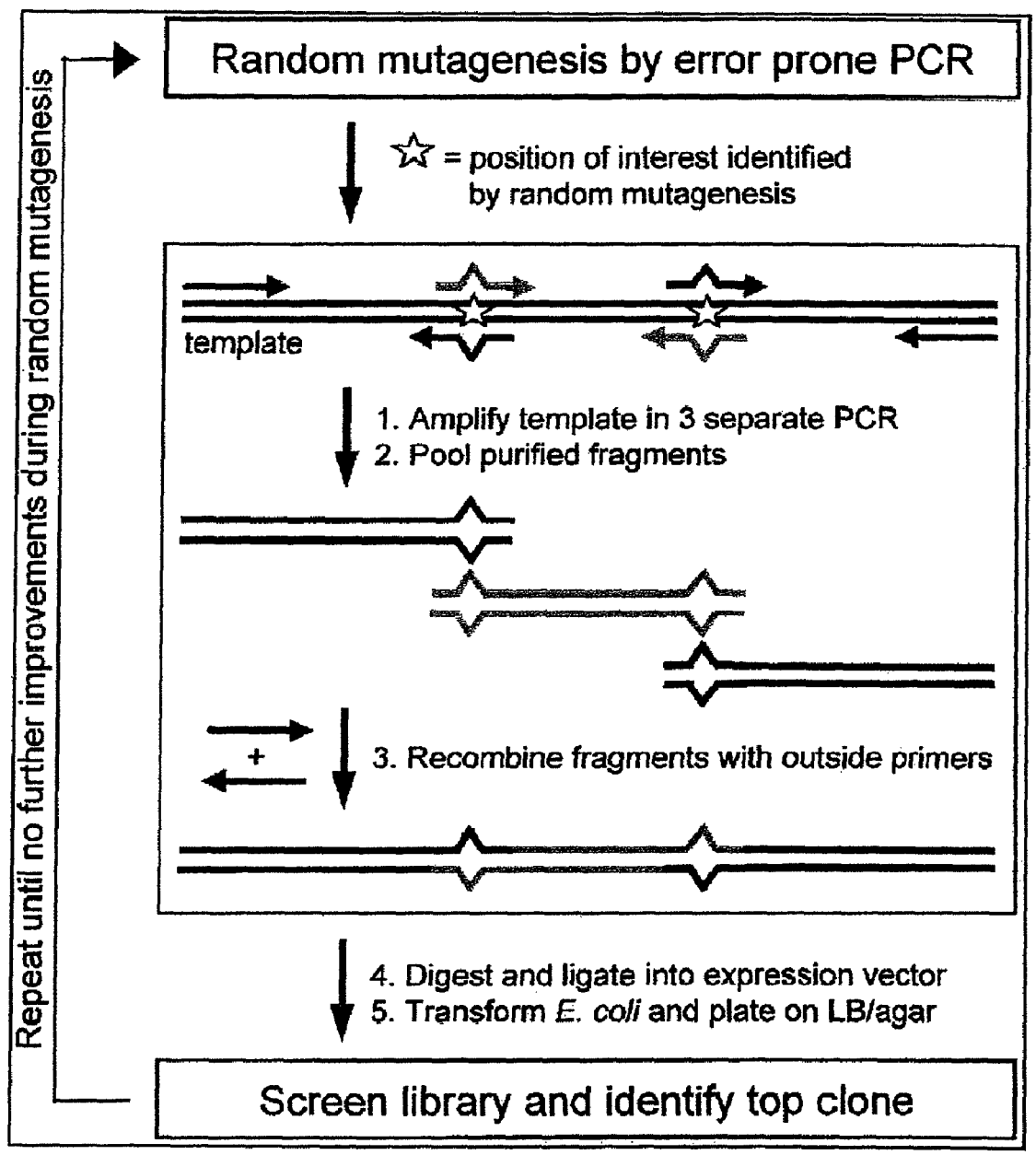
FIG. 7 shows a schematic representation of the directed evolution strategy of the present invention. Randomization at two positions is shown but the technique has been used with up to five fragments.

To reconstitute the red fluorescence of DsRed-I125R, the protein was subjected to iterative cycles of evolution. This accelerated evolution strategy used either random mutagenesis or semi-directed mutagenesis to create a library of mutated molecules, which can be screened for desirable characteristics. The directed evolution strategy of the present invention is shown in FIG. 7. Each cycle of the mutagenesis began with random mutagenesis to identify those positions that effected either the maturation or brightness of the red fluorescent protein. Once several residues were identified, expanded libraries were constructed in which several of these key positions were simultaneously mutated to a number of substitutions (see FIGS. 10-12). These directed libraries combine the benefits of shuffling of improved mutant genes with an efficient method of overcoming the limited number of substitutions accessible during random mutagenesis by error prone PCR. Most methods of in vitro recombination rely on random gene fragmentation. In contrast, the methods of the present invention use PCR to generate designed fragments that can be reassembled to give the full length shuffled gene.

Libraries of mutant red fluorescent proteins were screened in colonies of E. coli and were evaluated on both the magnitude of their red fluorescence under direct excitation at 540 nm and the ratio of emission intensities at 540 nm over 470 nm excitation. While the former constraint selected for very bright or fast maturing mutants, the latter constraint selected for mutants with decreased 470 nm excitation or red-shifted excitation spectra. Multiple cycles of random mutagenesis were used to find sequence locations that affected the maturation and brightness of the protein, and then expanded libraries of mutations at those positions were created and recombined to find optimal permutations.

Initial random mutagenesis of DsRed-I125R identified several beneficial mutations including K163Q or M, S179T and T217S. These three positions were included in our first directed library in which a total of seven residues were simultaneously mutated to a number of reasonable substitutions. The additional positions targeted in the first directed library included N42 and V44, residues that are critical for the fast phenotype of T1 (Bevis and Glick, *Nat. Biotechnol.*, 20:83-87 [2002]). Also included were I161 and S197, positions at which specific mutations contributed to the modest improvements of DSRed2 (CLONTECH) and the very similar 'E57' (Terskikh et al., *J. Biol. Chem.*, 277:7633-7636 [2002]). From this library, several clones were identified such as DsRed-I125R, S179T, T217A and DsRed-I125R, K163Q, T217A, but improvements were not dramatic.

As an alternative strategy, the DsRed variant fast tetramer T1 (Bevis and Glick, *Nat. Biotechnol.*, 20:83-87 [2002]) was also studied. Introduction of the I125R mutation into this protein (T1 DsRed-I125R polypeptide sequence provided in SEQ ID NO: 24) resulted in a dimer that matured in only a few days, which was comparable to the best DsRed dimers produced at that time. By further targeting those positions that had helped rescue DsRed-I125R, dramatic improvements in our first generation library were observed.

A similar directed mutagenesis strategy starting from T1-I125R (see FIG. 10A, library D1) was undertaken and eventually identified dimer1. Dimer1 was somewhat better than wt DsRed both in terms of brightness and rate of maturation but had a substantial green peak equivalent to that of T1. Dimer1 was also somewhat blue-shifted with an excitation maximum at 551 nm and an emission maximum at 579 nm. Error prone PCR on Dimer1 (FIG. 10A, library D2) resulted in the discovery of Dimer1.02 containing the mutation V71A in the hydrophobic core of the protein and effectively no green component in the excitation spectra. A second round of random mutagenesis (FIG. 10A, library D3) identified the mutations K70R which further decreased the green excitation, S197A which red-shifted the dimer back to DsRed wavelengths and T217S which greatly improved the rate of maturation. Unfortunately, K70R and S197A matured relatively slowly and T217S had a green excitation peak equivalent to DsRed. Using dimer1.02 as the template, two more rounds of directed mutagenesis were performed; the first focusing on the three positions identified above (FIG. 11A, library D3) and the second on C117, F118, F124, and V127 (FIG. 10A, library D4).

Continuing with the directed evolution strategy for a total of 4 generations, an optimal dimeric variant was produced, which was designated dimer2 (illustrated in FIG. 2B). This variant contains 17 mutations, of which eight are internal to the β-barrel (N42Q, V44A, V71A, F118L, K163Q, S179T, S197T and T217S), three are the aggregation reducing mutations found in T1 (R2A, K5E and N61) and see Bevis and Glick, *Nat. Biotechnol.*, 20:83-87 [2002]; and Yanushevich et al., *FEBS Lett.*, 511:11-14 [2002]), two are AB interface mutations (I125R and V127T), and 4 are miscellaneous surface mutations (T21S, H41T, C117T and S131P). The dimer2 nucleotide sequence is provided in SEQ ID NO: 7 and FIG. 21. The dimer2 polypeptide is provided in SEQ ID NO: 6 and FIG. 22A.

A variant of dimer2 (SEQ ID NO:6) may comprise one or more amino acid substitutions selected from amino acid substitutions at positions 22, 66, 105, and 124, and may also include terminal amino acids at the GFP terminus. A variant of dimer2 (SEQ ID NO:6) may have about 80%, or 85%, or 90%, or 91%, 92%, 93%, 94%, 95%, 96%, 97%, 98% or 99% sequence identity with the amino acid sequence of SEQ ID NO:6. For example, substitutions in the dimeric protein may be selected from one or more of V22M, Q66M, V104L, and F124M. In a preferred embodiment, the protein variant is dimer2.2MMM (dimer3) (dTomato) (SEQ ID NO: 81) having substitutions V22M, Q66M, V104L, and F124M with respect to SEQ ID NO: 6 and having GFP termini of MVSKGEE (SEQ ID NO: 14) (at the N-terminus) and GMDELYK (SEQ ID NO: 91) or YGMDELYK (SEQ ID NO: 110) at the C-terminus. The underlined residues were copied from the N- and C-termini of EGFP (containing mutations F64L, S65T; SEQ ID NO: 13) and replace the corresponding amino acids in DsRed and mRFP1, as illustrated in FIG. 22B. Also shown in FIG. 22B are the N-terminal amino acid sequences of DsRed (SEQ ID NO: 1) and mRFP1 (SEQ ID NO: 8).

As shown in the table of FIG. 32, dimer2.2MMM (dimer3) (dTomato) has an excitation wavelength peak at 554 nm and an emission wavelength peak at 581 nm, with an extinction coefficient of 70,000 $M^{-1}cm^{-1}$ and a quantum yield of 0.72. Dimer2.2NIMM (dimer3) (dTomato) has the highest extinction coefficient of the variants that have been made, and has improved quantum yield as compared to dimer2. Its excitation and emission wavelengths are most similar to the wild type DsRed, with has very little green component (having less green component than either wt DsRed or dimer2).

Construction of a Tandem Dimer of DsRed

In an attempt to produce a still further advantageous form of DsRed, an alternative novel strategy to synthesize a more stable DsRed dimer was devised. This approach utilized covalent tethering of two engineered monomeric DsRed units to yield a dimeric form of DsRed with advantageous properties. The basic strategy was to fuse two copies of an AC dimer with a polypeptide linker such that the critical dimer interactions could be satisfied through intramolecular contacts with the tandem partner encoded within the same polypeptide.

Based on the crystal structure of the DsRed tetramer (Yarbrough et al., *Proc. Natl. Acad. Sci. USA* 98:462-467 [2001]; and Wall et al., *Nature Struct. Biol.*, 7:1133-1138 [2000]), it was contemplated that a 10 to 20 residue linker could extend from the C-terminus of the A subunit to the N-terminus of the C subunit (~30 Å, see FIG. 1B), but not to the N-terminus of the B subunit (>70 Å). Using the optimized dimer2, a series of four tandem constructs were produced using linkers of varying lengths (9, 12, 13, or 22 amino acids) comprising a sequence similar to a known protease resistant linker (Whitlow et al. *Protein Eng.*, 6:989-995 [1993]).

Of the four constructions, only the tandem construct with the 9 residue linker was notable for a somewhat slower maturation. The other three constructs were practically indistinguishable in this respect, and thus, find equal use with the present invention. The tandem dimer construct with the 12 residue linker, designated tdimer2(12), was used in all subsequent experiments. As expected, dimer2 and tdimer2(12) have identical excitation and emission maximum and quantum yields (see FIG. 14). However, the extinction coefficient of tdimer2(12) is twice that of dimer2 due to the presence of two equally absorbing chromophores per polypeptide chain.

Evolution of a Monomeric DsRed

In an attempt to create improved dimers of DsRed would better tolerate disruption of the remaining interface, libraries were constructed where AC interface breaking mutations were incorporated into the tdimer2(12): An initial dimer library was reassembled using a 3' primer that encoded the mutations H222G and F224G (FIG. 10A, library D5). These two residues form the bulk of the dimer contacts in the C-terminal tail of DsRed that hooks around the C-terminal tail of the dimer partner. From this library the best two unique clones, HF2Ga and HF2Gb, were very similar in sequence to Dimer1 with the primary differences being the mutations F124L present in both clones, K163H in HF2 Gb and the H222G and F224G replacements. Both HF2Ga and HF2 Gb migrated as fluorescent dimers when loaded unboiled onto a 12% SDS-PAGE gel so they must maintain a stable dimer interface.

Simultaneously, a more direct approach to breaking up the AC interface through introduction of dimer-breaking mutations was undertaken. Dimer1 was the template for the first such library (FIG. 10A, library M1) in which nine different positions were targeted, including two key AC interface residues, H162 and A164, which were substituted for lysine or arginine, respectively. The brightest colonies from this library were difficult to distinguish from the background red fluorescence of the *E. coli* colonies even after prolonged imaging with a digital camera. Suspect colonies were restreaked on LB/agar, allowed to mature at room temperature for two weeks and a crude protein preparation analyzed by SDS-PAGE. Imaging of the gel revealed a single faint band consistent with the expected mass of the monomer. Thus, this species was termed mRFP0.1 (for monomeric Red Fluorescent Protein). Sequencing of this clone revealed that mRFP0.1 was equivalent to Dimer1 with mutations E144A, A145R, H162K, K163M, A164R, H222G and H224G.

Random mutagenesis on mRFP0.1 (FIG. 10A, library M2) resulted in the creation of the much brighter mRFP0.2, which gave an unambiguous red fluorescent and monomeric band by SDS-PAGE, and which contained the single additional mutation Y192C. Both mRFP0.1 and mRFP0.2 displayed at least 3-fold greater green fluorescence than red fluorescence, but as expected for the monomer, there was no FRET between the green and red components.

With the suspicion that mutations that were beneficial to the dimer could also benefit the monomer, a template mixture including mRFP0.2, Dimer1.56, HF2Ga and HG2Gb was subjected to a combination of PCR-based template shuffling and directed mutagenesis (FIG. 10A, library M3). The top clone identified in this library, mRFP0.3 was relatively bright and had a greatly diminished green fluorescent component. In addition, mRFP0.3 was approximately 10 nm red shifted from DsRed and was primarily derived from Dimer1.56.

The goal of the next directed library (FIG. 10B, library M4) was to investigate the effect of mutations at K83, which have previously been shown to cause a red shift in DsRed (Wall et al., *Nature Struct. Biol.*, 7:1133-1138 [2000]). The top two clones, designated mRFP0.4a and mRFP0.4b, contained the K83I or L mutation respectively, were 25 nm red shifted relative to DsRed and were very similar in terms of maturation rate and brightness. Unlike all the previous generations of the monomer, colonies of *E. coli* transformed with mRFP0.4a were red fluorescent within 12 h after transformation when excited with 540 nm light and viewed through a red filter.

A template mixture of mRFP0.4a and mRFP0.4b was subjected to random mutagenesis (FIG. 10B, library M5) and the resulting library was thoroughly screened. The 5 fastest maturing clones from this library were derived from mRFP0.4a and contained individual mutations L174P, V175A (two clones), F177C and F177S. The F177S clone or mRFP0.5a, appeared to mature slightly faster and had the smallest green peak in the absorbance spectra. One colony isolated from this library was exceptionally bright when grown on LB/agar but expressed very poorly when grown in liquid culture. This clone, designated mRFP0.5b, was derived from mRFP0.4b and contained two new mutations; L150M inside the barrel and V156A outside.

The next library (FIG. 10B, library M6) was intended to optimize the region around residues V175 and F177 in both mRFP0.5a and the increasingly divergent mRFP0.5b. The top clone in this library, designated mRFP0.6, was derived from mRFP0.5b, though of three other top clones, one was derived from mRFP0.5b; one from mRFP0.5a, and one appeared to have resulted from multiple crossovers between the two templates—The final library (FIG. 10B, library M7) targeted residues in the vicinity of L150 because this was the one remaining critical mutation that was derived from random mutagenesis and had not been reoptimized. Top clones had combinations of mutations at all targeted positions though the clone with the single mutation R153E was found to express slightly better in culture. This clone was further modified through deletion of the unnecessary V1a insertion and replacement of the cysteine at position 222 with a serine.

The final clone in this series, designated mRFP1, contained a total of 33 mutations (see FIG. 1C) relative to wild-type DsRed. Of these mutations, 13 are internal to the β-barrel (N42Q, V44A, V71A, K83L, F124L, L150M, K163M, V175A, F177V, S179T, V 195T, S197I and T217A). Of the 20 remaining external mutations, three are the aggregation reducing mutations from T1 (R2A, K5E and N61)), three are AB interface mutations (I125R, V127T and I180T), ten are AC interface mutations (R153E, H162K, A164R, L174D, Y192A, Y194K, H222S, L223T, F224G and L225A), and four additional mutations (T21S, H41T, C117E and V156A). The mRFP1 nucleotide and polypeptide sequences are provided in SEQ ID NOS: 9 and 8, respectively.

In other embodiments, the monomeric variant is a variant of mRFP1 (SEQ ID NO: 8). Based on indications that substitution of methionine at the first position in the chromophore had beneficial effects on maturation of the I125R dimeric variant of DsRed (Baird, G. S. (2001) *Ph.D. thesis*, University of California, San Diego), a directed library of residues near the chromophore was constructed, including randomization at position 66 in mRFP1. The Q66M substitution was found to have a large impact on the amount of protein that assumed the mature chromophore conformation relative to mRFP1, and the additional mutation T147S, present due to a PCR error in the Q66M mutant, was also found to be beneficial. In addition to allowing more complete maturation, the Q66M mutation also provides an additional red-shift of the excitation and emission spectra of approximately 5 nm relative to mRFP1. The Q66M, T147S mutant was designated mRFP1.1.

Because mRFP1 was found to be somewhat sensitive to N-terminal fusions, it was reasoned that changes to the N- and C-termini could potentially be beneficial to the protein in the context of fusions to other proteins. Thus, the first and last seven amino acids of mRFP 1.1 were replaced with the corresponding residues from GFP, with the hope that these residues would act as an "insulator" against adverse effects due to fusions to the N- or C-terminus of the resulting protein. This mutant was designated mRFP 1.2, and was found to be less sensitive to the presence of an N-terminal 6xHis (SEQ ID NO:120) tag than its predecessor. An additional benefit of these changes to the N- and &termini of mRFP is that primers used to amplify GFP-based proteins can now also be used for mRFP-based proteins as well, simplifying subcloning procedures.

While the substitution of the first and last seven amino acids of mRFP for the corresponding GFP residues was found to be beneficial, further reduction of the sensitivity of mRFP to fusions to its N-terminus was desirable. A library based on mRFP 1.2 was next constructed in which four additional randomized codons were inserted after position 6 in a construct that included an N-terminal 6×His (SEQ ID NO:120) tag. From this library, it was found that the insertion of the amino acid sequence NNMA (SEQ ID NO:112) gave the strongest fluorescence signal in bacteria, and so this clone was designated mRFP 1.3.

Additional random libraries based on mRFP1.3, as well as error-prone libraries of wavelength-shifted mRFP variants, were constructed. These libraries provided data that identified the V7I and M182K mutations as beneficial to efficient protein folding, and so these two mutations were added to mRFP1.3 to give mRFP1.4. It is worth noting that in homologous fluorescent proteins, position 182 is invariably occupied by a positively charged residue.

The chromophore-interacting residue 163 had not been re-investigated since early in the evolution of mRFP. Randomization of residue 163 showed that the substitution M163Q resulted in a nearly complete disappearance of the absorbance peak at ~510 nm present in all previous mRFP clones. This mutation additionally blue-shifted the excitation peak approximately 2 nm relative to mRFP 1.4 while having little impact on the emission peak of the protein, and so effectively increased the Stokes shift of this mRFP variant relative to previous clones. While this clone suffered from a reduced extinction coefficient, suggesting that it too did not fold efficiently, the additional mutation R17H restored an extinction coefficient nearly equivalent to mRFP 1.4, giving the variant mRFP 1.5, which is red-shifted 5 nm from mRFP1 and exhibits nearly complete maturation with kinetics as fast or faster than mRFP1.

An additional directed library of mRFP 1.5 was constructed that partially randomized positions 194, 195, 196, 197, and 199, based on evidence from wavelength-shifted mRFP variants that this region could influence solvent accessibility of the chromophore. From this library, the clone containing the mutations K194N, T195V, and D196N was found to have an enhanced extinction coefficient, while retaining the nearly complete lack of a 510 nm absorbance peak. This clone was designated mRFP1.5.4 (also termed mRFP2, or mCherry).

Dimer3

The dimer2 variant previously described possesses quite desirable properties, such as much faster maturation than wild-type DsRed and nearly complete maturation, as well as a high extinction coefficient and quantum yield relative to the fast-maturing mutant T1. In order to improve these properties, randomly mutagenized libraries of dimer2 were constructed. The V 104L mutation was identified as improving the brightness of the dimer, and subsequent analysis showed that the effect of this mutation was to significantly increase the quantum yield of the protein to a level comparable to wild-type DsRed. However, it was determined that this mutation alone was not clearly beneficial, as it also increased the proportion of protein trapped in an immature, green fluorescent state.

As with mRFP, a decrease in the dimer RFP's sensitivity to N- and C-terminal fusions was desired, and so, as with mRFP, its first and last seven amino acids were replaced with the corresponding GFP residues. The resulting protein was found to have more consistent brightness regardless of the N-terminal sequence attached to it. The V104L dimer variant with the GFP-type termini was designated dimer2.2.

Additional rounds of error-prone mutagenesis identified positions 22 and 124, both of which interact with the chromophore-containing central alpha-helix, to be important in improving the brightness of the dimer. Therefore, directed libraries were constructed at both of these positions; these libraries identified V22M and F124M as the optimal mutations. In addition, because the Q66M mutation had been shown to improve the properties of both wild-type DsRed and mRFP, this mutation was included in the resulting dimer, giving a protein differing from the original dimer2 by the mutations V22M, Q66M, V104L, and F124M, as well as the substitution of its first and last seven amino acids with the corresponding GFP residues. This final variant was designated dimer3 (dTomato), and has an improved extinction coefficient and quantum yield relative to dimer2, and also has improved maturation kinetics, leading to a decreased green fluorescent component relative to dimer2.

Wavelength-Shifted Variants of mRFP

Rather than attempting to monomerize novel fluorescent proteins, it was reasoned that it should be possible to alter the excitation and emission wavelength of mRFP by rational mutagenesis, as had been done with *Aequorea* GFP. Following the example of GFP, substitutions at the first chromophore residue, Q66, and in the stacking position homologous to T203 in GFP, mRFP I197 (S197 in wild-type DsRed) were explored.

The most significant wavelength shift we observed occurred when Q66 was substituted with either serine, threonine, or cysteine. All three substitutions gave a similar blue-shift in both excitation and emission wavelength, and led to a curious increase in pH sensitivity, characterized by an additional blue-shift in excitation and emission at alkaline pH. Such pH-sensitivity was obviously undesirable, and since the additionally blue-shifted chromophore species at high pH appeared to have increased extinction coefficient and quantum yield, we sought first to find mutants that favored this form of the chromophore and thus had reduced pH sensitivity.

Randomly mutagenized libraries of Q66C/S/T libraries identified the T195I mutation as important in reducing pH sensitivity and favoring the more blue-shifted form of the mOFP chromophore. Additional directed libraries at this and surrounding positions identified T195V as the optimal mutation for reducing pH sensitivity, and Q66T as having the highest quantum yield of the mOFP chromophores. This clone was designated mOFP.T.12, and, in addition to the modified N- and C-termini present in mRFP 1.4, has the additional mutations Q66T, K194M, T195V, D196S relative to mRFP1.4.

Randomization of the stacking position, 1197, in already blue-shifted mRFP variants led to the surprising discovery that a glutamate in this position provided an additional red-shift, yielding an mRFP variant with excitation and emission spectra unlike anything yet found in nature. This true yellow mRFP variant, designated mYOFP for yellow-orange fluorescent protein, was found initially to have extreme pH sensitivity as well as inefficient maturation: Additional mutations were discovered through several rounds of random and directed libraries that improved the folding efficiency and pH sensitivity of mYOFP variants, yielding the brightly fluorescent variant mYOFP 1.3, which, in addition to the modified N- and C-termini present in mRFP1.3, contains the mutations Q66C, A77T, D78G, L83F, T108A, T147S, D174S, V177T, M182K, K194I, T195A, D196G, I197E, L199I, and Q213L relative to mRFP1.3. Interestingly, in the case of mYOFP, the L199I mutation had the greatest effect on pH sensitivity, while in the case of mOFP, the T197V mutation had a similar effect, while mutations at L199 have little effect.

In order to mimic the red-shift of YFPs relative to GFP, aromatic residues were placed in the stacking position of mRFP and selected for variants with red-shifted excitation and emission spectra. Following several rounds of random and directed mutagenesis, we identified a clone, mFRFP.F2Q6, which has excitation and emission peaks ~20 nm red-shifted relative to mRFP2, or ~25 nm red-shifted relative to mRFP1. Significantly, this protein has an excitation maximum of 605 nm, which is beyond the generally agreed-upon barrier of hemoglobin and cytochrome absorbance in biological tissues. In addition to the modified N- and C-termini present in mRFP1.3, this variant contains the mutations V7I, E32K, A77P, L83M, R125H, T147S, M150L, I161V, T195L, and I197Y relative to mRFP1.3.

The properties of several variants of mRFP1 (SEQ ID NO:8) are presented in the table in FIG. 32. Nucleotide sequences coding for these variants are presented in FIGS. 34-37. A variant of mRFP1 (SEQ ID NO:8) may have about 80%, or 85%, or 90%, or 91%, 92%, 93%, 94%, 95%, 96%, 97%, 98% or 99% sequence identity with the amino acid sequence of SEQ ID NO:8. As indicated in FIG. 32, a variant of mRFP1 (SEQ ID NO:8) may comprise more than one amino acid substitution as compared to the wtDsRed sequence (SEQ ID NO: 1) or mRFP1 (SEQ ID NO: 8) and may also include terminal amino acid additions or substitutions selected from the insertions comprising one or more amino acids homologous to the amino acids at the GFP terminus, the amino acids DNMA (SEQ ID NO:111), and the amino acids NNMA SEQ ID NO:112). Amino acid substitutions found in the protein variants dimer 2.2MMM (dimer 3) (dTomato), mRFP1.5, OrS4-9, Y1.3 (mYOFP1.3) (mBanana), and mFRFP (F2Q6) (mGrape2) are indicated in FIG. 32, which also includes excitation/emission wavelength values, extinction coefficient values, quantum yield values, and comments on the properties of the variants.

Characterization of dimer2, tdimer2(12) and mRFP1

Figure 3A:
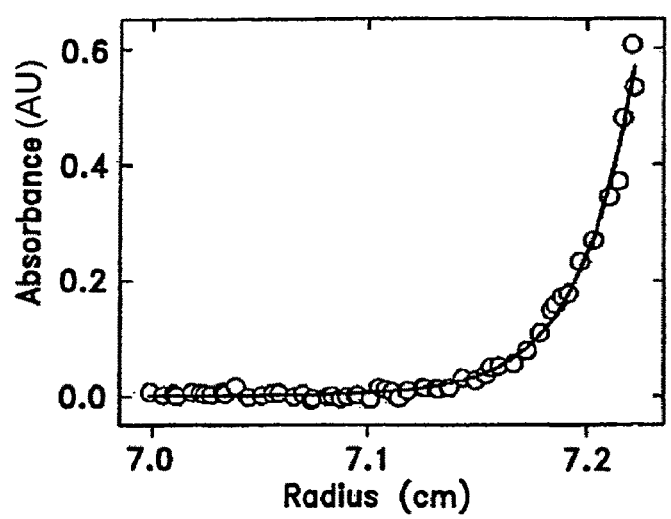
FIGS. 3A-3C show the results of an analytical ultracentrifugation analysis of DsRed, dimer2, and mRFP0.5a polypeptides, respectively. The equilibrium radial absorbance profiles at 20,000 rpm were modeled with a theoretical curve that allowed only the molecular weight to vary. The DsRed absorbance profile (FIG. 3A) was best fit with an apparent molecular weight of 120 kDa, consistent with a tetramer. The dimer2 absorbance profile (FIG. 3B) was best fit with an apparent molecular weight of 60 kDa, consistent with a dimer. The mRFP0.5a absorbance profile (FIG. 3C) was best fit with an apparent molecular weight of 32 kDa, consistent with a monomer containing an N-terminal polyhistidine affinity tag.
Figure 3B:
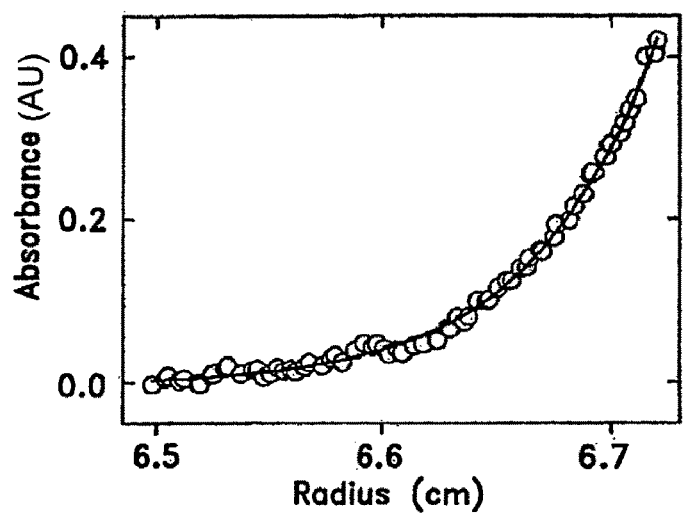
Figure 3C:
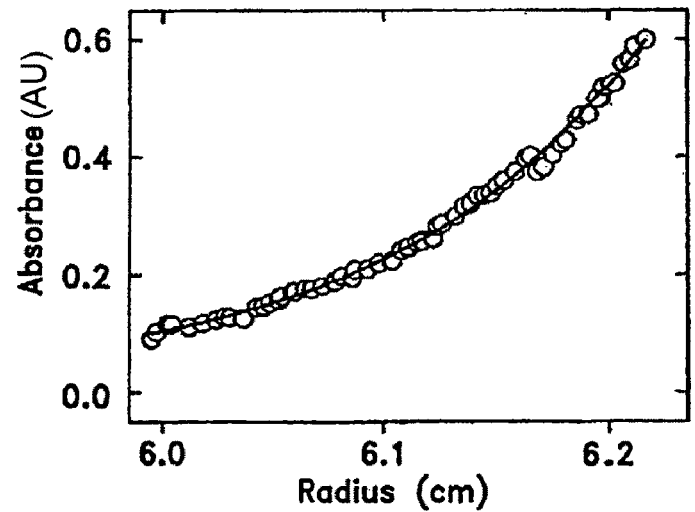

Initial evidence for the monomeric structure of mRFP1 and its precursors was based on SDS-PAGE results (see FIG. 8) and the lack of FRET between the green and red fluorescent components in early generations. Thus analytical equilibrium ultracentrifugation was performed on DsRed, dimer2, and mRFP0.5a (an evolutionary precursor to mRFP1). The mRFP0.5a polypeptide sequence is illustrated in FIGS. 20A-20D. The analytical equilibrium analysis confirmed the expected tetramer, dimer, and monomer configurations of the tested species (see FIGS. 3A-3C).

Figure 4A:
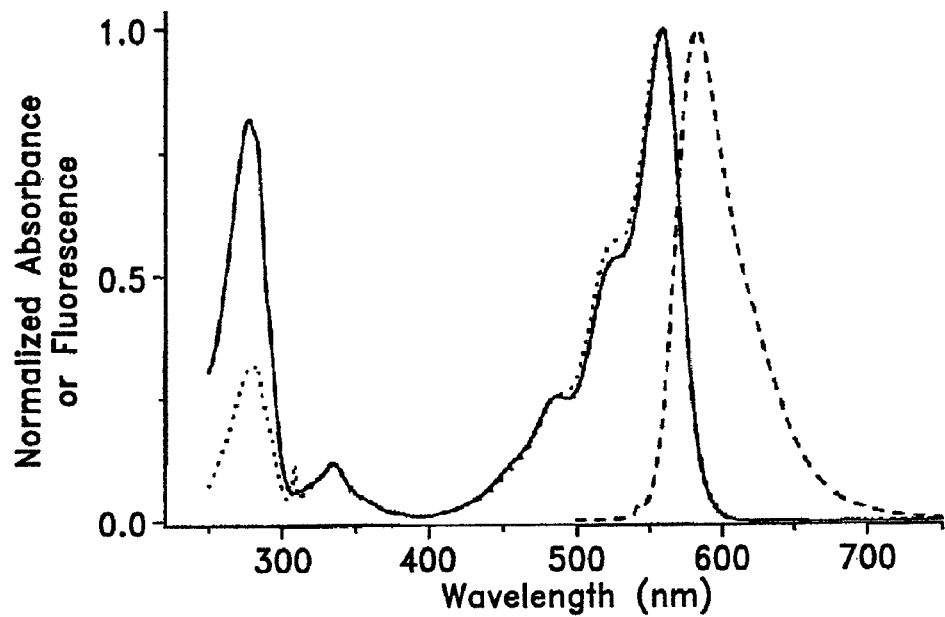
FIGS. 4A-4D show fluorescence and absorption spectra of DsRed, T1, dimer2 and tdimer2(12) and mRFP1, respectively. The absorbance spectrum is shown with a solid line, the excitation with a dotted line and the emission with a dashed line.
Figure 4C:
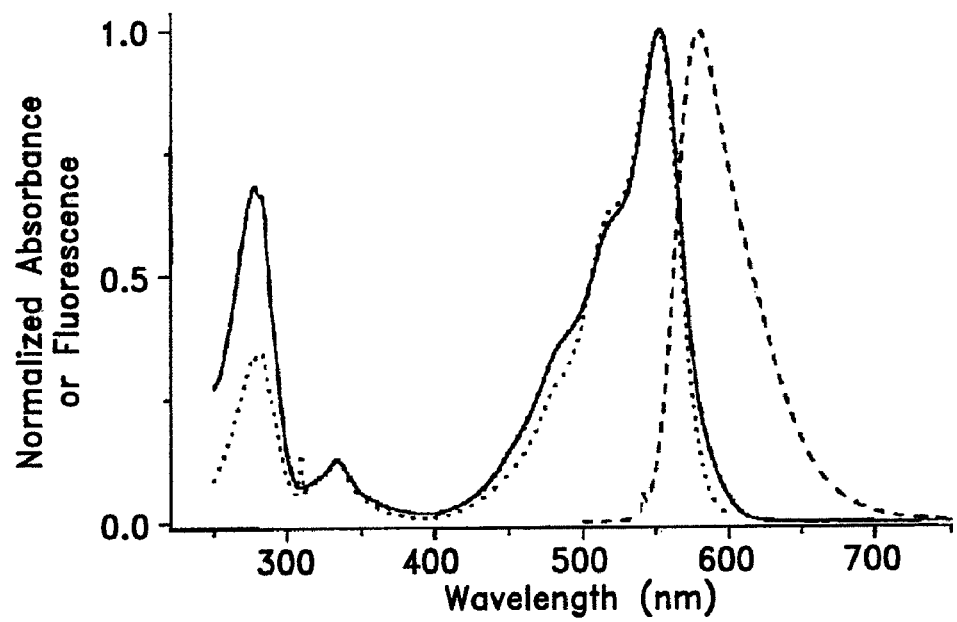
Figure 4B:
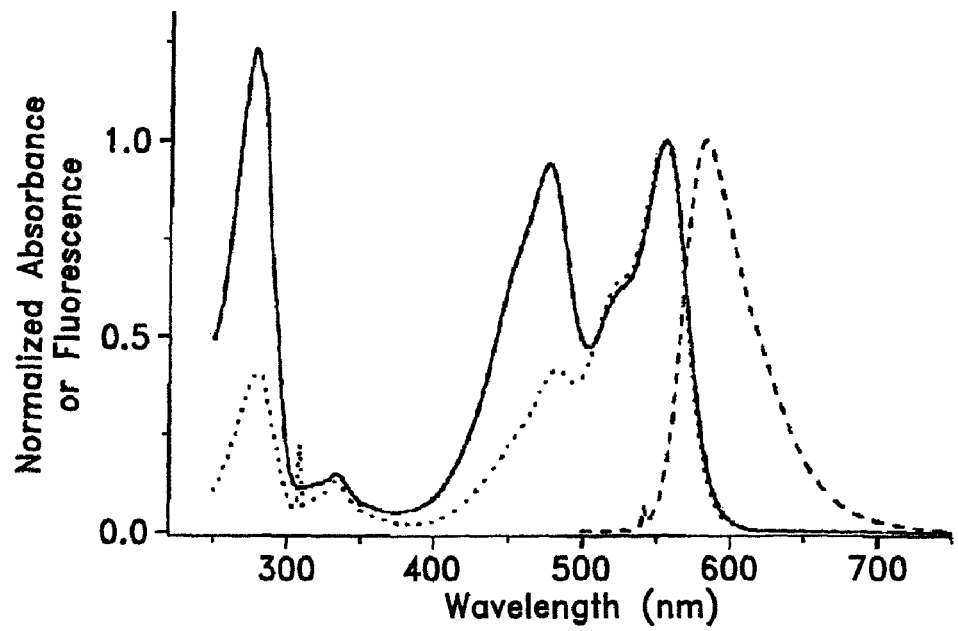
Figure 4D:
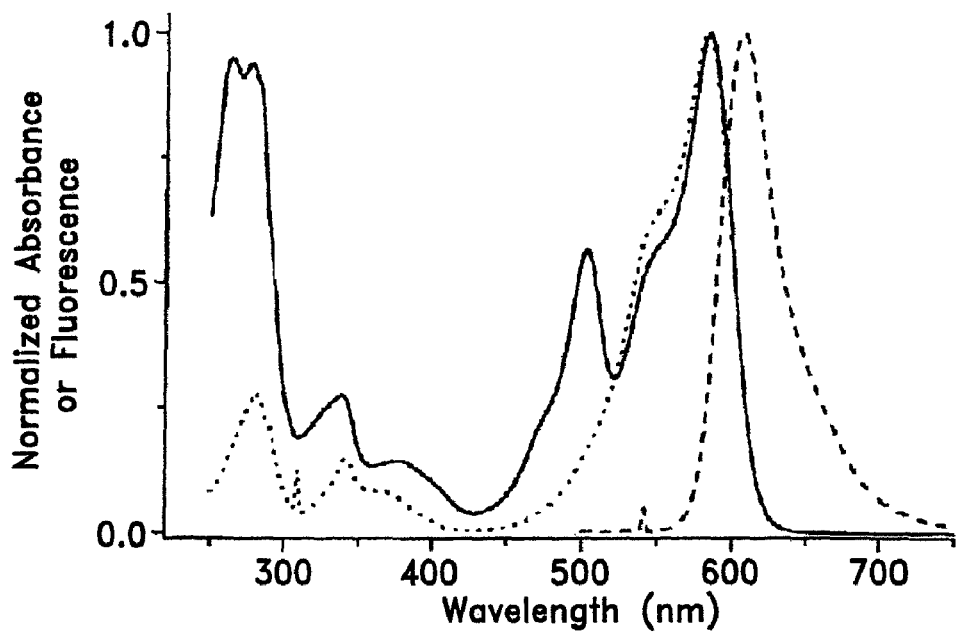

In a fluorescence and absorption spectra analysis, DsRed, T1 and dimer2 all have a fluorescent component that contributes at 475-486 nm to the excitation spectra due to FRET between oligomeric partners (see FIGS. 4A-4C). In this analysis, the T1 peak is quite pronounced (FIG. 4B), but in dimer2 (FIG. 4C), any excitation shoulder near 480 nm is almost obscured by the 5 nm blue-shifted excitation peak. The 25 nm red-shifted monomeric mRFP1 (FIG. 4D) also has a peak at 503 nm in the absorption spectra, but in contrast to the other variants, this species is non-fluorescent mutant and therefore does not show up in the excitation spectrum collected at any emission wavelength. When the 503 nm absorbing species is directly excited, negligible fluorescence emission is observed at any wavelength.

Figure 5:
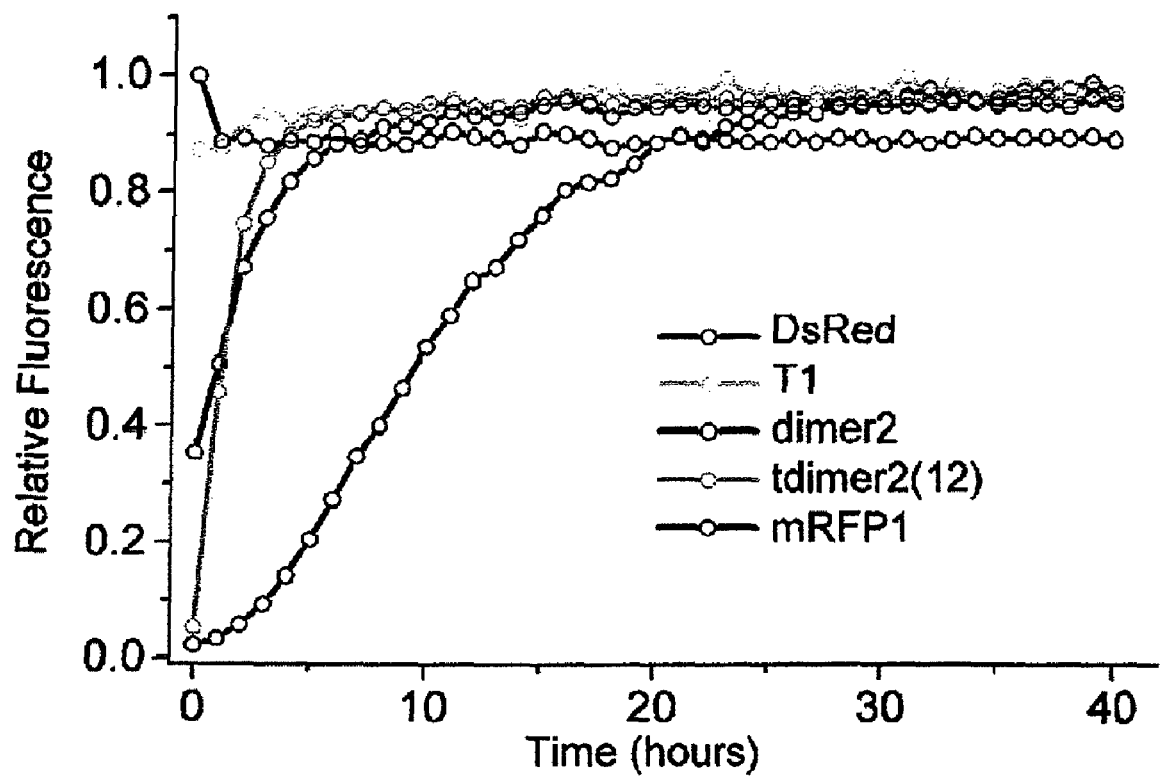
FIG. 5 shows a maturation time course of red fluorescence for DsRed, T1, dimer2, tdimer2(12) and mRFP1. The profiles are color coded, as indicated in the key. Log phase cultures of E. coli expressing the construct of interest were rapidly purified at 4° C. Maturation at 37° C. was monitored beginning at 2 hours post-harvest. The initial decrease in mRFP1 fluorescence is attributed to a slight quenching on warming from 4 to 37° C.
Figure 9:
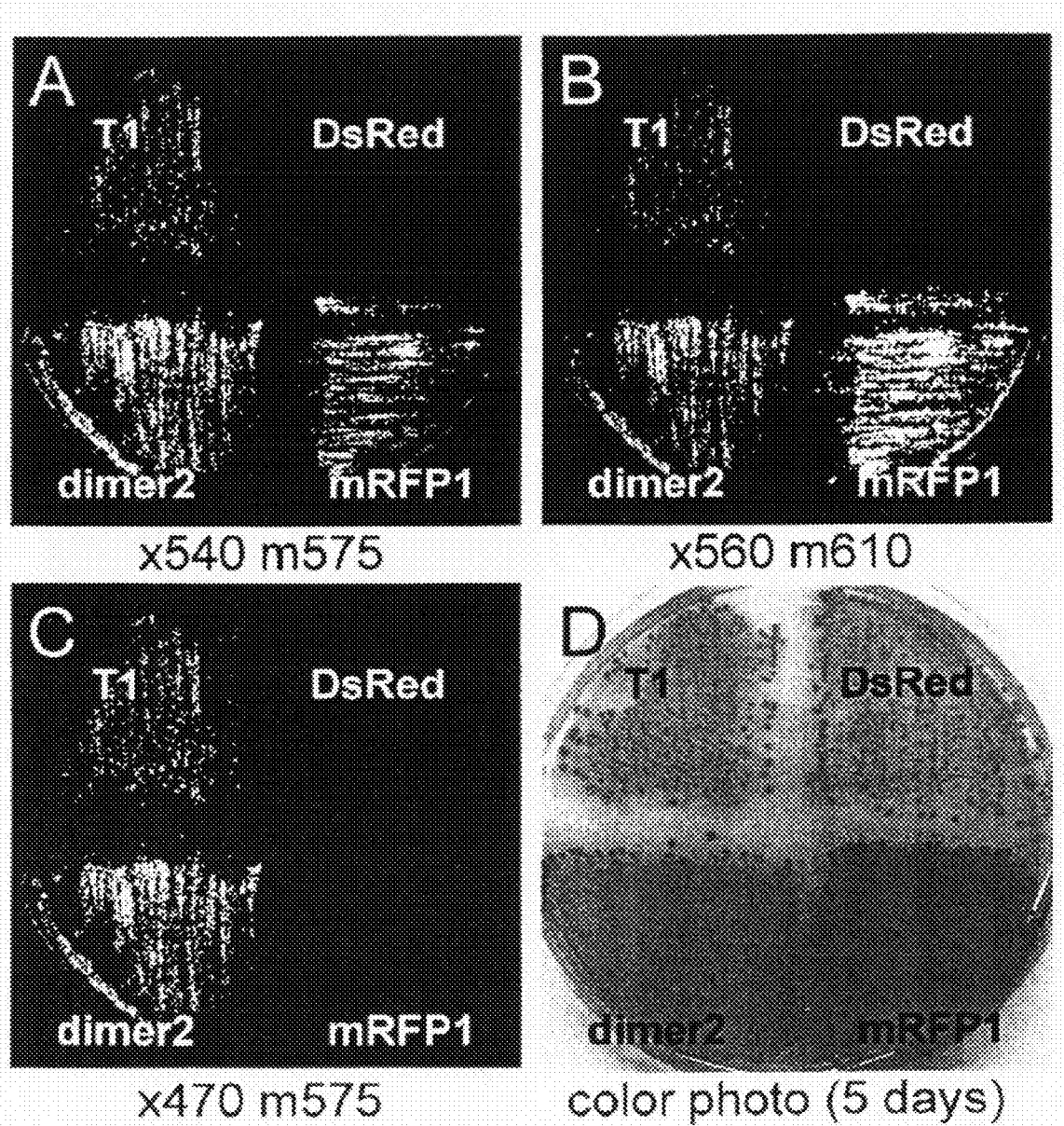
FIGS. 9A-9D show fluorescence images of red fluorescent proteins expressed in E. coli. E. coli strain JM109(DE3) was transformed with either DsRed, T1, dimer2 or mRFP1, plated on LB/agar supplemented with ampicillin, and incubated 12 hours at 37° C. then 8 hours at 20° C. before the plate was imaged with a digital camera.

As shown in FIG. 5, the rate of maturation of dimer2, tdimer2(12) and mRFP1 is greatly accelerated over that of DsRed; though only mRFP1 matures at least as quickly as T1. Based on data collected at 37° C., the $t_{0.5}$ for maturation of mRFP1 and T1 are less than 1 hour. E. coli colonies expressing either dimer2 or mRFP1 display similar or brighter levels of fluorescence to those expressing T1 after overnight incubation at 37° C. (see FIG. 9).

Expression of dimer2, tdimer2(12) and mRFP1 in Mammalian Cells

The fluorescence of the dimer2, tdimer2(12) and mRFP1 proteins in the context of mammalian cells was tested. Mammalian expression vectors encoding dimer2, tdimer2(12) and mRFP1 were expressed in transiently transfected HeLa cells. Within 12 hours the cells displayed strong red fluorescence evenly distributed throughout the nucleus and cytoplasm (data not shown).

Figure 6:
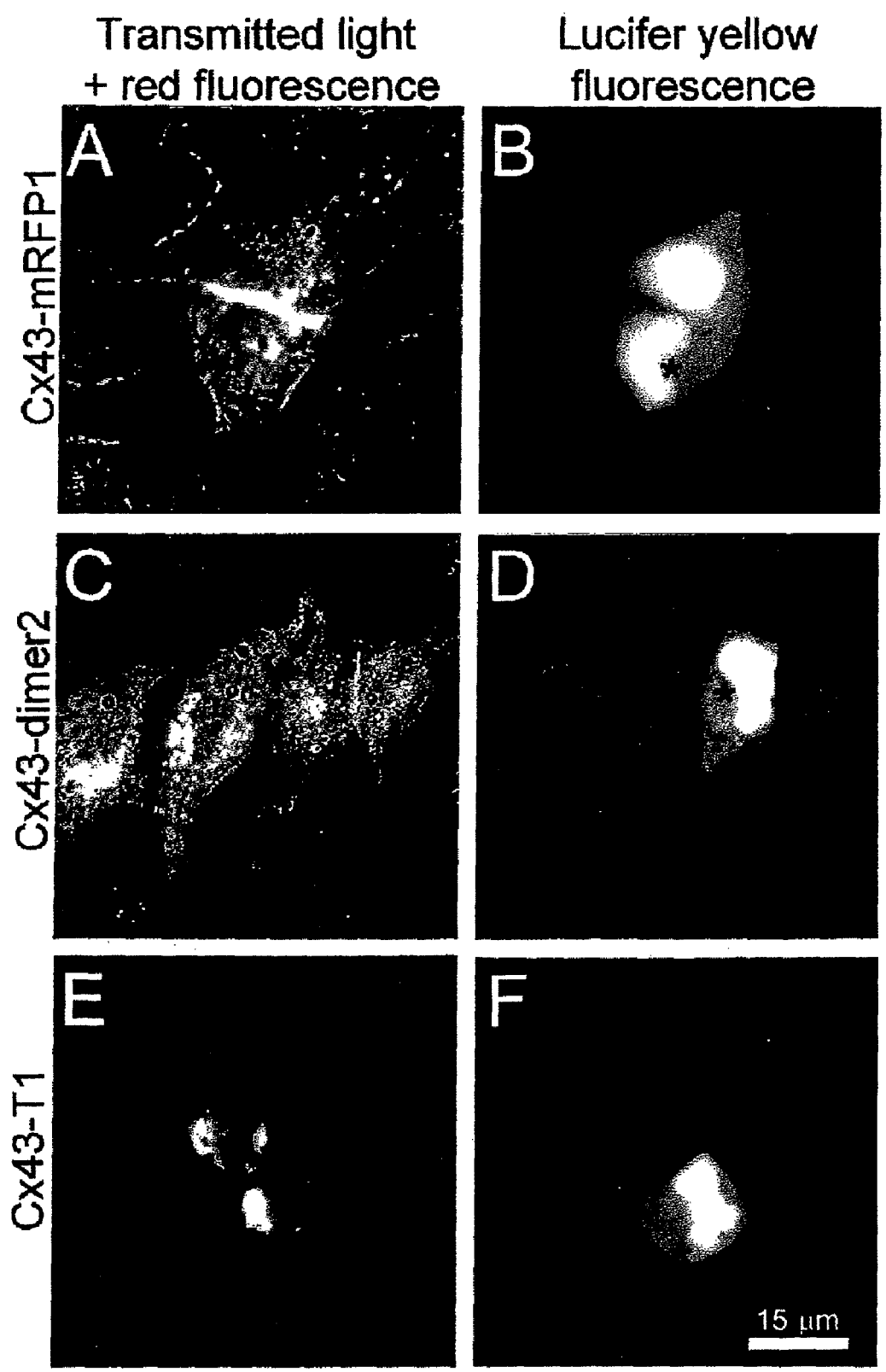
FIGS. 6A-6F show light and fluorescence microscopic images of HeLa cells expressing Cx43 fused with T1, dimer2 or mRFP1. Images 6A, 6C and 6E were acquired with excitation at 568 nm (55 nm bandwidth) and emission at 653 nm (95 nm bandwidth) with additional transmitted light. Lucifer yellow fluorescence (images 6B, 6D and 6F) was acquired with excitation at 425 nm (45 nm bandpass) and emission at 535 nm (55 nm bandpass).

In view of this result, it was tested whether an RFP-fusion polypeptide could be created, where the RFP moiety retains its fluorescence, and where the fused polypeptide partner retains a native biological activity. This experiment was conducted using the gap junction protein connexin43 (Cx43), which could demonstrate the advantage of a monomeric red fluorescent protein if the fused Cx43 polypeptide retained its biological activity. A series of constructs consisting of Cx43 fused to either GFP, T1, dimer2, tdimer2(12) or mRFP1 were expressed in HeLa cells, which do not express endogenous connexins. Following transfection, the red fluorescence of the cells was observed with a fluorescence microscope. The results of this experiment are shown in FIGS. 6A, 6C and 6E. As previously reported (Lauf et al., FEBS Lett. 498:11-15 [2001]), the Cx43-GFP fusion protein was properly trafficked to the membrane and was assembled into functional gap junctions (data not shown), whereas the Cx43-DsRed tetramer (i.e., the T1 tetramer) consistently formed perinuclear localized red fluorescent aggregates (FIG. 6E). Both Cx43-tdimer2(12) (not shown) and Cx43-dimer2 (FIG. 6C) were properly trafficked to the membrane though neither construct formed visible gap junctions. In contrast, the Cx43-mRFP1 construct behaved identically to Cx43-GFP and many red gap junctions were observed (FIG. 6A).

In another experiment, the transfected cells were microinjected with lucifer yellow to assess the functionality of the gap junctions (see FIGS. 6B, 6D and 6F; and FIG. 13). The Cx43-mRFP1 gap junctions rapidly and reliably passed dye (FIG. 6B), while neither Cx43-T1 transfected cells (FIG. 6E) nor non-transfected cells (not shown) passed dye. Both Cx43-dimer2 and Cx43-tdimer2(12) constructs slowly passed dye to a contacting transfected neighbor about one third of the time (FIG. 6D).

The above-described results demonstrate that the monomeric mRFP1 simultaneously overcomes the three critical problems associated with the wild-type tetrameric form of DsRed. Specifically mRFP1 is a monomer, it matures rapidly, and it has minimal emission when excited at wavelengths optimal for GFP. These features make mRFP1 a suitable red fluorescent protein for the construction of fusion proteins and multi-color labeling in combination with GFP. As demonstrated with the gap junction forming protein Cx43, mRFP1 fusion proteins are functional and trafficked in a manner identical to their GFP analogues.

Although the extinction coefficient and fluorescence quantum yield result in reduced brightness of fully mature mRFP1 compared to DsRed, this is not an obstacle to use of mRFP 1 in imaging experiments, as the reduced brightness is more than compensated for by the greater than 10-fold decrease in maturation time for mRFP1. Variant RFP polypeptides of the present invention, for example tdimer2(12), also find use as FRET based sensors. This species is sufficiently bright, and displays FRET with all variants of Aequorea GFP.

The present invention provides methods for the generation of still further advantageous RFP species. These methods use multistep evolutionary strategies involving one or multiple rounds of evolution with few mutational steps per cycle.

These methods also find use in the converting of other oligomeric fluorescent proteins into advantageous monomeric or dimeric forms.

Example 2

Preparation and Characterization of Fluorescent Protein Variants

This example demonstrates that mutations can be introduced into GFP spectral variants that reduce or eliminate the ability of the proteins to oligomerize.

ECFP (SEQ ID NO:11) and EYFP-V68L/Q69K (SEQ ID NO:12) at the dimer interface were subcloned into the bacterial expression vector pRSETB (Invitrogen Corp., La Jolla, Calif.), creating an N-terminal His$_6$ SEQ ID NO:120) tag on the of ECFP (SEQ ID NO: 11) and EYFP-V68L/Q69K (SEQ ID NO:12), which allowed purification of the bacterially expressed proteins on a nickel-agarose (Qiagen) affinity column. All dimer-related mutations in the cDNAs were created by site-directed mutagenesis using the QuickChange mutagenesis kit (Stratagene), then expressed and purified in the same manner. All cDNAs were sequenced to ensure that only the desired mutations existed.

EYFP-V68L/Q69K (SEQ ID NO: 12) was mutagenized using the QuickChange kit (Stratagene). The overlapping mutagenic primers were designated "top" for the 5' primer and "bottom" for the 3' primer and are designated according to the particular mutation introduced (see TABLE 1). All primers had a melting temperature greater than 70° C. The mutations were made as close to the center of the primers as possible and all primers were purified by polyacrylamide gel electrophoresis. The primers are shown in a 5' to Y orientation, with mutagenized codons underlined (TABLE 1).

TABLE 1

| Primer | Sequence | SEQ ID NO: |
|---|---|---|
| A206K top | CAG TCC AAG CTG AGC AAA GAC CCC AAC GAG AAG CGC GAT CAC | 25 |
| A206K bottom | GTG ATC GCG CTT CTC GTT GGG GTC TTT GCT CAG CTT GGA CTG | 26 |
| L221K top | CAC ATG GTC CTG AAG GAG TTC GTG ACC GCC GCC GGG | 27 |
| L221K bottom | CCC GGC GGC GGT CAC GAA CTC CTT CAG GAC CAT GTG | 28 |
| F223R top | CAC ATG GTC CTG CTG GAG CGC GTG ACC GCC GCC GGG | 29 |
| F223R bottom | CCC GGC GGC GGT CAC GCG CTC CAG CAG GAC CAT GTG | 30 |
| L221K/F223R top | CAC ATC GTC CTG AAG GAG CGC GTG ACC GCC GCC GGG | 31 |
| L221K/F223R bottom | CCC GGC GGC GGT CAC GCG CTC CTT CAG GAC CAT GTG | 32 |

For protein expression, plasmids containing cDNAs for the various EYFP-V68L/Q69K (SEQ ID NO: 12) mutants were transformed into *E. coli* strain JM109 and grown to an OD$_{600}$ of 0.6 in LB containing 100 μg/ml ampicillin at which time they were induced with 1 mM isopropyl β-D-thiogalactoside. The bacteria were allowed to express the protein at room temperature for 6 to 12 hr, then overnight at 4° C., then were pelleted by centrifugation, resuspended in phosphate buffered saline (pH 7.4), and lysed in a French press. Bacterial lysates were cleared by centrifugation at 30,000×g for 30 min. The proteins in the cleared lysates were affinity-purified on Ni-NTA-agarose (Qiagen).

All GFPs used in these experiments were 238 amino acids in length. Subcloning the cDNAs encoding the GFPs into pRSETB resulted in the fusion of an additional 33 amino acids to the N-terminus of the GFPs. The sequence of this tag is MRGSHHHHHHGMASMTGGQQMGRDLYD-DDDKDP (SEQ ID NO:22). Thus, the total length of the EYFP-V68L/Q69K (SEQ ID NO:12) mutants expressed from this cDNA was 271 amino acids. The His$_6$ (SEQ ID NO:120) tag was removed using EKMax (Invitrogen) to determine if the associative properties measured for the GFPs were affected by the presence of the N-terminal His$_6$-tag (SEQ ID NO:120). A dilution series of the enzyme and His$_6$-tagged (SEQ ID NO:120) GFP was made to determine the conditions necessary for complete removal of the His$_6$-tag SEQ ID NO:120). The purity of all expressed and purified proteins was analyzed by SDS-PAGE. In all cases, the expressed proteins were very pure, with no significant detectable contaminating proteins, and all were of the proper molecular weight. In addition, removal of the His$_6$ (SEQ ID NO:120) tag was very efficient, as determined by the presence of a single band migrating at the lower molecular weight than the His$_6$-EYFP-V68L/Q69K.

Spectrophotometric analysis of the purified proteins determined that there was no significant change in either the extinction coefficient as measured by chromophore denaturation (Ward et al., *In Green Fluorescent Protein: Properties, Applications and Protocols*," eds. Chalfie and Kain, Wiley-Liss [1998]) or quantum yield (the standard used for EYFP-V68L/Q69K and the mutants derived therefrom was fluorescein) of these proteins with respect to EYFP-V68L/Q69K (SEQ ID NO: 12; "wtEYFP"; Table 2). Fluorescence spectra were taken with a Fluorolog spectrofluorimeter. Absorbance spectra of proteins were taken with a Cary UV-Vis spectrophotometer. Extinction coefficients were determined by the denatured chromophore method (Ward et al., *In Green Fluorescent Protein: Properties, Applications and Protocols*," eds. Chalfie and Kain, Wiley-Liss [1998]).

TABLE 2

| Protein | Quantum Yield | Extinction Coefficient |
|---|---|---|
| WtEYFP | 0.71* | 62,000* |
| His$_6$ wtEYFP | 0.67 | 67,410 |
| His$_6$ wtEYFP L221K | 0.67 | 64,286 |
| His$_6$ wtEYFP F223R | 0.53 | 65,393 |
| His$_6$ wtEYFP A206K | 0.62 | 79,183 |

*published data (Cubitt et al., 1997)

To determine the degree of homoaffinity of the dimers, wtEYFP and the dimer mutants derived therefrom were subjected to sedimentation equilibrium analytical ultracentrifugation. Purified, recombinant proteins were dialyzed extensively against phosphate buffered saline (pH 7.4), and 125 μl samples of protein at concentrations ranging from 50 μM to 700 μM were loaded into 6-channel centrifugation cells with EPON centerpieces. Samples were blanked against the corresponding dialysis buffer. Sedimentation equilibrium experiments were performed on a Beckman Optima XL-I analytical ultracentrifuge at 20° C. measuring radial absorbance at 514 nm. Each sample was examined at three or more of the following speeds: 8,000 rpm, 10,000 rpm, 14,000 rpm, and 20,000 rpm. Periodic absorbance measurements at each speed ensured that the samples had reached equilibrium at each speed.

The data were analyzed globally at all rotor speeds by nonlinear least-squares analysis using the software package (Origin) supplied by Beckman. The goodness of fit was evaluated on the basis of the magnitude and randomness of the residuals, expressed as the difference between the experimental data and the theoretical curve and also by checking each of the tit parameters for physical reasonability. The molecular weight and partial specific volume of each protein were determined using Sedenterp v 1.01, and the data were factored into the equation for the determination of homoaffinity (TABLE 3).

TABLE 3

| Mutant | Molecular Weight | Partial Specific Volume |
|---|---|---|
| WtEYFP | 26796.23 | 0.7332 |
| His$_6$ wtEYFP | 30534.26 | 0.7273 |
| His$_6$ EYFP A206K | 30593.37 | 0.7277 |
| EYFP L221K | 30551.29 | 0.7270 |
| His$_6$ EYFP L221K | 30549.27 | 0.7271 |
| His$_6$ EYFP F223R | 30543.27 | 0.7270 |
| His$_6$EYFP L221K/F223R | 30560.30 | 0.7267 |

In addition, dissociation constants ($K_d$) derived from the data generated by analytical ultracentrifugation are shown for some proteins (TABLE 4).

TABLE 4

| Protein | $K_d$(mM) |
|---|---|
| His$_6$ wtEYFP | 0.11 |
| His$_6$ wtEYFP L221K | 9.7 |
| His$_6$ wtEYFP F223R | 4.8 |
| His$_6$ wtEYFP A206K | 74 |
| His$_6$ wtEYFP L221K/F223R | 2.4 |

For experiments in living cells, ECFP (SEQ ID NO: 11; "wtECFP") and EYFP-V68L/Q69K (SEQ ID NO: 12; "wtEYFP") targeted to the plasma membrane (PM) were subcloned into the mammalian expression vector, pcDNA3 (Invitrogen Corp.) and mutagenized and sequenced as described above. Targeting of the GFP variants to the PM was accomplished by making either N-terminal or C-terminal fusions of the GFP variant to short peptides containing a consensus sequence for acylation and/or prenylation (post-translational lipid modifications). The cDNAs of the PM targeted GFP variants were transfected and expressed in either HeLa cells or MDCK cells, and the expression pattern and degree of association were determined using fluorescent microscopy. FRET efficiency was measured to determine the degree of interaction of the PM-ECFP and PM-EYFP-V68L/Q69K. Analysis of the interactions by the FRET donor-dequench method (Miyawaki and Tsien, supra, 2000) demonstrated that the wtECFP and wtEYFP interacted in a manner that was dependent upon the association of the wtECFP and wtEYFP, and that this interaction was effectively eliminated by changing the amino acids in the hydrophobic interface to any one or a combination of the mutations A206K, L221K and F223R.

These results demonstrate that the solution oligomeric state of Aequorea GFP and its spectral variants, and dimer mutants derived therefrom, were accurately determined by analytical ultracentrifugation. The ECFP (SEQ ID NO: 11) and EYFP-V68L/Q69K (SEQ ID NO: 12) GFP spectral variants formed homodimers with a fairly high affinity of about 113 μM. By using site directed mutagenesis, the amino acid composition was altered so as to effectively eliminate dimerization and the cell biological problems associated with it. Thus, the modified fluorescent proteins provide a means to use FRET to measure the associative properties of host proteins fused to the modified CFP or YFP. The ambiguity and potential for false positive FRET results associated with ECFP (SEQ ID NO: 11) and EYFP-V68L/Q69K (SEQ ID NO: 12) dimerization have been effectively eliminated, as has the possibility of misidentification of the subcellular distribution or localization of a host protein due to dimerization of GFPs.

The-Renilla GFP and the Discosomd red fluorescent protein are obligate oligomers in solution. Because it was generally believed that Aequorea GFP could also dimerize in solution, and because GFP crystallizes as a dimer, the present investigation was designed to characterize the oligomeric state of GFP. The crystallographic interface between the two monomers included many hydrophilic contacts as well as several hydrophobic contacts (Yang et al., supra, 1996). It was not immediately clear, however, to what degree each type of interaction contributed to the formation of the dimer in solution.

As disclosed herein, the extent of GFP self-association was examined using sedimentation equilibrium, analytical ultracentrifugation, which is very useful for determining the oligomeric behavior of molecules both similar (self associating homomeric complexes) and dissimilar (heteromeric complexes; see Laue and Stafford, Ann. Rev. Biophys. Biomol. Struct. 28:75-100, 1999). In contrast to X-ray crystallography, the experimental conditions used in the analytical ultracentrifugation experiments closely approximated cellular physiological conditions. Monomer contact sites identified by X-ray crystallography within a multimeric complex are not necessarily the same as those in solution. Also in contrast to analytical ultracentrifugation, X-ray crystallography alone cannot provide definitive information about the affinity of the complex. The results of this investigation demonstrate that replacement of the hydrophobic residues A206, L221 and F223 with residues containing positively charged side chains (A206K, L221K and F223R) eliminated dimerization as determined by analytical ultracentrifugation in vitro and by analysis of the concentration dependence of FRET in intact cells.

Example 3

Characterization of the Coral Red Fluorescent Protein, DsRed, and Mutants Thereof This example describes the initial biochemical and biological characterization of DsRed and DsRed mutants.

The coding sequence for DsRed was amplified from pDsRed-N1 (Clontech Laboratories) with PCR primers that added an N terminal BamHI recognition site upstream of the initiator Met codon and a C terminal Eco RI site downstream of the STOP codon. After restriction digestion, the PCR product was cloned between the Bam HI and Eco RI sites of pRSET$_B$ (Invitrogen), and the resulting vector was amplified in DH5α bacteria. The resulting plasmid was used as a template for error-prone PCR (Heim and Tsien, Curr. Biol. 6:178-182, 1996, which is incorporated herein by reference) using primers that were immediately upstream and downstream of the DsRed coding sequence, theoretically allowing mutation of every coding base, including the initiator Met. The " mutagenized PCR fragment was digested with Eco RI and Bam HI and recloned into pRSET$_B$. Alternatively, the Quick-Change mutagenesis kit (Stratagene) was used to make directed mutations on the pRSET$_B$-DsRed plasmid.

In both random and directed mutagenesis studies, the mutagenized plasmid library was electroporated into JM109 bacteria, plated on LB plates containing ampicillin, and screened on a digital imaging device (Baird et al., *Proc. Natl. Acad. Sci., USA* 96:11242-11246, 1999, which is incorporated herein by reference). This device illuminated plates with light from a 150 Watt xenon arc lamp, filtered through bandpass excitation filters and directed onto the plates with two fiber optic bundles. Fluorescence emission from the plates was imaged through interference filters with a cooled CCD camera. Images taken at different wavelengths could be digitally ratioed using MetaMorph software (Universal Imaging) to allow identification of spectrally shifted mutants. Once selected, the mutant colonies were picked by hand into LB/Amp medium, after which the culture was used for protein preparation or for plasmid preparations. The DsRed mutant sequences were analyzed with dye-terminator dideoxy sequencing.

DsRed and its mutants were purified using the N-terminal polyhistidine tag (SEQ ID NO: 22; see Example 1) provided by the pRSETB expression vector (see Baird et al., supra, 1999). The proteins were microconcentrated and buffer exchanged into 10 mM Tris (pH 8.5) using a Microcon-30 (Amicon) for spectroscopic characterization. Alternatively, the protein was dialyzed against 10 mM Tris (pH 7.5) for oligomerization studies because microconcentration resulted in the production of large protein aggregates. To test for light sensitivity of protein maturation, the entire synthesis was repeated in the dark, with culture flasks wrapped in foil, and all purification was performed in a room that was dimly lit with red lights. There was no difference in protein yield or color when the protein was prepared in light or dark.

Numbering of amino acids conforms to the wild type sequence of drFP583 (DsRed; Matz et al., *Nature Biotechnology* 17:969-973 [1999]), in which residues 66-68, Gln-Tyr-Gly, are homologous to the chromophore-forming residues (65-67, Ser-Tyr-Gly) of GFP. The extra amino acid introduced by Clontech after the initiator Met was numbered "1a" and the residues of the N-terminal polyhistidine tag were numbered −33 to −1.

Fluorescence spectra were taken with a Fluorolog spectrofluorimeter. Absorbance spectra of proteins were taken with a Cary UV-Vis spectrophotometer. For quantum yield determination, the fluorescence of a solution of DsRed or DsRed K83M in phosphate buffered saline was compared to equally absorbing solutions of Rhodamine B and Rhodamine 101 in ethanol. Corrections were included in the quantum yield calculation for the refractive index difference between ethanol and water. For extinction coefficient determination; native protein absorbance was measured with the spectrophotometer, and protein concentration was measured by the BCA method (Pierce).

The pH sensitivity of DsRed was determined in a 96 well format by adding 100 µL of dilute DsRed in a weakly buffered solution to 100 µL of strongly buffered pH solutions in triplicate (total 200 µL per well) for pH 3 to pH 12. The fluorescence of each well was measured using a 525-555 nm bandpass excitation filter and a 575 nm long pass emission filter. After the 96 well fluorimeter measurements were taken, 100 µl of each pH buffered DsRed solution was analyzed on the spectrofluorimeter to observe pH-dependent spectral shape changes. For time-trials of DsRed maturation, a dilute solution of freshly synthesized and purified DsRed was made in 10 mM Tris (pH 8.5), and this solution was stored at room temperature in a stoppered cuvette (not airtight) and subjected to periodic spectral analysis. For mutant maturation data, fluorescence emission spectra (excitation at 475 nm or 558 nm) were taken directly after synthesis and purification, and then after more than 2 months storage at 4° C. or at room temperature.

Quantum yields for photodestruction were measured separately on a microscope stage or in a spectrofluorimeter. Microdroplets of aqueous DsRed solution were created under oil on a microscope slide and bleached with 1.2 W/cm$^2$ of light through a 525-555 nm bandpass filter. Fluorescence over time was monitored using the same filter and a 563-617 nm emission filter. For comparison, EGFP (containing mutations F64L, S65T; SEQ ID NO: 13) and EYFP-V68L/Q69K (also containing mutations S65G, S72A, T203Y; SEQ ID NO: 12) microdroplets were similarly bleached with 1.9 W/cm$^2$ at 460-490 nm while monitoring at 515-555 and 523-548 nm, respectively.

For the spectrofluorimeter bleaching experiment, a solution of DsRed was prepared in a rectangular microcuvette and overlaid with oil so that the entire 50 µL of protein solution resided in the 0.25 cm×0.2 cm×1 cm illumination volume. The protein solution was illuminated with 0.02 W/cm$^2$ light from the monochromator centered at 558 nm (5 nm bandwidth). Fluorescence over time was measured at 558 nm excitation (1.25 nm bandwidth) and 583 nm emission. Quantum yields ($\Phi$) for photobleaching were deduced from the equation $\Phi = (\epsilon \cdot I \cdot t_{90\%})^{-1}$, where $\epsilon$ is the extinction coefficient in cm$^2$mol$^{-1}$, I is the intensity of incident light in einsteins cm$^{-2}$s$^{-1}$ and $t_{90\%}$ is the time in seconds for the fluorophore to be 90% bleached (Adams et al., *J. Am. Chem. Soc.* 110:3312-3320, 1988, which is incorporated herein by reference).

Polyhistidine-tagged DsRed, DsRed K83M and wild type *Aequorea* GFP (SEQ ID NO: 10) were nm on a 15% polyacrylamide gel without denaturation. To prevent denaturation, protein solutions (in 10 mM Tris HCl, pH 7.5) were mixed 1:1 with 2×SDS-PAGE sample buffer (containing 200 mM dithiothreitol) and loaded directly onto the gel " without boiling. A broad range pre-stained molecular weight marker set (BioRad) was used as a size standard. The gel was then imaged on an Epson 1200 Perfection flatbed scanner.

Purified recombinant DsRed was dialyzed extensively against phosphate buffered saline (pH 7.4) or 10 mM Tris, 1 mM EDTA (pH 7.5). Sedimentation equilibrium experiments were performed on a Beckman Optima XL-I analytical ultracentrifuge at 20° C. measuring absorbance at 558 nm as a function of radius. 125 µL samples of DsRed at 3.57 µM (0.25 absorbance units) were loaded into 6 channel cells. The data were analyzed globally at 10,000, 14,000, and 20,000 rpm by nonlinear least-squares analysis using the Origin software package (Beckman). The goodness of fit was evaluated on the basis of the magnitude and randomness of the residuals, expressed as the difference between the experimental data and the theoretical curve and also by checking each of the fit parameters for physical reasonability.

FRET between immature green and mature red DsRed was examined in mammalian cells. DsRed in the vector pcDNA3 was transfected into HeLa cells using Lipofectin, and 24 hr later the cells were imaged on a fluorescence microscope. The fluorescences of the immature green. species (excitation 465-495 nm, 505 nm dichroic, emission 523-548 nm) and of mature red protein (excitation 529-552 nm, 570 nm dichroic, emission 563-618 nm) were measured with a cooled CCD camera. These measurements were repeated after selective photobleaching of the red component by illumination with light from the xenon lamp, filtered only by the 570 nm dichroic, for cumulative durations of 3, 6, 12, 24, and 49 min. By the final time, about 95% of the initial red emission had disappeared, whereas the green emission was substantially enhanced.

Yeast two hybrid assays were also performed. The DsRed coding region was cloned in-frame downstream of the Gal4 activation domains (the "bait"; amino acid residues 768-881) and DNA binding domains (the "prey"; amino acid residues 1-147) in the pGAD GH and pGBT9 vectors, respectively, (Clontech). These DsRed two hybrid plasmids were transformed into the HF7C strain of S. cerevisiae, which cannot synthesize histidine in the absence of interaction between the proteins fused to the Gal4 fragments. Yeast containing both DsRed-bait and DsRed-prey plasmids were streaked on medium lacking histidine and assayed for growth by visually inspecting the plates. Alternatively, the yeast were grown on filters placed on plates lacking tryptophan and leucine to select for the bait and prey plasmids. After overnight growth, the filters were removed from the plates, frozen in liquid nitrogen, thawed, and incubated in X-gal overnight at 30° C. and two days at 4° C. to test for β-galactosidase activity (assayed by blue color development). In both the β-galactosidase and histidine growth assays, negative controls consisted of yeast containing bait and prey plasmids, but only the bait or the prey was fused to DsRed.

Surprisingly, DsRed took days at room temperature to reach full red fluorescence. At room temperature, a sample of purified protein initially showed a major component of green fluorescence (excitation and emission maxima at 475 and 499 nm, respectively), which peaked in intensity at about 7 hr and decreased to nearly zero over two days. Meanwhile, the red fluorescence reached half its maximal fluorescence after approximately 27 hr and required more than 48 hr to reach greater than 90% of maximal fluorescence (see Baird et al., supra, 2000).

Fully matured DsRed had an extinction coefficient of 75,000 $M^{-1}cm^{-1}$ at its 558 nm absorbance maximum and a fluorescence quantum yield of 0.7, which is much higher than the values of 22,500 $M^{-1}cm^{-1}$ and 0.23 previously reported (Matz et al., *Nature Biotechnology* 17:969-973 [1999]). These properties make mature DsRed quite similar to rhodamine dyes in wavelength-and brightness. Unlike most GFP variants, DsRed displayed negligible (<10%) pH-dependence of absorbance or fluorescence from pH 5 to 12. (see Baird et al., supra, 2000). However, acidification to pH 4-4.5 depressed both the absorbance and excitation at 558 nm relative to the shorter wavelength shoulder at 526 nm, whereas the emission spectrum was unchanged in shape. DsRed was also relatively resistant to photobleaching. When exposed to a beam of 1.2 $W/cm^2$ of approximately 540 nm light in a microscope stage, microdroplets of DsRed under oil took 1 hr to bleach 90%, whereas 20 $mW/cm^2$ of 558 nm light in a spectrofluorimeter microcuvette required 83 hr to bleach 90%. The microscope and fluorimeter measurements, respectively, gave photobleach quantum efficiencies of $1.06 \times 10^{-6}$ and $4.8 \times 10^{-7}$ (mean of $7.7 \times 10^{-7}$). Analogous microscope measurements of EGFP (S65T; SEQ ID NO: 13) and EYFP-V68L/Q69K (SEQ ID NO: 12; including Q69K) gave $3 \times 10^{-6}$ and $5 \times 10^{-5}$, respectively.

In an effort to examine the nature of the red chromophore and to identify DsRed variants useful as biological indicators, DsRed was mutagenized randomly and at specific sites predicted by sequence alignment with GFP to be near the chromophore. Many mutants that matured more slowly or not at all were identified, but none were identified that matured faster than DsRed. Screening of random mutants identified mutants that appeared green or yellow, which was found to be due to substitutions K83E, K83R, S197T, and Y120H. The green fluorescence was due to a mutant species with excitation and emission maxima at 475 and 500 nm, respectively, whereas the yellow was due to a mixture of this green species with DsRed-like material, rather than to a single species at intermediate wavelengths.

The DsRed K83R mutant had the lowest percentage conversion to red in this series of experiments, and proved very useful as a stable version of the immature green-fluorescing form of DsRed (see Baird et al., supra, 2000). Further directed mutagenesis of K83 yielded more green and yellow mutants that were impaired in chromophore maturation. In many of the K83 mutants that matured slowly and incompletely, the red peak was at longer wavelengths than DsRed. K83M was particularly interesting because its final red-fluorescing species showed a 602 nm emission maximum, with relatively little residual green fluorescence and a respectable quantum yield, 0.44. However, its maturation was slower than that of the wild type DsRed. Y120H had a red shift similar to that of K83M and appeared to produce brighter bacterial colonies, but also maintained much more residual green fluorescence.

Spectroscopic data of the DsRed mutants are shown in FIG: 15. In this FIG., "maturation" of protein refers to the rate of appearance of the red fluorescence over the two days after protein synthesis. Because some maturation occurs during the synthesis and purification (which take 1-2 days), numerical quantification is not accurate. A simple +/−rating system was used, wherein (−−) means very little change, (−) means a 2-5 fold increase in red fluorescence, (+) means 5-20 fold increase, and (++) indicates the wild type increase (approximately 40 fold). The red green ratio was determined two months after protein synthesis by dividing the peak emission fluorescence obtained at 558 nm excitation by the 499 nm fluorescence obtained at 475 nm excitation from the same sample. This does not represent a molar ratio of the two species because the ratio does not correct for differences in extinction coefficient or quantum yields between the two species, or the possibility of FRET between the two species if they are in a macromolecular complex.

To determine whether Lys70 or Arg95 can form imines with the terminal carbonyl of a GFP-like chromophore (see Tsien, *Nature Biotechnol.*, 17:956-957, 1999), DsRed mutants K70M, K70R, and R95K were produced. K70M remained entirely green with no red component, whereas K70R matured slowly to a slightly red-shifted red species. The spectral similarity of K70R to wild type DsRed argues against covalent incorporation of either amino acid into the chromophore. No fluorescence at any visible wavelength was detected from R95K, which might be expected because Arg95 is homologous to Arg96-of GFP, which is conserved in all fluorescent proteins characterized to date (Matz et al., *Nature Biotechnology* 17:969-973 [1999]). The failure of R95K to form a green chromophore prevented testing whether Arg95 was also required for reddening.

In view of the propensity of *Aequorea* GFP to form dimers at high concentrations in solution and in some crystal forms, and the likelihood that *Renilla* GFP forms an obligate dimer (Ward et al., In *Green Fluorescent Protein: Properties, Applications and Protocols*," eds. Chalfie and Kain, Wiley-Liss [1998]), the ability of DsRed to oligomerize was examined. Initial examination of the expressed proteins by SDS-PAGE suggested that aggregates formed, in that polyhistidine-tagged proteins DsRed and DsRed K83R migrated as red and yellow-green bands, respectively, at an apparent molecular weight of greater than 110 kDa when mixed with 200 mM DTT and not heated before loading onto the gel (see Baird et al., supra, 2000). In comparison, *Aequorea* GFP, when treated similarly, ran as a fluorescent green band near its predicted monomer molecular weight of 30 kDa. The high molecular weight DsRed band was not observed when the sample was briefly boiled before electrophoresis (see Gross et al., supra, 2000). Under these conditions, a band near the predicted monomer molecular weight of 30 kDa predominated and was colorless without Coomassie staining.

To determine the oligomerization status more rigorously, the DsRed protein was subjected to analytical equilibrium centrifugation (Laue and Stafford, supra, 1999). Global curve fitting of the absorbance data determined from the radial scans of equilibrated DsRed indicated that DsRed exists as an obligate tetramer in solution (Baird et al., supra, 2000), in both low salt and physiological salt concentrations. When the data was modeled with a single-species tetramer, the fitted molecular weight was 119,083 Da, which is in excellent agreement with the theoretical molecular weight of 119,068 Da for the tetramer of polyHis-tagged DsRed. Attempts to fit the curves with alternative stoichiometries from monomer to pentamer failed to converge or gave unreasonable values for the floating variables and large, non-random residuals. The residuals for the tetramer fit were much smaller and more randomly distributed, but were somewhat further improved by extending the model to allow the obligate tetramer to dimerize into an octamer, with a fitted dissociation constant of 39 µM. Thus the 558-nm-absorbing species appears to be tetrameric over the range of monomer concentrations from 14 nM to 11 µM in vitro. The hint of octamer formation at the highest concentrations is only suggestive because the highest concentrations of tetramer achieved in the ultracentrifugation cell remained more than an order of magnitude below the fitted dissociation constant.

To confirm whether DsRed also oligomerizes in live cells, FRET analysis was performed in mammalian cells and in two hybrid assays in yeast cells. HeLa cells were transfected with wild type DsRed and imaged 24 hr later, when they contained a mixture of the immature green intermediate and the final red form. The green fluorescence was monitored intermittently before and during selective photobleaching of the red species over 49 min of intense orange illumination. If the two proteins were non-associated, bleaching the red species would be expected to have no effect on the green fluorescence. In fact, however, the green fluorescence increased by 2.7 to 5.8 fold in different cells, corresponding to FRET efficiencies of 63% to 83%. These values equal or surpass the highest FRET efficiencies ever observed between GFP mutants, 68% for cyan and yellow fluorescent proteins linked by a zinc ion-saturated zinc finger domain (Miyawaki and Tsien, supra, 2000).

Additional evidence of in vivo oligomerization was provided by the directed yeast two hybrid screen. When DsRed fusions to the Gal4 DNA binding domain and activation domain were expressed in HF7C yeast, the yeast demonstrated a his' phenotype and were able to grow without supplemental histidine, indicating a two hybrid interaction had occurred. Neither fusion construct alone (DsRed-DNA binding domain or DsRed-activation domain) produced the his+ phenotype, indicating that a DsRed-DsRed interaction, and not a non-specific DsRed-Gal4 interaction, was responsible for the positive result. In addition, the his+ yeast turned blue when lysed and incubated with X-gal, suggesting that the DsRed-DsRed interaction also drove transcription of the θ-galactosidase gene. Thus, two separate transcriptional measurements of the yeast two hybrid assay confirmed that DsRed associates in vivo.

This investigation of DsRed revealed that DsRed has many desirable properties, as well as some nonoptimal properties, with respect to its being useful to complement or as an alternative to GFPs. One of the most important favorable properties identified was that DsRed has a much higher extinction coefficient and fluorescence quantum yield (0.7) than was previously reported, such that the fluorescence brightness of the mature well-folded protein is comparable to rhodamine dyes and to the best GFPs.

DsRed also is quite resistant to photobleaching by intensities typical of spectrofluorimeters ($mW/cm^2$) or microscopes with arc lamp illumination and interference filters ($W/cm^2$), showing a photobleaching quantum yield on the order of $7 \times 10^{-7}$ in both regimes. This value is significantly better than those for two of the most popular green and yellow GFP mutants, EGFP ($3 \times 10^{-6}$) and EYFP-V68L/Q69K ($5 \times 10^{-5}$). The mean number of photons that a single molecule can emit before photobleaching is the ratio of the fluorescence and photobleaching quantum yields, or $1 \times 10^6$, $2 \times 10^5$, and $1.5 \times 10^4$ for DsRed, EGFP, and EYFP-V68L/Q69K, respectively. A caveat is that the apparent photobleaching quantum yield might well increase at higher light intensities and shorter times if the molecule can be driven into dark states such as triplets or tautomers from which it can recover its fluorescence. GFPs usually show a range of such dark states (Dickson et al., Nature 388:355-358, 1997; Schwille et al., Proc. Natl. Acad. Sci., USA 97:151-156, 2000), and there is no reason to expect that DsRed will be any simpler. The photobleaching measurements described herein were made over minutes to hours, and include ample time for such recovery. In contrast, fluorescence correlation spectroscopy and flow cytometry monitor single passages of molecules through a focused laser beam within microseconds to milliseconds, such that temporary dark states that last longer than the transit time count as photobleaching, raising the apparent quantum yield for bleaching. Techniques such as laser scanning confocal microscopy, in which identified molecules are repetitively scanned, will show intermediate degrees of photobleaching depending on the time scale of illumination and recovery.

Another desirable feature of DsRed is its negligible sensitivity to pH changes over the wide range (pH 4.5 to 12). The currently available brighter GFP mutants are more readily quenched than DsRed by acidic pH. Such pH sensitivity can be exploited under controlled conditions to sense pH changes, especially inside organelles or other specific compartments (see Llopis et al., Proc. Natl. Acad. Sci., USA 95:6803-6808, 1998), although this feature can cause artifacts in some applications.

DsRed mutants such as K83M demonstrate that DsRed can be pushed to longer wavelengths (564 and 602 nm excitation and emission maxima), while retaining adequate quantum efficiency (0.44). The 6 nm and 19 nm bathochromic shifts correspond to 191 $cm^{-1}$ and 541 $cm^{-1}$ in energy, which are of respectable magnitude for a single amino acid change that does not modify the chromophore. A homolog of DsRed recently cloned from a sea anemone has an absorbance maximum at 572 nm and extremely weak emission at 595 nm with quantum yield <0.001; one mutant had an emission peak at 610 nm but was very dim and slow to mature (Lukyanov et al., J. Biol. Chem. 275:25879-25882, 2000, which is incorporated herein by reference).

Less desirable features of DsRed include its slow and incomplete maturation, and its capacity to oligomerize. A maturation time on the order of days precludes a use of DsRed as a reporter for short term gene expression studies and for applications directed to tracking fusion proteins in organisms that have short generation times or fast development. Since maturation of GFPs was considerably accelerated by mutagenesis (Heim et al., Nature 373:663-664, 1995, which is incorporated herein by reference), DsRed similarly can be mutagenized and variants having faster maturation times can be isolated.

Because the Lys83 mutants all permitted at least some maturation, it is unlikely that the primary amine plays a direct catalytic role for this residue, a suggestion supported by the observation that the most chemically conservative replacement, Lys to Arg, impeded red development to the greatest extent. Ser197 provided a similar result, in that the most conservative possible substitution, Ser to Thr, also significantly slowed maturation. Mutations at the Lys83 and Ser197 sites appeared several times independently in separate random mutagenesis experiments and, interestingly, Lys83 and Ser197 are replaced by Leu and Thr, respectively, in the highly homologous cyan fluorescent protein dsFP483 from the same *Discosoma* species. Either of the latter two mutations could explain why dsFP483 never turns red. Residues other than Lys83 and Ser197 also affected maturation to the red.

The multimeric nature of DsRed was demonstrated by four separate lines of evidence, including slow migration on SDS-PAGE unless pre-boiled, analytical ultracentrifugation, strong FRET from the immature green to the final red form in mammalian cells, and directed two hybrid assays in yeast using HIS3 and LacZ reporter genes. Analytical ultracentrifugation provided the clearest evidence for an obligate stoichiometry of four over the entire range of monomer concentrations assayed ($10^{-8}$ to $10^{-5}$ M), with a hint that octamer formation can occur at yet higher concentrations. In addition, the tests in live cells confirmed that aggregation occurs under typical conditions of use, including the reducing environment of the cytosol and the presence of native proteins.

While oligomerization of DsRed does not preclude its use as a reporter of gene expression, it can result in artifactual results in applications where DsRed is fused to a host protein, for example, to report on the trafficking or interactions of the host protein in a cell. For a host protein of mass M without its own aggregation tendencies, fusion with DsRed can result in the formation of a complex of at least 4(M+26 kDa). Furthermore, since many proteins in signal transduction are activated by oligomerization, fusion to DsRed and consequent association can result in constitutive signaling. For host proteins that are oligomeric, fusion to DsRed can cause clashes of stoichiometry, steric conflicts of quaternary structures, or crosslinking into massive aggregates. In fact, red chameleons, i.e., fusions of cyan fluorescent protein, calmodulin, and calmodulin-binding peptide, and DsRed, are far more prone to form visible punctae in mammalian cells than the corresponding yellow chameleons with yellow fluorescent protein in place of DsRed (Miyawaki et al., *Proc. Natl. Acad. Sci., USA* 96:2135-2140, 1999).

The results disclosed above indicate that variants of DsRed, like those of the GFPs, can be produced such that the propensity of the fluorescent protein to oligomerize is reduced or eliminated. DsRed variants can be constructed and examined, for example, using a yeast two hybrid or other similar assay to identify and isolate non-aggregating mutants. In addition, the X-ray crystallographic structure of DsRed can be examined to confirm that optimal amino acid residues are modified to produce a form of DsRed having a reduced propensity to oligomerize.

Example 4

DsRed Variants Having Reduced Propensity to Oligomerize

This example demonstrates that mutations corresponding to those introduced into GFP variants to reduce or eliminate oligomerization also can be made in DsRed to reduce the propensity of DsRed to form tetramers.

In view of the results described in Example 1 and guided by the DsRed crystal structure, amino acid residues were identified as potentially being involved in DsRed oligomerization. One of these amino acids, isoleucine-125 (I125), was selected because, in the oligomer, the I125 residues of the subunits were close to, each other in a pairwise fashion; i.e., the side chain of I125 of the A subunit was about 4 Angstroms from the side chain of I125 of the C subunit, and the I125 residues in the B and D subunits were similarly positioned. In addition, the area in which the I125 side chains reside exhibited hydrophobicity, analogous to that identified in *Aequorea* GFP variants, which was demonstrated to be involved in the inter-subunit interaction. Based on these observations, DsRed mutants containing substitutions of positively charged amino acids, Lys (K) and Arg (R), for I125 were generated.

DsRed 11 25K and I125R were prepared with the Quick-Change Mutagenesis Kit using the DsRed cDNA (SEQ ID NO: 23; Clontech) subcloned into the expression vector pRSETB (Invitrogen) as the template for mutagenesis. The primers for mutagenesis, with the mutated codons underlined, were as follows:

TABLE 5

| Primer | Sequence | SEQ ID NO |
|---|---|---|
| I125K (forward) | 5'-TAC AAG GTG <u>AAG</u> TTC AAG GGC GTG AAC TTC CCC-3' | 33 |
| I125K (reverse) | 5'-GGG GAA GTT CAC GCC <u>CTT</u> GAA CTT CAC CTT GTA-3' | 34 |
| I125R (forward) | 5'-TAC AAG GTG AAG TTC <u>CGC</u> GGC GTG AAC TTC CCC-3' | 35 |
| I125R (reverse) | 5'-GGG GAA GTT CAC GCC <u>GCG</u> GAA CTT CAC CTT GTA-3' | 36 |

The mutant proteins were prepared following standard methodology and analyzed with polyacrylamide gel electrophoresis as described (Baird et al., supra, 2000). For further analysis, DsRed I125R was dialyzed extensively in PBS, then diluted in PBS until the absorbance of the solution at 558 nm was 0.1. This solution was centrifuged in a Beckman XL-1 analytical ultracentrifuge in PBS at 10,000 rpm, 12,000 rpm, 14,000 rpm, and 20,000 rpm. Absorbance at 558 nm versus radius was determined and compared to a wild type tetrameric DsRed control (Baird et al., supra, 2000).

The DsRed I125K yielded a protein that became red fluorescent and was a mixture of dimer and tetramer as analyzed by non-denaturing polyacrylamide gel electrophoresis of the native protein. The same analysis of DsRed I125R revealed that the protein was entirely dimeric. The dimeric status of DsRed I125R was confirmed by analytical ultracentrifugation; no residual tetramer was detected. These results demonstrate that the interaction between the A:C subunits and the B:D subunits can be disrupted, thereby reducing the propensity of the DsRed variant to oligomerize. No attempt was made to disrupt the A:B and C:D interfaces. These results demonstrate that the method of reducing or eliminating oligomerization of the GFP variants as described in Example 1 is generally applicable to other fluorescent proteins that have a propensity to oligomerize.

Example 5

Preparation and Characterization of Tandem DsRed Dimers

This example demonstrates that a tandem DsRed protein can be formed by linking two DsRed monomers, and that such tandem DsRed proteins maintain emission and excitation spectra characteristic of DsRed, but do not oligomerize.

To construct tandem DsRed (tDsRed), a 3' primer, 5'-CCGGATCCCCTTTGGTGCTGCCCTCTCCGCT-GCCAGGCTTGCCGCTGCCGCTG GTGCTGCCAAG-GAACAGATGGTGGCGTCCCTCG-3' (SEQ ID NO: 37), was designed that overlapped the last 25 by of DsRed (derived from the Clontech vector pDsRed-N1) and encoded for the linker sequence GSTSGSGKPGSGEGSTKG (SEQ ID NO: 38), followed by a Bam HI restriction site in frame with the BamHI site of $pRSET_B$ (Invitrogen). It was later determined that the above primer sequence contains three mismatches in the overlap region and contained several codons that were not optimal for mammalian expression. Accordingly, a new 3' primer, 5'-CCGGATCCCCCTTGGTGCTGCCCTC-CCCGCTGCCGGGCTTCCCGCTCCCGCTG GTGCT-GCCCAGGAACAGGTGGTGGCGGCCCTCG-3' (SEQ ID NO: 39), also was used. The 5' primer, 5'-GTACGACGAT-GACGATAAGGATCC-3' (SEQ ID NO: 40) also contained a Bam HI restriction site in frame with the Bam HI site of $pRSET_B$.

PCR amplification of DsRed and of DsRed-I125R with the new linker was accomplished with Taq DNA polymerase (Roche) and an annealing protocol that included 2 cycles at 40° C., 5 cycles at 43° C., 5 cycles at 45° C., and 15 cycles at 52° C. The resulting PCR product was purified by agarose gel-electrophoresis and digested with Bam HI (New England Biolabs). Bam HI and calf intestinal phosphatase (New England Biolabs) treated vector was prepared from pRSETB with DsRed or DsRed-I125R inserted in frame with the His-6 (SEQ ID NO:120) tag and between the 5' Bam HI and 3' Eco RI restriction sites.

Following ligation of the digested PCR products and vector with T4 DNA ligase (NEB), the mixture was used to transform competent *E. coli* DH5α by heat shock. Transformed colonies were grown on LB agar plates supplemented with the antibiotic ampicillin. Colonies were picked at random, and plasmid DNA was isolated through standard miniprep procedures (Qiagen). DNA sequencing was used to confirm the correct orientation of the inserted sequence.

In order to express protein; the isolated and sequenced vectors were used to transform competent *E. coli* JM109 (DE3). Single colonies grown on LB agar/ampicillin were used to inoculate 1 liter cultures of LB/ampicillin, then were grown with shaking at 225 rpm and 37° C. until the broth reached an $OD_{600}$ of 0.5-1.0. IPTG was added to a final concentration of 100 mg/l and the culture was grown for either 5 hr at 37° C. (tDsRed) or 24 hr at room temperature (RT; tDsRed-I125R). Cells were harvested by centrifugation (10 min, 5000 rpm), the pellet was resuspended in 50 mM Tris pH 7.5, and the cells were lysed by a single pass through a French press. Protein was purified by Ni-NTA (Qiagen) chromatography as described by the manufacturer and was stored in the elution buffer or was dialyzed into 50 mM Tris, pH 7.5.

With respect to the excitation and emission spectra as well as the maturation time of tDsRed and tDsRed-I125R, the proteins behaved identically to their untethered counterparts. As expected, tDsRed developed visible fluorescence within approximately 12 hr at room temperature, while tDsRed-I125R required several days before significant red color developed. The maturation of tDsRed-I125R continued for up to approximately 10 days. The excitation and emission maxima were unchanged at 558 nm and 583 nm, respectively.

The differences in the tandem dimer became apparent when the proteins were analyzed by SDS-polyacrylamide electrophoresis. Due to the high stability of the tetramer, DsRed that was not subjected to boiling migrated with an apparent molecular mass of about 110 kDa. In addition, the band on the gel, which corresponded to a DsRed tetramer, retained its red fluorescence, indicating that the rigid barrel structure of each monomer was intact. When the sample was boiled before loading, DsRed was non-fluorescent and presumably denatured, and ran as a monomer of approximately 32 kDa.

SDS-PAGE analysis confirmed the tandem structure of the expressed red fluorescent proteins, tDsRed and tDsRed-I125R. The unboiled tDsRed migrated at the same apparent molecular mass (about 110 kDa) as unboiled normal DsRed. The difference in their molecular structures only was apparent when the samples were boiled (denatured) before they were loaded onto the gel. Boiled tDsRed migrated with an apparent molecular mass of about 65 kDa, which is approximately the mass of two DsRed monomers, whereas boiled DsRed migrated at the monomer molecular mass of 32 kDa.

A similar comparison was made for DsRed-I125R and tDsRed-I125R. When they were not boiled prior to SDS-PAGE, tDsRed-I125R and DsRed-I125R both migrated as dimers with an apparent molecular mass of about 50 kDa. DsRed-I125R that was not boiled also had a large component that appeared to be denatured, though the fluorescent band for the dimer (50 kDa) was clearly visible. tDsRed-I125R also had a denatured component that migrated slower (65 kDa vs. 50 kDa) than the intact fluorescent species. However, when boiled, tDsRed-I125R migrated at approximately the same mass as two monomers (65 kDa), while DsRed-I125R migrated at the monomer molecular mass of 32 kDa.

These results demonstrate that linking two DsRed monomers to form an intramolecularly bound tandem dimer prevented formation of intermolecular oligomers, without affecting the emission or excitation spectra of the red fluorescent proteins.

Example 6

Red Fluorescent Proteins with Improvement Efficiency of Maturation Wild-Type DsRed and Q66M DsRed Maturation In an attempt to improve the speed and efficacy of maturation, Q66 of dsRed was converted by site-directed mutagenesis to every other naturally occurring amino acid. Only picking fluorescent colonies, it was determined that almost all single-mutations at this position (F, N, G, T, H, E, K, D, R, L, Q were deleterious, leading to loss of fluorescence, or inability to mature to a red fluorescent species. One substitution, however, Q66M, yielded a protein that had significantly improved properties.

Figure 26:
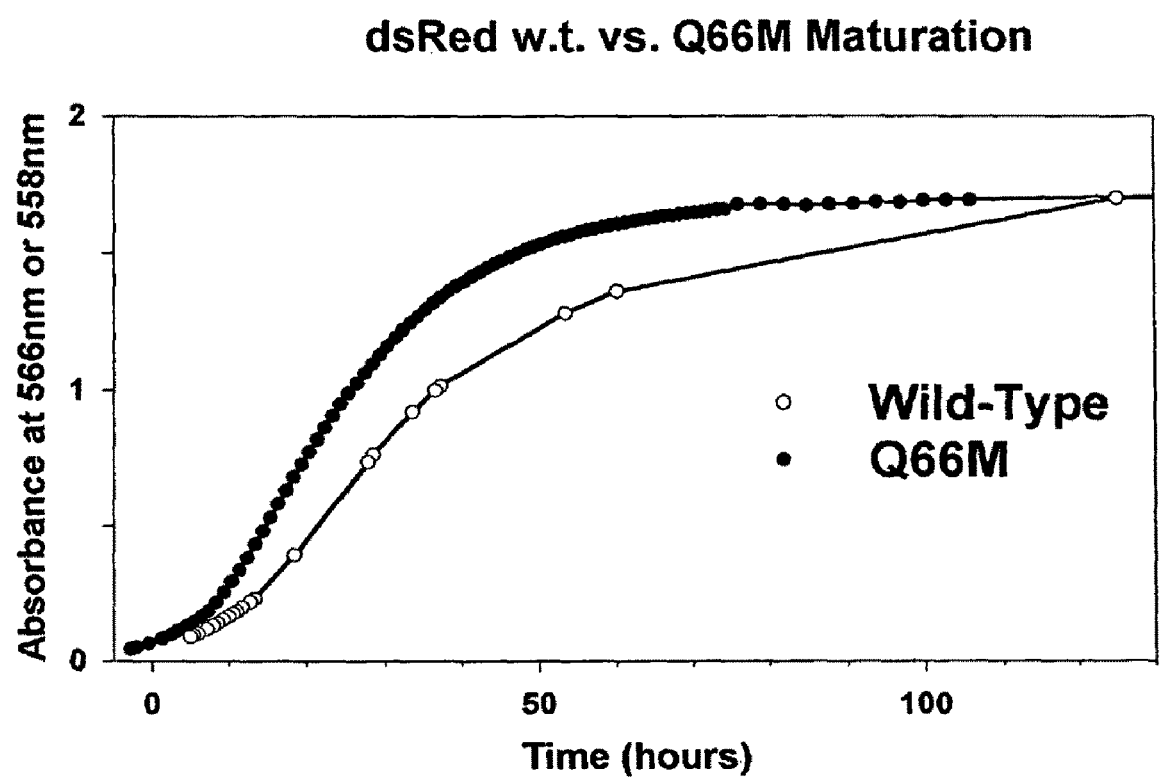
FIG. 26 illustrates the maturation of Q66M DsRed relative to the wild-type DsRed protein.

First, wild-type DsRed and Q66M DsRed were both produced in bacteria (*E. coli*) quickly purified, and allowed to mature in a cuvette sealed with parafilm. Parafilm was chosen to allow oxygen to diffuse into the protein solution, and to prevent the loss of water from the solution. The maturation was monitored by taking absorbance scans over time. FIG. 26 plots maturation as peak absorbance of the red chromophore versus time. Since the proteins were not expressed instantaneously or with the exact same efficiency, the two different curves did not both start at the same value, and they reached slightly different end values. To allow comparison, both curve amplitudes were first normalized to the same final absorbance. Then, the curves were fit to a three component kinetic model, and the time base for each scan was adjusted so that the curves intersected at zero time.

Wild-type DsRed and Q66M DsRed Fluorescence

Figure 27:
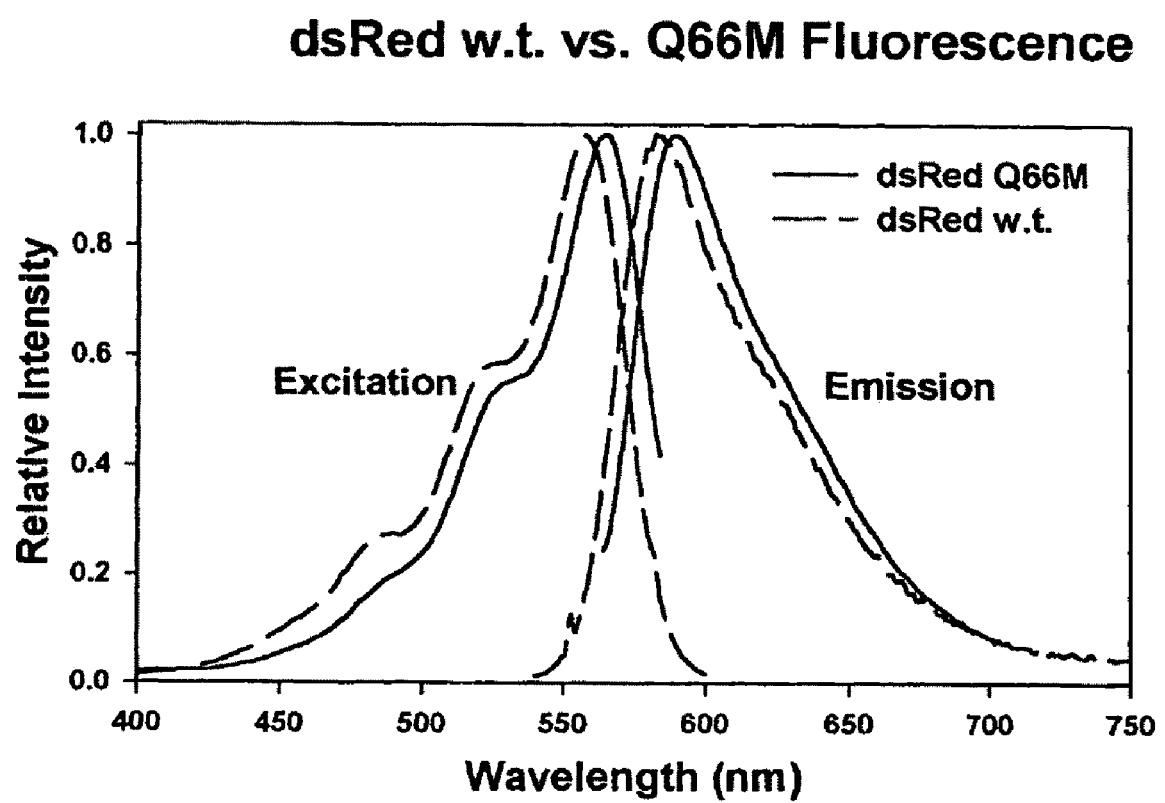
FIG. 27 shows the excitation and emission spectra of wild-type DsRed (dsRed w.t.) and Q66M DsRed (dsRED Q66M), plotting relative intensity as a function of wavelength.

Fluorescence emission and excitation spectra of wild-type DsRed and the Q66M DsRed variant were taken using 558 nm excitation or monitoring 583 nm emission for DsRed, and by using 566 nm excitation or monitoring 590 nm emission for Q66M DsRed. The results are shown in FIG. 27. Of note is the prominent red-shift of the entire Q66M DsRed fluorescence spectrum, as well as the marked depression of the excitation shoulder at 480 nm for Q66M DsRed relative to wild-type.

Q66M DsRed Completeness of Maturation

Figure 28:
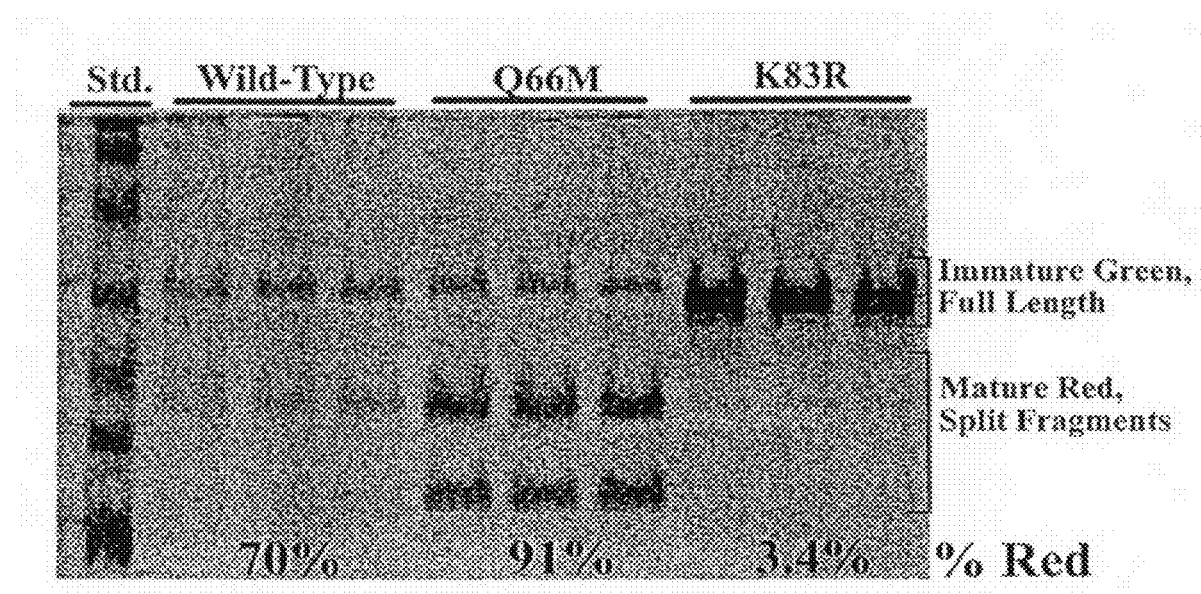
FIG. 28 shows Coomassie-stained bands on SDS-polyacrylamide gel, representative of wild-type DsRed, Q66M DsRed and K83DsRed after hydrolysis at pH 1. The completeness of red chromophore maturation for each species is given as a percentage of polypeptide hydrolysis at pH 1.0 (% Red).

Wild-type DsRed, Q66M DsRed, and another DsRed variant, K83R DsRed were subjected to brief boiling in pH 1 HCl, and then run on an SDS polyactylamide gel. Since red chromophore formation makes the protein acid labile at residue 66, the relative amount of hydrolysis products versus full-length protein is indicative of the completeness of maturation. The gel was Coomassie stained and imaged with a flat-bed scanner, and the relative intensity of all of the bands was then quantified using the software NIH Image. After normalizaation for molecular weights (since the darkness of a Coomassie-stainer band is related to the mass of protein in the band, not the molarity), the maturation completeness was calculated by dividing the normalized intensity of the split fragments' bands by the normalized intensity of the sum of all the bands. The results are shown in FIG. 28. As expected for K83R DsRed, which contains only a trace amount of red protein, only full-length protein is visible. However, wild-type DsRed is degraded roughly ⅔ into split fragments, and Q66M DsRed is almost completely degraded into split fragments.

In conclusion, when Q66M DsRed was expressed in bacteria, the bacteria appeared to become fluorescent slightly faster than bacteria expressing wild-type DsRed. Furthermore, the Q66M DsRed protein appeared to be a-deeper pink color than wild-type DsRed, which has an orange tinge. Finally, the excitation spectrum of Q66M DsRed has a significantly smaller hump at 480 nm than wild-type DsRed, suggesting that the species absorbing at 480 nm (the immature green form of the protein) was is less abundant. These data together show that Q66M DsRed has significantly improved properties over the wild-type DsRed protein.

Example 7

Preparation of a Further Improved Variant of the Monomeric Red Fluorescent Protein, mRFP1

The engineering of the monomeric DsRed, mRFP 1 (SEQ ID NO: 8), as described in the previous examples, has overcome at least three problems associated with the use of unmodified DsRed as a genetically encoded red fluorescent fusion label. Specifically, (1) mRFP1 is monomeric, (2) it matures rapidly, and (3) is not efficiently excited at wavelengths suitable for imaging of GFP. However mRFP1 is relatively dim (extinction coefficient (EC) of 44,000 $M^{-1}$ and quantum yield (QY) of 0.25) and therefore limited in certain applications. In an effort to improve the brightness of mRFP1 the strategy of directed evolution by randomizing specific residues has been continued, in the hope of finding variants with improved spectral properties.

Figure 29:
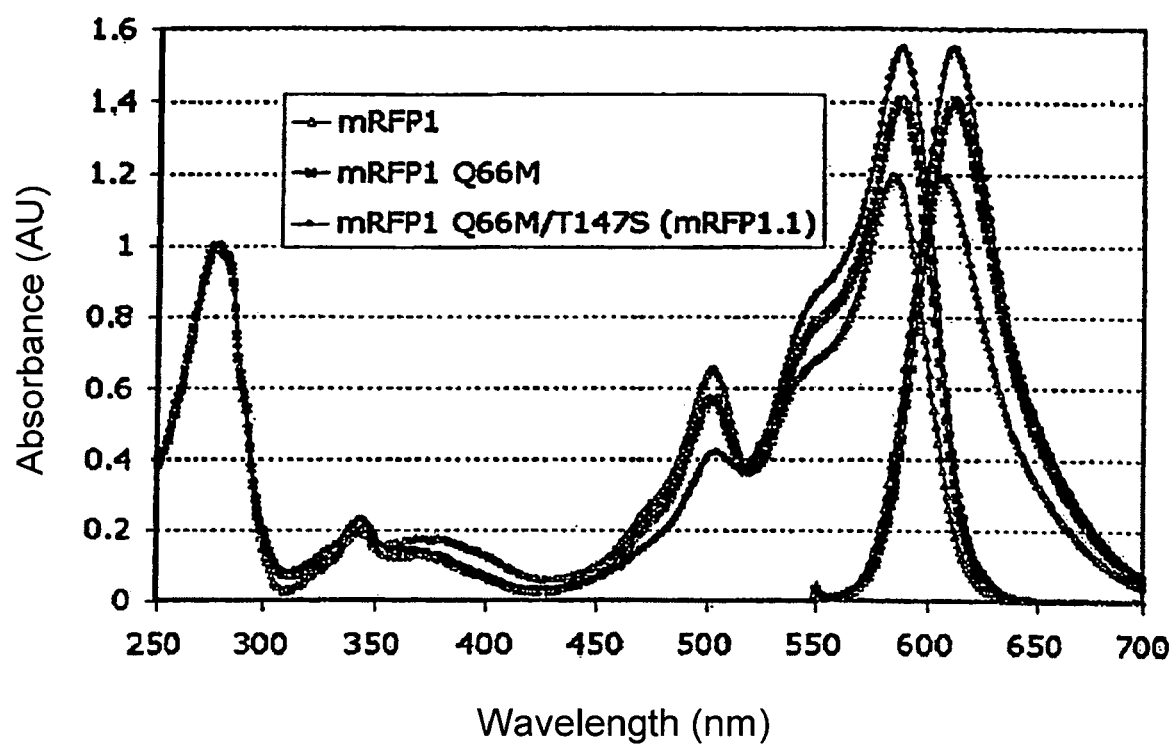
FIG. 29 shows the absorption spectrum of mRFP1, mRFP Q66M, and mRFP1.1. The absorption spectrum is normalized to the 280 nm peak which should approximate the total protein concentration. The emission spectrum (measured with excitation at 550 nm) is normalized to its respective absorption maximum for sake of representation.

In the first such library to improve the properties of mRFP 1 the following codon substitutions were made in the mRFP1 cDNA:

N42Q to NNK=all 20 amino acids
V44A to NNK=all 20 amino acids
L46 to MTC=1 or L
Q66 to NNK=all 20 amino acids
K70 to ARG=K or R
V71A to GYC=V or A This library contains a genetic diversity of 262,144 cDNAs which encode for 64,000 different amino acid sequences. This library was transformed into *E. coli* JM109(DE3) and bacterial colonies were manually screened (~50,000 independent colonies) as described in the previous examples. Colonies that exhibited improved brightness or were a different color were picked and the gene was sequenced to determine the amino acid substitution. Top clones identified from this library fell into several different categories including:

Red-Shifted Variants:
Q66M+T147S; x588m610, EC ~58,000 $M^{-1}$, QY ~0.25
Q66M; x588m610, EC ~52,000 $M^{-1}$, QY ~0.25
Blue-Shifted Variants:
Q66T+Q213L; x574m595, EC ~34,000 $M^{-1}$, QY ~0.25
Q66T; x564m581, EC ~23,000 $M^{-1}$, QY ~0.25
Q66S; x558m578, dimmer than Q66T
Other Interesting Variants:
N42H+Q66G; x504m516, dim
V44M+Q66G; x504m516, dim
Q66L; absorbance maximum at 502 nm, practically non-fluorescent The top mutant isolated from this library is mRFP1+Q66M/T147S, which has been designated mRFP 1.1. Although this variant does not improve the quantum yield relative to mRFP1, mRFP1.1 is ~30% brighter than mRFP1 due to an improved EC. This improvement is due to an apparent increase in the fraction of the protein that forms the mature red chromophore at the expense of the non-fluorescent species that absorbs at 502 nm (see FIG. 29, presenting the absorption and emission spectrum of mRFP1.1). The beneficial T147S mutant arose from an error during PCR amplification of the cDNA due to the use of Taq polymerise. The Q66M mutation has previously been shown to improve the fluorescence of the dimeric I125R variant of DsRed (Baird, G. S. (2001) *Ph.D. Thesis*, University of California, San Diego). The amino acid sequence of mRFP1.1 is shown in FIG. 30 (SEQ ID NO: 79), while the nucleotide sequence of mRFP1.1 is provided in FIG. 31 (SEQ ID NO: 80).

Example 8

Further Red Fluorescent Protein Variants

Further DsRed variants were produced using these methods. For example, FIG. 32 and TABLE 6 list some of these further variants. GFP termini are illustrated in FIG. 22B (SEQ ID NO:14 represents the N-terminus and SEQ ID NO:91 represents the C-terminus). An alternate variation of the C-terminal GFP sequence is provided in SEQ ID NO:110.

TABLE 6

| Designation | Mutations | Ex/Em | EC | QY |
|---|---|---|---|---|
| Dimer2.2MMM (dimer3) (dTomato) (SEQ ID NO: 81) | Dimer2 + GFP termini + V22M, Q66M, V104L, F124M | 554/581 | 70,000 | 0.72 |

TABLE 6-continued

| Designation | Mutations | Ex/Em | EC | QY |
|---|---|---|---|---|
| mRFP1.5 (SEQ ID NO: 83) | mRFP1.0 + GFP termini + ins(NNMA) after E6, V7I, T21S, Q66T, T147S, M182K, T195V | 585/612 | 60,000 | 0.25 |
| OrS4-9 (SEQ ID NO: 85) | mRFP1.0 + GFP termini + ins(NNMA) after E6, V7I, T21S, Q66T, T147S, M182K, T195V | 554/569 | 45,000 | 0.45 ± 0.05 |
| Y1.3 (mYOFP1.3) (mBanana) (SEQ ID NO: 87) | mRFP1.0 + GFP termini + ins(NNMA) after E6, Q66C, A77T, D78G, L83F, T108A, T147S, D174S, V177T, M182K, K194I, T195A, D196G, I197E, L199I, Q213L | 542/558 | 15,000 | 0.45 ± 0.05 |
| mFRFP (F2Q6) mGrape2 (SEQ ID NO: 89) | mRFP1.0 + GFP termini + ins(NNMA) after E6, V7I, E32K, Q66M, A77P, L83M, R125H, T147S, M150L, I161V, T195S, I197Y | 605/632 | 40,000 | 0.03 |

The dimer variant dimer2.2MMM (dimer3) (dTomato) (SEQ ID NO:81) is listed in Table 6. It has the highest extinction coefficient, and improved quantum yield compared to dimer2 (SEQ ID NO: 6). Dimer2.2MMM (dimer3) (dTomato) (SEQ ID NO:81) was also the dimer variant that had the extinction/emission ratio that was the most similar to the wild type DsRed, and had less green component than either wild-type DsRed or dimer2 (SEQ ID NO: 6). However, it does still have a residual green component.

Several monomer variants are also listed in Table 6. The monomer variant mRFP1.5 (SEQ ID NO: 83), had an emission peak that was red-shifted by about 5 nm, and significantly reduced green component, as compared with mRFP1.0. It also showed nearly complete maturation. However, its quantum yield is not extremely high. The monomer variant OrS4-9 (SEQ ID NO:85) was blue-shifted relative to mRFP and to wild-type. DsRed, with a higher quantum yield than mRFP1.0 or mRFP1.5, and had reduced pH sensitivity as compared with the original orange mRFP variants. However, its extinction coefficient is low, possibly due to difficulty in folding or incomplete maturation. The monomer variant Y1.3 (mYOFP1.3) (mBanana) (SEQ ID NO:87) had the largest blue-shift of any mRFP variant. It also had the highest quantum yield and a reduced pH sensitivity as compared with the original yellow mRFP variants, although its extinction coefficient is also low, possibly due to incomplete maturation. The monomer variant mFRFP (F2Q6) (mGrape2) (SEQ ID NO: 89) had the largest red-shift of any mRFP variant, and seems to have nearly complete maturation, although its quantum yield and its extinction coefficient are not extremely high.

Other monomeric variants may also be useful. For example, in some embodiments, a useful protein variant is selected from the group of variants including mRFP1.5 (SEQ ID NO: 83), OrS4-9 (SEQ ID NO: 85), Y1.3 (mYOFP1.3) (mBanana) (SEQ ID NO: 87), mFRFP (F2Q6) (mGrape2) (SEQ ID NO: 89), mRFP2 (mCherry) (SEQ ID NO: 92), mOFP (74-11) (SEQ ID NO: 94), mROFP (A2/6-6) (SEQ ID NO: 96), mStrawberry (SEQ ID NO: 98), mTangerine (SEQ ID NO: 100), mOrange (mOFP1) (SEQ ID NO: 102), mHoneydew (SEQ ID NO: 104), and mGrape1 (SEQ ID NO: 108).

As indicated above, dimeric variants may also be useful, and may include dimers including one or more of the monomers indicated above. Dimeric variants may also include a dimer subunit that is selected from, for example, Dimer1, dimer1.02, Dimer1.25, .dimer1.26, dimer 1.28, Dimer1.34, Dimer1.56, Dimer1.61, Dimer1.76, dimer2, dimer 2.2MMM (dimer 3) (dTomato) SEQ ID NO: 81) and tdTomato (SEQ ID NO: 106).

Example 9

Further Red Fluorescent Protein Variants

This example provides further discussion relating to the monomer variants. For example, one of the latest red versions matures more completely, is more tolerant of N-terminal fusions, and is over tenfold more photostable than mRFP1. Three new monomers with distinguishable hues from yellow-orange to red-orange have higher quantum efficiencies and suitability as re-emitting energy transfer acceptors.

Although mRFP1 overcame DsRed's tetramerization and sluggish maturation and exceeded DsRed's excitation and emission wavelengths by about 25 nm, the extinction coefficient, fluorescence quantum yield, and photostability decreased somewhat during the evolution of mRFP1[7]. To minimize these sacrifices, we have now subjected mRFP1 to many rounds of directed evolution using both manual and Fluorescence-activated cell sorting (FACS)-based screening. The resulting plethora of new variants include several new colors, increased tolerance of N-and C-terminal fusions, and improvements in extinction coefficients, quantum yields, and photostability, though no single variant is optimal by all criteria.

mCherry. The red chromophore of DsRed results from the autonomous multi-step post-translational modification of residues Gln66, Tyr67, and Gly68 into an imidazolidinone heterocycle with p-hydroxybenzylidene and acylimine substituents[8]. Based on the fact that introduction of Met at position 66 had a beneficial effect on the degree of maturation of the I125R dimeric variant of DsRed[9], our first attempt at improving the brightness of mRFP1 involved construction of a directed library in which residues near the chromophore, including position 66, were randomized. The top clone of this library, mRFP 1.1, contains the mutation Q66M (along with the complementary T147S), which, in addition to promoting more complete maturation, provides an additional 5 nm red-shift of both the excitation and emission spectra relative to mRFP1. We then noticed that the red fluorescence of both mRFP1 and mRFP1.1 could be drastically reduced by the presence of certain N-terminal fusions. Similarly, other researchers had noted that point mutations in the first few residues of tetrameric DsRed could provide dramatic increases in the observed fluorescent intensity[10]. We reasoned that since the N-terminal sequence of mRFP1 had been originally optimized for solubility of the unfused protein[6] rather than ability to tolerate fusions, this relatively arbitrary sequence could be far from ideal. Because *Aequorea* GFP is relatively indifferent to N- or C-terminal fusions, we eventually generated mRFP1.3 by replacing the first six amino acids of mRFP 1.1 with the corresponding residues from enhanced GFP (MVSKGEE, (SEQ ID NO:14)) followed by a spacer sequence NNMA (SEQ ID NO:112), and appending the last seven amino acids of GFP to the C-terminus. The 4 inserted residues NNMA (SEQ ID NO:112) are numbered 6a-d to preserve DsRed numbering for the rest of the protein.

Additional rounds of screening random libraries based on mRFP1.3 and wavelength-shifted mRFP variants identified the beneficial folding mutations V7I and M182K, which were incorporated into clone mRFP1.4. A library randomized at position 163 identified the substitution M163Q, resulting in a nearly complete disappearance of the absorbance peak at ~510 nm present in all previous mRFP clones, but a reduction in folding efficiency. The additional mutations R17H and N6aD (a substitution of N at position 6a, the numbering as explained, with D) restored an extinction coefficient to nearly equivalent to mRFP1.4. This variant, designated mRFP1.5, had excitation and emission 3 nm red-shifted from mRFP1 and exhibited nearly complete maturation with kinetics as fast or faster than mRFP1. Finally, an additional directed library constructed by partially randomizing positions 194, 195, 196, 197, and 199, resulted in the identification of a clone containing the mutations K194N, T195V, and D196N, which was found to have an enhanced extinction coefficient, while retaining the nearly complete lack of a 510 nm absorbance peak. This final clone was designated mCherry (See Table 7, FIGS. 47A and B, FIGS. 48A and B, and FIG. 50).

dTomato and tdTomato. The dimer2 variant previously described[7] possesses many desirable properties such as a faster and more complete maturation than wild-type DsRed and a greater fluorescent brightness than the fast-maturing mutant T1[6] (DsRed-Express). Through 5 rounds of directed evolution, we found the optimal combination of mutations V22M, Q66M, V105L, and F124M, which resulted in improved maturation kinetics, a significantly reduced 'dead-end' green component, and a small red-shift. The final clone, designated dTomato (see Table 7 and FIGS. 47A and 47B), additionally contains the GFP-type termini as described for mCherry (without the NNMA (SEQ ID NO:112) insertion), which result in a higher tolerance of N- and C-terminal fusions (data not shown). In order to construct a nonaggregating tag from the extremely bright dTomato, we genetically fused two copies of the gene to create a tandem dimer as previously reported. GFP-type termini were included at the N-terminus of the first copy of dTomato and at the C-terminus of the second copy of dTomato. The N-terminus of the second copy of dTomato consists of amino acids 2 through 6 of dimer2 followed by the NNMA (SEQ ID NO:112) insertion. This arrangement, designated tdTomato, provided the highest level of expression in *E. coli* while maintaining all of the desirable properties of the dimeric dTomato.

Wavelength-shifted variants of mRFP. Many new FPs with different colors have been discovered in diverse anthozoan species, but so far they all suffer from obligate tetramerization and would require efforts similar to the evolution of mRFP1 to produce widely useful fusion partners[11] Because such monomerization is usually tedious and often unsuccessful, it might be more efficient to alter the excitation and emission wavelength of mRFP through directed evolution. Following the example of GFP engineering[12, 13], we explored substitutions at Tyr 67, homologous to Tyr 66 in GFP, which contribute the core of the chromophore, and at Gln66, homologous to Ser 65 of GFP, which are the next most important contributors.

Starting with mRFP1.1, we replaced Tyr67 with either Phe, His, or Trp. The most promising clone contained the Tyr67Trp substitution, homologous to the main wavelength-shifting mutation in the cyan GFP mutant, CFP. Two further rounds of directed mutagenesis yielded our most blue-shifted mRFP variant, named "mHoneydew" which contains four additional substitutions (see FIG. 48A and FIG. 48B), but does not have optimized N- and C-termini. Like CFP, mHoneydew has relatively broad, double-peaked excitation and emission spectra, with excitation peaks at 487 and 504 nm, and emission peaks at 537 and 562 nm. Its extinction coefficient (17,000 $M^{-1}cm^{-1}$) and quantum yield (0.12) are quite low and proved relatively resistant to further improvements in initial libraries, and so was not evolved further in this study. Nevertheless, mHoneydew proves that the tryptophan-based chromophore of CFP can undergo a further maturation to a longer-wavelength chromophore, in analogy to the dehydrogenation of the tyrosine-derived GFP chromophore to the DsRed/mRFP chromophore.

Initial mutations of position 66 in mRFP1.1 indicated that the substitutions Gln66Ser, Gln66Thr, and Gln66Cys all yielded proteins significantly blue-shifted with respect to mRFP1. This led us to the development of "mTangerine," which contains the substitutions Gln66Cys and Gln213Leu with respect to mRFP1.1 (see FIGS. 48A and B), with excitation and emission peaks at 568 and 585 nm. While mTangerine has a respectable extinction coefficient (38,000 $M^{-1}cm^{-1}$) and quantum yield (0.3), we quickly moved on to development of Gln66-substituted mutants of mRFP1.4, with its optimized N- and C-termini.

In mRFP1.4, the substitutions Gln66Ser, Gln66Thr, and Gln66Cys all gave a similar blue-shift in both excitation and emission wavelength, and led to a curious increase in pH sensitivity that was characterized by an additional blue-shift at alkaline pH. Starting with mRFP1.4 M66T, through 6 additional rounds of directed, evolution, we arrived at the final orange fluorescent variant, mOrange, with excitation at 548 nm and emission at 562 nm (see Table 7, FIGS. 47A, 47B, 48A and 48B). mOrange has an extinction coefficient equivalent to mCherry, but more than 3-fold higher quantum yield. Interestingly, mOrange has excitation and emission maxima very close to a newly discovered tetrameric orange FP from *Cerianthus*[14] and a monomer evolved from a *Fulgia concinna* FP[15]. Though mOrange is the brightest true monomer in the present series, it does exhibit significant acid sensitivity, with a pKa of 6.5, and so is not yet optimal when pH insensitivity is required. However, the popular *Aequorea* GFP variant EYFP, with a pKa of 7.1[16], has been used successfully as a qualitative fusion tag by many researchers. Additionally, from the initial mRFP1.4 M66T clone, through 5 rounds of directed evolution, we created a pH-stable orange-red variant in which the longer-wavelength form of the Q66T chromophore has been enhanced. This variant, mStrawberry, has the highest extinction coefficient (90,000 $M^{-1}cm^{-1}$) of the true monomers. Its wavelengths (excitation 574 nm, emission 596 nm) and quantum yield (0.29) are intermediate between mCherry and mOrange (see Table 7, FIGS. 47A and B, and FIGS. 48A and B).

Figure 49:
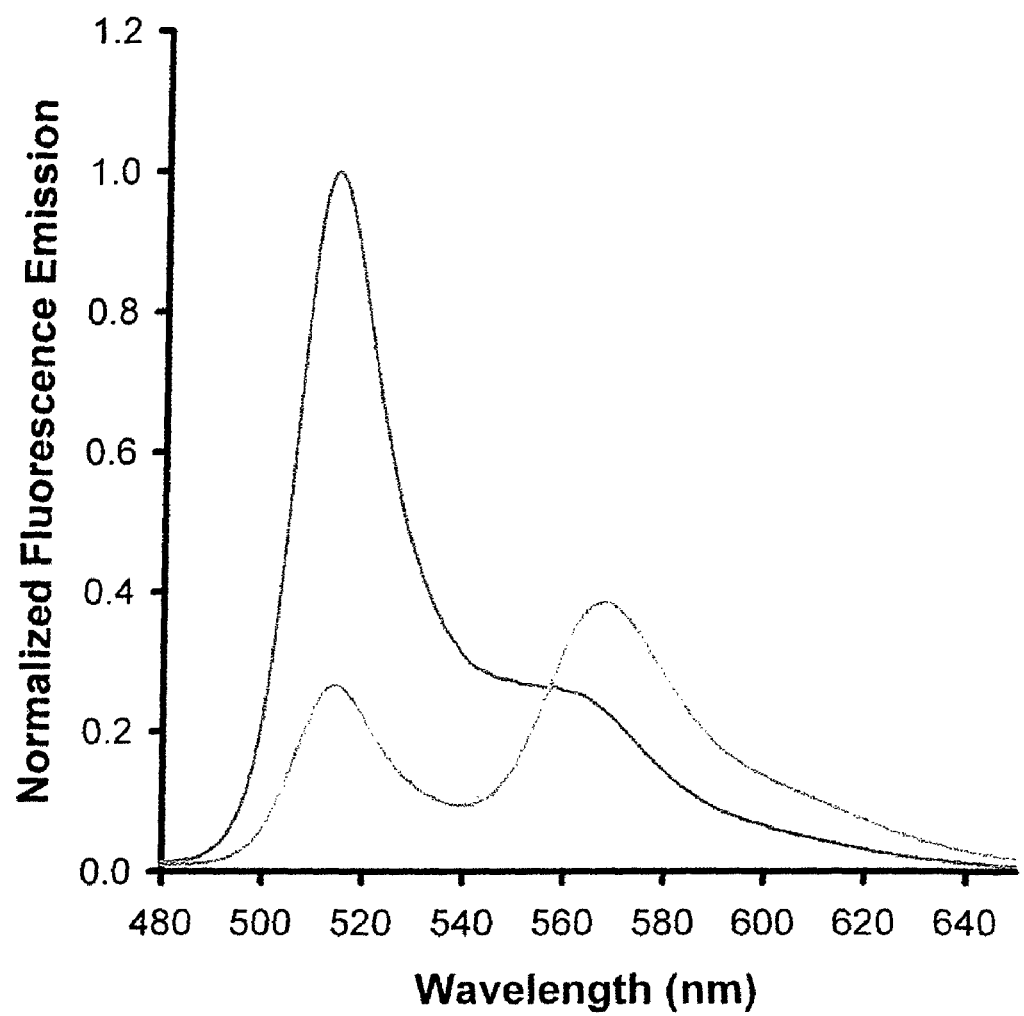
FIG. 49 provides emission spectra for 400 nm excitation for a zinc-finger fused with mOrange on its N-terminus and T-Sapphire on its C-terminus.

The high extinction coefficient and quantum yield of mOrange made it attractive as a potential FRET acceptor for GFP variants. As a test, we (assisted by Amy Palmer) constructed a new $Zn^{2+}$ sensor with mOrange and the violet-excited GFP mutant T-Sapphire[17] and compared it to the same sensor containing CFP and the Citrine variety[18] of YFP. T-Sapphire was chosen as donor because it is optimally excited below 425 nm, where mOrange is negligibly excited. The domain that changes its conformation upon binding $Zn^{2+}$ was modified from the original zif-268-derived version[19] by mutating the two $Zn^{2+}$-binding Cys to His to eliminate any possibility of oxidation. The fusion of CFP and Citrine respectively to the N- and C-terminii of the modified $Zn^{2+}$ finger displayed a 5.2 fold ratio change upon addition of $Zn^{2+}$, with an apparent $K_d$ of ~200 µM. Replacement of CFP by mOrange and Citrine by T-Sapphire yielded a sensor whose 562 nm to 514 nm emission ratio increased 6-fold upon $Zn^{2+}$ binding (FIG. 49). This demonstrates that mOrange and T-Sapphire make a good emission-ratiometric FRET pair with dynamic range at least equaling CFP and YFP but at longer emission wavelengths.

Position 197 stacks near the RFP chromophore in homology to Thr203 in GFP. Randomization of Ile 197 in mTangerine led to the surprising discovery that Glu provided an additional blue-shift. This variant was initially found to have extreme pH sensitivity as well as inefficient maturation. Eight rounds of directed evolution gradually improved the folding efficiency and pH sensitivity, eventually yielding mBanana, with excitation and emission peaks at 540 nm and 553 nm respectively and a high quantum yield (0.70). Unfortunately the fluorescence of mBanana is quite pH-sensitive, and the effective extinction coefficient remains quite low, only 6,000 $M^{-1}cm^{-1}$, probably due to incomplete maturation. Most of the protein seems trapped as a dead-end species absorbing at 385 nm. However, the increased quantum yield of mBanana partially compensates for its low extinction coefficient (see Table 7, FIGS. 47A and B, and FIGS. 48A and B).

What is the basis of the spectral shifts of these mRFP variants? The largest single effect is seen with substitutions at the first chromophore position, occupied by Gln in DsRed and mRFP1. Substitution of this residue with Ser, Thr, or Cys in mRFP1 or dimeric RFPs (data not shown) results in a significant blue-shift. In the absence of compensating mutations, the Q66S/T/C variants of mRFP1 all exhibit emission around 580 nm at neutral pH, but become brighter and more blue-shifted at high pH. The blue-shifted (mOrange) species is stabilized by T41F and L83F mutations, where the red-shifted (mStrawberry) form is favored by S62T, Q64N, and Q213L. In mBanana, the I197E mutation may contribute a hydrogen bond between the glutamate side chain and phenolate oxygen in the chromophore, resulting in a further redistribution of electron density.

Discrimination of Six FPs

Figure 52:
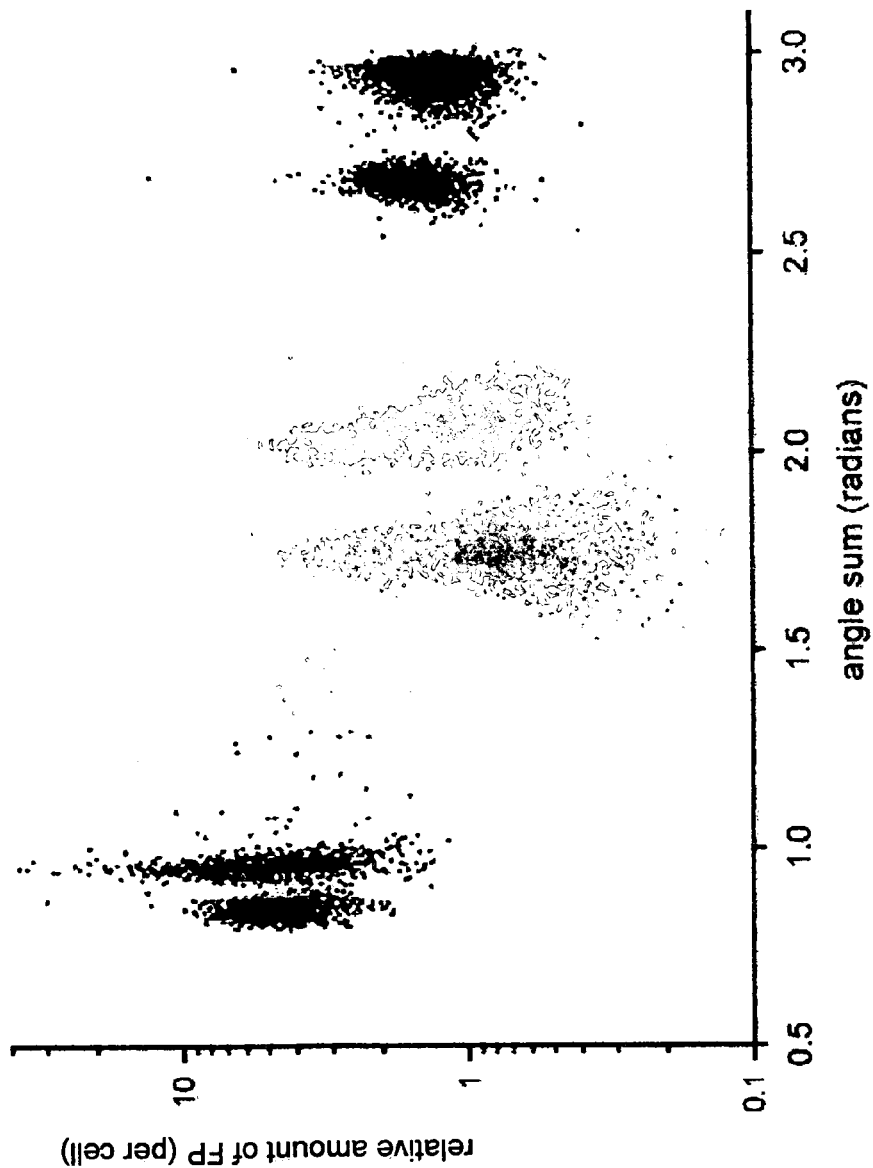
FIG. 52 illustrates discrimination of *E. coli* transfected with six different fluorescent proteins (FPs).

An obvious application of the proliferation of FP colors is to discriminate many cell types, transcriptional activities, or fusion proteins. In the most general case where a cell or voxel could contain arbitrary concentrations of n FPs mixed together, determination of the n independent concentrations or quantities of each of the FPs requires spectral or lifetime unmixing of at least n measurements, preferably many more to confer statistical robustness. However, there is an-important special case where each cell or nonoverlapping subcellular structure has been tagged with a different FP. When a cell or voxel contains at most one FP, how many measurements are required to decide its identity and concentration? To test such discrimination experimentally, bacteria separately transfected with EGFP, Citrine, mBanana, mOrange, mStrawberry, or mCherry were mixed and analyzed by flow cytometry, with excitation at 514 nm and emission simultaneously measured through three bandpass filters, 540-560 nm, 564-606 nm, and 595-635 nm respectively. Transformation of the three signals to polar coordinates enabled easy discrimination of the six constituent populations and the relative amounts of FP per cell (FIG. 52). Thus three simple emission measurements are sufficient.

Photostability Measurements

We compared the photostability of mRFP1 with that of its descendants and with EGFP by making microdroplets of purified protein solutions in phosphate-buffered saline under mineral oil, illuminating them on a fluorescence microscope at irradiances of several watts/cm$^2$, and recording the time course of gradual loss of fluorescence due to bleaching (see Methods below). In order to make fair comparisons between proteins with different extinction coefficients, overlaps with excitation filters, and quantum yields, we normalized the bleach rates to an initial emission rate from each molecule of 1000 photons/sec. The resulting bleach curves (shown in FIG. 51) varied greatly in absolute rate but were generally far from single exponentials. Most showed an initial fast phase in which over 50% of the initial emission was lost, followed by a lower amplitude, much slower decay phase. This complexity makes it difficult to extract a meaningful single number for the quantum efficiency of photobleaching. Another common previous figure of merit for fluorophore photostability is the mean number of photons emitted before photobleaching, ideally corresponding to the total area under each curve. However, this integral is usually dominated by the dim slow-bleaching component, whose low intensity would hinder discrimination from background autofluorescence in a real biological experiment, and which might not even have the same excitation and emission spectra as the original protein. We believe a more realistic figure of merit for typical cell biological experiments is the time for the emission to drop to 50% of its initial value. These values are listed in Table 7. By this criterion, the best performers are tdTomato and mCherry, which are both more than tenfold better than mRFP1 and nearly as good as EGFP.

For example, we investigated the mutations responsible for increased photostability of mCherry relative to mRFP1 by measuring the photostability of several intermediate mutants. We found that the increase in photostability occurred between the mutants mRFP1.4 and mRFP1.5, which differ by the N6aD (a substitution of N at position 6a, the numbering as explained, with D), R17H, and M163Q mutations, of which only M163Q is internal and interacts with the chromophore, and so is likely to be responsible for the increase in photostability. The photostability of mRFP1.5 and mCherry is practically identical, indicating that the mutations that occurred between these two variants had no effect on the photostability. When the mutation M163Q is introduced into other variants, such as mOrange and mStrawberry, it also provides a significant increase in photostability, though other properties of these variants, such as the maturation rate and quantum yield, are adversely affected by this mutation.

The highest brightness (product of extinction coefficient, 138,000 $M^{-1}cm^{-1}$, and quantum yield, 0.69) and photostability are found in tdTomato, at the cost of doubling the molecular weight. A previous tandem dimer, t-HcRed1, was reported to have an extinction coefficient and quantum yield of 160,000 $M^{-1}cm^{-1}$ and 0.04[20], whose product is about 15-fold smaller than tdTomato's. Among the true monomers, mCherry offers the longest wavelengths, the highest photostability, the fastest maturation, and excellent pH resistance. Its excitation and emission maxima are just 3 nm longer than those of mRFP1, for which it is the closest upgrade. Although mCherry's quantum efficiency is slightly lower (0.22 vs. 0.25 for mRFP1), its increased extinction coefficient (due to near-complete maturation), tolerance of N-terminal fusions, and photostability make mRFP1 obsolete. For applications such as dual-emission FRET where the acceptor's quantum yield must be maximized, mOrange is the current favorite (e.g. FIG. 49), though its maturation time, pH sensitivity, and photostability are currently far from optimal. Additional colors for multiwavelength tracking of distinct cells or substructures are available from mStrawberry, mTangerine, mBanana, and mHoneydew in descending order of wavelengths and brightnesses.

Methods

Mutagenesis and Screening. mRFP1 and dimer2[7] were used as the initial templates for construction of genetic libraries by a combination of saturation or partial saturation mutagenesis at particular residues and random mutagenesis of the whole gene. Random mutagenesis was performed by error-prone PCR as described[18] or by using the GeneMorph I or GeneMorph II kit (Stratagene). Mutations at specific residues were introduced as described, or by sequential QuikChange (Stratagene), or by QuikChange Multi (Stratagene), or by a ligation-based method (description follows). Briefly, oligonucleotide primers containing the degenerate codons of interest at their 5' ends preceded by a SapI restriction site were used to amplify the RFP in two separate PCR reactions using PfuTurbo polymerase (Stratagene). Each PCR fragment was cut with SapI (New England Biolabs) to produce a 3-base overhang compatible with the other digested fragment, and purified digested fragments were ligated with T4 DNA ligase (New England Biolabs). Full length ligation products inserts were gel purified and cut with EcoRI/BamHI (New England Biolabs) and inserted into pRSET$_B$ or a modified pBAD vector (Invitrogen). For all library construction methods, chemically competent or electrocompetent *Escherichia coli* strain JM109(DE3) (for pRSET$_B$) or LMG194 (for pBAD)[26] were transformed and grown overnight on LB/agar (supplemented with 0.02% L-arabinose (Fluka) for pBAD constructs) at 37° C. and maintained thereafter at room temperature. LB/agar plates were manually screened as previously described[27]. JM109(DE3) colonies of interest were cultured overnight in 2 ml LB supplemented with ampicillin. LMG194 colonies of interest were cultured for 8 hours in 2 ml RM supplemented with ampicillin and 0.2% D-glucose, and then culture volume was increased to 4 ml with LB/ampicillin and RFP expression was induced by adding L-arabinose to a final concentration of 0.2% and cultures were allowed to continue growing overnight. For both JM109(DE3) and LMG194, a fraction of the cell pellet was extracted with B-PER II (Pierce), and spectra were obtained using a Safire 96-well plate reader with monochromators (TECAN, Männendorf, Switzerland). DNA was purified from the remaining pellet by QIAprep spin column (Qiagen) and submitted for sequencing.

Construction of Tandem Dimer and FRET Constructs. To construct tdTomato with a 12-residue linker (GHGTGSTGSGSS; SEQ ID NO:17), dRFP3 was amplified in two separate PCR reactions, the first retaining the 7-residue GFP-type N-terminus (MVSKGEE; SEQ ID NO:14) but deleting the 7-residue GFP-type C-terminus and adding the first half of the 12-residue linker followed by a SapI restriction site, and the second adding the remaining half of the 12-residue linker followed by the sequence ASSEDNNMA (SEQ ID NO:121) before residue 7 of dRFP3, and ending with the 7-residue GFP-type C-terminus (GMDELYK; SEQ ID NO:91). Gel purified PCR products were digested with SapI , gel purified, and ligated with T4 DNA ligase. Full length ligation product was gel purified, cut with EcoRI/BamHI, and ligated into a modified pBAD vector. For FRET constructs, the original $Zn^{2+}$ sensor[19] was modified such that the two $Zn^{2+}$ ligating Cys residues were mutated to His. The modified $Zn^{2+}$ finger domain, HERPYAHPVESHDRFSRSDELTRHIR-IHTGQK (SEQ ID NO:122) ($Zn^{2+}$ ligating residues in bold, mutated residues underlined), was cloned between CFP and citrine with SphI and SacI sites as linkers. PCR-amplified mOrange and T-Sapphire[17] were inserted into BamHI/SphI and EcoRI/SacI sites, replacing CFP and citrine.

Protein Production and Characterization. RFPs were expressed from pBAD vectors in *E. coli* LMG194 by growing single colonies in 40 ml RM/Amp supplemented with 0.2% D-glucose for 8 hours, adding 40 ml LB/Amp and adding L-arabinose to a final concentration of 0.2%, and incubating overnight at 37° C. For maturation experiments, flasks were sealed with parafilm upon induction to restrict oxygen availability. All proteins were purified by Ni-NTA chromatography (Qiagen) and dialyzed into PBS. Biochemical and fluorescence characterization experiments were performed as described. For FRET measurements, purified $Zn^{2+}$ sensor proteins were diluted in 10 mM MOPS, 100 mM KCl, pH 7.4 with either 1 mM EDTA or 1 mM $ZnCl_2$ and fluorescence emission spectra were collected with excitation near the peak donor excitation wavelength.

Fluorescence Activated Cell Sorting. A modified version of the protocol described by Daugherty et al. was used for FACS screening of large libraries of FP mutants[28]. Briefly, *E. coli* LMG194 were electroporated with a modified pBAD vector containing the gene library and the transformed cells were grown in 30 ml RM supplemented with ampicillin and 0.2% D-glucose. After 8 hours, RFP expression was induced by adding L-arabinose to a final concentration of 0.2%. Overnight induced cultures were diluted 1:100 into DPBS supplemented with ampicillin prior to FACS sorting. Multiple rounds of cell sorting were performed on a FACSDiva (BD Biosciences) in yield mode for the first sort and purity or single cell mode for subsequent sorts of the same library. Sorted cells were grown overnight in 4 ml RM/amp with 0.2% D-glucose and the resulting saturated culture was diluted 1:100 into 30 ml RM/Amp with 0.2% D-glucose to start the next culture to be sorted. After 3 to 4 rounds of FACS sorting, the bacteria were plated onto LB/agar supplemented with 0.02% L-arabinose and grown overnight, after which individual clones were screened manually as described above.

Photobleaching measurements. Aqueous droplets of purified protein in phosphate-buffered saline were formed under mineral oil in a chamber on the fluorescence microscope stage. For reproducible results it proved essential to pre-extract the oil with aqueous buffer, which would remove any traces of autoxidized or acidic contaminants. The droplets were small enough (5-10 µm diameter) so that all the molecules would see the same incident intensity. The absolute excitation irradiance in photons/($cm^2$·s·nm) as a function of wavelength was computed from the spectra of a xenon lamp, the transmission of the excitation filter, the reflectance of the dichroic mirror, the manufacturer-supplied absolute spectral sensitivity of a miniature integrating-sphere detector (SPD024 head and ILC1700 meter, International Light Corp., Newburyport, Mass.), and the measured detector current. The predicted rate of initial photon emission (before any photobleaching had occurred) was calculated from the excitation irradiance and absorbance spectrum (both as functions of wavelength), and the quantum yield. These rates varied from 180 $s^{-1}$ for mHoneydew to 3300 $s^{-1}$ for mStrawberry. To normalize the observed photobleaching time courses to a common arbitrary standard of 1000 emitted photons/sec, the time axes were correspondingly scaled by factors of 0.18 to 3.3, assuming that emission and photobleach rates are both proportional to excitation intensity at intensities typical of microscopes with arc lamp sources, as is known to be the case for GFP[29].

TABLE 7

| Fluorescent protein | Excitation maximum, nm | Emission maximum, nm | Extinction coefficient per chain[a], $M^{-1}cm^{-1}$ | Fluorescence quantum yield | Brightness of fully mature protein (% of DsRed) | $pK_a$ | $t_{0.5}$ for maturation at 37° C. | $t_{0.5}$ for bleach[b], sec |
|---|---|---|---|---|---|---|---|---|
| DsRed | 558 | 583 | 75,000 | 0.79 | 100 | 4.7 | ~10 hr | ND |
| T1 | 555 | 584 | 38,000 | 0.51 | 33 | 4.8 | <1 hr | ND |

TABLE 7-continued

| Fluorescent protein | Excitation maximum, nm | Emission maximum, nm | Extinction coefficient per chain[a], M$^{-1}$cm$^{-1}$ | Fluorescence quantum yield | Brightness of fully mature protein (% of DsRed) | pK$_a$ | t$_{0.5}$ for maturation at 37° C. | t$_{0.5}$ for bleach[b], sec |
|---|---|---|---|---|---|---|---|---|
| Dimer2 | 552 | 579 | 69,000 | 0.69 | 80 | 4.9 | ~2 hr | ND |
| mRFP1 | 584 | 607 | 50,000 | 0.25 | 21 | 4.5 | <1 hr | 6.2 |
| mHoneydew | 487/504 | 537/562 | 17,000 | 0.12 | 3 | <4.0 | ND | 5.9 |
| mBanana | 540 | 553 | 6,000 | 0.70 | 7 | 6.7 | 1 hr | 1.4 |
| mOrange | 548 | 562 | 71,000 | 0.69 | 83 | 6.5 | 2.5 hr | 6.4 |
| dTomato | 554 | 581 | 69,000 | 0.69 | 80 | 4.7 | 1 hr, | 64. |
| tdTomato | 554 | 581 | 138,000 | 0.69 | 160 | 4.7 | 1 hr | 70. |
| mTangerine | 568 | 585 | 38,000 | 030 | 19 | 5.7 | ND | 5.1 |
| mStrawberry | 574 | 596 | 90,000 | 0.29 | 44 | <4.5 | 50 min | 11. |
| mCherry | 587 | 610 | 72,000 | 0.22 | 27 | <4.5 | 15 min | 68. |

[a]Extinction coefficients were measured by the alkali denaturation method and are believed to be more accurate than the previously reported values for DsRed, T1, dimer2, and mRFP1[7]
[b]Time (s) to bleach to 50% emission intensity, at an illumination level that causes each molecule to emit 1000 photons/sec initially, i.e. before any bleaching has occurred. See Materials and Methods for more details. For comparison, the value for EGFP is 115 sec, assuming an extinction coefficient of 56,000 and quantum efficiency of 0.60.

Figure Legends Referred to in Example 9

Figure 47:
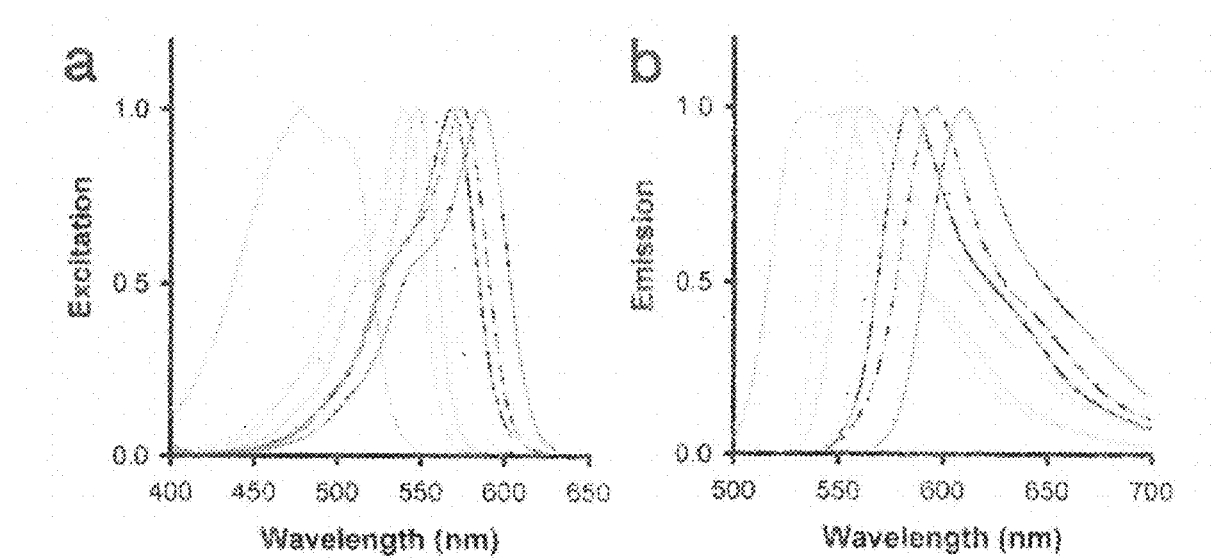
FIG. 47A provides excitation spectra for new RFP variants. Spectra are normalized to the excitation and emission peak for each protein. Excitation curves are shown as solid or dashed lines for mRFP1 variants and as a dotted-line for dTomato and tdTomato, with colors corresponding to the color of each variant.
FIG. 47B provides emission spectra for new RFP variants. Spectra are normalized to the excitation and emission peak for each protein. Emission curves are shown as solid or dashed lines for mRFP1 variants and as a dotted line for dTomato and tdTomato, with colors corresponding to the color of each variant.

FIGS. 47A and 47B: Excitation and emission spectra for new RFP variants. Spectra are normalized to the excitation and emission peak for each protein. Excitation (a) and emission (b) curves are shown as solid or dashed lines for mRFP1 variants and as a dotted line for dTomato and tdTomato, with colors corresponding to the color of each variant.

Figure 48B:
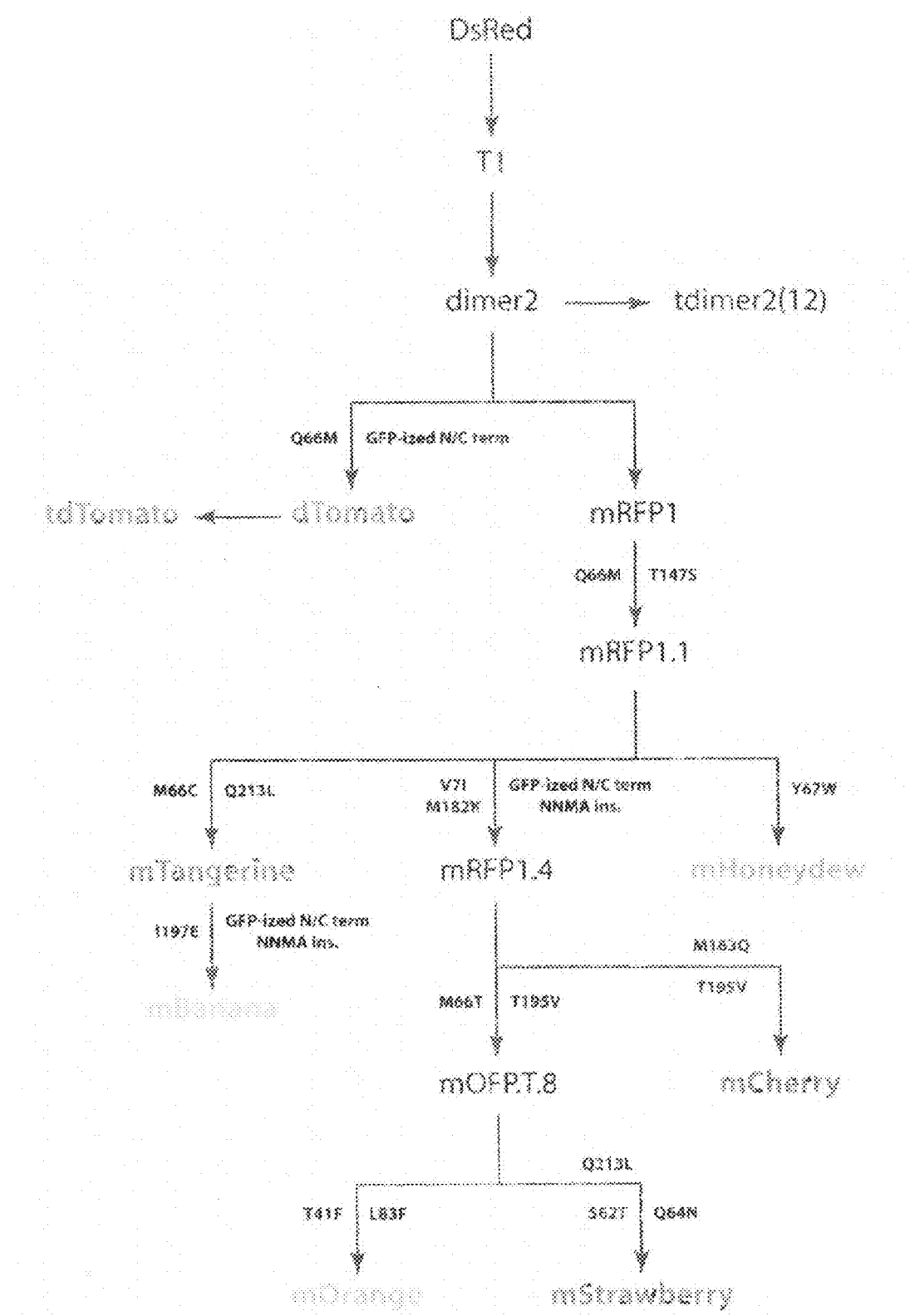
FIG. 48B provides genealogy of DsRed-derived variants, with mutations critical to the phenotype of each new variant (e.g., NNMA ins. (SEQ ID NO:112)).

FIGS. 48A and 48B: Sequences and genealogy. (a) Sequence alignment of new mRFP variants with wild-type DsRed and mRFP1. Internal residues are shaded. mRFP1 mutations are shown in blue, and critical mutations in mCherry, mStrawberry, mTangerine, mOrange, mBanana, and mHoneydew are shown in colors corresponding to the color of each variant. GFP-type termini on new mRFP variants are shown in green. (b) A genealogy of DsRed-derived variants, with mutations critical to the phenotype of each new variant.

FIG. 49: T-Sapphire-mOrange FRET. Emission spectra for 400 nm excitation for a zinc-finger fused with mOrange on its N-terminus and T-Sapphire on its C-terminus. Emission in the presence of 1 mM EDTA in zinc-free buffer is represented by the green line, and emission in the presence of 1 mM ZnCl$_2$ is represented by the orange line.

Figure 50:
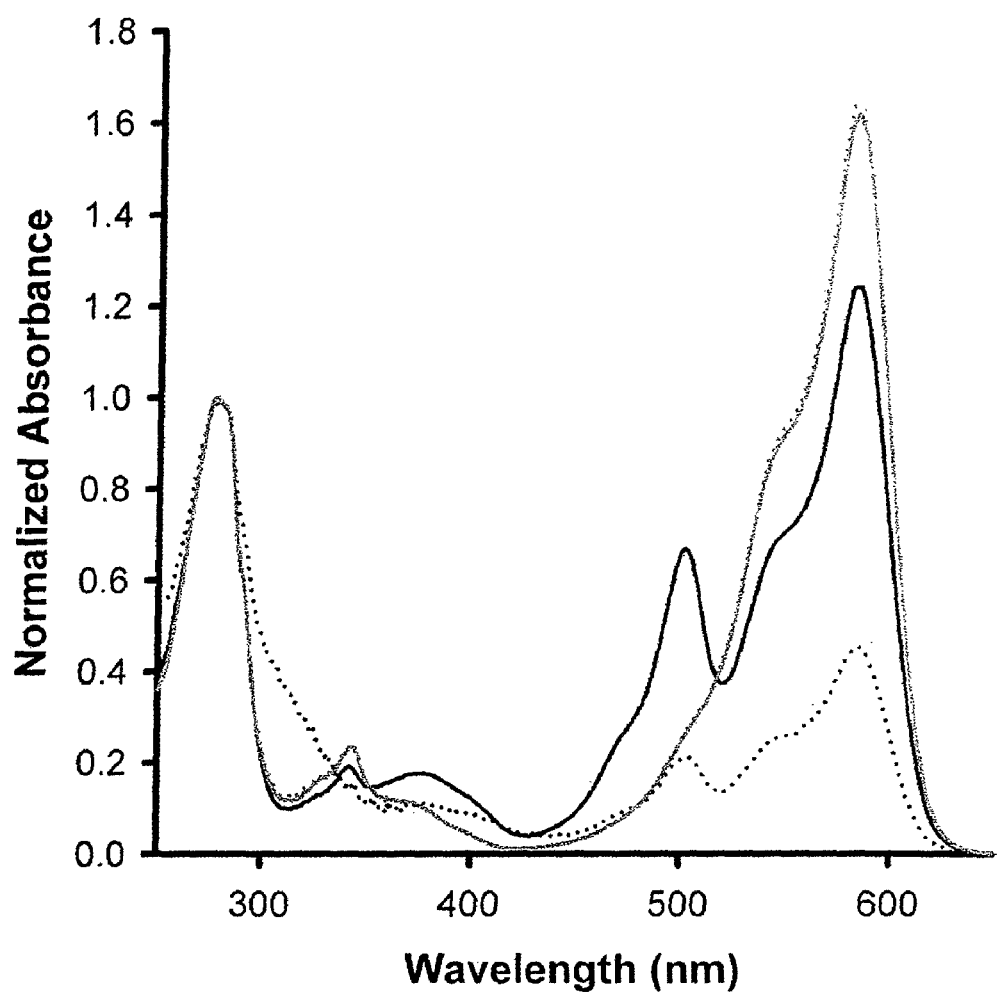
FIG. 50 provides mRFP1 and mCherry C-/N-terminal 6×His (SEQ ID NO:120) tag absorbance spectra, illustrating sensitivity to N- and C-terminal fusions.

FIG. 50: Sensitivity to N- and C-terminal fusions. mRFP1 and mCherry C-/N-terminal 6×His (SEQ ID NO:120) tag absorbance spectra. mRFP1 and mCherry with N-terminal leader sequence containing a 6×His (SEQ ID NO:120) tag (derived from pRSET$_B$) or C-terminal tail with Myc-tag and 6×His (SEQ ID NO:120) tag (derived from pBAD-Myc-His-A (Invitrogen)) were purified on Ni-NTA Agarose beads in parallel with extensive washes. Absorbance spectra were taken and normalized to the 280 nm peak for each. Absorbance curves for mRFP1 are plotted in red, and those from mCherry are plotted in blue. Solid lines correspond to N-terminal 6×His-tagged (SEQ ID NO:120) protein, and dotted lines correspond to C-terminal 6×His-tagged (SEQ ID NO:120) protein. While mRFP1 exhibited greatly reduced expression and apparent extinction coefficient (approximately 4-fold lower) when expressed with the C-terminal tag, mCherry produced nearly identical results with either N-terminal or C-terminal tags.

Figure 51:
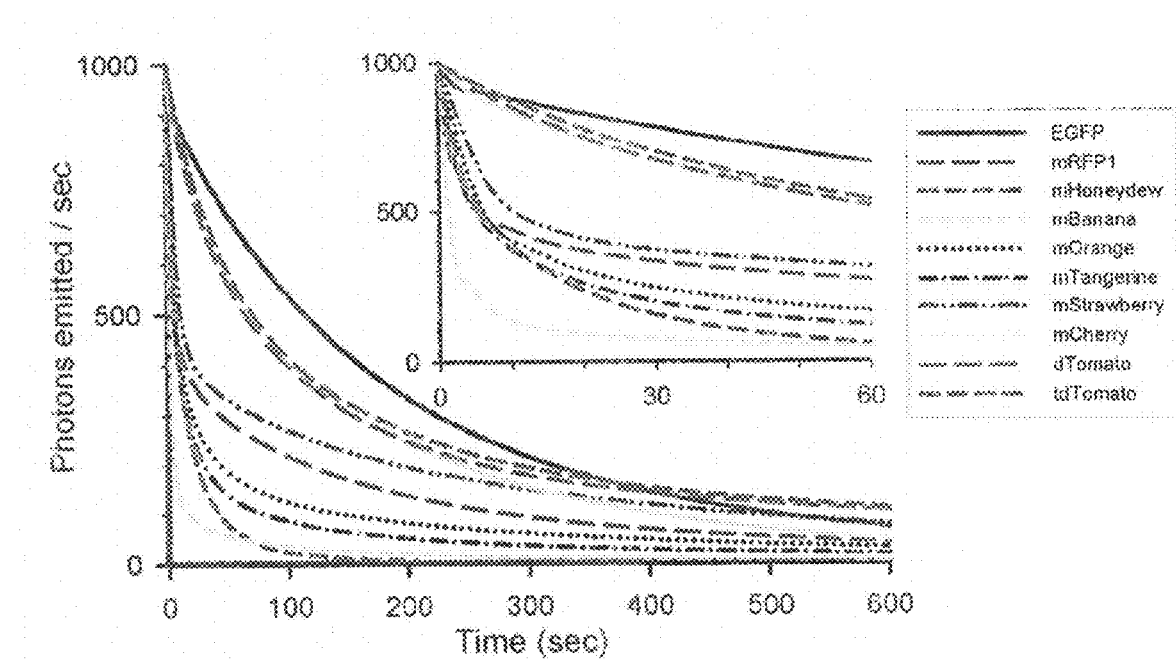
FIG. 51 provides photobleaching curves for new RFP variants.

FIG. 51: Photobleaching curves for new RFP variants. Curves for mRFP1 and EGFP are included for comparison. All curves are normalized to illumination intensities calculated to cause each molecule to emit 1000 photons/sec at time=0 before photobleaching.

FIG. 52: Discrimination of E. coli transfected with six different FPs. Bacteria separately transformed with different FPs were mixed and analyzed by flow cytometry for a total of about 10,000 events. Excitation was at 514 nm from an argon-ion laser. Emissions $E_1$, $E_2$, and $E_3$ were simultaneously collected with 540-560 nm, 564-606 nm, and 595-635 nm bandpass filters respectively. Normalized fluorescences $F_i$ were calculated as $E_i$/(mean of all $E_i$ values) for i=1, 2, 3. The root-mean-square intensity (ordinate) was defined as $[E_1^2+E_2^2+E_3^2]^{1/2}$, while the angle sum (abscissa) was $\tan^{-1}(E_2/E_1)+\tan^{-1}(E_3/E_2)$ in radians. Each dot represents a cell. Control runs with pure populations verified that the blue-green dots represent GFP-expressing cells, green dots mean Citrine YFP, yellows mean mBanana, oranges mean mOrange, reds mean mStrawberry, and magentas mean mCherry.

REFERENCES REFERRED TO IN EXAMPLE 9

1. Tsien, R. Y. The green fluorescent protein. Annu Rev Biochem 67, 509-544 (1998).
2. Zhang, J., Campbell, R. E., Ting, A. Y. & Tsien, R. Y. Creating new fluorescent probes for cell biology. Nat Rev Mol Cell Biol 3, 906-918 (2002).
3. Lauf, U., Lopez, P. & Falk, M. M. Expression of fluorescently tagged connexins: a novel approach to rescue function of oligomeric DsRed-tagged proteins. FEBS Lett 498, 11-15 (2001).
4. Matz, M. V. et al. Fluorescent proteins from nonbioluminescent Anthozoa species. Nat Biotechnol 17, 969-973 (1999).
5. Baird, G. S., Zacharias, D. A. & Tsien, R. Y. Biochemistry, mutagenesis, and oligomerization of DsRed, a red fluorescent protein from coral. Proc Mad Acad Sci USA 97, 11984-11989 (2000).
6. Bevis, B. J. & Glick, B. S. Rapidly maturing variants of the Discosoma red fluorescent protein (DsRed). Nat Biotechnol 20, 83-87 (2002).
7. Campbell, R. E. et al. A monomeric red fluorescent protein. Proc Nad Acad Sci USA 99, 7877-7882 (2002).
8. Gross, L. A., Baird, G. S., Hoffman, R. C., Baldridge, K. K. & Tsien, R. Y. The structure of the chromophore within DsRed, a red fluorescent protein from coral. Proc Nad Acad Sci USA 97, 11990-11995 (2000).
9. Baird, G. S. (Univ. of California, San Diego, 2001).
10. Sorensen, M. et al. Rapidly maturing red fluorescent protein variants with strongly enhanced brightness in bacteria. FEBS Lett 552, 110-114 (2003).

11. Verkhusha, V. V. & Lukyanov, K. A. The molecular properties and applications of Anthozoa fluorescent proteins and chromoproteins. *Nat Biotechnol* 22, 289-296 (2004).
12. Heim, R., Cubitt, A. B. & Tsien, R. Y. Improved green fluorescence. *Nature* 373, 663-664 (1995).
13. Heim, R., Prasher, D. C. & Tsien, R. Y. Wavelength mutations and posttranslational autoxidation of green fluorescent protein. *Proc Nad Acad Sci USA* 91, 12501-12504 (1994).
14. Ip, D. T. et al. Crystallization and preliminary crystallographic analysis of a novel orange fluorescent protein from the Cnidaria tube anemone *Cerianthus* sp. *Acta Crystallogr D Biol Crystallogr* 60, 340-341 (2004).
15. Karasawa, S., Araki, T., Nagai, T., Mizuno, H. & Miyawaki, A. Cyan-emitting and orange-emitting fluorescent proteins as a donor/acceptor pair for fluorescence resonance energy transfer. *Biochem J* 381, 307-312 (2004).
16. Llopis, J., McCaffery, J. M., Miyawaki, A., Farquhar, M. G. & Tsien, R. Y. Measurement of cytosolic, mitochondrial, and Golgi pH in single living cells with green fluorescent proteins. *Proc Natl Acad Sci USA* 95, 6803-6808 (1998).
17. Zapata-Hommer, O. & Griesbeck, O. Efficiently folding and circularly permuted variants of the Sapphire mutant of GFP. *BMC Biotechnol* 3, 5 (2003).
18. Griesbeck, 0., Baird, G. S., Campbell, R. E., Zacharias, D. A. & Tsien, R. Y. Reducing the environmental sensitivity of yellow fluorescent protein. Mechanism and applications. *J Biol Chem* 276, 29188-29194 (2001).
19. Miyawaki, A. & Tsien, R. Y. Monitoring protein conformations and interactions by fluorescence resonance energy transfer between mutants of green fluorescent protein. *Methods Enzymol* 327, 472-500 (2000).
20. Fradkov, A. F. et al. Far-red fluorescent tag for protein labelling. *Biochem J* 368, 17-21 (2002).
21. Chudakov, D. M. et al. Kindling fluorescent proteins for precise in vivo photolabeling. *Nat Biotechnol* 21, 191-194 (2003).
22. Chudakov, D. M., Feofanov, A. V., Mudrik, N, N., Lukyanov, S. & Lukyanov, K. A. Chromophore environment provides clue to "kindling fluorescent protein" riddle. *J Biol Chem* 278, 7215-7219 (2003).
23. Mizuno, H. et al. Photo-induced peptide cleavage in the green-to-red conversion of a fluorescent protein. *Mol Cell* 12, 1051-1058 (2003).
24. Ando, R., Hama, H., Yamamoto-Hino, M., Mizuno, H. & Miyawaki, A. An optical marker based on the UV-induced green-to-red photoconversion of a fluorescent protein. *Proc Natl Acad Sci USA* 99, 12651-12656 (2002).
25. Petersen, J. et al. The 2.0-A crystal structure of eqFP611, a far red fluorescent protein from the sea anemone *Entacmaea quadricolor*. *J Biol Chem* 278, 44626-44631 (2003).
26. Guzman, L. M., Belin, D., Carson, M. J. & Beckwith, J. Tight regulation, modulation, and high-level expression by vectors containing the arabinose PBAD promoter. *J Bacteriol* 177, 4121-4130 (1995).
27. Baird, G. S., Zacharias, D. A. & Tsien, R. Y. Circular permutation and receptor insertion within green fluorescent proteins. *Proc Nad Acad Sci USA* 96, 11241-11246 (1999).
28. Daugherty, P. S., Olsen, M. J., Iverson, B. L. & Georgiou, G. Development of an optimized expression system for the screening of antibody libraries displayed on the *Escherichia coli* surface. *Protein Eng* 12, 613-621 (1999).
29. Chiu, C. S., Kartalov, E., Unger, M., Quake, S. & Lester, H. A. Single-molecule measurements calibrate green fluorescent protein surface densities on transparent beads for use with 'knock-in' animals and other expression systems. *J Neurosci Methods* 105, 55-63 (2001).

All publications, GenBank Accession Number sequence submissions, patents and published patent applications mentioned in the above specification are herein incorporated by reference in their entirety. Various modifications and variations of the described compositions and methods of the invention will be apparent to those skilled in the art without departing from the scope and spirit of the invention. Although the invention has been described in connection with various specific embodiments, it should be understood that the invention as claimed should not be unduly limited to such specific embodiments. Indeed, various modifications of the described modes for carrying out the invention which are obvious to those skilled in protein chemistry or molecular biological arts or related fields are intended to be within the scope of the following claims.

What is claimed is:

1. An isolated polynucleotide encoding a Discosoma red fluorescent protein (DsRed) variant, wherein the variant comprises an amino acid sequence that is at least 90% identical over the entire length of SEQ ID NO:8.

2. The polynucleotide of claim 1, wherein the variant comprises an amino acid sequence that is at least 95% identical over the entire length of SEQ ID NO:8.

3. The polynucleotide of claim 1, wherein the encoded DsRed variant has improved fluorescence maturation relative to the polypeptide of SEQ ID NO:1.

4. The polynucleotide of claim 1, wherein the encoded DsRed variant is a monomer.

5. A vector comprising a polynucleotide of claim 1.

6. The vector of claim 5, wherein the vector is an expression vector.

7. A host cell comprising the vector of claim 5.

8. A kit, comprising a polynucleotide of claim 1.

* * * * *

UNITED STATES PATENT AND TRADEMARK OFFICE
CERTIFICATE OF CORRECTION

PATENT NO. : 7,906,636 B2  
APPLICATION NO. : 12/618624  
DATED : March 15, 2011  
INVENTOR(S) : Robert E. Campbell, Nathan C. Shaner and Roger Y. Tsien Page 1 of 1

It is certified that error appears in the above-identified patent and that said Letters Patent is hereby corrected as shown below:

On the Cover Page: Item [75] Inventors should read in order as shown

Section (75)   Inventors:   Robert E. Campbell, Edmonton (CA);  
Nathan C. Shaner, La Jolla (US);  
Roger Y. Tsien, La Jolla (US)

In the Specification:

Column 1, Paragraph 2: Please replace the paragraph under STATEMENT AS TO RIGHTS TO INVENTIONS MADE UNDER FEDERALLY SPONSORED RESEARCH OR DEVELOPMENT to read:

-- This invention was made with government support under Grant No. NS27177, awarded by the National Institute of Neurological Disorders and Stroke, and under Grant No. GM62114-01, awarded by the National Institute of General Medical Sciences. The government has certain rights in the invention. --

Signed and Sealed this  
Twenty-first Day of June, 2011

David J. Kappos  
*Director of the United States Patent and Trademark Office*

SEQUENCE LISTING

```
<160> NUMBER OF SEQ ID NOS: 122

<210> SEQ ID NO 1
<211> LENGTH: 225
<212> TYPE: PRT
<213> ORGANISM: Discosoma sp.
<220> FEATURE:
<223> OTHER INFORMATION: Discosoma corallimorph Anthozoan wild-type
      red fluorescent protein (DsRed, drFP583)

<400> SEQUENCE: 1

Met Arg Ser Ser Lys Asn Val Ile Lys Glu Phe Met Arg Phe Lys Val
 1               5                  10                  15

Arg Met Glu Gly Thr Val Asn Gly His Glu Phe Glu Ile Glu Gly Glu
            20                  25                  30

Gly Glu Gly Arg Pro Tyr Glu Gly His Asn Thr Val Lys Leu Lys Val
        35                  40                  45

Thr Lys Gly Gly Pro Leu Pro Phe Ala Trp Asp Ile Leu Ser Pro Gln
    50                  55                  60
```

```
Phe Gln Tyr Gly Ser Lys Val Tyr Val Lys His Pro Ala Asp Ile Pro
 65                  70                  75                  80

Asp Tyr Lys Lys Leu Ser Phe Pro Glu Gly Phe Lys Trp Glu Arg Val
                 85                  90                  95

Met Asn Phe Glu Asp Gly Gly Val Val Thr Val Thr Gln Asp Ser Ser
            100                 105                 110

Leu Gln Asp Gly Cys Phe Ile Tyr Lys Val Lys Phe Ile Gly Val Asn
        115                 120                 125

Phe Pro Ser Asp Gly Pro Val Met Gln Lys Lys Thr Met Gly Trp Glu
130                 135                 140

Ala Ser Thr Glu Arg Leu Tyr Pro Arg Asp Gly Val Leu Lys Gly Glu
145                 150                 155                 160

Ile His Lys Ala Leu Lys Leu Lys Asp Gly Gly His Tyr Leu Val Glu
                165                 170                 175

Phe Lys Ser Ile Tyr Met Ala Lys Lys Pro Val Gln Leu Pro Gly Tyr
            180                 185                 190

Tyr Tyr Val Asp Ser Lys Leu Asp Ile Thr Ser His Asn Glu Asp Tyr
        195                 200                 205

Thr Ile Val Glu Gln Tyr Glu Arg Thr Glu Gly Arg His His Leu Phe
    210                 215                 220

Leu
225

<210> SEQ ID NO 2
<211> LENGTH: 678
<212> TYPE: DNA
<213> ORGANISM: Discosoma sp.
<220> FEATURE:
<223> OTHER INFORMATION: Discosoma corallimorph Anthozoan wild-type
      red fluorescent protein (DsRed, drFP583) open reading frame

<400> SEQUENCE: 2
atgaggtctt ccaagaatgt tatcaaggag ttcatgaggt ttaaggttcg catggaagga      60
acggtcaatg ggcacgagtt tgaaatagaa ggcgaaggag aggggaggcc atacgaaggc     120
cacaataccg taaagcttaa ggtaaccaag gggggacctt tgccatttgc ttgggatatt     180
ttgtcaccac aatttcagta tggaagcaag gtatatgtca agcaccctgc cgacatacca     240
gactataaaa gctgtcatt tcctgaagga tttaatggg aaagggtcat gaactttgaa     300
gacggtggcg tcgttactgt aacccaggat ccagtttgc aggatggctg tttcatctac     360
aaggtcaagt tcattggcgt gaactttcct tccgatggac ctgttatgca aagaagaca     420 atgggctggg aagccagcac tgagcgtttg tatcctcgtg atggcgtgtt gaaaggagag     480
attcataagg ctctgaagct gaaagacggt ggtcattacc tagttgaatt caaaagtatt     540
tacatggcaa agaagcctgt gcagctacca gggtactact atgttgactc caaactggat     600
ataacaagcc acaacgaaga ctatacaatc gttgagcagt atgaaagaac cgagggacgc     660
caccatctgt tcctttaa                                                   678

<210> SEQ ID NO 3
<211> LENGTH: 681
<212> TYPE: DNA
<213> ORGANISM: Artificial Sequence
<220> FEATURE:
<223> OTHER INFORMATION: Description of Artificial Sequence:Discosoma
      corallimorph Anthozoan red fluorescent protein
      (DsRed) with mammalian codon usage

<400> SEQUENCE: 3
```

-continued

```
atggtgcgct cctccaagaa cgtcatcaag gagttcatgc gcttcaaggt gcgcatggag    60
ggcaccgtga acggccacga gttcgagatc gagggcgagg gcgagggccg ccctacgag     120 ggccacaaca ccgtgaagct gaaggtgacc aagggcggcc ccctgccctt cgcctgggac    180
atcctgtccc cccagttcca gtacggctcc aaggtgtacg tgaagcaccc cgccgacatc    240
cccgactaca agaagctgtc cttccccgag ggcttcaagt gggagcgcgt gatgaacttc    300
gaggacggcg gcgtggtgac cgtgacccag gactcctccc tgcaggacgg ctgcttcatc    360
tacaaggtga agttcatcgg cgtgaacttc ccctccgacg gccccgtaat gcagaagaag    420
accatgggct gggaggcctc caccgagcgc ctgtaccccc gcgacggcgt gctgaagggc    480
gagatccaca aggccctgaa gctgaaggac ggcggccact acctggtgga gttcaagtcc    540
atctacatgg ccaagaagcc cgtgcagctg cccggctact actacgtgga ctccaagctg    600
gacatcacct cccacaacga ggactacacc atcgtggagc agtacgagcg caccgagggc    660
cgccaccacc tgttcctgta g                                              681
```

<210> SEQ ID NO 4
<211> LENGTH: 225
<212> TYPE: PRT
<213> ORGANISM: Artificial Sequence
<220> FEATURE:
<223> OTHER INFORMATION: Description of Artificial Sequence:Discosoma
      corallimorph Anthozoan red fluorescent protein
      (DsRed) variant fast T1

<400> SEQUENCE: 4

Met Ala Ser Ser Glu Asp Val Ile Lys Glu Phe Met Arg Phe Lys Val
1               5                   10                  15

Arg Met Glu Gly Ser Val Asn Gly His Glu Phe Glu Ile Glu Gly Glu
            20                  25                  30

Gly Glu Gly Arg Pro Tyr Glu Gly Thr Gln Thr Ala Lys Leu Lys Val
        35                  40                  45

Thr Lys Gly Gly Pro Leu Pro Phe Ala Trp Asp Ile Leu Ser Pro Gln
    50                  55                  60

Phe Gln Tyr Gly Ser Lys Val Tyr Val Lys His Pro Ala Asp Ile Pro
65                  70                  75                  80

Asp Tyr Lys Lys Leu Ser Phe Pro Glu Gly Phe Lys Trp Glu Arg Val
                85                  90                  95

Met Asn Phe Glu Asp Gly Gly Val Val Thr Val Thr Gln Asp Ser Ser
            100                 105                 110

Leu Gln Asp Gly Ser Phe Ile Tyr Lys Val Lys Phe Ile Gly Val Asn
        115                 120                 125

Phe Pro Ser Asp Gly Pro Val Met Gln Lys Lys Thr Met Gly Trp Glu
    130                 135                 140

Ala Ser Thr Glu Arg Leu Tyr Pro Arg Asp Gly Val Leu Lys Gly Glu
145                 150                 155                 160

Ile His Lys Ala Leu Lys Leu Lys Asp Gly Gly His Tyr Leu Val Glu
                165                 170                 175

Phe Lys Ser Ile Tyr Met Ala Lys Lys Pro Val Gln Leu Pro Gly Tyr
            180                 185                 190

Tyr Tyr Val Asp Ser Lys Leu Asp Ile Thr Ser His Asn Glu Asp Tyr
        195                 200                 205

Thr Ile Val Glu Gln Tyr Glu Arg Ala Glu Gly Arg His His Leu Phe
    210                 215                 220

Leu
225

<210> SEQ ID NO 5
<211> LENGTH: 678
<212> TYPE: DNA
<213> ORGANISM: Artificial Sequence
<220> FEATURE:
<223> OTHER INFORMATION: Description of Artificial Sequence:Discosoma
    corallimorph Anthozoan red fluorescent protein
    (DsRed) variant fast T1 cDNA

<400> SEQUENCE: 5

```
atggcctcct ccgaggacgt catcaaggag ttcatgcgct tcaaggtgcg catggagggc    60
tccgtgaacg gccacgagtt cgagatcgag ggcgagggcg agggccgccc ctacgagggc   120
acccagaccg ccaagctgaa ggtgaccaag ggcggccccc tgcccttcgc ctgggacatc   180
ctgtcccccc agttccagta cggctccaag gtgtacgtga agcaccccgc cgacatcccc   240
gactacaaga agctgtcctt ccccgagggc ttcaagtggg agcgcgtgat gaacttcgag   300
gacggcggcg tggtgaccgt gacccaggac tcctccctgc aggacggctc cttcatctac   360
aaggtgaagt tcatcggcgt gaacttcccc tccgacggcc ccgtaatgca gaagaagact   420
atgggctggg aggcctccac cgagcgcctg tacccccgcg acggcgtgct gaagggcgag   480
atccacaagg ccctgaagct gaaggacggc ggccactacc tggtggagtt caagtccatc   540
tacatggcca gaagcccgt gcagctgccc ggctactact acgtggactc caagctggac   600
atcacctccc acaacgagga ctacaccatc gtggagcagt acgagcgcgc cgagggccgc   660
caccacctgt tcctgtag                                                  678
```

<210> SEQ ID NO 6
<211> LENGTH: 226
<212> TYPE: PRT
<213> ORGANISM: Artificial Sequence
<220> FEATURE:
<223> OTHER INFORMATION: Description of Artificial Sequence:Discosoma
    corallimorph Anthozoan red fluorescent protein
    (DsRed) tandem dimer subunit variant dimer2

<400> SEQUENCE: 6

```
Met Val Ala Ser Ser Glu Asp Val Ile Lys Glu Phe Met Arg Phe Lys
  1               5                  10                  15

Val Arg Met Glu Gly Ser Val Asn Gly His Glu Phe Glu Ile Glu Gly
             20                  25                  30

Glu Gly Glu Gly Arg Pro Tyr Glu Gly Thr Gln Thr Ala Lys Leu Lys
         35                  40                  45

Val Thr Lys Gly Gly Pro Leu Pro Phe Ala Trp Asp Ile Leu Ser Pro
     50                  55                  60

Gln Phe Gln Tyr Gly Ser Lys Ala Tyr Val Lys His Pro Ala Asp Ile
 65                  70                  75                  80

Pro Asp Tyr Lys Lys Leu Ser Phe Pro Glu Gly Phe Lys Trp Glu Arg
                 85                  90                  95

Val Met Asn Phe Glu Asp Gly Gly Val Val Thr Val Thr Gln Asp Ser
            100                 105                 110

Ser Leu Gln Asp Gly Thr Leu Ile Tyr Lys Val Lys Phe Arg Gly Thr
        115                 120                 125

Asn Phe Pro Pro Asp Gly Pro Val Met Gln Lys Lys Thr Met Gly Trp
    130                 135                 140

Glu Ala Ser Thr Glu Arg Leu Tyr Pro Arg Asp Gly Val Leu Lys Gly
145                 150                 155                 160

Glu Ile His Gln Ala Leu Lys Leu Lys Asp Gly Gly His Tyr Leu Val
```

```
                      165                 170                 175
Glu Phe Lys Thr Ile Tyr Met Ala Lys Lys Pro Val Gln Leu Pro Gly
            180                 185                 190

Tyr Tyr Tyr Val Asp Thr Lys Leu Asp Ile Thr Ser His Asn Glu Asp
        195                 200                 205

Tyr Thr Ile Val Glu Gln Tyr Glu Arg Ser Glu Gly Arg His His Leu
    210                 215                 220

Phe Leu
225

<210> SEQ ID NO 7
<211> LENGTH: 681
<212> TYPE: DNA
<213> ORGANISM: Artificial Sequence
<220> FEATURE:
<223> OTHER INFORMATION: Description of Artificial Sequence:Discosoma
      corallimorph Anthozoan red fluorescent protein
      (DsRed) tandem dimer subunit variant dimer2 open
      reading frame

<400> SEQUENCE: 7
atggtggcct cctccgagga cgtcatcaaa gagttcatgc gcttcaaggt gcgcatggag     60
ggctccgtga acggccacga gttcgagatc gagggcgagg gcgagggccg cccctacgag    120
ggcacccaga ccgccaagct gaaggtgacc aagggcggcc ccctgccctt cgcctgggac    180
atcctgtccc cccagttcca gtacggctcc aaggcgtacg tgaagcaccc cgccgacatc    240
cccgactaca gaagctgtc cttccccgag ggcttcaagt gggagcgcgt gatgaacttc    300
gaggacggcg gcgtggtgac cgtgacccag gactcctccc tgcaggacgg cacgctgatc    360
tacaaggtga agttccgcgg caccaacttc ccccccgacg ccccgtaat gcagaagaag    420 accatgggct gggaggcctc caccgagcgc ctgtacccccc gcgacggcgt gctgaagggc    480
gagatccacc aggccctgaa gctgaaggac ggcggccact acctggtgga gttcaagacc    540
atctacatgg ccaagaagcc cgtgcagctg cccggctact actacgtgga caccaagctg    600
gacatcacct cccacaacga ggactacacc atcgtggaac agtacgagcg ctccgagggc    660
cgccaccacc tgttcctgta g                                              681

<210> SEQ ID NO 8
<211> LENGTH: 225
<212> TYPE: PRT
<213> ORGANISM: Artificial Sequence
<220> FEATURE:
<223> OTHER INFORMATION: Description of Artificial Sequence:Discosoma
      corallimorph Anthozoan red fluorescent protein
      (DsRed) monomeric variant mRFP1

<400> SEQUENCE: 8

Met Ala Ser Ser Glu Asp Val Ile Lys Glu Phe Met Arg Phe Lys Val
 1               5                  10                  15

Arg Met Glu Gly Ser Val Asn Gly His Glu Phe Glu Ile Glu Gly Glu
            20                  25                  30

Gly Glu Gly Arg Pro Tyr Glu Gly Thr Gln Thr Ala Lys Leu Lys Val
        35                  40                  45

Thr Lys Gly Gly Pro Leu Pro Phe Ala Trp Asp Ile Leu Ser Pro Gln
    50                  55                  60

Phe Gln Tyr Gly Ser Lys Ala Tyr Val Lys His Pro Ala Asp Ile Pro
65                  70                  75                  80

Asp Tyr Leu Lys Leu Ser Phe Pro Glu Gly Phe Lys Trp Glu Arg Val
                85                  90                  95
```

```
Met Asn Phe Glu Asp Gly Gly Val Val Thr Val Thr Gln Asp Ser Ser
            100                 105                 110
Leu Gln Asp Gly Glu Phe Ile Tyr Lys Val Lys Leu Arg Gly Thr Asn
            115                 120                 125
Phe Pro Ser Asp Gly Pro Val Met Gln Lys Lys Thr Met Gly Trp Glu
        130                 135                 140
Ala Ser Thr Glu Arg Met Tyr Pro Glu Asp Gly Ala Leu Lys Gly Glu
145                 150                 155                 160
Ile Lys Met Arg Leu Lys Leu Lys Asp Gly Gly His Tyr Asp Ala Glu
                165                 170                 175
Val Lys Thr Thr Tyr Met Ala Lys Lys Pro Val Gln Leu Pro Gly Ala
            180                 185                 190
Tyr Lys Thr Asp Ile Lys Leu Asp Ile Thr Ser His Asn Glu Asp Tyr
            195                 200                 205
Thr Ile Val Glu Gln Tyr Glu Arg Ala Glu Gly Arg His Ser Thr Gly
        210                 215                 220
Ala
225

<210> SEQ ID NO 9
<211> LENGTH: 678
<212> TYPE: DNA
<213> ORGANISM: Artificial Sequence
<220> FEATURE:
<223> OTHER INFORMATION: Description of Artificial Sequence:Discosoma
      corallimorph Anthozoan red fluorescent protein
      (DsRed) monomeric variant mRFP1

<400> SEQUENCE: 9
atggcctcct ccgaggacgt catcaaggag ttcatgcgct tcaaggtgcg catggagggc      60
tccgtgaacg gccacgagtt cgagatcgag ggcgagggcg agggccgccc ctacgagggc     120
acccagaccg ccaagctgaa ggtgaccaag ggcggccccc tgcccttcgc ctgggacatc     180
ctgtccccte agttccagta cggctccaag gcctacgtga agcaccccgc cgacatcccc     240
gactacttga agctgtcctt ccccgagggc ttcaagtggg agcgcgtgat gaacttcgag     300
gacggcggcg tggtgaccgt gacccaggac tcctccctgc aggacggcga gttcatctac     360
aaggtgaagc tgcgcggcac caacttcccc tccgacggcc ccgtaatgca gaagaagacc     420
atgggctggg aggcctccac cgagcggatg taccccgagg acggcgccct gaagggcgag     480
atcaagatga ggctgaagct gaaggacggc ggccactacg acgccgaggt caagaccacc     540
tacatggcca agaagcccgt gcagctgccc ggcgcctaca agaccgacat caagctggac     600
atcacctccc acaacgagga ctacaccatc gtggaacagt acgagcgcgc cgagggccgc     660
cactccaccg gcgcctaa                                                   678

<210> SEQ ID NO 10
<211> LENGTH: 238
<212> TYPE: PRT
<213> ORGANISM: Aequorea victoria
<220> FEATURE:
<223> OTHER INFORMATION: Pacific Northwest jellyfish wild-type
      (native) green fluorescent protein (GFP)

<400> SEQUENCE: 10

Met Ser Lys Gly Glu Glu Leu Phe Thr Gly Val Val Pro Ile Leu Val
  1               5                  10                  15
Glu Leu Asp Gly Asp Val Asn Gly His Lys Phe Ser Val Ser Gly Glu
             20                  25                  30
```

-continued

Gly Glu Gly Asp Ala Thr Tyr Gly Lys Leu Thr Leu Lys Phe Ile Cys
            35                  40                  45

Thr Thr Gly Lys Leu Pro Val Pro Trp Pro Thr Leu Val Thr Thr Phe
 50                  55                  60

Ser Tyr Gly Val Gln Cys Phe Ser Arg Tyr Pro Asp His Met Lys Gln
 65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Asn Ser His Asn Val Tyr Ile Met Ala Asp Lys Gln Lys Asn Gly
145                 150                 155                 160

Ile Lys Val Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
    210                 215                 220

Thr Ala Ala Gly Ile Thr His Gly Met Asp Glu Leu Tyr Lys
225                 230                 235

<210> SEQ ID NO 11
<211> LENGTH: 239
<212> TYPE: PRT
<213> ORGANISM: Artificial Sequence
<220> FEATURE:
<223> OTHER INFORMATION: Description of Artificial Sequence:enhanced
      cyan fluorescent protein (ECFP, wtECFP)

<400> SEQUENCE: 11

Met Val Ser Lys Gly Glu Glu Leu Phe Thr Gly Val Val Pro Ile Leu
 1               5                  10                  15

Val Glu Leu Asp Gly Asp Val Asn Gly His Arg Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
 50                  55                  60

Leu Thr Trp Gly Val Gln Cys Phe Ser Arg Tyr Pro Asp His Met Lys
 65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Ile Ser His Asn Val Tyr Ile Thr Ala Asp Lys Gln Lys Asn
145                 150                 155                 160

```
Gly Ile Lys Ala His Phe Lys Ile Arg His Asn Ile Glu Asp Gly Ser
            165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
            195                 200                 205

Ser Lys Asp Pro Asn Glu Lys Arg Asp His Met Val Leu Leu Glu Phe
            210                 215                 220

Val Thr Ala Ala Gly Ile Thr Leu Gly Met Asp Glu Leu Tyr Lys
225                 230                 235

<210> SEQ ID NO 12
<211> LENGTH: 239
<212> TYPE: PRT
<213> ORGANISM: Artificial Sequence
<220> FEATURE:
<223> OTHER INFORMATION: Description of Artificial Sequence:enhanced
      yellow fluorescent protein (EYFP, wtEYFP) variant V68L/Q69K

<400> SEQUENCE: 12

Met Val Ser Lys Gly Glu Glu Leu Phe Thr Gly Val Val Pro Ile Leu
  1               5                  10                  15

Val Glu Leu Asp Gly Asp Val Asn Gly His Lys Phe Ser Val Ser Gly
             20                  25                  30

Glu Gly Glu Gly Asp Ala Thr Tyr Gly Lys Leu Thr Leu Lys Phe Ile
         35                  40                  45

Cys Thr Thr Gly Lys Leu Pro Val Pro Trp Pro Thr Leu Val Thr Thr
     50                  55                  60

Phe Gly Tyr Gly Leu Lys Cys Phe Ala Arg Tyr Pro Asp His Met Lys
 65                  70                  75                  80

Gln His Asp Phe Phe Lys Ser Ala Met Pro Glu Gly Tyr Val Gln Glu
                 85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
            115                 120                 125

Ile Asp Phe Lys Glu Asp Gly Asn Ile Leu Gly His Lys Leu Glu Tyr
            130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
            165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Tyr Gln Ser Ala Leu
            195                 200                 205

Ser Lys Asp Pro Asn Glu Lys Arg Asp His Met Val Leu Leu Glu Phe
            210                 215                 220

Val Thr Ala Ala Gly Ile Thr Leu Gly Met Asp Glu Leu Tyr Lys
225                 230                 235

<210> SEQ ID NO 13
<211> LENGTH: 239
<212> TYPE: PRT
<213> ORGANISM: Artificial Sequence
<220> FEATURE:
<223> OTHER INFORMATION: Description of Artificial Sequence:enhanced
      green fluorescent protein (EGFP)
```

-continued

```
<400> SEQUENCE: 13

Met Val Ser Lys Gly Glu Glu Leu Phe Thr Gly Val Val Pro Ile Leu
  1               5                  10                  15

Val Glu Leu Asp Gly Asp Val Asn Gly His Lys Phe Ser Val Ser Gly
             20                  25                  30

Glu Gly Glu Gly Asp Ala Thr Tyr Gly Lys Leu Thr Leu Lys Phe Ile
         35                  40                  45

Cys Thr Thr Gly Lys Leu Pro Val Pro Trp Pro Thr Leu Val Thr Thr
 50                  55                  60

Leu Thr Tyr Gly Val Gln Cys Phe Ser Arg Tyr Pro Asp His Met Lys
 65                  70                  75                  80

Gln His Asp Phe Phe Lys Ser Ala Met Pro Glu Gly Tyr Val Gln Glu
                 85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys
225                 230                 235

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence:EGFP
      N-terminus, 7-residue GFP-type N-terminus

<400> SEQUENCE: 14

Met Val Ser Lys Gly Glu Glu
  1               5

<210> SEQ ID NO 15
<211> LENGTH: 239
<212> TYPE: PRT
<213> ORGANISM: Artificial Sequence
<220> FEATURE:
<223> OTHER INFORMATION: Description of Artificial Sequence:enhanced
      yellow fluorescent protein (EYFP)

<400> SEQUENCE: 15

Met Val Ser Lys Gly Glu Glu Leu Phe Thr Gly Val Val Pro Ile Leu
  1               5                  10                  15

Val Glu Leu Asp Gly Asp Val Asn Gly His Lys Phe Ser Val Ser Gly
             20                  25                  30

Glu Gly Glu Gly Asp Ala Thr Tyr Gly Lys Leu Thr Leu Lys Phe Ile
```

```
               35                  40                  45
Cys Thr Thr Gly Lys Leu Pro Val Pro Trp Pro Thr Leu Val Thr Thr
             50                  55                  60

Phe Gly Tyr Gly Val Gln Cys Phe Ala Arg Tyr Pro Asp His Met Lys
 65                  70                  75                  80

Gln His Asp Phe Phe Lys Ser Ala Met Pro Glu Gly Tyr Val Gln Glu
                 85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Tyr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys
225                 230                 235

<210> SEQ ID NO 16
<211> LENGTH: 9
<212> TYPE: PRT
<213> ORGANISM: Artificial Sequence
<220> FEATURE:
<223> OTHER INFORMATION: Description of Artificial Sequence:9 residue
      peptide linker

<400> SEQUENCE: 16

Arg Met Gly Thr Gly Ser Gly Gln Leu
  1               5

<210> SEQ ID NO 17
<211> LENGTH: 12
<212> TYPE: PRT
<213> ORGANISM: Artificial Sequence
<220> FEATURE:
<223> OTHER INFORMATION: Description of Artificial Sequence:12 residue
      peptide linker

<400> SEQUENCE: 17

Gly His Gly Thr Gly Ser Thr Gly Ser Gly Ser Ser
  1               5                  10

<210> SEQ ID NO 18
<211> LENGTH: 13
<212> TYPE: PRT
<213> ORGANISM: Artificial Sequence
<220> FEATURE:
<223> OTHER INFORMATION: Description of Artificial Sequence:13 residue
      peptide linker

<400> SEQUENCE: 18

Arg Met Gly Ser Thr Ser Gly Ser Thr Lys Gly Gln Leu
  1               5                  10
```

-continued

<210> SEQ ID NO 19
<211> LENGTH: 22
<212> TYPE: PRT
<213> ORGANISM: Artificial Sequence
<220> FEATURE:
<223> OTHER INFORMATION: Description of Artificial Sequence:22 residue
      peptide linker

<400> SEQUENCE: 19

Arg Met Gly Ser Thr Ser Gly Ser Gly Lys Pro Gly Ser Gly Glu Gly
 1               5                  10                  15

Ser Thr Lys Gly Gln Leu
            20

<210> SEQ ID NO 20
<211> LENGTH: 225
<212> TYPE: PRT
<213> ORGANISM: Artificial Sequence
<220> FEATURE:
<223> OTHER INFORMATION: Description of Artificial Sequence:Discosoma
      corallimorph Anthozoan red fluorescent protein
      (DsRed) with I125R replacement, DsRed-I125R mutant

<400> SEQUENCE: 20

Met Arg Ser Ser Lys Asn Val Ile Lys Glu Phe Met Arg Phe Lys Val
 1               5                  10                  15

Arg Met Glu Gly Thr Val Asn Gly His Glu Phe Glu Ile Glu Gly Glu
            20                  25                  30

Gly Glu Gly Arg Pro Tyr Glu Gly His Asn Thr Val Lys Leu Lys Val
        35                  40                  45

Thr Lys Gly Gly Pro Leu Pro Phe Ala Trp Asp Ile Leu Ser Pro Gln
    50                  55                  60

Phe Gln Tyr Gly Ser Lys Val Tyr Val Lys His Pro Ala Asp Ile Pro
65                  70                  75                  80

Asp Tyr Lys Lys Leu Ser Phe Pro Glu Gly Phe Lys Trp Glu Arg Val
                85                  90                  95

Met Asn Phe Glu Asp Gly Gly Val Val Thr Val Thr Gln Asp Ser Ser
            100                 105                 110

Leu Gln Asp Gly Cys Phe Ile Tyr Lys Val Lys Phe Arg Gly Val Asn
        115                 120                 125

Phe Pro Ser Asp Gly Pro Val Met Gln Lys Lys Thr Met Gly Trp Glu
    130                 135                 140

Ala Ser Thr Glu Arg Leu Tyr Pro Arg Asp Gly Val Leu Lys Gly Glu
145                 150                 155                 160

Ile His Lys Ala Leu Lys Leu Lys Asp Gly Gly His Tyr Leu Val Glu
                165                 170                 175

Phe Lys Ser Ile Tyr Met Ala Lys Lys Pro Val Gln Leu Pro Gly Tyr
            180                 185                 190

Tyr Tyr Val Asp Ser Lys Leu Asp Ile Thr Ser His Asn Glu Asp Tyr
        195                 200                 205

Thr Ile Val Glu Gln Tyr Glu Arg Thr Glu Gly Arg His His Leu Phe
    210                 215                 220

Leu
225

<210> SEQ ID NO 21
<211> LENGTH: 716
<212> TYPE: DNA
<213> ORGANISM: Aequorea victoria
<220> FEATURE:

<223> OTHER INFORMATION: Pacific Northwest jellyfish wild-type (native) green fluorescent protein (GFP) cDNA

<400> SEQUENCE: 21

```
atgagtaaag gagaagaact tttcactgga gttgtcccaa ttcttgttga attagatggt      60
gatgttaatg ggcacaaatt ttctgtcagt ggagagggtg aaggtgatgc aacatacgga     120
aaacttaccc ttaaatttat ttgcactact ggaaaactac ctgttccatg gccaacactt     180
gtcactactt tctcttatgg tgttcaatgc ttttcaagat acccagatca tatgaaacag     240
catgactttt tcaagagtgc catgcccgaa ggttatgtac aggaaagaac tatattttc      300
aaagatgacg ggaactacaa gacacgtgct gaagtcaagt ttgaaggtga tacccttgtt     360
aatagaatcg agttaaaagg tattgatttt aaagaagatg gaacattct tggacacaaa      420
ttggaataca actataactc acacaatgta tacatcatgg cagacaaaca aaagaatgga     480
atcaaagtta acttcaaaat tagacacaac attgaagatg gaagcgttca actagcagac     540
cattatcaac aaaatactcc aattggcgat ggccctgtcc ttttaccaga caaccattac     600
ctgtccacac aatctgccct ttcgaaagat cccaacgaaa agagagacca catggtcctt     660
cttgagtttg taacagctgc tgggattaca catggcatgg atgaactata caaata        716
```

<210> SEQ ID NO 22
<211> LENGTH: 33
<212> TYPE: PRT
<213> ORGANISM: Artificial Sequence
<220> FEATURE:
<223> OTHER INFORMATION: Description of Artificial Sequence:N-terminal polyhistidine tag, pRSET-B GFP subclone additional N-terminal additional 33 amino acids

<400> SEQUENCE: 22

Met Arg Gly Ser His His His His His His Gly Met Ala Ser Met Thr
1               5                   10                  15
Gly Gly Gln Gln Met Gly Arg Asp Leu Tyr Asp Asp Asp Lys Asp
            20                  25                  30
Pro

<210> SEQ ID NO 23
<211> LENGTH: 681
<212> TYPE: DNA
<213> ORGANISM: Artificial Sequence
<220> FEATURE:
<223> OTHER INFORMATION: Description of Artificial Sequence:modified Discosoma corallimorph Anthozoan wild-type red fluorescent protein (DsRed) open reading frame amended to accomodate mammalian codon usage utilization preferences

<400> SEQUENCE: 23

```
atggtgcgct cctccaagaa cgtcatcaag gagttcatgc gcttcaaggt gcgcatggag      60
ggcaccgtga acggccacga gttcgagatc gagggcgagg gcgagggccg cccctacgag     120
ggccacaaca ccgtgaagct gaaggtgacc aagggcggcc ccctgccctt cgcctgggac     180
atcctgtccc ccagttcca gtacggctcc aaggtgtacg tgaagcaccc cgccgacatc     240
cccgactaca agaagctgtc cttccccgag ggcttcaagt gggagcgcgt gatgaacttc     300
gaggacggcg gcgtggtgac cgtgacccag gactcctccc tgcaggacgg ctgcttcatc     360
tacaaggtga agttcatcgg cgtgaacttc ccctccgacg gccccgtaat gcagaagaag     420
accatgggct gggaggcctc caccgagcgc ctgtaccccc gcgacggcgt gctgaagggc     480
gagatccaca aggccctgaa gctgaaggac ggcggccact acctggtgga gttcaagtcc     540
```

```
atctacatgg ccaagaagcc cgtgcagctg cccggctact actacgtgga ctccaagctg    600
gacatcacct cccacaacga ggactacacc atcgtggagc agtacgagcg caccgagggc    660
cgccaccacc tgttcctgta g                                              681
```

<210> SEQ ID NO 24
<211> LENGTH: 225
<212> TYPE: PRT
<213> ORGANISM: Artificial Sequence
<220> FEATURE:
<223> OTHER INFORMATION: Description of Artificial Sequence:Discosoma corallimorph Anthozoan red fluorescent protein (DsRed) variant fast T1 with I125R mutation

<400> SEQUENCE: 24

```
Met Ala Ser Ser Glu Asp Val Ile Lys Glu Phe Met Arg Phe Lys Val
 1               5                  10                  15

Arg Met Glu Gly Ser Val Asn Gly His Glu Phe Glu Ile Glu Gly Glu
            20                  25                  30

Gly Glu Gly Arg Pro Tyr Glu Gly Thr Gln Thr Ala Lys Leu Lys Val
        35                  40                  45

Thr Lys Gly Gly Pro Leu Pro Phe Ala Trp Asp Ile Leu Ser Pro Gln
50                  55                  60

Phe Gln Tyr Gly Ser Lys Val Tyr Val Lys His Pro Ala Asp Ile Pro
65                  70                  75                  80

Asp Tyr Lys Lys Leu Ser Phe Pro Glu Gly Phe Lys Trp Glu Arg Val
                85                  90                  95

Met Asn Phe Glu Asp Gly Gly Val Val Thr Val Thr Gln Asp Ser Ser
            100                 105                 110

Leu Gln Asp Gly Ser Phe Ile Tyr Lys Val Lys Phe Arg Gly Val Asn
        115                 120                 125

Phe Pro Ser Asp Gly Pro Val Met Gln Lys Lys Thr Met Gly Trp Glu
130                 135                 140

Ala Ser Thr Glu Arg Leu Tyr Pro Arg Asp Gly Val Leu Lys Gly Glu
145                 150                 155                 160

Ile His Lys Ala Leu Lys Leu Lys Asp Gly Gly His Tyr Leu Val Glu
                165                 170                 175

Phe Lys Ser Ile Tyr Met Ala Lys Lys Pro Val Gln Leu Pro Gly Tyr
            180                 185                 190

Tyr Tyr Val Asp Ser Lys Leu Asp Ile Thr Ser His Asn Glu Asp Tyr
        195                 200                 205

Thr Ile Val Glu Gln Tyr Glu Arg Ala Glu Gly Arg His His Leu Phe
210                 215                 220

Leu
225
```

<210> SEQ ID NO 25
<211> LENGTH: 42
<212> TYPE: DNA
<213> ORGANISM: Artificial Sequence
<220> FEATURE:
<223> OTHER INFORMATION: Description of Artificial Sequence:5' overlapping mutagenic primer A206K top

<400> SEQUENCE: 25

```
cagtccaagc tgagcaaaga ccccaacgag aagcgcgatc ac                        42
```

<210> SEQ ID NO 26
<211> LENGTH: 42
<212> TYPE: DNA

```
<213> ORGANISM: Artificial Sequence
<220> FEATURE:
<223> OTHER INFORMATION: Description of Artificial Sequence:3'
      overlapping mutagenic primer A206K bottom

<400> SEQUENCE: 26
gtgatcgcgc ttctcgttgg ggtctttgct cagcttggac tg                              42

<210> SEQ ID NO 27
<211> LENGTH: 36
<212> TYPE: DNA
<213> ORGANISM: Artificial Sequence
<220> FEATURE:
<223> OTHER INFORMATION: Description of Artificial Sequence:5'
      overlapping mutagenic primer L221K top

<400> SEQUENCE: 27
cacatggtcc tgaaggagtt cgtgaccgcc gccggg                                     36

<210> SEQ ID NO 28
<211> LENGTH: 36
<212> TYPE: DNA
<213> ORGANISM: Artificial Sequence
<220> FEATURE:
<223> OTHER INFORMATION: Description of Artificial Sequence:3'
      overlapping mutagenic primer L221K bottom

<400> SEQUENCE: 28
cccggcggcg gtcacgaact ccttcaggac catgtg                                     36

<210> SEQ ID NO 29
<211> LENGTH: 36
<212> TYPE: DNA
<213> ORGANISM: Artificial Sequence
<220> FEATURE:
<223> OTHER INFORMATION: Description of Artificial Sequence:5'
      overlapping mutagenic primer F223R top

<400> SEQUENCE: 29
cacatggtcc tgctggagcg cgtgaccgcc gccggg                                     36

<210> SEQ ID NO 30
<211> LENGTH: 36
<212> TYPE: DNA
<213> ORGANISM: Artificial Sequence
<220> FEATURE:
<223> OTHER INFORMATION: Description of Artificial Sequence:3'
      overlapping mutagenic primer F223R bottom

<400> SEQUENCE: 30
cccggcggcg gtcacgcgct ccagcaggac catgtg                                     36

<210> SEQ ID NO 31
<211> LENGTH: 36
<212> TYPE: DNA
<213> ORGANISM: Artificial Sequence
<220> FEATURE:
<223> OTHER INFORMATION: Description of Artificial Sequence:5'
      overlapping mutagenic primer L221K/F223R top

<400> SEQUENCE: 31
cacatcgtcc tgaaggagcg cgtgaccgcc gccggg                                     36

<210> SEQ ID NO 32
<211> LENGTH: 36
<212> TYPE: DNA
<213> ORGANISM: Artificial Sequence
<220> FEATURE:
```

-continued

```
<223> OTHER INFORMATION: Description of Artificial Sequence:3'
      overlapping mutagenic primer L221K/F223R bottom

<400> SEQUENCE: 32
cccggcggcg gtcacgcgct ccttcaggac catgtg                                    36

<210> SEQ ID NO 33
<211> LENGTH: 33
<212> TYPE: DNA
<213> ORGANISM: Artificial Sequence
<220> FEATURE:
<223> OTHER INFORMATION: Description of Artificial Sequence:mutagenesis
      primer I125K (forward)

<400> SEQUENCE: 33
tacaaggtga agttcaaggg cgtgaacttc ccc                                       33

<210> SEQ ID NO 34
<211> LENGTH: 33
<212> TYPE: DNA
<213> ORGANISM: Artificial Sequence
<220> FEATURE:
<223> OTHER INFORMATION: Description of Artificial Sequence:mutagenesis
      primer I125K (reverse)

<400> SEQUENCE: 34
ggggaagttc acgcccttga acttcacctt gta                                       33

<210> SEQ ID NO 35
<211> LENGTH: 33
<212> TYPE: DNA
<213> ORGANISM: Artificial Sequence
<220> FEATURE:
<223> OTHER INFORMATION: Description of Artificial Sequence:mutagenesis
      primer I125R (forward)

<400> SEQUENCE: 35
tacaaggtga agttccgcgg cgtgaacttc ccc                                       33

<210> SEQ ID NO 36
<211> LENGTH: 33
<212> TYPE: DNA
<213> ORGANISM: Artificial Sequence
<220> FEATURE:
<223> OTHER INFORMATION: Description of Artificial Sequence:mutagenesis
      primer I125R (reverse)

<400> SEQUENCE: 36
ggggaagttc acgccgcgga acttcacctt gta                                       33

<210> SEQ ID NO 37
<211> LENGTH: 86
<212> TYPE: DNA
<213> ORGANISM: Artificial Sequence
<220> FEATURE:
<223> OTHER INFORMATION: Description of Artificial Sequence:chimeric 3'
      primer containing 3 mismatches in the overlap
      region to construct tandem DsRed (tDsRed) encoding
      linker sequence

<400> SEQUENCE: 37
ccggatcccc tttggtgctg ccctctccgc tgccaggctt gccgctgccg ctggtgctgc          60
caaggaacag atggtggcgt ccctcg                                               86

<210> SEQ ID NO 38
<211> LENGTH: 18
<212> TYPE: PRT
```

```
<213> ORGANISM: Artificial Sequence
<220> FEATURE:
<223> OTHER INFORMATION: Description of Artificial Sequence:linker
      sequence encoded by chimeric 3' primer containing 3
      mismatches in the overlap region to construct
      tandem DsRed (tDsRed)

<400> SEQUENCE: 38

Gly Ser Thr Ser Gly Ser Gly Lys Pro Gly Ser Gly Glu Gly Ser Thr
 1               5                  10                  15

Lys Gly

<210> SEQ ID NO 39
<211> LENGTH: 86
<212> TYPE: DNA
<213> ORGANISM: Artificial Sequence
<220> FEATURE:
<223> OTHER INFORMATION: Description of Artificial Sequence:chimeric 3'
      primer to construct tandem DsRed (tDsRed) with
      codon usage optimized for mammalian expression

<400> SEQUENCE: 39
ccggatcccc cttggtgctg ccctccccgc tgccgggctt cccgctcccg ctggtgctgc      60
ccaggaacag gtggtggcgg ccctcg                                          86

<210> SEQ ID NO 40
<211> LENGTH: 24
<212> TYPE: DNA
<213> ORGANISM: Artificial Sequence
<220> FEATURE:
<223> OTHER INFORMATION: Description of Artificial Sequence:5' primer
      to construct tandem DsRed (tDsRed) with BamHI restriction site

<400> SEQUENCE: 40
gtacgacgat gacgataagg atcc                                            24

<210> SEQ ID NO 41
<211> LENGTH: 24
<212> TYPE: DNA
<213> ORGANISM: Artificial Sequence
<220> FEATURE:
<223> OTHER INFORMATION: Description of Artificial Sequence:vector
      backbone primer, PRSET_BamH1_FW PCR primer for general use

<400> SEQUENCE: 41
gtacgacgat gacgataagg atcc                                            24

<210> SEQ ID NO 42
<211> LENGTH: 24
<212> TYPE: DNA
<213> ORGANISM: Artificial Sequence
<220> FEATURE:
<223> OTHER INFORMATION: Description of Artificial Sequence:vector
      backbone primer, PRSET_EcoR1_RV PCR primer for general use

<400> SEQUENCE: 42
gcagccggat caagcttcga attc                                            24

<210> SEQ ID NO 43
<211> LENGTH: 46
<212> TYPE: DNA
<213> ORGANISM: Artificial Sequence
<220> FEATURE:
<223> OTHER INFORMATION: Description of Artificial Sequence:mutagenic
      primer, N42X_V44X_FW PCR primer used to construct
      libraries for DsRed dimer evolution

<400> SEQUENCE: 43
```
cgcccctacg agggccacmw saccvycaag ctgaaggtga ccaagg      46

<210> SEQ ID NO 44
<211> LENGTH: 46
<212> TYPE: DNA
<213> ORGANISM: Artificial Sequence
<220> FEATURE:
<223> OTHER INFORMATION: Description of Artificial Sequence:mutagenic
      primer, N42X_V44X_RV PCR primer used to construct
      libraries for DsRed dimer evolution

<400> SEQUENCE: 44
ccttggtcac cttcagcttg rbggtswkgt ggccctcgta ggggcg      46

<210> SEQ ID NO 45
<211> LENGTH: 42
<212> TYPE: DNA
<213> ORGANISM: Artificial Sequence
<220> FEATURE:
<223> OTHER INFORMATION: Description of Artificial Sequence:mutagenic
      primer, K70X_V71X_FW PCR primer used to construct
      libraries for DsRed dimer evolution
<220> FEATURE:
<221> NAME/KEY: modified_base
<222> LOCATION: (1)..(42)
<223> OTHER INFORMATION: n = g, a, c or t

<400> SEQUENCE: 45
cagttccagt acggctccnn knyctacgtg aagcaccccg cc      42

<210> SEQ ID NO 46
<211> LENGTH: 42
<212> TYPE: DNA
<213> ORGANISM: Artificial Sequence
<220> FEATURE:
<223> OTHER INFORMATION: Description of Artificial Sequence:mutagenic
      primer, K70X_V71X_RV PCR primer used to construct
      libraries for DsRed dimer evolution
<220> FEATURE:
<221> NAME/KEY: modified_base
<222> LOCATION: (1)..(42)
<223> OTHER INFORMATION: n = g, a, c or t

<400> SEQUENCE: 46
ggcggggtgc ttcacgtagr nmnnggagcc gtactggaac tg      42

<210> SEQ ID NO 47
<211> LENGTH: 48
<212> TYPE: DNA
<213> ORGANISM: Artificial Sequence
<220> FEATURE:
<223> OTHER INFORMATION: Description of Artificial Sequence:mutagenic
      primer, C117X_V127T_FW PCR primer used to
      construct libraries for DsRed dimer evolution
<220> FEATURE:
<221> NAME/KEY: modified_base
<222> LOCATION: (1)..(48)
<223> OTHER INFORMATION: n = g, a, c or t

<400> SEQUENCE: 47
caggacggcr vsntsatcta caaggtgaag ntscgcggca ccaacttc      48

<210> SEQ ID NO 48
<211> LENGTH: 48
<212> TYPE: DNA
<213> ORGANISM: Artificial Sequence
<220> FEATURE:
<223> OTHER INFORMATION: Description of Artificial Sequence:mutagenic
      primer, C117X_V127T_RV PCR primer used to
      construct libraries for DsRed dimer evolution

```
<220> FEATURE:
<221> NAME/KEY: modified_base
<222> LOCATION: (1)..(48)
<223> OTHER INFORMATION: n = g, a, c or t

<400> SEQUENCE: 48
gaagttggtg ccgcgsanct tcaccttgta gatsansbyg ccgtcctg                        48

<210> SEQ ID NO 49
<211> LENGTH: 46
<212> TYPE: DNA
<213> ORGANISM: Artificial Sequence
<220> FEATURE:
<223> OTHER INFORMATION: Description of Artificial Sequence:mutagenic
      primer, I161X_K163X_FW PCR primer used to
      construct libraries for DsRed dimer evolution

<400> SEQUENCE: 49
ggcgtgctga agggcgagvy ccacmwsgcc ctgaagctga aggacg                         46

<210> SEQ ID NO 50
<211> LENGTH: 46
<212> TYPE: DNA
<213> ORGANISM: Artificial Sequence
<220> FEATURE:
<223> OTHER INFORMATION: Description of Artificial Sequence:mutagenic
      primer, I161X_K163X_RV PCR primer used to
      construct libraries for DsRed dimer evolution

<400> SEQUENCE: 50
cgtccttcag cttcagggcs wkgtggrbct cgcccttcag cacgcc                         46

<210> SEQ ID NO 51
<211> LENGTH: 31
<212> TYPE: DNA
<213> ORGANISM: Artificial Sequence
<220> FEATURE:
<223> OTHER INFORMATION: Description of Artificial Sequence:mutagenic
      primer, S179X_FW PCR primer used to construct
      libraries for DsRed dimer evolution
<220> FEATURE:
<221> NAME/KEY: modified_base
<222> LOCATION: (14)
<223> OTHER INFORMATION: n = g, a, c or t

<400> SEQUENCE: 51
ggtggagttc aagnccatct acatggccaa g                                         31

<210> SEQ ID NO 52
<211> LENGTH: 31
<212> TYPE: DNA
<213> ORGANISM: Artificial Sequence
<220> FEATURE:
<223> OTHER INFORMATION: Description of Artificial Sequence:mutagenic
      primer, S179X_RV PCR primer used to construct
      libraries for DsRed dimer evolution
<220> FEATURE:
<221> NAME/KEY: modified_base
<222> LOCATION: (18)
<223> OTHER INFORMATION: n = g, a, c or t

<400> SEQUENCE: 52
cttggccatg tagatggnct tgaactccac c                                         31

<210> SEQ ID NO 53
<211> LENGTH: 34
<212> TYPE: DNA
<213> ORGANISM: Artificial Sequence
<220> FEATURE:
<223> OTHER INFORMATION: Description of Artificial Sequence:mutagenic
``` primer, S197X_A_FW PCR primer used to construct
libraries for DsRed dimer evolution
<220> FEATURE:
<221> NAME/KEY: modified_base
<222> LOCATION: (17)
<223> OTHER INFORMATION: n = g, a, c or t

<400> SEQUENCE: 53
ctactactac gtggacncca agctggacat cacc                                    34

<210> SEQ ID NO 54
<211> LENGTH: 34
<212> TYPE: DNA
<213> ORGANISM: Artificial Sequence
<220> FEATURE:
<223> OTHER INFORMATION: Description of Artificial Sequence:mutagenic
primer, S197X_A_RV PCR primer used to construct
libraries for DsRed dimer evolution
<220> FEATURE:
<221> NAME/KEY: modified_base
<222> LOCATION: (1)
<223> OTHER INFORMATION: n = 5' phosphorylated g
<220> FEATURE:
<221> NAME/KEY: modified_base
<222> LOCATION: (18)
<223> OTHER INFORMATION: n = g, a, c or t

<400> SEQUENCE: 54
ngtgatgtcc agcttgkngt ccacgtagta gtag                                    34

<210> SEQ ID NO 55
<211> LENGTH: 34
<212> TYPE: DNA
<213> ORGANISM: Artificial Sequence
<220> FEATURE:
<223> OTHER INFORMATION: Description of Artificial Sequence:mutagenic
primer, S197_B_FW PCR primer used to construct
libraries for DsRed dimer evolution
<220> FEATURE:
<221> NAME/KEY: modified_base
<222> LOCATION: (17)..(18)
<223> OTHER INFORMATION: n = g, a, c or t

<400> SEQUENCE: 55
ctactactac gtggacnnka agctggacat cacc                                    34

<210> SEQ ID NO 56
<211> LENGTH: 34
<212> TYPE: DNA
<213> ORGANISM: Artificial Sequence
<220> FEATURE:
<223> OTHER INFORMATION: Description of Artificial Sequence:mutagenic
primer, S197_B_RV PCR primer used to construct
libraries for DsRed dimer evolution
<220> FEATURE:
<221> NAME/KEY: modified_base
<222> LOCATION: (17)..(18)
<223> OTHER INFORMATION: n = g, a, c or t

<400> SEQUENCE: 56
ggtgatgtcc agcttmnngt ccacgtagta gtag                                    34

<210> SEQ ID NO 57
<211> LENGTH: 27
<212> TYPE: DNA
<213> ORGANISM: Artificial Sequence
<220> FEATURE:
<223> OTHER INFORMATION: Description of Artificial Sequence:mutagenic
primer, T217X_FW PCR primer used to construct
libraries for DsRed dimer evolution
<220> FEATURE:
<221> NAME/KEY: modified_base

```
<222> LOCATION: (13)
<223> OTHER INFORMATION: n = g, a, c or t

<400> SEQUENCE: 57
cagtacgagc gcnccgaggg ccgccac                                           27

<210> SEQ ID NO 58
<211> LENGTH: 27
<212> TYPE: DNA
<213> ORGANISM: Artificial Sequence
<220> FEATURE:
<223> OTHER INFORMATION: Description of Artificial Sequence:mutagenic
      primer, T217X_RV PCR primer used to construct
      libraries for DsRed dimer evolution
<220> FEATURE:
<221> NAME/KEY: modified_base
<222> LOCATION: (15)
<223> OTHER INFORMATION: n = g, a, c or t

<400> SEQUENCE: 58
gtggcggccc tcggngcgct cgtactg                                           27

<210> SEQ ID NO 59
<211> LENGTH: 39
<212> TYPE: DNA
<213> ORGANISM: Artificial Sequence
<220> FEATURE:
<223> OTHER INFORMATION: Description of Artificial Sequence:mutagenic
      primer, K70X_K83X_FW PCR primer used for DsRed
      monomer evolution

<400> SEQUENCE: 59
aagcaccccg ccgacatccc cgactacwwk aagctgtcc                              39

<210> SEQ ID NO 60
<211> LENGTH: 42
<212> TYPE: DNA
<213> ORGANISM: Artificial Sequence
<220> FEATURE:
<223> OTHER INFORMATION: Description of Artificial Sequence:mutagenic
      primer, K70X_K83X_RV PCR primer used for DsRed
      monomer evolution

<400> SEQUENCE: 60
gatgtcggcg gggtgcttca cgtagrccyt ggagccgtac tg                          42

<210> SEQ ID NO 61
<211> LENGTH: 39
<212> TYPE: DNA
<213> ORGANISM: Artificial Sequence
<220> FEATURE:
<223> OTHER INFORMATION: Description of Artificial Sequence:mutagenic
      primer, C117X_S131X_FW PCR primer used for DsRed
      monomer evolution
<220> FEATURE:
<221> NAME/KEY: modified_base
<222> LOCATION: (7)

<400> SEQUENCE: 61
gtgaagntsc gcggcaccaa cttccccycc gacggcccc                              39

<210> SEQ ID NO 62
<211> LENGTH: 48
<212> TYPE: DNA
<213> ORGANISM: Artificial Sequence
<220> FEATURE:
<223> OTHER INFORMATION: Description of Artificial Sequence:mutagenic
      primer, C117X_S131X_RV PCR primer used for DsRed
      monomer evolution
<220> FEATURE:
```

```
<221> NAME/KEY: modified_base
<222> LOCATION: (18)
<223> OTHER INFORMATION: n = g, a, c or t

<400> SEQUENCE: 62
gaagttggtg ccgcgsanct tcaccttgta gatgaasbyg ccgtcctg                48

<210> SEQ ID NO 63
<211> LENGTH: 66
<212> TYPE: DNA
<213> ORGANISM: Artificial Sequence
<220> FEATURE:
<223> OTHER INFORMATION: Description of Artificial Sequence:mutagenic
      primer, E144X_A164X_FW PCR primer used for DsRed
      monomer evolution
<220> FEATURE:
<221> NAME/KEY: modified_base
<222> LOCATION: (1)..(66)
<223> OTHER INFORMATION: n = g, a, c or t

<400> SEQUENCE: 63
ctgtaccccc gcgacggcgt gctgaagggc gagnhcargn wsargctgaa gctgaaggac    60
ggcggc                                                              66

<210> SEQ ID NO 64
<211> LENGTH: 66
<212> TYPE: DNA
<213> ORGANISM: Artificial Sequence
<220> FEATURE:
<223> OTHER INFORMATION: Description of Artificial Sequence:mutagenic
      primer, E144X_A164X_RV PCR primer used for DsRed
      monomer evolution

<400> SEQUENCE: 64
cttcagcacg ccgtcgcggg ggtacaggcg ctcggtgsts bbsbbccagc ccatrgtctt    60
cttctg                                                              66

<210> SEQ ID NO 65
<211> LENGTH: 42
<212> TYPE: DNA
<213> ORGANISM: Artificial Sequence
<220> FEATURE:
<223> OTHER INFORMATION: Description of Artificial Sequence:mutagenic
      primer, A145X_V156X_FW PCR primer used for DsRed
      monomer evolution
<220> FEATURE:
<221> NAME/KEY: modified_base
<222> LOCATION: (13)
<223> OTHER INFORMATION: n = g, a, c or t

<400> SEQUENCE: 65
tccaccgagc rsntstaccc cvasgacggc rbcctgaagg gc                      42

<210> SEQ ID NO 66
<211> LENGTH: 42
<212> TYPE: DNA
<213> ORGANISM: Artificial Sequence
<220> FEATURE:
<223> OTHER INFORMATION: Description of Artificial Sequence:mutagenic
      primer, A145X_V156X_RV PCR primer used for DsRed
      monomer evolution
<220> FEATURE:
<221> NAME/KEY: modified_base
<222> LOCATION: (18)
<223> OTHER INFORMATION: n = g, a, c or t

<400> SEQUENCE: 66
gccgtcstbg gggtasansy gctcggtgga ggctcccag cc                       42
```

<210> SEQ ID NO 67
<211> LENGTH: 39
<212> TYPE: DNA
<213> ORGANISM: Artificial Sequence
<220> FEATURE:
<223> OTHER INFORMATION: Description of Artificial Sequence:mutagenic
     primer, H162X_A164X_FW PCR primer used for DsRed
     monomer evolution

<400> SEQUENCE: 67
ctgaagggcg agatcargmw sargctgaag ctgaaggac                    39

<210> SEQ ID NO 68
<211> LENGTH: 39
<212> TYPE: DNA
<213> ORGANISM: Artificial Sequence
<220> FEATURE:
<223> OTHER INFORMATION: Description of Artificial Sequence:mutagenic
     primer, H162X_A164X_RV PCR primer used for DsRed
     monomer evolution

<400> SEQUENCE: 68
gtccttcagc ttcagcytsw kcytgatctc gcccttcag                    39

<210> SEQ ID NO 69
<211> LENGTH: 39
<212> TYPE: DNA
<213> ORGANISM: Artificial Sequence
<220> FEATURE:
<223> OTHER INFORMATION: Description of Artificial Sequence:mutagenic
     primer, L174X_180X_FW PCR primer used for DsRed
     monomer evolution
<220> FEATURE:
<221> NAME/KEY: modified_base
<222> LOCATION: (1)..(39)
<223> OTHER INFORMATION: n = g, a, c or t

<400> SEQUENCE: 69
ggccactacv vcnycgagny caagaccayc tacatggcc                    39

<210> SEQ ID NO 70
<211> LENGTH: 39
<212> TYPE: DNA
<213> ORGANISM: Artificial Sequence
<220> FEATURE:
<223> OTHER INFORMATION: Description of Artificial Sequence:mutagenic
     primer, L174X_180X_RV PCR primer used for DsRed
     monomer evolution
<220> FEATURE:
<221> NAME/KEY: modified_base
<222> LOCATION: (1)..(39)
<223> OTHER INFORMATION: n = g, a, c or t

<400> SEQUENCE: 70
ggccatgtag rtggtcttgr nctcgrngbb gtagtggcc                    39

<210> SEQ ID NO 71
<211> LENGTH: 39
<212> TYPE: DNA
<213> ORGANISM: Artificial Sequence
<220> FEATURE:
<223> OTHER INFORMATION: Description of Artificial Sequence:mutagenic
     primer, Y192X_Y194X_FW PCR primer used for DsRed
     monomer evolution

<400> SEQUENCE: 71
gtgcagctgc ccggcgccta cgccgtggac accaagctg                    39

<210> SEQ ID NO 72

```
<211> LENGTH: 39
<212> TYPE: DNA
<213> ORGANISM: Artificial Sequence
<220> FEATURE:
<223> OTHER INFORMATION: Description of Artificial Sequence:mutagenic
      primer, Y192X_Y194X_RV PCR primer used for DsRed
      monomer evolution

<400> SEQUENCE: 72
cagcttggtg tccacggcgt aggcgccggg cagctgcac                          39

<210> SEQ ID NO 73
<211> LENGTH: 36
<212> TYPE: DNA
<213> ORGANISM: Artificial Sequence
<220> FEATURE:
<223> OTHER INFORMATION: Description of Artificial Sequence:mutagenic
      primer, Y192X_S197X_FW PCR primer used for DsRed
      monomer evolution

<400> SEQUENCE: 73
ggcrmstacr msrycgacry caagctggac atcacc                             36

<210> SEQ ID NO 74
<211> LENGTH: 36
<212> TYPE: DNA
<213> ORGANISM: Artificial Sequence
<220> FEATURE:
<223> OTHER INFORMATION: Description of Artificial Sequence:mutagenic
      primer, Y192X_S197X_RV PCR primer used for DsRed
      monomer evolution

<400> SEQUENCE: 74
cttgrygtcg ryskygtask ygccgggcag ctgcac                             36

<210> SEQ ID NO 75
<211> LENGTH: 43
<212> TYPE: DNA
<213> ORGANISM: Artificial Sequence
<220> FEATURE:
<223> OTHER INFORMATION: Description of Artificial Sequence:mutagenic
      primer, T217X_L225X_RV PCR primer used for DsRed
      monomer evolution

<400> SEQUENCE: 75
cgaattctta skygccskyg ccgtggcggc cctcgghgcg ctc                     43

<210> SEQ ID NO 76
<211> LENGTH: 40
<212> TYPE: DNA
<213> ORGANISM: Artificial Sequence
<220> FEATURE:
<223> OTHER INFORMATION: Description of Artificial Sequence:mutagenic
      primer, H222G_F224G_RV PCR primer used for DsRed
      monomer evolution
<220> FEATURE:
<221> NAME/KEY: modified_base
<222> LOCATION: (1)
<223> OTHER INFORMATION: n = 5'-phosphorylated g

<400> SEQUENCE: 76
ncttcgaatt cttacaggcc caggccgtgg cggccctcgg                         40

<210> SEQ ID NO 77
<211> LENGTH: 30
<212> TYPE: DNA
<213> ORGANISM: Artificial Sequence
<220> FEATURE:
<223> OTHER INFORMATION: Description of Artificial Sequence:mutagenic
      primer, V1a_deI_FW PCR primer used for DsRed
```

-continued monomer evolution

<400> SEQUENCE: 77
aaggatccga tggcctcctc cgaggacgtc                                              30

<210> SEQ ID NO 78
<211> LENGTH: 33
<212> TYPE: DNA
<213> ORGANISM: Artificial Sequence
<220> FEATURE:
<223> OTHER INFORMATION: Description of Artificial Sequence:mutagenic
      primer, H222S_REV PCR primer used for DsRed
      monomer evolution

<400> SEQUENCE: 78
ttcgaattct taggcgccgg tggagtggcg gcc                                          33

<210> SEQ ID NO 79
<211> LENGTH: 225
<212> TYPE: PRT
<213> ORGANISM: Artificial Sequence
<220> FEATURE:
<223> OTHER INFORMATION: Description of Artificial Sequence:Discosoma
      corallimorph Anthozoan red fluorescent protein
      (DsRed) mutant variant mRFP1.1 (mRFP1 + Q66M/T147S)

<400> SEQUENCE: 79

Met Ala Ser Ser Glu Asp Val Ile Lys Glu Phe Met Arg Phe Lys Val
  1               5                  10                  15

Arg Met Glu Gly Ser Val Asn Gly His Glu Phe Glu Ile Glu Gly Glu
             20                  25                  30

Gly Glu Gly Arg Pro Tyr Glu Gly Thr Gln Thr Ala Lys Leu Lys Val
         35                  40                  45

Thr Lys Gly Gly Pro Leu Pro Phe Ala Trp Asp Ile Leu Ser Pro Gln
     50                  55                  60

Phe Met Tyr Gly Ser Lys Ala Tyr Val Lys His Pro Ala Asp Ile Pro
 65                  70                  75                  80

Asp Tyr Leu Lys Leu Ser Phe Pro Glu Gly Phe Lys Trp Glu Arg Val
                 85                  90                  95

Met Asn Phe Glu Asp Gly Gly Val Val Thr Val Thr Gln Asp Ser Ser
            100                 105                 110

Leu Gln Asp Gly Glu Phe Ile Tyr Lys Val Lys Leu Arg Gly Thr Asn
        115                 120                 125

Phe Pro Ser Asp Gly Pro Val Met Gln Lys Lys Thr Met Gly Trp Glu
    130                 135                 140

Ala Ser Ser Glu Arg Met Tyr Pro Glu Asp Gly Ala Leu Lys Gly Glu
145                 150                 155                 160

Ile Lys Met Arg Leu Lys Leu Lys Asp Gly Gly His Tyr Asp Ala Glu
                165                 170                 175

Val Lys Thr Thr Tyr Met Ala Lys Lys Pro Val Gln Leu Pro Gly Ala
            180                 185                 190

Tyr Lys Thr Asp Ile Lys Leu Asp Ile Thr Ser His Asn Glu Asp Tyr
        195                 200                 205

Thr Ile Val Glu Gln Tyr Glu Arg Ala Glu Gly Arg His Ser Thr Gly
    210                 215                 220

Ala
225

<210> SEQ ID NO 80
<211> LENGTH: 678

```
<212> TYPE: DNA
<213> ORGANISM: Artificial Sequence
<220> FEATURE:
<223> OTHER INFORMATION: Description of Artificial Sequence:Discosoma
      corallimorph Anthozoan red fluorescent protein
      (DsRed) mutant variant mRFP1.1 (mRFP1 + Q66M/T147S)

<400> SEQUENCE: 80
atggcctcct ccgaggacgt catcaaggag ttcatgcgct tcaaggtgcg catggagggc     60
tccgtgaacg gccacgagtt cgagatcgag ggcgagggcg agggccgccc ctacgagggc    120
acccagaccg ccaagctgaa ggtgaccaag ggcggccccc tgcccttcgc ctgggacatc    180
ctgtcccctc agttcatgta cggctccaag gcctacgtga agcaccccgc cgacatcccc    240
gactacttga agctgtcctt ccccgagggc ttcaagtggg agcgcgtgat gaacttcgag    300
gacggcggcg tggtgaccgt gacccaggac tcctccctgc aggacggcga gttcatctac    360
aaggtgaagc tgcgcggcac caacttcccc tccgacggcc ccgtaatgca gaagaagacc    420
atgggctggg aggcctcctc cgagcggatg taccccgagg acggcgccct gaagggcgag    480
atcaagatga ggctgaagct gaaggacggc ggccactacg acgccgaggt caagaccacc    540
tacatggcca gaagcccgt gcagctgccc ggcgcctaca agaccgacat caagctggac    600
atcacctccc acaacgagga ctacaccatc gtggaacagt acgagcgcgc cgagggccgc    660
cactccaccg gcgcctaa                                                   678

<210> SEQ ID NO 81
<211> LENGTH: 234
<212> TYPE: PRT
<213> ORGANISM: Artificial Sequence
<220> FEATURE:
<223> OTHER INFORMATION: Description of Artificial Sequence:Discosoma
      corallimorph Anthozoan red fluorescent protein
      (DsRed) mutant dimeric variant dimer2.2MMM
      (dimer3, dTomato)

<400> SEQUENCE: 81

Met Val Ser Lys Gly Glu Glu Val Ile Lys Glu Phe Met Arg Phe Lys
 1               5                  10                  15

Val Arg Met Glu Gly Ser Met Asn Gly His Glu Phe Glu Ile Glu Gly
            20                  25                  30

Glu Gly Glu Gly Arg Pro Tyr Glu Gly Thr Gln Thr Ala Lys Leu Lys
        35                  40                  45

Val Thr Lys Gly Gly Pro Leu Pro Phe Ala Trp Asp Ile Leu Ser Pro
    50                  55                  60

Gln Phe Met Tyr Gly Ser Lys Ala Tyr Val Lys His Pro Ala Asp Ile
65                  70                  75                  80

Pro Asp Tyr Lys Lys Leu Ser Phe Pro Glu Gly Phe Lys Trp Glu Arg
                85                  90                  95

Val Met Asn Phe Glu Asp Gly Gly Leu Val Thr Val Thr Gln Asp Ser
            100                 105                 110

Ser Leu Gln Asp Gly Thr Leu Ile Tyr Lys Val Lys Met Arg Gly Thr
        115                 120                 125

Asn Phe Pro Pro Asp Gly Pro Val Met Gln Lys Lys Thr Met Gly Trp
    130                 135                 140

Glu Ala Ser Thr Glu Arg Leu Tyr Pro Arg Asp Gly Val Leu Lys Gly
145                 150                 155                 160

Glu Ile His Gln Ala Leu Lys Leu Lys Asp Gly Gly His Tyr Leu Val
                165                 170                 175

Glu Phe Lys Thr Ile Tyr Met Ala Lys Lys Pro Val Gln Leu Pro Gly
```

```
              180                 185                 190
Tyr Tyr Tyr Val Asp Thr Lys Leu Asp Ile Thr Ser His Asn Glu Asp
        195                 200                 205

Tyr Thr Ile Val Glu Gln Tyr Glu Arg Ser Glu Gly Arg His His Leu
        210                 215                 220

Phe Leu Tyr Gly Met Asp Glu Leu Tyr Lys
225                 230

<210> SEQ ID NO 82
<211> LENGTH: 705
<212> TYPE: DNA
<213> ORGANISM: Artificial Sequence
<220> FEATURE:
<223> OTHER INFORMATION: Description of Artificial Sequence:Discosoma
      corallimorph Anthozoan red fluorescent protein
      (DsRed) mutant dimeric variant dimer2.2MMM
      (dimer3, dTomato)

<400> SEQUENCE: 82
atggtgagca agggcgagga ggtcatcaaa gagttcatgc gcttcaaggt gcgcatggag      60
ggctccatga acggccacga gttcgagatc gagggcgagg cgagggccg ccctacgag      120 ggcacccaga ccgccaagct gaaggtgacc aagggcggcc cctgcccctt cgcctgggac     180
atcctgtccc cccagttcat gtacggctcc aaggcgtacg tgaagcaccc cgccgacatc     240
cccgattaca agaagctgtc cttccccgag ggcttcaagt gggagcgcgt gatgaacttc     300
gaggacggcg gtctggtgac cgtgacccag gactcctccc tgcaggacgg cacgctgatc     360
tacaaggtga agatgcgcgg caccaacttc ccccccgacg gccccgtaat gcagaagaag     420
accatgggct gggaggcctc caccgagcgc ctgtaccccc gcgacggcgt gctgaagggc     480
gagatccacc aggccctgaa gctgaaggac ggcggccact acctggtgga gttcaagacc     540
atctacatgg ccaagaagcc cgtgcaactg cccggctact actacgtgga caccaagctg     600
gacatcacct cccacaacga ggactacacc atcgtggaac agtacgagcg ctccgagggc     660
cgccaccacc tgttcctgta cggcatggac gagctgtaca agtaa                    705

<210> SEQ ID NO 83
<211> LENGTH: 236
<212> TYPE: PRT
<213> ORGANISM: Artificial Sequence
<220> FEATURE:
<223> OTHER INFORMATION: Description of Artificial Sequence:Discosoma
      corallimorph Anthozoan red fluorescent protein
      (DsRed) mutant monomer variant mRFP1.5

<400> SEQUENCE: 83

Met Val Ser Lys Gly Glu Glu Asp Asn Met Ala Ile Ile Lys Glu Phe
  1               5                  10                  15

Met Arg Phe Lys Val His Met Glu Gly Ser Val Asn Gly His Glu Phe
                 20                  25                  30

Glu Ile Glu Gly Glu Gly Glu Gly Arg Pro Tyr Glu Gly Thr Gln Thr
             35                  40                  45

Ala Lys Leu Lys Val Thr Lys Gly Gly Pro Leu Pro Phe Ala Trp Asp
         50                  55                  60

Ile Leu Ser Pro Gln Phe Met Tyr Gly Ser Lys Ala Tyr Val Lys His
 65                  70                  75                  80

Pro Ala Asp Ile Pro Asp Tyr Leu Lys Leu Ser Phe Pro Glu Gly Phe
                 85                  90                  95

Lys Trp Glu Arg Val Met Asn Phe Glu Asp Gly Gly Val Val Thr Val
                100                 105                 110
```

```
Thr Gln Asp Ser Ser Leu Gln Asp Gly Glu Phe Ile Tyr Lys Val Lys
            115                 120                 125

Leu Arg Gly Thr Asn Phe Pro Ser Asp Gly Pro Val Met Gln Lys Lys
130                 135                 140

Thr Met Gly Trp Glu Ala Ser Ser Glu Arg Met Tyr Pro Glu Asp Gly
145                 150                 155                 160

Ala Leu Lys Gly Glu Ile Lys Gln Arg Leu Lys Leu Lys Asp Gly Gly
            165                 170                 175

His Tyr Asp Ala Glu Val Lys Thr Thr Tyr Lys Ala Lys Lys Pro Val
            180                 185                 190

Gln Leu Pro Gly Ala Tyr Lys Thr Asp Ile Lys Leu Asp Ile Thr Ser
            195                 200                 205

His Asn Glu Asp Tyr Thr Ile Val Glu Gln Tyr Glu Arg Ala Glu Gly
            210                 215                 220

Arg His Ser Thr Gly Gly Met Asp Glu Leu Tyr Lys
225                 230                 235
```

<210> SEQ ID NO 84
<211> LENGTH: 711
<212> TYPE: DNA
<213> ORGANISM: Artificial Sequence
<220> FEATURE:
<223> OTHER INFORMATION: Description of Artificial Sequence:Discosoma
      corallimorph Anthozoan red fluorescent protein
      (DsRed) mutant monomer variant mRFP1.5

<400> SEQUENCE: 84

```
atggtgagca agggcgagga ggataacatg gccatcatca aggagttcat gcgcttcaag    60
gtgcacatgg agggctccgt gaacggccac gagttcgaga tcgagggcga gggcgagggc   120
cgcccctacg agggcaccca gaccgccaag ctgaaggtga ccaagggtgg ccccctgccc   180
ttcgcctggg acatcctgtc ccctcagttc atgtacggct ccaaggccta cgtgaagcac   240
cccgccgaca tccccgacta cttgaagctg tccttccccg agggcttcaa gtgggagcgc   300
gtgatgaact tcgaggacgg cggcgtggtg accgtgaccc aggactcctc cctgcaggac   360
ggcgagttca tctacaaggt gaagctgcgc ggcaccaact tccctccga cggccccgta   420
atgcagaaga agaccatggg ctgggaggcc tcctccgagc ggatgtaccc cgaggacggc   480
gccctgaagg gcgagatcaa gcagaggctg aagctgaagg acggcggcca ctacgacgct   540
gaggtcaaga ccacctacaa ggccaagaag cccgtgcagc tgcccggcgc ctacaagacc   600
gacatcaagt tggacatcac ctcccacaac gaggactaca ccatcgtgga acagtacgaa   660
cgcgccgagg gccgccactc caccggcggc atggacgagc tgtacaagta a             711
```

<210> SEQ ID NO 85
<211> LENGTH: 236
<212> TYPE: PRT
<213> ORGANISM: Artificial Sequence
<220> FEATURE:
<223> OTHER INFORMATION: Description of Artificial Sequence:Discosoma
      corallimorph Anthozoan red fluorescent protein
      (DsRed) mutant monomer variant OrS4-9

<400> SEQUENCE: 85

```
Met Val Ser Lys Gly Glu Glu Asn Asn Met Ala Ile Ile Lys Glu Phe
1               5                   10                  15

Met Arg Phe Lys Val Arg Met Glu Gly Ser Val Asn Gly His Glu Phe
                20                  25                  30

Glu Ile Glu Gly Glu Gly Glu Gly Arg Pro Tyr Glu Gly Thr Gln Thr
```

```
                    35                  40                  45
Ala Lys Leu Lys Val Thr Lys Gly Gly Pro Leu Pro Phe Ala Trp Asp
 50                  55                  60

Ile Leu Ser Pro Gln Phe Thr Tyr Gly Ser Lys Ala Tyr Val Lys His
 65                  70                  75                  80

Pro Ala Asp Ile Pro Asp Tyr Leu Lys Leu Ser Phe Pro Glu Gly Phe
                 85                  90                  95

Lys Trp Glu Arg Val Met Asn Phe Glu Asp Gly Gly Val Thr Val
                100                 105                 110

Thr Gln Asp Ser Ser Leu Gln Asp Gly Glu Phe Ile Tyr Lys Val Lys
                115                 120                 125

Leu Arg Gly Thr Asn Phe Pro Ser Asp Gly Pro Val Met Gln Lys Lys
130                 135                 140

Thr Met Gly Trp Glu Ala Ser Ser Glu Arg Met Tyr Pro Glu Asp Gly
145                 150                 155                 160

Ala Leu Lys Gly Glu Ile Lys Met Arg Leu Lys Leu Lys Asp Gly Gly
                165                 170                 175

His Tyr Asp Ala Glu Val Lys Thr Thr Tyr Lys Ala Lys Lys Pro Val
                180                 185                 190

Gln Leu Pro Gly Ala Tyr Lys Val Asp Ile Lys Leu Asp Ile Thr Ser
                195                 200                 205

His Asn Glu Asp Tyr Thr Ile Val Glu Gln Tyr Glu Arg Ala Glu Gly
                210                 215                 220

Arg His Ser Thr Gly Gly Met Asp Glu Leu Tyr Lys
225                 230                 235

<210> SEQ ID NO 86
<211> LENGTH: 711
<212> TYPE: DNA
<213> ORGANISM: Artificial Sequence
<220> FEATURE:
<223> OTHER INFORMATION: Description of Artificial Sequence:Discosoma
      corallimorph Anthozoan red fluorescent protein
      (DsRed) mutant monomer variant OrS4-9

<400> SEQUENCE: 86
atggtgagca agggcgagga gaataacatg gccatcatca aggagttcat gcgcttcaag      60
gtacgcatgg agggctccgt gaacggccac gagttcgaga ttgagggcga gggcgagggc     120
cgcccctacg agggcaccca gaccgccaag ttgaaggtga ccaagggtgg ccccctgccc     180
ttcgcctggg acatcctgtc ccctcagttc acctacggct ccaaggccta cgtgaagcac     240
cccgccgaca tccccgacta cttgaagctg tccttccccg agggcttcaa gtgggaacgc     300
gtgatgaact tcgaggacgg cggcgtggtg accgtgacac aggactcctc cctgcaggac     360
ggcgagttca tctacaaggt gaagctgcgc ggcaccaact tccccctccga cggccccgta     420 atgcagaaga agaccatggg ctgggaggcc tcctccgagc ggatgtaccc cgaggacggc     480
gccctgaagg gcgagatcaa gatgaggctg aagctgaagg acggcggcca ctacgacgct     540
gaggtcaaga ccacctacaa ggccaagaag cccgtgcagc tgcccggcgc ctacaaggtc     600
gacatcaagc tggacatcac ctcccacaac gaggactaca ccatcgtgga acagtacgaa     660
cgcgccgagg gccgccactc caccggcggc atggacgagc tgtacaagta a              711

<210> SEQ ID NO 87
<211> LENGTH: 236
<212> TYPE: PRT
<213> ORGANISM: Artificial Sequence
<220> FEATURE:
```

-continued

<223> OTHER INFORMATION: Description of Artificial Sequence:Discosoma
    corallimorph Anthozoan red fluorescent protein
    (DsRed) mutant monomer variant Y1.3 (mYOFP1.3
    (yellow-orange fluorescent protein), mBanana)

<400> SEQUENCE: 87

Met Val Ser Lys Gly Glu Glu Asn Asn Met Ala Val Ile Lys Glu Phe
1               5                   10                  15

Met Arg Phe Lys Val Arg Met Glu Gly Ser Val Asn Gly His Glu Phe
            20                  25                  30

Glu Ile Glu Gly Glu Gly Glu Gly Arg Pro Tyr Glu Gly Thr Gln Thr
        35                  40                  45

Ala Lys Leu Lys Val Thr Lys Gly Gly Pro Leu Pro Phe Ala Trp Asp
    50                  55                  60

Ile Leu Ser Pro Gln Phe Cys Tyr Gly Ser Lys Ala Tyr Val Lys His
65                  70                  75                  80

Pro Thr Gly Ile Pro Asp Tyr Phe Lys Leu Ser Phe Pro Glu Gly Phe
                85                  90                  95

Lys Trp Glu Arg Val Met Asn Phe Glu Asp Gly Gly Val Val Thr Val
            100                 105                 110

Ala Gln Asp Ser Ser Leu Gln Asp Gly Glu Phe Ile Tyr Lys Val Lys
        115                 120                 125

Leu Arg Gly Thr Asn Phe Pro Ser Asp Gly Pro Val Met Gln Lys Lys
    130                 135                 140

Thr Met Gly Trp Glu Ala Ser Ser Glu Arg Met Tyr Pro Glu Asp Gly
145                 150                 155                 160

Ala Leu Lys Gly Glu Ile Lys Met Arg Leu Lys Leu Lys Asp Gly Gly
                165                 170                 175

His Tyr Ser Ala Glu Thr Lys Thr Thr Tyr Lys Ala Lys Lys Pro Val
            180                 185                 190

Gln Leu Pro Gly Ala Tyr Ile Ala Gly Glu Lys Ile Asp Ile Thr Ser
        195                 200                 205

His Asn Glu Asp Tyr Thr Ile Val Glu Leu Tyr Glu Arg Ala Glu Gly
    210                 215                 220

Arg His Ser Thr Gly Gly Met Asp Glu Leu Tyr Lys
225                 230                 235

<210> SEQ ID NO 88
<211> LENGTH: 711
<212> TYPE: DNA
<213> ORGANISM: Artificial Sequence
<220> FEATURE:
<223> OTHER INFORMATION: Description of Artificial Sequence:Discosoma
    corallimorph Anthozoan red fluorescent protein
    (DsRed) mutant monomer variant Y1.3 (mYOFP1.3
    (yellow-orange fluorescent protein), mBanana)

<400> SEQUENCE: 88
atggtgagca agggcgagga gaataacatg gccgtcatca aggagttcat gcgcttcaag      60
gtgcgcatgg agggctccgt gaacggccac gagttcgaga tcgagggcga gggcgagggc     120
cgcccctacg agggcaccca gaccgccaag ctgaaggtga ccaagggtgg ccccctgccc     180
ttcgcctggg acatcctgtc ccctcagttc tgctacggct ccaaggccta cgtgaagcac     240
cccactggta tccccgacta cttcaagctg tccttccccg agggcttcaa gtgggagcgc     300
gtgatgaact tcgaggacgg cggcgtggtg accgtggctc aggactcctc cctgcaggac     360
ggcgagttca tctacaaggt gaagctgcgc ggcaccaact tcccctccga cggccccgta     420
atgcagaaga agaccatggg ctgggaggcc tcctccgagc ggatgtaccc cgaggacggc     480

```
gccctgaagg gcgagatcaa gatgaggctg aagctgaagg acggcggcca ctacagcgcc      540
gagaccaaga ccacctacaa ggccaagaag cccgtgcagt tgcccggcgc ctacatagcc      600
ggcgagaaga tcgacatcac ctcccacaat gaggactaca ctatcgtgga attgtacgag      660
cgcgccgagg gccgccactc caccggcggc atggacgagc tgtacaagta a              711
```

<210> SEQ ID NO 89
<211> LENGTH: 236
<212> TYPE: PRT
<213> ORGANISM: Artificial Sequence
<220> FEATURE:
<223> OTHER INFORMATION: Description of Artificial Sequence:Discosoma
     corallimorph Anthozoan red fluorescent protein
     (DsRed) mutant monomer variant mFRFP (F2Q6,
     mGrape2)

<400> SEQUENCE: 89

```
Met Val Ser Lys Gly Glu Glu Asn Asn Met Ala Val Ile Lys Glu Phe
 1               5                  10                  15

Met Arg Phe Lys Val Arg Met Glu Gly Ser Val Asn Gly His Glu Phe
             20                  25                  30

Glu Ile Glu Gly Lys Gly Glu Gly Arg Pro Tyr Glu Gly Thr Gln Thr
         35                  40                  45

Ala Lys Leu Lys Val Thr Lys Gly Gly Pro Leu Pro Phe Ala Trp Asp
     50                  55                  60

Ile Leu Ser Pro Gln Phe Met Tyr Gly Ser Lys Ala Tyr Val Lys His
 65                  70                  75                  80

Pro Pro Asp Ile Pro Asp Tyr Met Lys Leu Ser Phe Pro Glu Gly Phe
                 85                  90                  95

Lys Trp Glu Arg Val Met Asn Phe Glu Asp Gly Gly Val Val Thr Val
            100                 105                 110

Thr Gln Asp Ser Ser Leu Gln Asp Gly Glu Phe Ile Tyr Lys Val Lys
        115                 120                 125

Leu His Gly Thr Asn Phe Pro Ser Asp Gly Pro Val Met Gln Lys Lys
    130                 135                 140

Thr Met Gly Trp Glu Ala Ser Ser Glu Arg Leu Tyr Pro Glu Asp Gly
145                 150                 155                 160

Ala Leu Lys Gly Glu Val Lys Met Arg Leu Lys Leu Lys Asp Gly Gly
                165                 170                 175

His Tyr Asp Ala Glu Val Lys Thr Thr Tyr Met Ala Lys Lys Pro Val
            180                 185                 190

Gln Leu Pro Gly Ala Tyr Lys Leu Asp Tyr Lys Leu Asp Ile Thr Ser
        195                 200                 205

His Asn Glu Asp Tyr Thr Ile Val Glu Gln Tyr Glu Arg Ala Glu Gly
    210                 215                 220

Arg His Ser Thr Gly Gly Met Asp Glu Leu Tyr Lys
225                 230                 235
```

<210> SEQ ID NO 90
<211> LENGTH: 711
<212> TYPE: DNA
<213> ORGANISM: Artificial Sequence
<220> FEATURE:
<223> OTHER INFORMATION: Description of Artificial Sequence:Discosoma
     corallimorph Anthozoan red fluorescent protein
     (DsRed) mutant monomer variant mFRFP (F2Q6,
     mGrape2)

<400> SEQUENCE: 90

```
atggtgagca agggcgagga gaataacatg ccgtcatca aggagttcat gcgcttcaag      60
gtgcgcatgg agggctccgt gaacggccac gagttcgaga tcgagggcaa gggcgagggc     120
cgcccctacg agggcaccca gaccgccaag ctgaaggtga ccaagggcgg ccccctgccc     180
ttcgcctggg acatcctgtc ccctcagttc atgtacggct ccaaggccta cgtgaagcac     240
cccccctgaca tccccgacta catgaagctg tccttccccg agggcttcaa gtgggagcgc    300
gtgatgaact cgaggacgg cggcgtggtg accgtgaccc aggactcctc cctgcaggac      360
ggcgagttca tctacaaggt gaagctgcac ggcaccaact tccccctccga cggccccgta    420
atgcagaaga gaccatggg ctgggaggcc tcctccgagc ggttgtaccc cgaggacggc      480
gccctgaagg gcgaggtcaa gatgaggctg aagctgaagg acggcggcca ctacgacgcc     540
gaggtcaaga ccacctacat ggccaagaag cccgtgcagc tgcccggcgc ctacaagctc     600
gactacaagc tggacatcac ctcccacaac gaggactaca ccatcgtgga acagtacgag     660
cgcgccgagg ccgccactc caccggcggc atggacgagc tgtacaagta a               711
```

<210> SEQ ID NO 91
<211> LENGTH: 7
<212> TYPE: PRT
<213> ORGANISM: Artificial Sequence
<220> FEATURE:
<223> OTHER INFORMATION: Description of Artificial Sequence:EGFP
      C-terminus, 7-residue GFP-type C-terminus

<400> SEQUENCE: 91

Gly Met Asp Glu Leu Tyr Lys
 1               5

<210> SEQ ID NO 92
<211> LENGTH: 236
<212> TYPE: PRT
<213> ORGANISM: Artificial Sequence
<220> FEATURE:
<223> OTHER INFORMATION: Description of Artificial Sequence:Discosoma
      corallimorph Anthozoan red fluorescent protein
      (DsRed) monomer variant mRFP2 (mCherry)

<400> SEQUENCE: 92

Met Val Ser Lys Gly Glu Glu Asp Asn Met Ala Ile Ile Lys Glu Phe
 1               5                  10                  15

Met Arg Phe Lys Val His Met Glu Gly Ser Val Asn Gly His Glu Phe
                20                  25                  30

Glu Ile Glu Gly Glu Gly Glu Gly Arg Pro Tyr Glu Gly Thr Gln Thr
            35                  40                  45

Ala Lys Leu Lys Val Thr Lys Gly Gly Pro Leu Pro Phe Ala Trp Asp
        50                  55                  60

Ile Leu Ser Pro Gln Phe Met Tyr Gly Ser Lys Ala Tyr Val Lys His
 65                  70                  75                  80

Pro Ala Asp Ile Pro Asp Tyr Leu Lys Leu Ser Phe Pro Glu Gly Phe
                85                  90                  95

Lys Trp Glu Arg Val Met Asn Phe Glu Asp Gly Gly Val Val Thr Val
            100                 105                 110

Thr Gln Asp Ser Ser Leu Gln Asp Gly Glu Phe Ile Tyr Lys Val Lys
        115                 120                 125

Leu Arg Gly Thr Asn Phe Pro Ser Asp Gly Pro Val Met Gln Lys Lys
    130                 135                 140

Thr Met Gly Trp Glu Ala Ser Ser Glu Arg Met Tyr Pro Glu Asp Gly
145                 150                 155                 160

```
Ala Leu Lys Gly Glu Ile Lys Gln Arg Leu Lys Leu Lys Asp Gly Gly
            165                 170                 175

His Tyr Asp Ala Glu Val Lys Thr Thr Tyr Lys Ala Lys Lys Pro Val
            180                 185                 190

Gln Leu Pro Gly Ala Tyr Asn Val Asn Ile Lys Leu Asp Ile Thr Ser
            195                 200                 205

His Asn Glu Asp Tyr Thr Ile Val Glu Gln Tyr Glu Arg Ala Glu Gly
            210                 215                 220

Arg His Ser Thr Gly Gly Met Asp Glu Leu Tyr Lys
225                 230                 235

<210> SEQ ID NO 93
<211> LENGTH: 711
<212> TYPE: DNA
<213> ORGANISM: Artificial Sequence
<220> FEATURE:
<223> OTHER INFORMATION: Description of Artificial Sequence:Discosoma
      corallimorph Anthozoan red fluorescent protein
      (DsRed) monomer variant mRFP2 (mCherry)

<400> SEQUENCE: 93
atggtgagca agggcgagga ggataacatg gccatcatca aggagttcat gcgcttcaag      60
gtgcacatgg agggctccgt gaacggccac gagttcgaga tcgagggcga gggcgagggc     120
cgcccctacg agggcaccca gaccgccaag ctgaaggtga ccaagggtgg ccccctgccc     180
ttcgcctggg acatcctgtc cctcagttc atgtacggct ccaaggccta cgtgaagcac      240
cccgccgaca tccccgacta cttgaagctg tccttcccg agggcttcaa gtgggagcgc      300
gtgatgaact tcgaggacgg cggcgtggtg accgtgaccc aggactcctc cctgcaggac     360
ggcgagttca tctacaaggt gaagctgcgc ggcaccaact cccctccga cggccccgta      420 atgcagaaga gaccatgggc tgggaggcc cctccgagc ggatgtaccc cgaggacggc       480
gccctgaagg gcgagatcaa gcagaggctg aagctgaagg acggcggcca ctacgacgct    540
gaggtcaaga ccacctacaa ggccaagaag cccgtgcagc tgcccggcgc ctacaacgtc    600
aacatcaagt tggacatcac ctcccacaac gaggactaca ccatcgtgga acagtacgaa    660
cgcgccgagg gccgccactc caccggcggc atggacgagc tgtacaagta a             711

<210> SEQ ID NO 94
<211> LENGTH: 235
<212> TYPE: PRT
<213> ORGANISM: Artificial Sequence
<220> FEATURE:
<223> OTHER INFORMATION: Description of Artificial Sequence:Discosoma
      corallimorph Anthozoan red fluorescent protein
      (DsRed) monomer variant mOFP (74-11)
<220> FEATURE:
<221> NAME/KEY: MOD_RES
<222> LOCATION: (62)
<223> OTHER INFORMATION: Xaa = any amino acid

<400> SEQUENCE: 94

Met Val Ser Lys Gly Glu Glu Asn Asn Met Ala Ile Ile Lys Glu Phe
  1               5                  10                  15

Met Arg Phe Lys Val Arg Met Glu Gly Ser Val Asn Gly His Glu Phe
                 20                  25                  30

Glu Ile Glu Gly Glu Gly Glu Gly Arg Pro Tyr Glu Gly Phe Gln Thr
            35                  40                  45

Ala Lys Leu Lys Val Thr Lys Gly Gly Pro Leu Pro Phe Xaa Trp Asp
        50                  55                  60

Ile Leu Ser Pro Gln Phe Thr Tyr Gly Ser Lys Ala Tyr Val Lys His
```

-continued

```
                65                  70                  75                  80
Pro Ala Asp Ile Pro Asp Tyr Leu Lys Leu Ser Phe Pro Glu Gly Phe
                        85                  90                  95
Lys Trp Glu Arg Val Met Asn Phe Glu Asp Gly Gly Val Val Thr Val
                    100                 105                 110
Thr Gln Asp Ser Ser Leu Gln Asp Gly Glu Phe Ile Tyr Lys Val Lys
                115                 120                 125
Leu Arg Gly Thr Asn Phe Pro Ser Asp Gly Pro Val Met Gln Lys Lys
            130                 135                 140
Thr Met Gly Trp Glu Ala Ser Ser Glu Arg Met Tyr Pro Glu Asp Gly
145                 150                 155                 160
Ala Leu Lys Gly Glu Ile Lys Met Arg Leu Lys Leu Lys Asp Gly Gly
                165                 170                 175
His Tyr Thr Ser Glu Val Lys Thr Thr Tyr Lys Ala Lys Lys Pro Val
                180                 185                 190
Gln Leu Pro Gly Ala Tyr Ile Val Gly Ile Lys Leu Asp Ile Thr Ser
            195                 200                 205
His Asn Glu Asp Tyr Thr Ile Val Glu Gln Tyr Glu Arg Ala Glu Gly
        210                 215                 220
Arg His Ser Thr Gly Gly Met Asp Glu Leu Lys
225                 230                 235

<210> SEQ ID NO 95
<211> LENGTH: 708
<212> TYPE: DNA
<213> ORGANISM: Artificial Sequence
<220> FEATURE:
<223> OTHER INFORMATION: Description of Artificial Sequence:Discosoma
      corallimorph Anthozoan red fluorescent protein
      (DsRed) monomer variant mOFP (74-11)
<220> FEATURE:
<221> NAME/KEY: modified_base
<222> LOCATION: (185)
<223> OTHER INFORMATION: n = g, a, c or t

<400> SEQUENCE: 95
atggtgagca agggcgagga gaataacatg gccatcatca aggagttcat gcgcttcaag      60
gtgcgcatgg agggctccgt gaacggccac gagttcgaga tcgagggcga gggcgagggc     120
cgcccctacg agggctttca gaccgctaag ctgaaggtga ccaagggtgg cccccctgccc    180 ttcgnctggg acatcctgtc ccctcagttc acctacggct ccaaggccta cgtgaagcac     240
cccgccgaca tccccgacta cttgaagctg tccttccccg agggcttcaa gtgggagcgc     300
gtgatgaact tcgaggacgg cggcgtggtg accgtgaccc aggactcctc cctgcaggac     360
ggcgagttca tctacaaggt gaagctgcgc ggcaccaact tccctccga cggccccgta      420 atgcagaaga agaccatggg ctgggaggcc tcctccgagc ggatgtaccc cgaggacggc     480
gccctgaagg gcgagatcaa gatgaggctg aagctgaagg acggcggcca ctacacctcc    540
gaggtcaaga ccacctacaa ggccaagaag cccgtgcagc tgcccggcgc ctacatcgtc    600
ggcatcaagt tggacatcac ctcccacaac gaggactaca ccatcgtgga acagtacgaa    660
cgcgccgagg gccgccactc caccggcggc atggacgagc ttaagtaa                 708

<210> SEQ ID NO 96
<211> LENGTH: 236
<212> TYPE: PRT
<213> ORGANISM: Artificial Sequence
<220> FEATURE:
<223> OTHER INFORMATION: Description of Artificial Sequence:Discosoma
      corallimorph Anthozoan red fluorescent protein
```

(DsRed) monomer variant mROFP (A2/6-6)

<400> SEQUENCE: 96

Met Val Ser Lys Gly Glu Glu Asn Asn Met Ala Ile Ile Lys Glu Phe
1               5                   10                  15

Met Arg Phe Lys Val Arg Met Glu Gly Ser Val Asn Gly His Glu Phe
            20                  25                  30

Glu Ile Glu Gly Glu Gly Glu Gly Arg Pro Tyr Glu Gly Thr Gln Thr
        35                  40                  45

Ala Lys Leu Lys Val Thr Lys Gly Gly Pro Leu Pro Phe Ala Trp Asp
    50                  55                  60

Ile Leu Thr Pro Asn Phe Thr Tyr Gly Ser Lys Ala Tyr Val Lys His
65              70                  75                  80

Pro Ala Asp Ile Pro Asp Tyr Leu Lys Leu Ser Phe Pro Glu Gly Phe
                85                  90                  95

Lys Trp Glu Arg Val Met Asn Phe Glu Asp Gly Gly Val Val Thr Val
            100                 105                 110

Thr Gln Asp Ser Ser Leu Gln Asp Gly Glu Phe Ile Tyr Lys Val Lys
        115                 120                 125

Leu Arg Gly Thr Asn Phe Pro Ser Asp Gly Pro Val Met Gln Lys Lys
    130                 135                 140

Thr Met Gly Trp Glu Ala Ser Ser Glu Arg Met Tyr Pro Glu Asp Gly
145             150                 155                 160

Ala Leu Lys Gly Glu Ile Lys Met Arg Leu Lys Leu Lys Asp Gly Gly
                165                 170                 175

His Tyr Asp Ala Glu Val Lys Thr Thr Tyr Lys Ala Lys Lys Pro Val
            180                 185                 190

Gln Leu Pro Gly Ala Tyr Ile Val Gly Ile Lys Leu Asp Ile Thr Ser
        195                 200                 205

His Asn Glu Asp Tyr Thr Ile Val Glu Leu Tyr Glu Arg Ala Glu Gly
    210                 215                 220

Arg His Ser Thr Gly Gly Met Asp Glu Leu Tyr Lys
225                 230                 235

<210> SEQ ID NO 97
<211> LENGTH: 711
<212> TYPE: DNA
<213> ORGANISM: Artificial Sequence
<220> FEATURE:
<223> OTHER INFORMATION: Description of Artificial Sequence:Discosoma
      corallimorph Anthozoan red fluorescent protein
      (DsRed) monomer variant mROFP (A2/6-6)

<400> SEQUENCE: 97
atggtgagca agggcgagga gaataacatg gccatcatca aggagttcat gcgcttcaag    60
gtgcgcatgg agggctccgt gaacggccac gagttcgaga tcgagggcga gggcgagggc   120
cgcccctacg agggcaccca gaccgccaag ctgaaggtga ccaagggtgg ccccctgccc   180
ttcgcctggg acatcctaac ccccaacttc acctacggct ccaaggccta cgtgaagcac   240
cccgccgaca tccccgacta cttgaagctg tccttccccg agggcttcaa gtgggagcgc   300
gtgatgaact tcgaggacgg cggcgtggtg accgtgaccc aggactcctc cctgcaggac   360
ggcgagttca tctacaaggt gaagctgcgc ggcaccaact tccctccga cggccccgta   420 atgcagaaga agaccatggg ctgggaggcc tcctccgagc ggatgtaccc cgaggacggc   480
gccctgaagg gcgagatcaa gatgaggctg aagctgaagg acggcggcca ctacgacgct   540
gaggtcaaga ccacctacaa ggccaagaag cccgtgcagc tgcccggcgc ctacatcgtc   600
ggcatcaagt tggacatcac ctcccacaac gaggactaca ccatcgtgga actgtacgaa       660
cgcgccgagg gccgccactc caccggcggc atggacgagc tgtacaagta a                711

<210> SEQ ID NO 98
<211> LENGTH: 236
<212> TYPE: PRT
<213> ORGANISM: Artificial Sequence
<220> FEATURE:
<223> OTHER INFORMATION: Description of Artificial Sequence:Discosoma
      corallimorph Anthozoan red fluorescent protein
      (DsRed) monomer variant mStrawberry

<400> SEQUENCE: 98

Met Val Ser Lys Gly Glu Glu Asn Asn Met Ala Ile Ile Lys Glu Phe
1               5                   10                  15

Met Arg Phe Lys Val Arg Met Glu Gly Ser Val Asn Gly His Glu Phe
            20                  25                  30

Glu Ile Glu Gly Glu Gly Glu Gly Arg Pro Tyr Glu Gly Thr Gln Thr
        35                  40                  45

Ala Lys Leu Lys Val Thr Lys Gly Gly Pro Leu Pro Phe Ala Trp Asp
    50                  55                  60

Ile Leu Thr Pro Asn Phe Thr Tyr Gly Ser Lys Ala Tyr Val Lys His
65                  70                  75                  80

Pro Ala Asp Ile Pro Asp Tyr Leu Lys Leu Ser Phe Pro Glu Gly Phe
                85                  90                  95

Lys Trp Glu Arg Val Met Asn Phe Glu Asp Gly Gly Val Val Thr Val
            100                 105                 110

Thr Gln Asp Ser Ser Leu Gln Asp Gly Glu Phe Ile Tyr Lys Val Lys
        115                 120                 125

Leu Arg Gly Thr Asn Phe Pro Ser Asp Gly Pro Val Met Gln Lys Lys
    130                 135                 140

Thr Met Gly Trp Glu Ala Ser Ser Glu Arg Met Tyr Pro Glu Asp Gly
145                 150                 155                 160

Ala Leu Lys Gly Glu Ile Lys Met Arg Leu Lys Leu Lys Asp Gly Gly
                165                 170                 175

His Tyr Asp Ala Glu Val Lys Thr Thr Tyr Lys Ala Lys Lys Pro Val
            180                 185                 190

Gln Leu Pro Gly Ala Tyr Ile Val Gly Ile Lys Leu Asp Ile Thr Ser
        195                 200                 205

His Asn Glu Asp Tyr Thr Ile Val Glu Leu Tyr Glu Arg Ala Glu Gly
    210                 215                 220

Arg His Ser Thr Gly Gly Met Asp Glu Leu Tyr Lys
225                 230                 235

<210> SEQ ID NO 99
<211> LENGTH: 711
<212> TYPE: DNA
<213> ORGANISM: Artificial Sequence
<220> FEATURE:
<223> OTHER INFORMATION: Description of Artificial Sequence:Discosoma
      corallimorph Anthozoan red fluorescent protein
      (DsRed) monomer variant mStrawberry

<400> SEQUENCE: 99
atggtgagca agggcgagga gaataacatg gccatcatca aggagttcat gcgcttcaag       60
gtgcgcatgg agggctccgt gaacggccac gagttcgaga tcgagggcga gggcgagggc      120
cgcccctacg agggcaccca gaccgccaag ctgaaggtga ccaagggtgg ccccctgccc      180

```
ttcgcctggg acatcctaac ccccaacttc acctacggct ccaaggccta cgtgaagcac      240
cccgccgaca tccccgacta cttgaagctg tccttccccg agggcttcaa gtgggagcgc      300
gtgatgaact tcgaggacgg cggcgtggtg accgtgaccc aggactcctc cctgcaggac      360
ggcgagttca tctacaaggt gaagctgcgc ggcaccaact tcccctccga cggccccgta      420
atgcagaaga agaccatggg ctgggaggcc tcctccgagc ggatgtaccc cgaggacggc      480
gccctgaagg gcgagatcaa gatgaggctg aagctgaagg acggcggcca ctacgacgct      540
gaggtcaaga ccacctacaa ggccaagaag cccgtgcagc tgcccggcgc ctacatcgtc      600
ggcatcaagt tggacatcac ctcccacaac gaggactaca ccatcgtgga actgtacgaa      660
cgcgccgagg gccgccactc caccggcggc atggacgagc tgtacaagta a               711
```

<210> SEQ ID NO 100
<211> LENGTH: 225
<212> TYPE: PRT
<213> ORGANISM: Artificial Sequence
<220> FEATURE:
<223> OTHER INFORMATION: Description of Artificial Sequence:Discosoma
      corallimorph Anthozoan red fluorescent protein
      (DsRed) monomer variant mTangerine

<400> SEQUENCE: 100

Met Ala Ser Ser Glu Asp Val Ile Lys Glu Phe Met Arg Phe Lys Val
1               5                   10                  15

Arg Met Glu Gly Ser Val Asn Gly His Glu Phe Glu Ile Glu Gly Glu
            20                  25                  30

Gly Glu Gly Arg Pro Tyr Glu Gly Thr Gln Thr Ala Lys Leu Lys Val
        35                  40                  45

Thr Lys Gly Gly Pro Leu Pro Phe Ala Trp Asp Ile Leu Ser Pro Gln
    50                  55                  60

Phe Cys Tyr Gly Ser Lys Ala Tyr Val Lys His Pro Ala Asp Ile Pro
65                  70                  75                  80

Asp Tyr Leu Lys Leu Ser Phe Pro Glu Gly Phe Lys Trp Glu Arg Val
                85                  90                  95

Met Asn Phe Glu Asp Gly Gly Val Val Thr Val Thr Gln Asp Ser Ser
            100                 105                 110

Leu Gln Asp Gly Glu Phe Ile Tyr Lys Val Lys Leu Arg Gly Thr Asn
        115                 120                 125

Phe Pro Ser Asp Gly Pro Val Met Gln Lys Lys Thr Met Gly Trp Glu
    130                 135                 140

Ala Ser Ser Glu Arg Met Tyr Pro Glu Asp Gly Ala Leu Lys Gly Glu
145                 150                 155                 160

Ile Lys Met Arg Leu Lys Leu Lys Asp Gly Gly His Tyr Asp Ala Glu
                165                 170                 175

Val Lys Thr Thr Tyr Met Ala Lys Lys Pro Val Gln Leu Pro Gly Ala
            180                 185                 190

Tyr Lys Thr Asp Ile Lys Leu Asp Ile Thr Ser His Asn Glu Asp Tyr
        195                 200                 205

Thr Ile Val Glu Leu Tyr Glu Arg Ala Glu Gly Arg His Ser Thr Gly
    210                 215                 220

Ala
225

<210> SEQ ID NO 101
<211> LENGTH: 678
<212> TYPE: DNA
<213> ORGANISM: Artificial Sequence
<220> FEATURE:
<223> OTHER INFORMATION: Description of Artificial Sequence:Discosoma
      corallimorph Anthozoan red fluorescent protein
      (DsRed) monomer variant mTangerine

<400> SEQUENCE: 101

```
atggcctcct ccgaggacgt catcaaggag ttcatgcgct tcaaggtgcg catggagggc     60
tccgtgaacg gccacgagtt cgagatcgag ggcgagggcg agggccgccc ctacgagggc    120
acccagaccg ccaagctgaa ggtgaccaag ggcggccccc tgcccttcgc ctgggacatc    180
ctgtcccctc agttctgtta cggctccaag gcctacgtga agcacccgc cgacatcccc     240
gactacttga agctgtcctt ccccgagggc ttcaagtggg agcgcgtgat gaacttcgag    300
gacggcggcg tggtgaccgt gacccaggac tcctccctgc aggacggcga gttcatctac    360
aaggtgaagc tgcgcggcac caacttcccc tccgacggcc ccgtaatgca gaagaagacc    420
atgggctggg aggcctcctc cgagcggatg taccccgagg acggcgccct gaagggcgag    480
atcaagatga ggctgaagct gaaggacggc ggccactacg acgccgaggt caagaccacc    540
tacatggcca agaagcccgt gcagctgccc ggcgcctaca agaccgacat caagctggac    600
atcacctccc acaacgagga ctacaccatc gtggaattgt acgagcgcgc cgagggccgc    660
cactccaccg gcgcctaa                                                  678
```

<210> SEQ ID NO 102
<211> LENGTH: 236
<212> TYPE: PRT
<213> ORGANISM: Artificial Sequence
<220> FEATURE:
<223> OTHER INFORMATION: Description of Artificial Sequence:Discosoma
      corallimorph Anthozoan red fluorescent protein
      (DsRed) monomer variant mOrange (mOFP1)

<400> SEQUENCE: 102

```
Met Val Ser Lys Gly Glu Glu Asn Asn Met Ala Ile Ile Lys Glu Phe
  1               5                  10                  15

Met Arg Phe Lys Val Arg Met Glu Gly Ser Val Asn Gly His Glu Phe
                 20                  25                  30

Glu Ile Glu Gly Glu Gly Glu Gly Arg Pro Tyr Glu Gly Phe Gln Thr
             35                  40                  45

Ala Lys Leu Lys Val Thr Lys Gly Gly Pro Leu Pro Phe Ala Trp Asp
         50                  55                  60

Ile Leu Ser Pro Gln Phe Thr Tyr Gly Ser Lys Ala Tyr Val Lys His
 65                  70                  75                  80

Pro Ala Asp Ile Pro Asp Tyr Phe Lys Leu Ser Phe Pro Glu Gly Phe
                 85                  90                  95

Lys Trp Glu Arg Val Met Asn Phe Glu Asp Gly Gly Val Val Thr Val
            100                 105                 110

Thr Gln Asp Ser Ser Leu Gln Asp Gly Glu Phe Ile Tyr Lys Val Lys
        115                 120                 125

Leu Arg Gly Thr Asn Phe Pro Ser Asp Gly Pro Val Met Gln Lys Lys
    130                 135                 140

Thr Met Gly Trp Glu Ala Ser Ser Glu Arg Met Tyr Pro Glu Asp Gly
145                 150                 155                 160

Ala Leu Lys Gly Glu Ile Lys Met Arg Leu Lys Leu Lys Asp Gly Gly
                165                 170                 175

His Tyr Thr Ser Glu Val Lys Thr Thr Tyr Lys Ala Lys Lys Pro Val
            180                 185                 190

Gln Leu Pro Gly Ala Tyr Ile Val Gly Ile Lys Leu Asp Ile Thr Ser
```

```
              195                 200                 205
His Asn Glu Asp Tyr Thr Ile Val Glu Gln Tyr Glu Arg Ala Glu Gly
            210                 215                 220

Arg His Ser Thr Gly Gly Met Asp Glu Leu Tyr Lys
225                 230                 235
```

<210> SEQ ID NO 103
<211> LENGTH: 711
<212> TYPE: DNA
<213> ORGANISM: Artificial Sequence
<220> FEATURE:
<223> OTHER INFORMATION: Description of Artificial Sequence:Discosoma
      corallimorph Anthozoan red fluorescent protein
      (DsRed) monomer variant mOrange (mOFP1)

<400> SEQUENCE: 103

```
atggtgagca agggcgagga gaataacatg gccatcatca aggagttcat gcgcttcaag    60
gtgcgcatgg agggctccgt gaacggccac gagttcgaga tcgagggcga gggcgagggc   120
cgcccctacg agggctttca gaccgctaag ctgaaggtga ccaagggtgg cccctgccc    180
ttcgcctggg acatcctgtc ccctcagttc acctacggct ccaaggccta cgtgaagcac   240
cccgccgaca tccccgacta cttcaagctg tccttcccg agggcttcaa gtgggagcgc    300
gtgatgaact tcgaggacgg cggcgtggtg accgtgaccc aggactcctc cctgcaggac   360
ggcgagttca tctacaaggt gaagctgcgc ggcaccaact cccctccga cggccccgta    420
atgcagaaga agaccatggg ctgggaggcc tcctccgagc ggatgtaccc cgaggacggc   480
gccctgaagg gcgagatcaa gatgaggctg aagctgaagg acggcggcca ctacacctcc   540
gaggtcaaga ccacctacaa ggccaagaag cccgtgcagc tgcccggcgc ctacatcgtc   600
ggcatcaagt tggacatcac ctcccacaac gaggactaca ccatcgtgga aacagtacgaa   660
cgcgccgagg ccgccactc caccggcggc atggacgagc tgtacaagta a              711
```

<210> SEQ ID NO 104
<211> LENGTH: 225
<212> TYPE: PRT
<213> ORGANISM: Artificial Sequence
<220> FEATURE:
<223> OTHER INFORMATION: Description of Artificial Sequence:Discosoma
      corallimorph Anthozoan red fluorescent protein
      (DsRed) monomer variant mHoneydew

<400> SEQUENCE: 104

```
Met Ala Ser Ser Glu Asp Val Ile Lys Glu Phe Met Arg Phe Lys Val
  1               5                  10                  15

Arg Met Glu Gly Ser Val Asn Gly His Glu Phe Glu Ile Glu Gly Glu
             20                  25                  30

Gly Glu Gly Arg Pro Tyr Glu Gly Thr Gln Thr Ala Lys Leu Lys Val
         35                  40                  45

Thr Lys Gly Gly Pro Leu Pro Phe Ala Trp Asp Ile Leu Ser Pro Gln
     50                  55                  60

Phe Met Trp Gly Ser Lys Ala Tyr Val Lys His Pro Ala Asp Ile Pro
 65                  70                  75                  80

Asp Tyr Leu Lys Leu Ser Phe Pro Glu Gly Phe Lys Trp Glu Arg Val
                 85                  90                  95

Met Asn Phe Glu Asp Gly Gly Val Val Thr Val Thr Gln Asp Ser Ser
            100                 105                 110

Leu Gln Asp Gly Glu Phe Ile Tyr Lys Val Lys Leu Arg Gly Thr Asn
        115                 120                 125
```

```
Phe Pro Ser Asp Gly Pro Val Met Gln Lys Lys Thr Met Gly Trp Ala
    130                 135                 140

Ala Thr Thr Glu Arg Met Tyr Pro Glu Asp Gly Ala Leu Lys Gly Glu
145                 150                 155                 160

Ile Lys Met Arg Leu Lys Leu Lys Asp Gly Gly His Tyr Asp Ala Glu
                165                 170                 175

Val Lys Thr Thr Tyr Met Ala Lys Lys Pro Val Gln Leu Pro Gly Ala
            180                 185                 190

Tyr Lys Ile Asp Gly Lys Leu Asp Ile Thr Ser His Asn Glu Asp Tyr
        195                 200                 205

Thr Ile Val Glu Gln Tyr Glu Arg Ala Glu Gly Arg His Ser Thr Gly
    210                 215                 220

Ala
225

<210> SEQ ID NO 105
<211> LENGTH: 678
<212> TYPE: DNA
<213> ORGANISM: Artificial Sequence
<220> FEATURE:
<223> OTHER INFORMATION: Description of Artificial Sequence:Discosoma
      corallimorph Anthozoan red fluorescent protein
      (DsRed) monomer variant mHoneydew

<400> SEQUENCE: 105
atggcctcct ccgaggacgt catcaaggag ttcatgcgct tcaaggtgcg catggagggc    60
tccgtgaacg gccacgagtt cgagatcgag ggcgagggcg agggccgccc ctacgagggc   120
acccagaccg ccaagctgaa ggtgaccaag gcggccccc tgcccttcgc ctgggacatc   180
ctgtcccctc agttcatgtg gggctccaag gcctacgtga agcaccccgc cgacatcccc   240
gactacttga agctgtcctt ccccgagggc ttcaagtggg agcgcgtgat gaacttcgag   300
gacggcggcg tggtgaccgt gacccaggac tcctccctgc aggacggcga gttcatctac   360
aaggtgaagc tgcgcggcac caacttcccc tccgacggcc ccgtaatgca agaagaagacc   420 atgggctggg cggccaccac cgagcggatg taccccgagg acggcgccct gaagggcgag   480
atcaagatga ggctgaagct gaaggacggc ggccactacg acgccgaggt caagaccacc   540
tacatggcca agaagcccgt gcagctgccc ggcgcctaca agattgacgg gaagctggac   600
atcacctccc acaacgagga ctacaccatc gtggaacagt acgagcgcgc cgagggccgc   660
cactccaccg gcgcctaa                                                 678

<210> SEQ ID NO 106
<211> LENGTH: 456
<212> TYPE: PRT
<213> ORGANISM: Artificial Sequence
<220> FEATURE:
<223> OTHER INFORMATION: Description of Artificial Sequence:Discosoma
      corallimorph Anthozoan red fluorescent protein
      (DsRed) tandem dimeric variant tdTomato

<400> SEQUENCE: 106

Met Val Ser Lys Gly Glu Glu Val Ile Lys Phe Met Arg Phe Lys
1               5                   10                  15

Val Arg Met Glu Gly Ser Met Asn Gly His Glu Phe Glu Ile Glu Gly
                20                  25                  30

Glu Gly Glu Gly Arg Pro Tyr Glu Gly Thr Gln Thr Ala Lys Leu Lys
            35                  40                  45

Val Thr Lys Gly Gly Pro Leu Pro Phe Ala Trp Asp Ile Leu Ser Pro
        50                  55                  60
```

```
Gln Phe Met Tyr Gly Ser Lys Ala Tyr Val Lys His Pro Ala Asp Ile
 65                  70                  75                  80

Pro Asp Tyr Lys Lys Leu Ser Phe Pro Glu Gly Phe Lys Trp Glu Arg
             85                  90                  95

Val Met Asn Phe Glu Asp Gly Gly Leu Val Thr Val Thr Gln Asp Ser
            100                 105                 110

Ser Leu Gln Asp Gly Thr Leu Ile Tyr Lys Val Lys Met Arg Gly Thr
        115                 120                 125

Asn Phe Pro Pro Asp Gly Pro Val Met Gln Lys Lys Thr Met Gly Trp
    130                 135                 140

Glu Ala Ser Thr Glu Arg Leu Tyr Pro Arg Asp Gly Val Leu Lys Gly
145                 150                 155                 160

Glu Ile His Gln Ala Leu Lys Leu Lys Asp Gly Gly His Tyr Leu Val
                165                 170                 175

Glu Phe Lys Thr Ile Tyr Met Ala Lys Lys Pro Val Gln Leu Pro Gly
            180                 185                 190

Tyr Tyr Tyr Val Asp Thr Lys Leu Asp Ile Thr Ser His Asn Glu Asp
        195                 200                 205

Tyr Thr Ile Val Glu Gln Tyr Glu Arg Ser Glu Gly Arg His His Leu
    210                 215                 220

Phe Leu Gly His Gly Thr Gly Ser Thr Gly Ser Gly Ser Ser Gly Thr
225                 230                 235                 240

Ala Ser Ser Glu Asp Asn Asn Met Ala Val Ile Lys Glu Phe Met Arg
                245                 250                 255

Phe Lys Val Arg Met Glu Gly Ser Met Asn Gly His Glu Phe Glu Ile
            260                 265                 270

Glu Gly Glu Gly Glu Gly Arg Pro Tyr Glu Gly Thr Gln Thr Ala Lys
        275                 280                 285

Leu Lys Val Thr Lys Gly Gly Pro Leu Pro Phe Ala Trp Asp Ile Leu
    290                 295                 300

Ser Pro Gln Phe Met Tyr Gly Ser Lys Ala Tyr Val Lys His Pro Ala
305                 310                 315                 320

Asp Ile Pro Asp Tyr Lys Lys Leu Ser Phe Pro Glu Gly Phe Lys Trp
                325                 330                 335

Glu Arg Val Met Leu Ile Tyr Lys Val Lys Met Arg Gly Thr Asn Phe
            340                 345                 350

Pro Pro Asp Gly Pro Val Met Gln Lys Lys Thr Met Gly Trp Glu Ala
        355                 360                 365

Ser Thr Glu Arg Leu Tyr Pro Arg Asp Gly Val Leu Lys Gly Glu Ile
    370                 375                 380

His Gln Ala Leu Lys Leu Lys Asp Gly Gly His Tyr Leu Val Glu Phe
385                 390                 395                 400

Lys Thr Ile Tyr Met Ala Lys Lys Pro Val Gln Leu Pro Gly Tyr Tyr
                405                 410                 415

Tyr Val Asp Thr Lys Leu Asp Ile Thr Ser His Asn Glu Asp Tyr Thr
            420                 425                 430

Ile Val Glu Gln Tyr Glu Arg Ser Glu Gly Arg His His Leu Phe Leu
        435                 440                 445

Tyr Gly Met Asp Glu Leu Tyr Lys
    450                 455

<210> SEQ ID NO 107
<211> LENGTH: 1431
<212> TYPE: DNA
```

<213> ORGANISM: Artificial Sequence
<220> FEATURE:
<223> OTHER INFORMATION: Description of Artificial Sequence:Discosoma
    corallimorph Anthozoan red fluorescent protein
    (DsRed) tandem dimeric variant tdTomato

<400> SEQUENCE: 107

```
atggtgagca agggcgagga ggtcatcaaa gagttcatgc gcttcaaggt gcgcatggag      60
ggctccatga acggccacga gttcgagatc gagggcgagg gcgagggccg cccctacgag     120
ggcacccaga ccgccaagct gaaggtgacc aagggcggcc ccctgccctt cgcctgggac     180
atcctgtccc cccagttcat gtacggctcc aaggcgtacg tgaagcaccc cgccgacatc     240
cccgattaca agaagctgtc cttccccgag ggcttcaagt gggagcgcgt gatgaacttc     300
gaggacggcg gtctggtgac cgtgacccag gactcctccc tgcaggacgg cacgctgatc     360
tacaaggtga agatgcgcgg caccaacttc ccccccgacg gccccgtaat gcagaagaag     420
accatgggct gggaggcctc caccgagcgc ctgtaccccc gcgacggcgt gctgaagggc     480
gagatccacc aggccctgaa gctgaaggac ggcggccact acctggtgga gttcaagacc     540
atctacatgg ccaagaagcc cgtgcaactg cccggctact actacgtgga caccaagctg     600
gacatcacct cccacaacga ggactacacc atcgtggaac agtacgagcg ctccgagggc     660
cgccaccacc tgttcctggg catggaccc ggcagcaccg gcagcggcag ctccggcacc     720
gcctcctccg aggacaacaa catggccgtc atcaaagagt tcatgcgctt caaggtgcgc     780
atggagggct ccatgaacgg ccacgagttc gagatcgagg cgagggcga gggccgcccc     840
tacgagggca cccagaccgc caagctgaag gtgaccaagg gcggcccct gcccttcgcc     900
tgggacatcc tgtcccccca gttcatgtac ggctccaagg cgtacgtgaa gccccccgcc     960
gacatccccg attacaagaa gctgtccttc cccgagggct tcaagtggga gcgcgtgatg    1020
aacttcgagg acggcggtct ggtgaccgtg acccaggact cctccctgca ggacggcacg    1080
ctgatctaca aggtgaagat gcgcggcacc aacttccccc ccgacggccc cgtaatgcag    1140
aagaagacca tgggctggga ggcctccacc gagcgcctgt accccgca cggcgtgctg    1200
aagggcgaga tccaccaggc cctgaagctg aaggacggcg gccactacct ggtggagttc    1260
aagaccatct acatggccaa gaagcccgtg caactgcccg gctactacta cgtggacacc    1320
aagctggaca tcacctccca caacgaggac tacaccatcg tggaacagta cgagcgctcc    1380
gagggccgcc accacctgtt cctgtacggc atggacgagc tgtacaagta a             1431
```

<210> SEQ ID NO 108
<211> LENGTH: 225
<212> TYPE: PRT
<213> ORGANISM: Artificial Sequence
<220> FEATURE:
<223> OTHER INFORMATION: Description of Artificial Sequence:Discosoma
    corallimorph Anthozoan red fluorescent protein
    (DsRed) monomer variant mGrape1

<400> SEQUENCE: 108

```
Met Ala Ser Ser Glu Asp Val Ile Lys Glu Phe Met Arg Phe Lys Val
  1               5                  10                  15

Arg Met Glu Gly Ser Val Asn Gly His Glu Phe Glu Ile Glu Gly Glu
             20                  25                  30

Gly Glu Gly Arg Pro Tyr Glu Gly Thr Gln Thr Ala Lys Leu Lys Val
         35                  40                  45

Thr Lys Gly Gly Pro Leu Pro Phe Ala Trp Asp Ile Leu Ser Pro Gln
     50                  55                  60
```

```
Phe Met Tyr Gly Ser Lys Ala Tyr Val Lys His Pro Ala Asp Ile Pro
 65                  70                  75                  80

Asp Tyr Leu Lys Leu Ser Phe Pro Glu Gly Phe Lys Trp Glu Arg Val
                 85                  90                  95

Met Asn Phe Glu Asp Gly Gly Val Val Thr Val Thr Gln Asp Ser Ser
            100                 105                 110

Leu Gln Asp Gly Glu Phe Ile Tyr Lys Val Lys Leu Arg Gly Thr Asn
        115                 120                 125

Phe Pro Ser Asp Gly Pro Val Met Gln Lys Lys Thr Met Gly Trp Glu
130                 135                 140

Ala Ser Ser Glu Arg Leu Tyr Pro Glu Asp Gly Ala Leu Lys Gly Glu
145                 150                 155                 160

Ile Lys Met Arg Leu Lys Leu Lys Asp Gly Gly His Tyr Asp Ala Glu
                165                 170                 175

Ala Lys Thr Thr Tyr Met Ala Lys Lys Pro Val Gln Leu Pro Gly Ala
            180                 185                 190

Tyr Lys Leu Asp Tyr Lys Leu Asp Ile Thr Ser His Asn Glu Asp Tyr
        195                 200                 205

Thr Ile Val Glu Gln Tyr Glu Arg Ala Glu Gly Arg His Ser Thr Gly
    210                 215                 220

Ala
225

<210> SEQ ID NO 109
<211> LENGTH: 678
<212> TYPE: DNA
<213> ORGANISM: Artificial Sequence
<220> FEATURE:
<223> OTHER INFORMATION: Description of Artificial Sequence:Discosoma
      corallimorph Anthozoan red fluorescent protein
      (DsRed) monomer variant mGrape1

<400> SEQUENCE: 109
atggcctcct ccgaggacgt catcaaggag ttcatgcgct tcaaggtgcg catggagggc      60
tccgtgaacg gccacgagtt cgagatcgag ggcgagggcg agggccgccc ctacgagggc     120
acccagaccg ccaagctgaa ggtgaccaag ggcggccccc tgcccttcgc ctgggacatc     180
ctgtcccctc agttcatgta cggctccaag gcctacgtga agcacccgc cgacatcccc      240 gactacctga agctgtcctt ccccgagggc ttcaagtggg agcgcgtgat gaacttcgag     300
gacggcggcg tggtgaccgt gacccaggac tcctccctgc aggacggcga gttcatctac     360
aaggtgaagc tgcgcggcac caacttcccc tccgacggcc ccgtaatgca gaagaagacc     420
atgggctggg aggcctcctc cgagcggctg tacccegagg acggcgccct gaagggcgag     480
atcaagatga ggctgaagct gaaggacggc ggccactacg acgccgaggc caagaccacc     540
tacatggcca agaagcccgt gcagctgccc ggcgcctaca agctcgacta caagctggac     600
atcacctccc acaacgagga ctacaccatc gtggaacagt acgagcgcgc cgagggccgc     660
cactccaccg gcgcctaa                                                  678

<210> SEQ ID NO 110
<211> LENGTH: 8
<212> TYPE: PRT
<213> ORGANISM: Artificial Sequence
<220> FEATURE:
<223> OTHER INFORMATION: Description of Artificial Sequence:alternate
      variation of EGFP C-terminus

<400> SEQUENCE: 110
```

```
Tyr Gly Met Asp Glu Leu Tyr Lys
  1               5

<210> SEQ ID NO 111
<211> LENGTH: 4
<212> TYPE: PRT
<213> ORGANISM: Artificial Sequence
<220> FEATURE:
<223> OTHER INFORMATION: Description of Artificial Sequence:4 residue
      insert after position E6, residues 6a-6d

<400> SEQUENCE: 111

Asp Asn Met Ala
  1

<210> SEQ ID NO 112
<211> LENGTH: 4
<212> TYPE: PRT
<213> ORGANISM: Artificial Sequence
<220> FEATURE:
<223> OTHER INFORMATION: Description of Artificial Sequence:4 residue
      insert after position E6, residues 6a-6d, spacer
      sequence

<400> SEQUENCE: 112

Asn Asn Met Ala
  1

<210> SEQ ID NO 113
<211> LENGTH: 10
<212> TYPE: PRT
<213> ORGANISM: Artificial Sequence
<220> FEATURE:
<223> OTHER INFORMATION: Description of Artificial Sequence:N-terminal
      end of wtDsRed

<400> SEQUENCE: 113

Met Arg Ser Ser Lys Asn Val Ile Lys Glu
  1               5                  10

<210> SEQ ID NO 114
<211> LENGTH: 6
<212> TYPE: PRT
<213> ORGANISM: Artificial Sequence
<220> FEATURE:
<223> OTHER INFORMATION: Description of Artificial Sequence:C-terminal
      end of wtDsRed

<400> SEQUENCE: 114

Arg His His Leu Phe Leu
  1               5

<210> SEQ ID NO 115
<211> LENGTH: 10
<212> TYPE: PRT
<213> ORGANISM: Artificial Sequence
<220> FEATURE:
<223> OTHER INFORMATION: Description of Artificial Sequence:N-terminal
      end of mRFP1

<400> SEQUENCE: 115

Met Ala Ser Ser Glu Asp Val Ile Lys Glu
  1               5                  10

<210> SEQ ID NO 116
<211> LENGTH: 6
<212> TYPE: PRT
<213> ORGANISM: Artificial Sequence
<220> FEATURE:
```

```
<223> OTHER INFORMATION: Description of Artificial Sequence:C-terminal
      end of mRFP1

<400> SEQUENCE: 116

Arg His Ser Thr Gly Ala
  1               5

<210> SEQ ID NO 117
<211> LENGTH: 15
<212> TYPE: PRT
<213> ORGANISM: Artificial Sequence
<220> FEATURE:
<223> OTHER INFORMATION: Description of Artificial Sequence:N-terminal
      end of wtDsRed or mRFP1 replaced with "GFP termini"

<400> SEQUENCE: 117

Met Val Ser Lys Gly Glu Glu Asn Asn Met Ala Val Ile Lys Glu
  1               5                  10                  15

<210> SEQ ID NO 118
<211> LENGTH: 12
<212> TYPE: PRT
<213> ORGANISM: Artificial Sequence
<220> FEATURE:
<223> OTHER INFORMATION: Description of Artificial Sequence:C-terminal
      end of wtDsRed or mRFP1 replaced with "GFP termini"

<400> SEQUENCE: 118

Arg His Ser Thr Gly Gly Met Asp Glu Leu Tyr Lys
  1               5                  10

<210> SEQ ID NO 119
<211> LENGTH: 225
<212> TYPE: PRT
<213> ORGANISM: Artificial Sequence
<220> FEATURE:
<223> OTHER INFORMATION: Description of Artificial Sequence:Discosoma
      corallimorph Anthozoan red fluorescent protein
      (DsRed) monomer variant mHoneydew from Figure 48A

<400> SEQUENCE: 119

Met Ala Ser Ser Glu Asp Val Ile Lys Glu Phe Met Arg Phe Lys Val
  1               5                  10                  15

Arg Met Glu Gly Ser Val Asn Gly His Glu Phe Glu Ile Glu Gly Glu
                 20                  25                  30

Gly Glu Gly Arg Pro Tyr Glu Gly Thr Gln Thr Ala Lys Leu Lys Val
             35                  40                  45

Thr Lys Gly Gly Pro Leu Pro Phe Ala Trp Asp Ile Leu Ser Pro Gln
 50                  55                  60

Phe Met Trp Gly Ser Lys Ala Tyr Val Lys His Pro Ala Asp Ile Pro
 65                  70                  75                  80

Asp Tyr Leu Lys Leu Ser Phe Pro Glu Gly Phe Lys Trp Glu Arg Val
                 85                  90                  95

Met Asn Phe Glu Asp Gly Gly Val Val Thr Val Thr Gln Asp Ser Ser
            100                 105                 110

Leu Gln Asp Gly Glu Phe Ile Tyr Lys Val Lys Leu Arg Gly Thr Asn
        115                 120                 125

Phe Pro Ser Asp Gly Pro Val Met Gln Lys Lys Thr Met Gly Trp Ala
    130                 135                 140

Ala Thr Ser Glu Arg Met Tyr Pro Glu Asp Gly Ala Leu Lys Gly Glu
145                 150                 155                 160

Ile Lys Met Arg Leu Lys Leu Lys Asp Gly Gly His Tyr Asp Ala Glu
                165                 170                 175
```

```
Val Lys Thr Thr Tyr Met Ala Lys Lys Pro Val Gln Leu Pro Gly Ala
            180                 185                 190

Tyr Lys Ile Asp Gly Lys Leu Asp Ile Thr Ser His Asn Glu Asp Tyr
        195                 200                 205

Thr Ile Val Glu Gln Tyr Glu Arg Ala Glu Gly Arg His Ser Thr Gly
    210                 215                 220

Ala
225

<210> SEQ ID NO 120
<211> LENGTH: 6
<212> TYPE: PRT
<213> ORGANISM: Artificial Sequence
<220> FEATURE:
<223> OTHER INFORMATION: Description of Artificial Sequence:N-terminal
      6xHis tag, polyhistidine tag, His-6 tag,
      nickel-agarose affinity tag

<400> SEQUENCE: 120

His His His His His His
  1               5

<210> SEQ ID NO 121
<211> LENGTH: 9
<212> TYPE: PRT
<213> ORGANISM: Artificial Sequence
<220> FEATURE:
<223> OTHER INFORMATION: Description of Artificial Sequence:sequence
      following 12-residue linker before residue 7 of
      dRFP3

<400> SEQUENCE: 121

Ala Ser Ser Glu Asp Asn Asn Met Ala
  1               5

<210> SEQ ID NO 122
<211> LENGTH: 32
<212> TYPE: PRT
<213> ORGANISM: Artificial Sequence
<220> FEATURE:
<223> OTHER INFORMATION: Description of Artificial Sequence:modified
      2+-Zn finger domain with two 2+Zn-ligating Cys residues
      mutated to His

<400> SEQUENCE: 122

His Glu Arg Pro Tyr Ala His Pro Val Glu Ser His Asp Arg Phe Ser
  1               5                  10                  15

Arg Ser Asp Glu Leu Thr Arg His Ile Arg Ile His Thr Gly Gln Lys
             20                  25                  30
```